(12) United States Patent
Davies et al.

(10) Patent No.: US 8,304,423 B2
(45) Date of Patent: Nov. 6, 2012

(54) MODULATORS OF MUSCARINIC RECEPTORS

(75) Inventors: Robert J. Davies, Watertown, MA (US); Jinwang Xu, Framingham, MA (US)

(73) Assignee: Vertex Pharmaceutical Incorporated, Cambridge, MA (US)

(*) Notice: Subject to any disclaimer, the term of this patent is extended or adjusted under 35 U.S.C. 154(b) by 0 days.

(21) Appl. No.: 13/171,652

(22) Filed: Jun. 29, 2011

(65) Prior Publication Data

US 2012/0004226 A1 Jan. 5, 2012
US 2012/0196857 A9 Aug. 2, 2012

Related U.S. Application Data

(62) Division of application No. 11/709,662, filed on Feb. 22, 2007, now Pat. No. 8,003,660.

(60) Provisional application No. 60/775,813, filed on Feb. 22, 2006.

(51) Int. Cl.
*A61K 31/5355* (2006.01)
*A61K 31/438* (2006.01)
*C07D 417/12* (2006.01)
*C07D 413/12* (2006.01)
*C07D 405/12* (2006.01)
*C07D 401/04* (2006.01)
*C07D 401/12* (2006.01)
*C07D 221/20* (2006.01)

(52) U.S. Cl. ....... 514/278; 514/235.5; 546/17; 540/543; 544/70

(58) Field of Classification Search .................. 514/278, 514/235.5; 546/17; 540/543; 544/70
See application file for complete search history.

(56) References Cited

U.S. PATENT DOCUMENTS

| | | | |
|---|---|---|---|
| 3,654,287 A | 4/1972 | Dykstra | |
| 3,666,764 A | 5/1972 | Campbell et al. | |
| 3,959,475 A | 5/1976 | Bauer et al. | |
| 3,962,259 A | 6/1976 | Bauer et al. | |
| 4,233,307 A | 11/1980 | Ono et al. | |
| 4,349,549 A | 9/1982 | Roszkowski et al. | |
| 4,558,049 A | 12/1985 | Bernardi et al. | |
| 5,091,387 A | 2/1992 | Evans et al. | |
| 5,219,860 A | 6/1993 | Chambers et al. | |
| 5,324,733 A | 6/1994 | Billington et al. | |
| 5,457,207 A | 10/1995 | Efange et al. | |
| 5,576,321 A | 11/1996 | Krushinski, Jr. et al. | |
| 5,578,593 A | 11/1996 | Chen et al. | |
| 5,614,523 A | 3/1997 | Audia et al. | |
| 5,627,196 A | 5/1997 | Audia et al. | |
| 5,652,235 A | 7/1997 | Chen et al. | |
| 5,658,921 A | 8/1997 | Perregaard et al. | |
| 5,693,643 A | 12/1997 | Gilbert et al. | |
| 5,741,789 A | 4/1998 | Hibschman et al. | |
| 5,789,402 A | 8/1998 | Audia et al. | |
| 5,817,679 A | 10/1998 | Shen et al. | |
| 5,885,999 A | 3/1999 | Elliott et al. | |
| 6,013,652 A | 1/2000 | Maccoss et al. | |
| 6,130,217 A | 10/2000 | Arnold et al. | |
| 6,166,037 A | 12/2000 | Budhu et al. | |
| 6,166,040 A | 12/2000 | Fairhurst et al. | |
| 6,294,534 B1 | 9/2001 | Nargund et al. | |
| 6,316,437 B1 | 11/2001 | Hoffman | |
| 6,326,375 B1 | 12/2001 | Fukami et al. | |
| 6,413,961 B1 | 7/2002 | Demopulos et al. | |
| 6,436,962 B1 | 8/2002 | Hoffman et al. | |
| 6,566,367 B2 | 5/2003 | Bakthavatchalam et al. | |
| 6,576,664 B1 | 6/2003 | Yao et al. | |
| 6,713,487 B2 | 3/2004 | Yu et al. | |
| 6,720,324 B2 | 4/2004 | Marzabadi et al. | |
| 6,828,440 B2 | 12/2004 | Goehring et al. | |
| 6,869,960 B2 | 3/2005 | Ito et al. | |
| 6,943,199 B2 | 9/2005 | De Lombaert et al. | |
| 7,045,527 B2 | 5/2006 | Chen et al. | |
| 7,205,417 B2 | 4/2007 | Fukami et al. | |
| 7,279,471 B2 | 10/2007 | Mueller et al. | |
| 7,351,706 B2 | 4/2008 | Bissantz et al. | |
| 7,491,715 B2 | 2/2009 | Ek et al. | |
| 2002/0188124 A1 | 12/2002 | Fukami et al. | |
| 2003/0036652 A1 | 2/2003 | Bakthavatchalam et al. | |
| 2003/0082623 A1 | 5/2003 | Borowsky et al. | |
| 2003/0158219 A1 | 8/2003 | Ito et al. | |
| 2004/0038855 A1 | 2/2004 | Salon et al. | |
| 2004/0050285 A1 | 3/2004 | Zozulya et al. | |
| 2004/0054177 A1 | 3/2004 | Otake et al. | |
| 2004/0072847 A1 | 4/2004 | Bakthavatchalam et al. | |
| 2004/0082623 A1 | 4/2004 | Rochhi et al. | |
| 2004/0122074 A1 | 6/2004 | Dow et al. | |
| 2004/0142956 A1 | 7/2004 | Chen et al. | |
| 2004/0204397 A1 | 10/2004 | Chaturvedula et al. | |
| 2004/0214837 A1 | 10/2004 | Griffith et al. | |

(Continued)

FOREIGN PATENT DOCUMENTS

CN 1535967 A 10/2004

(Continued)

OTHER PUBLICATIONS

Rosenberg et al. Am. J. Psychiatry, 2006, 163, 1884-1890.*
Luo et al. Cell, 2009, 136, pp. 823-837.*
Abdel-Madid, A., et al., "Reductive Amination of Aldehydes and Ketones with Sodium Tracetoxyborohydride. Studies on Direct and Indirect Reductive Amination Procedures1", J. Org. Chem. (1996) vol. 61, pp. 3849-3862.
Berney, D., et al., Helvetica Chimica Acta, (1974), vol. 57, pp. 1198-1204.
Bignan, G.C., et al., "Preparation of 3-Spirocyclic Indolin-2-ones as Ligands for the ORL-1 Receptor," Bioorganic and Medicinal Chem. Lett, (2005) vol. 15, pp. 5022-5026.
Butera, J.A., et al., "Recent Approaches to the Treatment of Urinary Incontinence: A Survey of Patent Activity from 1995 to 1998," Expert Opinion on Therapeutic Patents (1998) vol. 8, No. 8, pp. 1017-1035.

(Continued)

*Primary Examiner* — Joseph Kosack
*Assistant Examiner* — Matthew Coughlin
(74) *Attorney, Agent, or Firm* — Honigman Miller Schwartz and Cohn LLP; Christopher C. Forbes; Jonathan P. O'Brien

(57) ABSTRACT

The present invention relates to modulators of muscarinic receptors. The present invention also provides compositions comprising such modulators, and methods therewith for treating muscarinic receptor mediated diseases.

20 Claims, No Drawings

U.S. PATENT DOCUMENTS

| | | | |
|---|---|---|---|
| 2005/0033048 A1 | 2/2005 | Bakthavatchalam et al. |
| 2005/0143372 A1 | 6/2005 | Ghosh et al. |
| 2005/0153998 A1 | 7/2005 | Ito et al. |
| 2005/0176703 A1 | 8/2005 | Gabriel et al. |
| 2005/0215576 A1 | 9/2005 | Degnan et al. |
| 2005/0261332 A1 | 11/2005 | Distefano et al. |
| 2006/0019962 A1 | 1/2006 | Makings et al. |
| 2006/0040964 A1 | 2/2006 | Bakthavatchalam et al. |
| 2006/0058778 A1 | 3/2006 | Arcusa Villacampa et al. |
| 2006/0106045 A1 | 5/2006 | Hughes et al. |
| 2006/0111380 A1 | 5/2006 | Otake et al. |
| 2006/0173027 A1 | 8/2006 | Marzabadi et al. |
| 2006/0183904 A1 | 8/2006 | Guo et al. |
| 2006/0211722 A1 | 9/2006 | Jiao et al. |
| 2006/0217372 A1 | 9/2006 | Blanco-Pillado et al. |
| 2006/0270673 A1 | 11/2006 | Duggan et al. |
| 2007/0043023 A1 | 2/2007 | Makings et al. |
| 2007/0149502 A1 | 6/2007 | Chaturvedula et al. |
| 2007/0213315 A1 | 9/2007 | Davies et al. |
| 2007/0254903 A1 | 11/2007 | Boatman et al. |
| 2008/0033002 A1 | 2/2008 | Bandarage et al. |
| 2008/0171753 A1 | 7/2008 | Jitsuoka et al. |

FOREIGN PATENT DOCUMENTS

| | | |
|---|---|---|
| DE | 3433327 A1 | 3/1985 |
| EP | 0070171 A1 | 1/1983 |
| EP | 0128886 A2 | 12/1984 |
| EP | 0414289 A1 | 2/1991 |
| EP | 0444945 A2 | 9/1991 |
| EP | 0445974 A2 | 9/1991 |
| EP | 0486280 A2 | 5/1992 |
| EP | 0518805 A1 | 12/1992 |
| EP | 0722941 A2 | 7/1996 |
| GB | 1575800 | 10/1980 |
| GB | 2308064 A | 6/1997 |
| JP | 2001/278886 A | 10/2001 |
| JP | 2002/316987 A | 10/2002 |
| WO | 94/22846 A1 | 10/1994 |
| WO | 95/11029 A1 | 4/1995 |
| WO | 95/14025 A1 | 5/1995 |
| WO | 95/28389 A1 | 10/1995 |
| WO | 97/41878 A1 | 11/1997 |
| WO | 97/41879 A1 | 11/1997 |
| WO | 99/06434 A1 | 2/1999 |
| WO | 99/32489 A1 | 7/1999 |
| WO | 00/06146 A1 | 2/2000 |
| WO | 00/06153 A1 | 2/2000 |
| WO | 00/06545 A1 | 2/2000 |
| WO | 00/38720 A1 | 7/2000 |
| WO | 01/02386 A1 | 1/2001 |
| WO | 01/22919 A2 | 4/2001 |
| WO | 01/29027 A1 | 4/2001 |
| WO | 01/45707 A1 | 6/2001 |
| WO | 01/64213 A1 | 9/2001 |
| WO | 02/094825 A1 | 11/2002 |
| WO | 03/095427 A1 | 11/2003 |
| WO | 2004/010942 A2 | 2/2004 |
| WO | 2004/010943 A2 | 2/2004 |
| WO | 2004/011427 A2 | 2/2004 |
| WO | 2005/065779 A1 | 7/2005 |
| WO | 2005/111003 A1 | 11/2005 |
| WO | 2006/001958 A2 | 1/2006 |

OTHER PUBLICATIONS

Bymaster, F.P., et al., "Xanomiline: A Selective Muscarinic Agonist for the Treatment of Alzheimer's Disease," Drug Development Research (1997) vol. 40, pp. 158-170.

CAS Registry entry for Registry No. 878376-80-8, which entered STN on Mar. 28, 2006.

Caufield, M.P., et al., "International Union of Pharmacology. XVII. Classification of Muscarinic Acetylcholine Receptors," Pharmacol. Rev., (1998) vol. 50, No. 2, pp. 279-290.

Caufield, M.P., "Muscarinic Receptors—Characterization, Coupling and Function," Pharmac. Ther. (1993) vol. 58, pp. 319-379.

Chambers, M.S., et al., "Spiropiperidines as High-Affinity, Selective s Ligands," J. Med. Chem., (1992), vol. 35, No. 11, pp. 2033-2039.

Cheng, Y., et al., "Solid Phase Synthesis of Spiroindoline," Tet. Lett. (1997) vol. 38, No. 9, pp. 1497-1500.

Chiavarelli, S., et al., "Ricerche nella serle della 4-feniipiperidina. Nota v. Derivati della 4,4'-spiro-(1"metilpiperidin)-1,2,3,4,-tetraidroisochinolina," Gazzetta Chimica Italiana (1960) vol. 90, pp. 189-195.

Custers, F.G.J., et al., "Vesamicol and Some of its Derivatives: Questionable Ligands for Selectively Labeling Acetylcholine Transporters in Rat Brain," Eur. Jour. of Pharm. (1997) vol. 338, pp. 177-183.

deLaszlo, S.E., et al., "A Nonpeptidic Agonist Ligand of the Human C5A Receptor: Synthesis, Binding Affinity Optimization and Functional Characterization," Bioorganic and Medicinal Chem. Lett. (1997) vol. 7, No. 2, pp. 213-218.

Dhar, T.G.M., et al., "Design and Synthesis of Novel α1a Adrenoceptor-selective Antagonists," Journal of Medicinal Chemistry (1999) vol. 42, No. 23, pp. 4778-4793.

Efange, S.M.N., et al., "(+)-p-([18F]Fluorobenzyl)Spirotrozamicol {(+)-[18F]Spiro-FBT}: Synthesis and Biological Evaluation of a High-Affinity Ligand for the Vesicular Acetylcholine Transporter (VAChT)," Nuclear Medicine and Biology (1999) vol. 26, pp. 189-192.

Efange, S.M.N., et al., "Comparative Tissue Distribution of Conformationally Restricted Radioiodinated Vesamicol Receptor Ligands," Nuclear Medicine and Biology (1995) vol. 22, No. 4, pp. 437-444.

Efange, S.M.N., et al., "Spirovesamicols: Conformationally Restricted Analogs of 2-(4-Phenylpiperidino) Cyclohexnol (Vesamicol, AH5183) as Potential Modulators of Presynaptic Cholinergic Function," Journal of Medicinal Chemistry (1994) vol. 37, No. 16, pp. 2574-2582.

Efange, S.M.N., et al., "N-Hydroxyalkyl Derivatives of 3β-Phenyltropane and Methylspiro[1H-indoline-3,4'-piperidine]: Vesamicol Analogues with Affinity of Monoamine Transporters," J. Med. Chem. (1997) vol. 40, pp. 3905-3914.

Efange, S.M.N., et al., "Vesamicol Analogs as Sigma Ligands. Molecular Determinants of Selectivity at the Vesamicol Receptor," Biochem. Pharm. (1995) vol. 49, No. 6, pp. 791-797.

Evans, B.E., et al., "Orally Active, Nonpeptide Oxytocin Antagonists," Journal of Medicinal Chemistry (1992) vol. 35, No. 21, pp. 3919-3927.

Felder, C.C., et al., "Therapeutic Opportunities for Muscarinic Receptors in the Central Nervous System," J. Med. Chem. (2000) vol. 43, No. 23, pp. 4333-4353.

Freireich, E.J., et al., "Quantitative Comparison of Toxicity of Anticancer Agents in Mouse, Rat, Hamster, Dog, Monkey and Man," Cancer Chemother, Rep. (1966) vol. 50, pp. 219-244.

Hulme, E.C., et al., "Muscarinic Receptor Subtypes," Annu. Rev. Pharmacol. Toxicol. (1990) vol. 30, pp. 633-673.

Kim, D., et al., "Discovery of Human CCR5 Antagonists Containing Hydantoins for the Treatment of HIV-1 Infection," Bioorganic and Medicinal Chem. Lett. (2001) vol. 11, pp. 3099-3102.

Maligres, P.E., et al., "Synthesis of the Orally Active Spiroindoline-Based Growth Hormone Secretagogue, MK-677," Tetrahedron (1997) vol. 53, No. 32, pp. 10983-10992.

Malstrom, R.E., et al., "Pharmacology of H 394/84, a Dihydropyridine Neuropeptide Y Y1 Receptor Antagonist, in Vivo," Eur. Jour. of Pharm. (2001) vol. 418, pp. 95-104.

Matier, W.L., et al., "Novel Cyclizations and Ring-Opening Reactions of 3-Phenylindene Derivatives," J. Org. Chem. (1971) vol. 36, No. 5, pp. 650-654.

Moltzen, E.K., et al., "σ Ligands with Subnanomolar Affinity and Preference for the σ2 Binding Site," Journal of Medicinal Chemistry (1995) vol. 38, No. 11, pp. 2009-2017.

Morrow, D.F., et al., "Synthesis of Some New 17-Spiro-Substituted Steroids," J. Med. Chem. (1967) vol. 10, No. 2, pp. 133-138.

Nargund, R.P., et al., "Peptidomimetic Growth Hormone Secretagogues: Synthesis and Biological Activities of Analogs Varied at the Indole Nucleus of the Prototypical Spiropiperidine L-162,752," Bioorganic and Medicinal Chem. Lett. (1996) vol. 6, No. 14, pp. 1731-1736.

Nargund, R.P., et al., "Synthesis and Biological Activities of Camphor-Based Non-Peptide Growth Hormone Secretagogues," Bioorganic and Medicinal Chem. Lett. (1996) vol. 6, No. 11, pp. 1265-1270.

Oprea, T.I., et al., "Is There a Difference Between Leads and Drugs? A Historical Perspective," J. Chem. Inf. Comput. Sci. (2001) vol. 41, pp. 1308-1315.

Pasternak, S., et al., "Potent, Orally Bioavailable Somatostatin Agonists: Good Absorption Achieved by Urea Backbone Cyclization," Bioorganic and Medicinal Chem. Lett. (1999) vol. 9, pp. 491-496.

Patchett, A.A., et al., "The Synthesis of 17β-Amino-17 α-(2'-carboxyethyl)androstane Lacatama1," J. Org. Chem. (1962) vol. 27, pp. 3822-3828.

Patrick, G.L., J. Chem. Soc. Perkin Trans I, (1995), vol. 10, pp. 1273-1279.

Pettibone, D.J., et al., "Identification of an Orally Active, Nonpeptidyl Oxytocin Antagonist," Journal of Pharm. and Experimental Therap. (1993) vol. 264, No. 1, pp. 308-314.

Reimann, E., et al., "Synthese und Pharmakologische Prüfung Holologer und Hydroxylierter 3,4-Dihydro-1'-methyispiro[naphthalin-(2H),4'-piperidine]," Archiv. Der. Pharmazie, VCH Verlagsgesellschaft MBH, Weinheim, DE, (1990) vol. 323, pp. 35-39.

Rubin, B.K., et al., "Novel Medications for Asthma: A Look into the Future," Exper. Opinion on Investigational Drugs (2007) vol. 16, No. 6, pp. 889-897.

Takemoto, T., et al., "Asymmetric Synthesis of Enantiomerically Pure Spiro[((2S)-hydroxy)indane-1,4'-piperidine]," Tetrahedron Asymmetry (1999) vol. 10, pp. 1787-1793.

Tata, J.R., et al., "The Synthesis and Activity of Spiroindine Growth Hormone Secretagogues," Bioorganic and Medicinal Chem. Lett. (1997) vol. 7, No. 6, pp. 663-668.

Williams, P.D., et al., "1-(((7,7-Dimethyl-2(S)-(2(S)-amino-4-(methylsulfonyl)butyramido)bicyclo[2.2.1]-heptan-1(S)-yl)methyl)sulfonyl)-4-2(2-methylphenyl)piperazine (L-368,899): An Orally Bioavailable, Non-Peptide Oxytocin Antagonist with Potential Utility for Managing Preterm Labor," J. Med. Chem. (1994) vol. 37, pp. 555-571.

Yang, L., et al., "Potent 3-Spiropiperidine Growth Hormone Secretagogues," Bioorganic & Medicinal Chemistry Letters (1998) vol. 8, No. 1, pp. 107-112.

Yang, L., et al., "The Design and Synthesis of non-peptide Somatostatin Receptor Agonists," Peptides for the New Millennium, Proceedings of the American Peptide Symposium, 16th, Minneapolis, MN, Jun. 26-Jul. 1999 (2000), Meeting Date 1999, pp. 250-252.

* cited by examiner

MODULATORS OF MUSCARINIC RECEPTORS

CLAIM OF PRIORITY

This application is a divisional application which claims priority under 35 U.S.C. §121 to U.S. application Ser. No. 11/709,662, filed on Feb. 22, 2007, which claims priority to U.S. Provisional Application Ser. No. 60/775,813, filed on Feb. 22, 2006. Both applications are hereby incorporated by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43(23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors—Characterization, Coupling, and Function," Pharmacol. Ther., 58, pp. 319-379 (1993); Caulfield, M. P. et al., International Union of Pharmacology. XVII. Classification of Muscarinic Acetylcholine Receptors," Pharmacol. Rev., 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating the activity of a muscarinic receptor (e.g., $M_1$, $M_2$, $M_3$, $M_4$, $M_5$, or combinations thereof) using compounds of formula I:

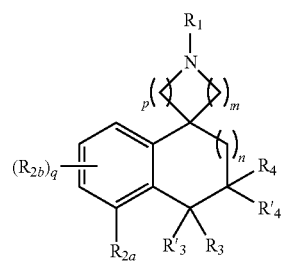

or a pharmaceutically acceptable salt thereof, wherein $R_1$, $R_{2a}$, $R_{2b}$, $R_3$, $R'_3$, $R_4$, $R'_4$, n, m, p, and q are described below.

Another aspect of the present invention provides methods of treating or reducing the severity of a muscarinic receptor mediated disease in a mammal, comprising the step of administering to said mammal a compound as described above. In several embodiments, the muscarinic receptor is $M_4$. In others, the muscarinic receptor is $M_1$.

Another aspect of the present invention provides methods of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis associated with CNS disorders including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances, and wound healing, wherein said method comprises the step of contacting said patient with a compound as described above.

Another aspect of the present invention provides pharmaceutical compositions comprising a compound described above and a pharmaceutical carrier.

DETAILED DESCRIPTION

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, or heterocycloaliphaticamino]; sulfonyl [e.g., aliphatic-$S(O)_2$—]; sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroaralkoxy; alkoxycarbonyl; alkylcarbonyloxy; or hydroxy. Without limitation, some examples of substituted alkyls include carboxyalkyl (such as HOOC-alkyl, alkoxycarbonylalkyl, and alkylcarbonyloxyalkyl); cyanoalkyl; hydroxyalkyl; alkoxyalkyl; acylalkyl; aralkyl; (alkoxyaryl)alkyl; (sulfonylamino)alkyl (such as alkyl-$S(O)_2$-aminoalkyl); aminoalkyl; amidoalkyl; (cycloaliphatic)alkyl; or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo; cycloaliphatic [e.g., cycloalkyl or cycloalkenyl]; heterocycloaliphatic [e.g., heterocycloalkyl or heterocycloalkenyl]; aryl; heteroaryl; alkoxy; aroyl; heteroaroyl; acyl [e.g., (aliphatic)carbonyl, (cycloaliphatic)carbonyl, or (heterocycloaliphatic)carbonyl]; nitro; cyano; amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, alkylaminocarbonyl, cycloalkylaminocarbonyl, heterocycloalkylaminocarbonyl, arylaminocarbonyl, or heteroarylaminocarbonyl]; amino [e.g., aliphaticamino, cycloaliphaticamino, heterocycloaliphaticamino, or aliphaticsulfonylamino]; sulfonyl [e.g., alkyl-$S(O)_2$—, cycloaliphatic-$S(O)_2$—, or aryl-$S(O)_2$—]; sulfinyl; sulfanyl; sulfoxy; urea; thiourea; sulfamoyl; sulfamide; oxo; carboxy; carbamoyl; cycloaliphaticoxy; heterocycloaliphaticoxy; aryloxy; heteroaryloxy; aralkyloxy; heteroaralkoxy; alkoxycarbonyl; alkylcarbonyloxy; or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$S(O)_2$-aminoalkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl; heteroaroyl; alkoxy; cycloalkyloxy; heterocycloalkyloxy; aryloxy; heteroaryloxy; aralkyloxy; nitro; carboxy; cyano; halo; hydroxy; sulfo; mercapto; sulfanyl [e.g., aliphatic-S— or cycloaliphatic-S—]; sulfinyl [e.g., aliphatic-S(O)— or cycloaliphatic-S(O)—]; sulfonyl [e.g., aliphatic-$S(O)_2$—, aliphaticamino-$S(O)_2$—, or cycloaliphatic-$S(O)_2$—]; amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl]; urea; thiourea; sulfamoyl; sulfamide; alkoxycarbonyl; alkylcarbonyloxy; cycloaliphatic; heterocycloaliphatic; aryl; heteroaryl; acyl [e.g., (cycloaliphatic)carbonyl or (heterocycloaliphatic)carbonyl]; amino [e.g., aliphaticamino]; sulfoxy; oxo; carbamoyl; (cycloaliphatic)oxy; (heterocycloaliphatic)oxy; or (heteroaryl)alkoxy.

As used herein, an "amido" encompasses both "aminocarbonyl" and "carbonylamino". These terms when used alone or in connection with another group refers to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic) carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl, (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic) carbonyl]; sulfonyl [e.g., aliphatic-S(O)$_2$— or amino-S(O)$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl) carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl) aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (amino sulfonyl)aryl]; (alkylsulfonyl)aryl; (cyano)aryl; (hydroxyalkyl)aryl; ((alkoxy)alkyl)aryl; (hydroxy)aryl, ((carboxy) alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl]; cycloaliphatic [e.g., cycloalkyl or cycloalkenyl]; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino]; cyano; halo; hydroxy; acyl; mercapto; alkylsulfanyl; sulfoxy; urea; thiourea; sulfamoyl; sulfamide; oxo; or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2] octyl, bicyclo[3.3.1]nonyl, bicyclo[3.3.2.]decyl, bicyclo [2.2.2]octyl, adamantyl, azacycloalkyl, or ((aminocarbonyl) cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as aliphatic [e.g., alkyl, alkenyl, or alkynyl]; cycloaliphatic; (cycloaliphatic) aliphatic; heterocycloaliphatic; (heterocycloaliphatic) aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl]; cyano; halo; hydroxy; mercapto; sulfonyl [e.g., alkyl-S(O)$_2$— and aryl-S(O)$_2$—]; sulfinyl

[e.g., alkyl-S(O)—]; sulfanyl [e.g., alkyl-S—]; sulfoxy; urea; thiourea; sulfamoyl; sulfamide; oxo; or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety such as tetrahydroisoquinoline to produce a heteroaryl group.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S).

Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino]; nitro; carboxy [e.g., HOOC—, alkoxycarbonyl, or alkylcarbonyloxy]; acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl]; nitro; cyano; halo; hydroxy; mercapto; sulfonyl [e.g., alkylsulfonyl or arylsulfonyl]; sulfinyl [e.g., alkylsulfinyl]; sulfanyl [e.g., alkylsulfanyl]; sulfoxy; urea; thiourea; sulfamoyl; sulfamide; oxo; or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-S(O)$_2$— or amino-S(O)$_2$—]; sulfinyl [e.g., aliphatic-S(O)—]; sulfanyl [e.g., aliphatic-S—]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)heteroaryl; (hydroxy)heteroaryl; ((carboxy)alkyl)heteroaryl; [((dialkyl)amino)alkyl]heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl, and (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (e.g., carboxyalkyl, hydroxyalkyl, and haloalkyl such as trifluoromethyl); alkenyl; alkynyl; cycloalkyl; (cycloalkyl)alkyl; heterocycloalkyl; (heterocycloalkyl)alkyl; aryl; heteroaryl; alkoxy; cycloalkyloxy; heterocycloalkyloxy; aryloxy; heteroaryloxy; aralkyloxy; heteroaralkyloxy; aroyl; heteroaroyl; nitro; carboxy; alkoxycarbonyl; alkylcarbonyloxy; aminocarbonyl; alkylcarbonylamino; cycloalkylcarbonylamino; (cycloalkylalkyl)carbonylamino; arylcarbonylamino; aralkylcarbonylamino; (heterocycloalkyl)carbonylamino; (heterocycloalkylalkyl)carbonylamino; heteroarylcarbonylamino; heteroaralkylcarbonylamino; cyano; halo; hydroxy; acyl; mercapto; alkylsulfanyl; sulfoxy; urea; thiourea; sulfamoyl; sulfamide; oxo; or carbamoyl.

As used herein, an "acyl" group refers to a formyl group or Rx—C(O)— (such as -alkyl-C(O)—, also referred to as "alkylcarbonyl") where Rx and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)—when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidino" group refers to the structure —N=C(N(R$^X$R$^Y$))N(R$^X$R$^Y$) wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, the term "amidino" group refers to the structure —C=(NR$^X$)N(R$^X$R$^Y$) wherein R$^X$ and R$^Y$ have been defined above.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic group" or "cyclic moiety" include mono-, bi-, and tri-cyclic ring systems including cycloaliphatic, heterocycloaliphatic, aryl, or heteroaryl, each of which has been previously defined.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$- where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_{2a}$, $R_{2b}$, $R_3$, $R'_3$, $R_4$, $R'_4$, and other variables contained therein formulae I encompass specific groups, such as alkyl and aryl. Unless otherwise noted, each of the specific groups for the variables $R_1$, $R_{2a}$, $R_{2b}$, $R_3$, $R'_3$, $R_4$, $R'_4$, and other variables contained therein can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich, et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

II. Compounds

A. Generic Compounds

The present invention provides methods of modulating activity of a muscarinic receptor comprising the step of contacting said receptor with a compound of formula I:

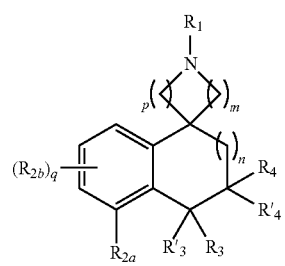

or a pharmaceutically acceptable salt thereof.

$R_1$ is a branched or straight $C_{1-12}$ aliphatic optionally substituted with 1-3 of $R^A$, wherein up to 3 carbon units of $R_1$ are optionally and independently replaced by —CO—, —CS—, —CONR$^F$—, —CONR$^F$NR$^F$—, —CO$_2$—, —OCO—, —NR$^F$CO$_2$—, —O—, —NR$^F$CONR$^F$—, —OCONR$^F$—, —NR$^F$NR$^F$—, —NR$^F$CO—, —S—, —S(O)—, —S(O)$_2$—, —NR$^F$—, —S(O)$_2$NR$^F$—, —NR$^F$SO$_2$—, or —NR$^F$S(O)$_2$NR$^F$. Each $R^A$ is independently halo, —OH, —NH$_2$, —NO$_2$, —CN, or —OCF$_3$. Each $R^F$ is independently hydrogen, or a branched or straight $C_{1-8}$ aliphatic group optionally substituted with 1-3 of $R^A$.

$R_{2a}$ is —$Z^B R_5$, wherein each $Z^B$ is independently a bond or an optionally substituted branched or straight $C_{1-4}$ aliphatic chain wherein up to two carbon units of $Z^B$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —S(O)—, —S(O)$_2$—, —NR$^B$—, —S(O)$_2$NR$^B$—, —NR$^B$S(O)$_2$—, or —NR$^B$S(O)$_2$NR$^B$—. Each $R_5$ is independently $R^B$, halo, —OH, —CN, or —OCF$_3$. Each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

Alternatively, $R_{2a}$ and $R_3$ together with the atoms to which they are attached form a 5-7 membered partially unsaturated optionally substituted cyclic group optionally having 1-2 heteroatoms independently selected from N, O and S.

Each $R_{2b}$ is independently —$Z^E R_8$, wherein each $Z^E$ is independently a bond or an optionally substituted branched or straight $C_{1-4}$ aliphatic chain wherein up to two carbon units of $Z^E$ are optionally and independently replaced by —CO—, —CS—, —CONR$^G$—, —CONR$^G$NR$^G$—, —CO$_2$—, —OCO—, —NR$^G$CO$_2$—, —O—, —NR$^G$CONR$^G$—, —OCONR$^G$—, —NR$^G$NR$^G$—, —NR$^G$CO—, —S—, —S(O)—, —S(O)$_2$—, —NR$^G$—, —S(O)$_2$NR$^G$—, —NR$^G$S(O)$_2$—, or —NR$^G$S(O)$_2$NR$^G$—. Each $R_8$ is independently $R^G$, halo, —OH, —CN, or —OCF$_3$. Each $R^G$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

Alternatively, $R_{2a}$ and one $R_{2b}$ together with the atoms to which they are attached form a 5-7 membered partially unsaturated optionally substituted cyclic group optionally having 1-2 heteroatoms independently selected from N, O, and S, wherein $R_{2b}$ is attached to a carbon atom vicinal to the carbon atom to which $R_{2a}$ is attached on the fused phenyl of formula I; or two of $R_{2b}$ together with the atoms to which they are attached form a 5-7 membered partially unsaturated optionally substituted cyclic group optionally containing 1-2 heteroatoms independently selected from N, O, and S, wherein each $R_{2b}$ is attached to a vicinal carbon atom on the fused phenyl of formula I.

$R_3$ and $R'_3$ together form an oxo group, or each is independently —$Z^C R_6$, wherein each $Z^C$ is independently a bond or an optionally substituted branched or straight $C_{1-4}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—. Each $R_6$ is independently $R^C$, halo, —OH, —NH$_2$, —NO$_2$, —CN, or —OCF$_3$. Each $R^C$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

Alternatively, $R_3$ and $R_4$ together with the atoms to which they are attached form a 5-6 membered optionally substituted cycloaliphatic or a 5-6 membered optionally substituted heterocycloaliphatic.

$R_4$ and $R'_4$ together form an oxo group, or each is independently —$Z^D R_7$, wherein each $Z^D$ is independently a bond or an optionally substituted branched or straight $C_{1-4}$ aliphatic chain wherein up to two carbon units of $Z^D$ are optionally and independently replaced by —CO—, —CS—, —CONR$^D$—, —CONR$^D$NR$^D$—, —CO$_2$—, —OCO—, —NR$^D$CO$_2$—, —O—, —NR$^D$CONR$^D$—, —OCONR$^D$—, —NR$^D$NR$^D$—, —NR$^D$CO—, —S—, —S(O)—, —S(O)$_2$—, —NR$^D$—, —S(O)$_2$NR$^D$—, —NR$^D$S(O)$_2$—, or —NR$^D$S(O)$_2$NR$^D$—. Each $R_7$ is independently $R^D$, halo, —OH, —NH$_2$, —NO$_2$, —CN, or —OCF$_3$. Each $R^D$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

m is 0-3, p is 0-3, and m+p is 3, 4, 5, or 6.

n is 0-2.

q is 0-3.

B. Specific Compounds

1. Substituent $R_1$:

$R_1$ is a branched or straight $C_{1-12}$ aliphatic optionally substituted with 1-3 of $R^A$, wherein up to 3 carbon units of $R_1$ are optionally and independently replaced by —CO—, —CS—, —CONR$^F$—, —CONR$^F$NR$^F$—, —CO$_2$—, —OCO—, —NR$^F$CO$_2$—, —O—, —NR$^F$CONR$^F$—, —OCONR$^F$—, —NR$^F$NR$^F$—, —NR$^F$CO—, —S—, —S(O)—, —S(O)$_2$—, —NR$^F$—, —S(O)$_2$NR$^F$—, —NR$^F$S(O)$_2$—, or —NR$^F$S(O)$_2$NR$^F$—; each $R^A$ is halo, —OH, —NH$_2$, —NO$_2$, —CN, or —OCF$_3$; each $R^F$ is hydrogen, or a branched or straight $C_{1-8}$ aliphatic group optionally substituted with 1-3 of $R^A$.

In several embodiments, $R_1$ is an optionally substituted straight or branched $C_{1-12}$ aliphatic, wherein up to 3 carbon units of $R_1$ are optionally and independently replaced with —C(O)—, —S(O)$_2$—, —S—, —O—, or combinations thereof.

In several embodiments, $R_1$ is an optionally substituted straight $C_{1-10}$ aliphatic. For example, $R_1$ is a straight $C_{1-10}$ alkyl, a straight $C_{2-10}$ alkenyl, or a straight $C_{2-10}$ alkynyl, each of which is optionally substituted with 1-3 of halo, hydroxy, cyano, or combinations thereof. In several examples, $R_1$ is a straight $C_{1-10}$ alkyl, a straight $C_{2-10}$ alkenyl, or a straight $C_{2-10}$ alkynyl, each of which is unsubstituted. In alternative examples, $R_1$ is a straight $C_{1-10}$ alkyl that is optionally substituted with 1-3 of halo or cyano. In additional examples, $R_1$ is a $C_{2-10}$ alkenyl having 1-2 C—C double bonds that is optionally substituted with 1-3 of halo, hydroxy, cyano, or combinations thereof. In additional examples, $R_1$ is an optionally substituted $C_{2-10}$ alkynyl.

In several examples, $R_1$ is an optionally substituted branched $C_{3-12}$ aliphatic. For example, $R_1$ is a branched $C_{3-12}$ alkyl, a branched $C_{3-12}$ alkenyl, or a branched $C_{3-12}$ alkynyl, each of which is optionally substituted with 1-3 of halo, hydroxy, cyano, or combinations thereof. In several examples, $R_1$ is a branched $C_{3-10}$ alkyl, a branched $C_{3-10}$ alkenyl, or a branched $C_{3-10}$ alkynyl, each of which is unsubstituted. In alternative examples, $R_1$ is an alkyl that is optionally substituted with 1-3 of halo or cyano. In additional examples, $R_1$ is an alkenyl having 1-2 C—C double bonds and is optionally substituted. In additional examples, $R_1$ is an optionally substituted branched $C_{2-12}$ alkynyl.

In several embodiments, $R_1$ is a straight $C_{1-10}$ aliphatic or a branched $C_{3-12}$ aliphatic, each of which is optionally substituted with 1-3 of halo, hydroxy, cyano, or combinations thereof.

In several embodiments, up to 2 carbon units of $R_1$ are optionally and independently replaced with —C(O)—, —S(O)$_2$—, —S—, —O—, —NR$^F$—, or combinations thereof.

In several embodiments, $R_1$ is a straight $C_{1-10}$ alkyl, straight $C_{2-10}$ alkenyl, straight $C_{2-10}$ alkynyl, branched $C_{3-12}$ alkyl, branched $C_{3-12}$ alkenyl, or branched $C_{3-12}$ alkynyl, each of which is optionally substituted with 1-3 of $R^A$.

In several embodiments, $R_1$ is a straight $C_{2-10}$ alkenyl having 1-2 C—C double bonds or a branched $C_{3-12}$ alkenyl having 1-2 C—C double bonds, each of which is optionally substituted.

In several embodiments, $R_1$ is an optionally substituted straight or branched $C_{1-12}$ aliphatic wherein 1-2 of the carbon units have been optionally replaced with —S— or —S(O)$_2$—. In other embodiments, $R_1$ is an optionally substituted straight or branched aliphatic wherein 1-2 of the carbon units have been optionally replaced with —S—. In several embodiments, $R_1$ is aliphatic-S(O)$_2$-aliphatic or aliphatic-S-aliphatic, each of which is optionally substituted with 1-3 of halo, hydroxy, cyano, nitro, alkoxy, or combinations thereof. For example, $R_1$ is an (alkylsulfonyl)alkyl or (alkylsulfanyl)alkyl, each of which is optionally substituted.

In several embodiments, $R_1$ is an optionally substituted straight or branched $C_{1-12}$ aliphatic wherein 1-2 of the carbon units have been optionally replaced with —C(O)—, —O—, or —CO$_2$—. In several embodiments, $R_1$ is an optionally substituted straight or branched $C_{1-12}$ aliphatic wherein one carbon unit has been replaced with —C(O)—, and another carbon unit has been replaced by —O—. In several embodiments, $R_1$ is an acyl [e.g., (aliphatic)carbonyl], (aliphatic(carbonyl))aliphatic, (aliphaticoxy(carbonyl))aliphatic, or carboxy [e.g. (aliphaticoxy)carbonyl], each of which is optionally substituted with 1-3 of halo, hydroxy, cyano, nitro, or combinations thereof.

In several embodiments, $R_1$ is one selected from:

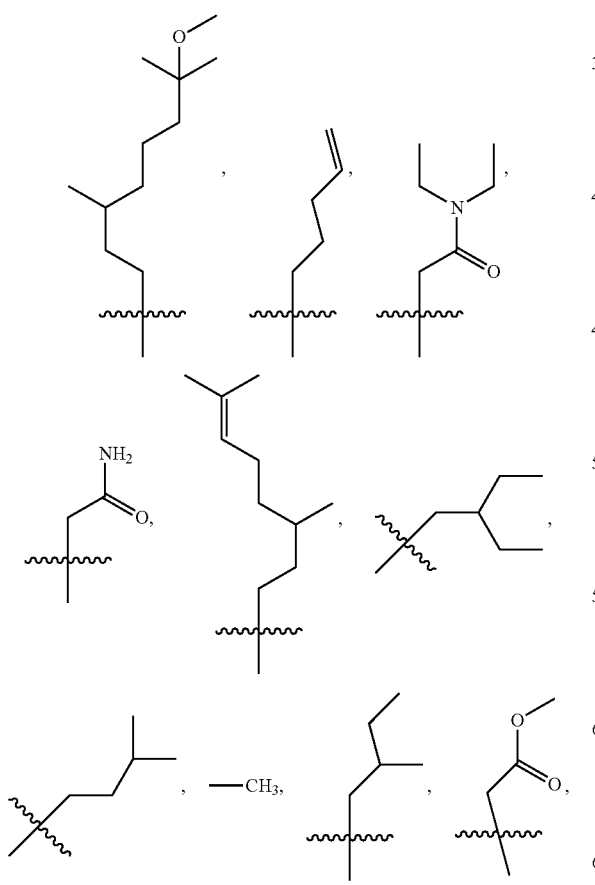

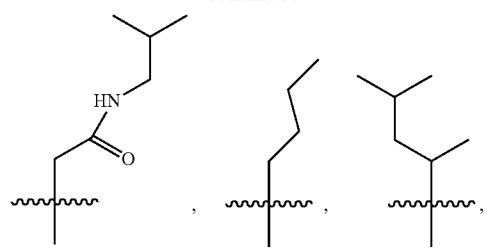

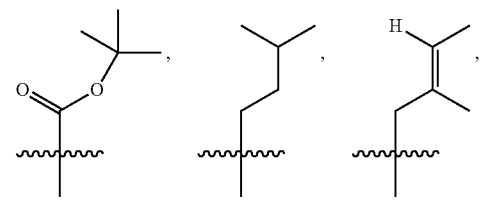

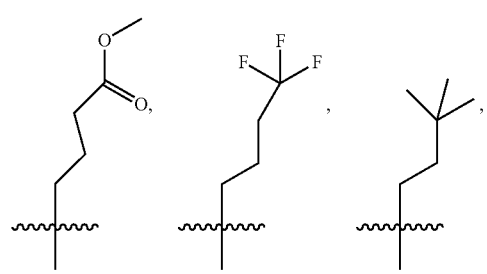

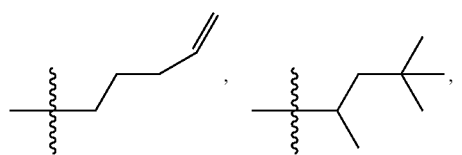

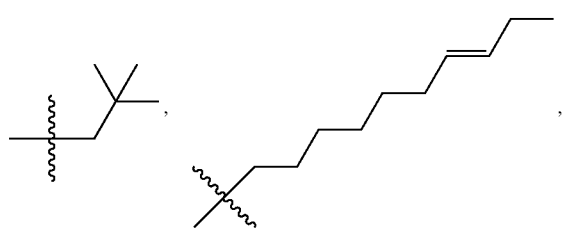

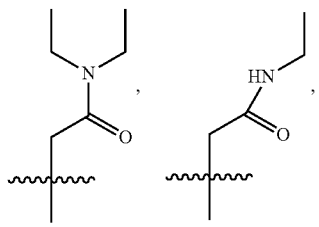

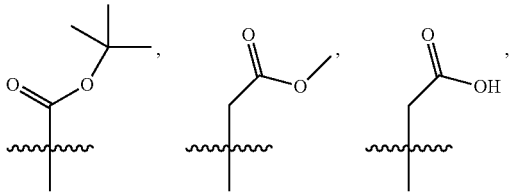

-continued

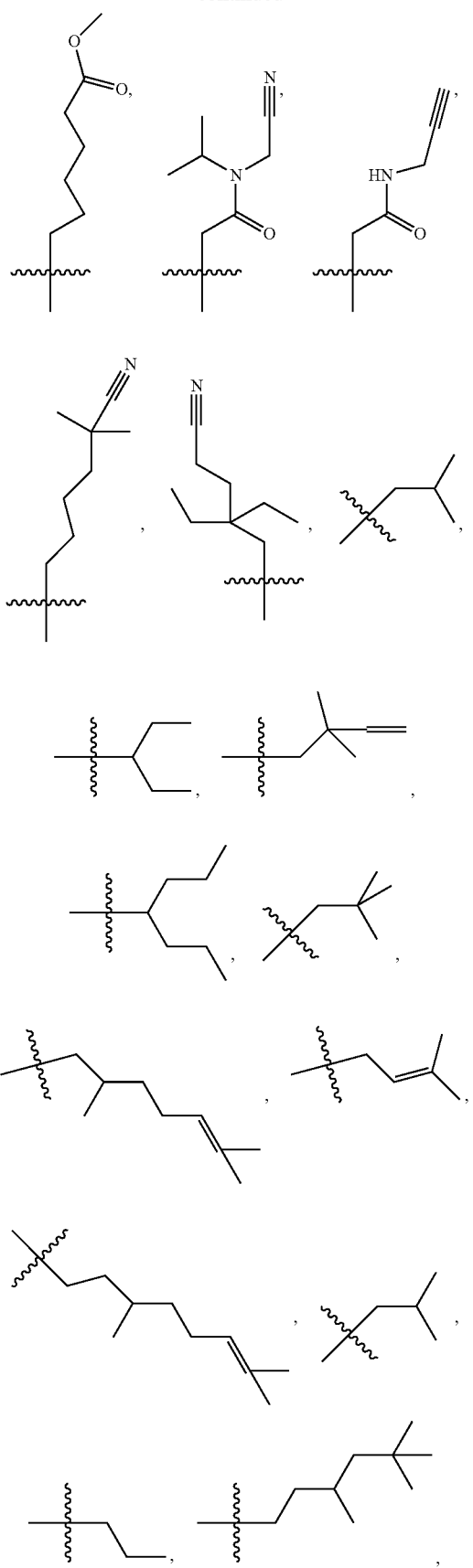

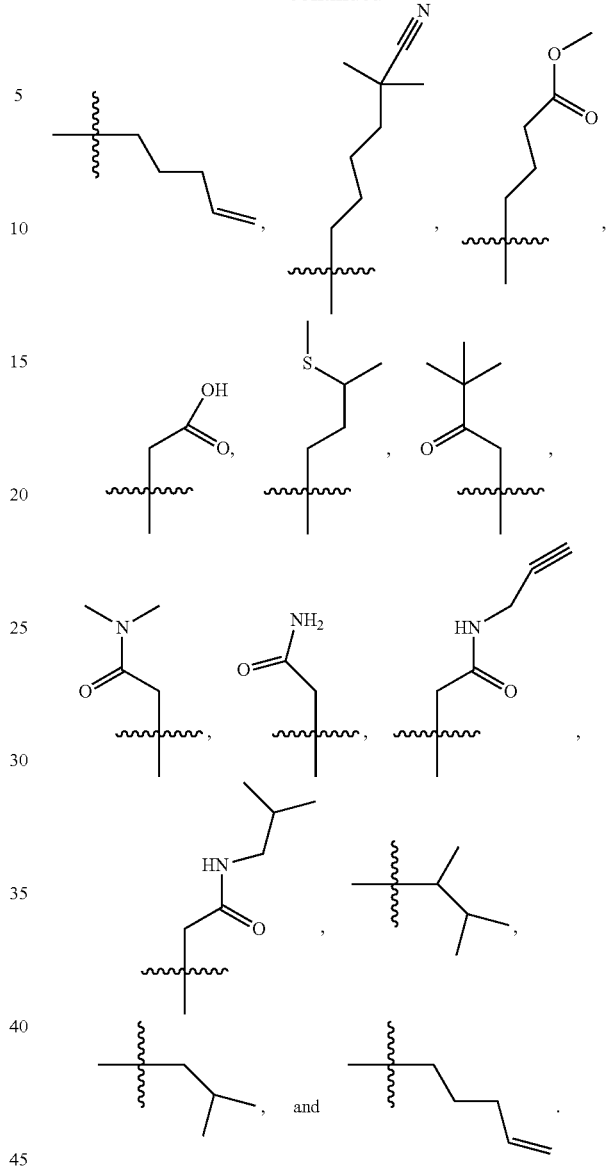

2. Substituents $R_{2a}$ and $R_{2b}$:

$R_{2a}$ is —$Z^B R_5$, wherein each $Z^B$ is independently a bond or an optionally substituted branched or straight $C_{1-4}$ aliphatic chain wherein up to two carbon units of $Z^B$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —S(O)—, —S(O)$_2$—, —NO—, —S(O)$_2$NR$^B$—, —NR$^B$S(O)$_2$—, or —NR$^B$S(O)$_2$NR$^B$—. Each $R_5$ is independently $R^B$, halo, —OH, —CN, or —OCF$_3$. Each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl. Alternatively, $R_{2a}$ and $R_3$ together with the atoms to which they are attached form a 5-7 membered partially unsaturated optionally substituted cyclic group optionally containing 1-2 heteroatoms independently selected from N, O, and S. Each $R_{2b}$ is independently —$Z^E R_8$, wherein each $Z^E$ is independently a bond or an optionally substituted branched or straight $C_{1-4}$ aliphatic chain wherein up to two carbon units of $Z^E$ are optionally and independently replaced by —CO—, —CS—, —CONR$^G$—, —CONR$^G$NR$^G$—, —CO$_2$—, —OCO—, —NR$^G$CO$_2$—, —O—, —NR$^G$CONR$^G$—, —OCONR$^G$—, —NR$^G$NR$^G$—, —NR$^G$CO—, —S—, —S(O)—, —S(O)$_2$—, —NR$^G$—, —S(O)$_2$NR$^G$—, —NR$^G$S(O)$_2$—, or —NR$^G$S(O)$_2$NR$^G$—. Each $R_8$ is independently $R^G$, halo, —OH, —CN, or —OCF$_3$. Each $R^G$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

Alternatively, $R_{2a}$ and one $R_{2b}$ together with the atoms to which they are attached form an 5-7 membered partially unsaturated optionally substituted cyclic group optionally having 1-2 heteroatoms independently selected from N, O, and S, wherein $R_{2b}$ is attached to a carbon atom vicinal to the carbon atom to which $R_{2a}$ is attached on the fused phenyl of formula I.

Alternatively, two of $R_{2b}$ together with the atoms to which they are attached form an 5-7 membered partially unsaturated optionally substituted cyclic group optionally having 1-2 heteroatoms independently selected from N, O, and S, wherein each $R_{2b}$ is attached to a vicinal carbon atom on the fused phenyl of formula I.

In several embodiments, $R_{2a}$ or $R_{2b}$ is hydrogen. For example, in some embodiments, q is 0 and $R_{2a}$ is hydrogen.

In several embodiments, when q is 1, 2, or 3, $R_{2b}$ is attached to the core structure of formula I at the 6 position, 7 position, 8 position, or combinations thereof. For example, $R_{2b}$ is attached at the 6 or 7 position, or combinations thereof.

In several embodiments, $R_{2a}$ or $R_{2b}$ is an optionally substituted amino. For example, $R_{2a}$ or $R_{2b}$ is an (aliphatic)amino, (cycloaliphatic)amino, or combinations thereof, each of which is optionally substituted.

In several embodiments, $R_{2a}$ or $R_{2b}$ is an optionally substituted amido. For example, $R_{2a}$ or $R_{2b}$ is an (alkyl(carbonyl)) amino, (cycloalkyl(carbonyl))amino, (alkyl(amino))carbonyl, (cycloalkyl(amino))carbonyl, or combination thereof, each of which is optionally substituted.

In several embodiments, $R_{2a}$ or $R_{2b}$ is an optionally substituted (alkyl(amino))carbonyl, an optionally substituted (aliphatic)carbonyl, or an optionally substituted (alkoxy)carbonyl. For example, $R_{2a}$ or $R_{2b}$ is a (methyl(amino))carbonyl, (ethyl(amino))carbonyl, (propyl(amino))carbonyl, or combinations thereof, each of which is optionally substituted. In other examples, $R_{2a}$ or $R_{2b}$ is a (methoxy)carbonyl, (ethoxy) carbonyl, (propoxy)carbonyl, (butoxy)carbonyl, or combinations thereof, each of which is optionally substituted. Additional examples of $R_{2a}$ or $R_{2b}$ include (methyl)carbonyl, (ethyl)carbonyl, (propyl)carbonyl, (butyl)carbonyl, or combinations thereof, each of which is optionally substituted.

In several embodiments, q is 2 and two of $R_{2b}$ taken together with the carbon atoms to which they are attached form a 5-7 membered partially unsaturated optionally substituted cyclic group optionally having 1-2 heteroatoms independently selected from N, O, and S, wherein each $R_{2b}$ is attached to the phenyl of formula I on a carbon atom adjacent to the carbon atom substituted with the other $R_{2b}$. For example, two of $R_{2b}$ and the atoms to which they are attached and the phenyl of formula I form an optionally substituted benzo[d][1,3]dioxolyl.

In several embodiments, q is 0; and $R_{2a}$ and $R_3$ taken together with the atoms to which they are attached form a 5-7 membered partially unsaturated optionally substituted heterocycloaliphatic. For example, $R_{2a}$ and $R_3$ taken together with the atoms to which they are attached form optionally substituted 1H-pyrrol-2(5H)-onyl. In other examples, $R_{2a}$ and $R_3$ taken together with the atoms to which they are attached form a 1H-pyrrol-2(5H)-onyl that is optionally substituted with 1-2 oxo groups.

In several embodiments, q is 1 or 2, and each $R_{2b}$ is independently halo, or methoxy.

In several embodiments, $R_{2a}$ or $R_{2b}$ is halo, hydrogen, or methoxy. Other embodiments include 2 $R_{2b}$ groups (i.e., q=2), wherein each is methoxy.

3. Substituents $R_3$ and $R'_3$:

$R_3$ and $R'_3$ together form an oxo group, or each is independently —$Z^C R_6$, wherein each $Z^C$ is independently a bond or an optionally substituted branched or straight $C_{1-4}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—; each $R_6$ is independently $R^C$, halo, —OH, —NH$_2$, —NO$_2$, —CN, or —OCF$_3$; each $R^C$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl; or $R_3$ and $R_4$ together with the atoms to which they are attached form a 5-7 membered optionally substituted cycloaliphatic or a 5-7 membered optionally substituted heterocycloaliphatic.

In several embodiments, one of $R_3$ and $R'_3$ is independently an optionally substituted branched or straight $C_{1-4}$ aliphatic wherein up to two carbon units of $R_3$ or $R'_3$ is optionally and independently replaced by —C(O)—, —NH—, —S(O)$_2$—, or combinations thereof; and the remaining $R_3$ or $R'_3$ is hydrogen. In several embodiments, one of $R_3$ and $R'_3$ are straight optionally substituted $C_{2-4}$ aliphatic groups wherein a first carbon unit is optionally and independently replaced by —NH—, and a second carbon unit is optionally and independently replaced by —C(O)—; and the remaining $R_3$ or $R'_3$ is hydrogen. In another embodiment, one of $R_3$ and $R'_3$ is optionally substituted (methylcarbonyl)amino and the remaining $R_3$ or $R'_3$ is hydrogen. In other embodiments, each of $R_3$ and $R'_3$ is independently hydrogen or a methylcarbonylamino, N,N-dimethylaminocarbonylamino, ethylcarbonylamino, pyrrolidine-2,5-dion-1-yl, piperidin-2-one-1-yl, methylaminocarbonyl, N,N-dimethylaminocarbonyl, aminocarbonyl, cyano, or methoxycarbonylamino, each of which is optionally substituted.

In several embodiments, one of $R_3$ and $R'_3$ is an optionally substituted heterocycloaliphatic, and the remaining $R_3$ or $R'_3$ is hydrogen. In several examples, one of $R_3$ and $R'_3$ is an optionally substituted 5-7 membered heterocycloaliphatic having 1-2 heteroatoms independently selected from N, O, and S, and the remaining $R_3$ or $R'_3$ is hydrogen. In other examples, one of $R_3$ and $R'_3$ is a 5-7 membered heterocycloaliphatic group optionally substituted with 1-3 of halo, hydroxy, cyano, aryl, heteroaryl, cycloaliphatic, heterocycloaliphatic, aliphatic, alkoxy, oxo, or combinations thereof; and the remaining $R_3$ or $R'_3$ is hydrogen. In several examples, one of $R_3$ and $R'_3$ is an optionally substituted 5-7 membered heterocycloaliphatic optionally substituted with 1-2 oxo groups, and the remaining $R_3$ or $R'_3$ is hydrogen. For example, one of $R_3$ and $R'_3$ is pyrrolidinyl, tetrahydrofuranyl, 1,3-dioxolanyl, pyrazolidinyl, tetrahydropyranyl, thiomorpholinyl, morpholinyl, piperidinyl, piperazinyl, 1,4-dioxanyl, or 1,4-dithianyl, each of which is optionally substituted with 1-3 of halo, hydroxy, cyano, aryl, heteroaryl, cycloaliphatic, heterocycloaliphatic, aliphatic, alkoxy, oxo, or combinations thereof; and the remaining $R_3$ or $R'_3$ is hydrogen.

In several embodiments, $R_3$ and $R'_3$ are each independently hydrogen or halo.

In several embodiments, $R_3$ and $R'_3$ are independently —$Z^C R_6$, wherein each $Z^C$ is a independently a bond or an optionally substituted straight $C_{1-4}$ aliphatic chain wherein up to two carbon units of $Z^C$ are optionally and independently replaced by —CO—, or —NH—. $R_6$ is an optionally substituted cycloaliphatic or hydrogen. For example, $R_6$ is cyclopropyl, cyclobutyl, cyclopentyl, cycloheptyl, or cyclohexyl, each of which is optionally substituted.

In several embodiments, $R_3$ and $R_4$ together with the atoms to which they are attached form a 5-6 membered optionally substituted heterocycloaliphatic. For example, $R_3$ and $R_4$ taken together with the atoms to which they are attached form an optionally substituted 5-6 membered heterocycloaliphatic having 1-2 heteroatoms selected from N, O, and S. In other examples, $R_3$ and $R_4$ taken together with the atoms to which they are attached form an optionally substituted 5-6 membered heterocycloaliphatic that is optionally substituted with 1-2 oxo groups. For example, $R_3$ and $R_4$ together form pyrrolidin-2-onyl, imidazolidin-2-onyl, or oxazolidin-2-onyl, each of which is optionally substituted.

In several embodiments, $R_3$ and $R'_3$ together with the carbon atom to which they are attached form an oxo group, or $R_3$ and $R'_3$ are each independently selected from hydrogen,

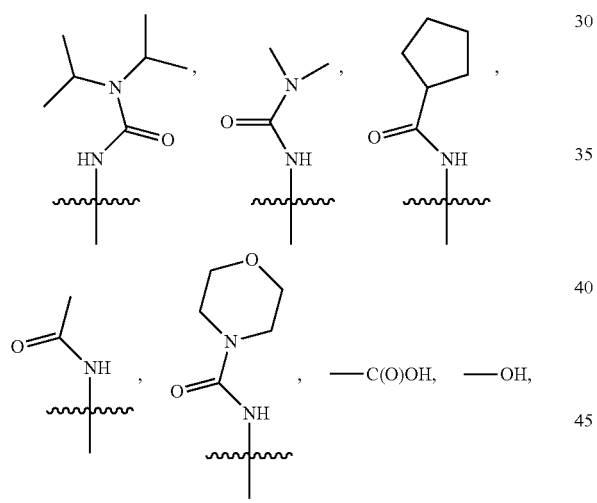

—C(O)OH, —OH,

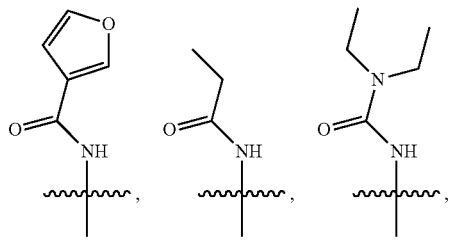

-continued

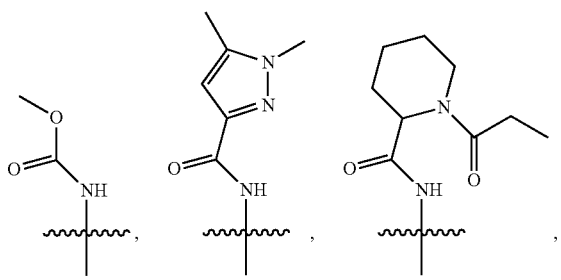

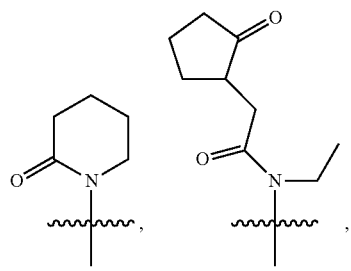

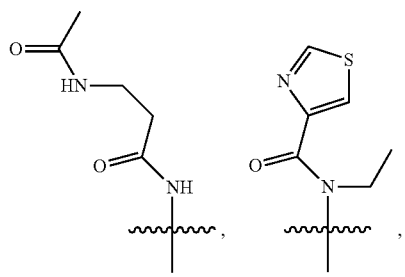

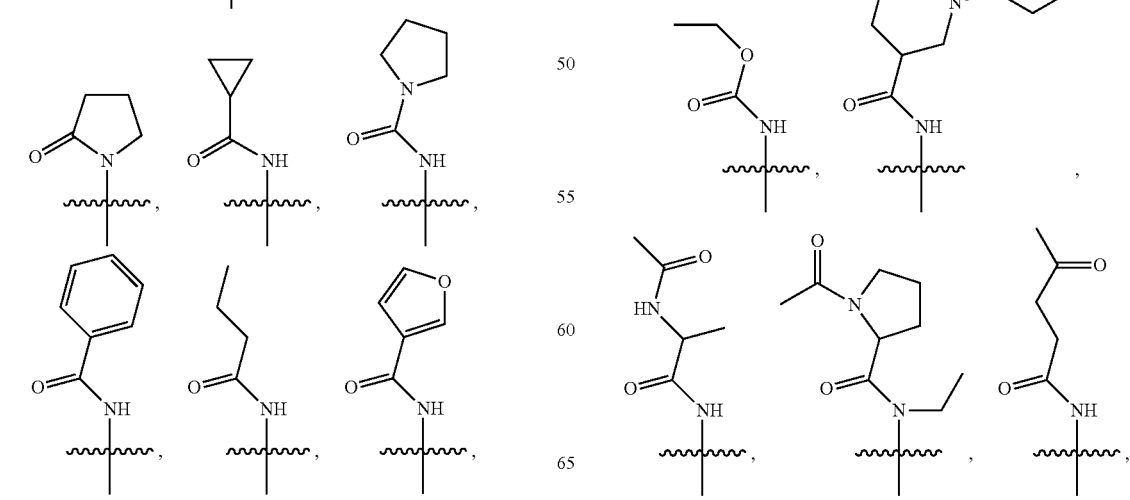

-continued
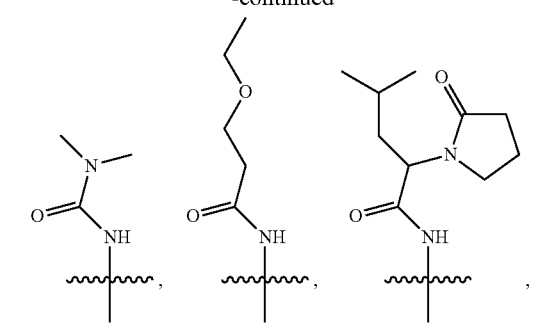
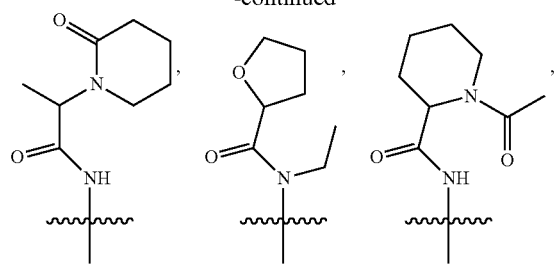
-continued
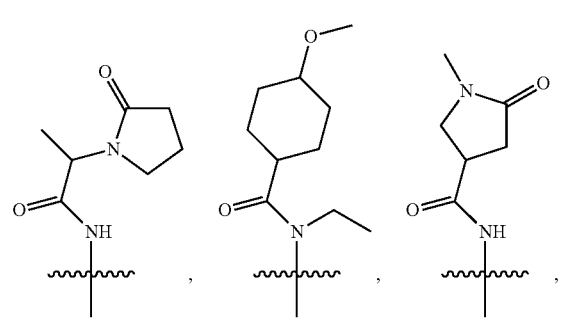
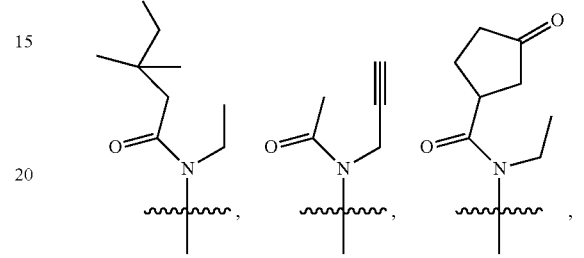
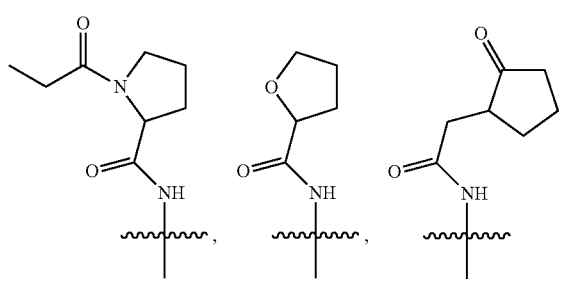
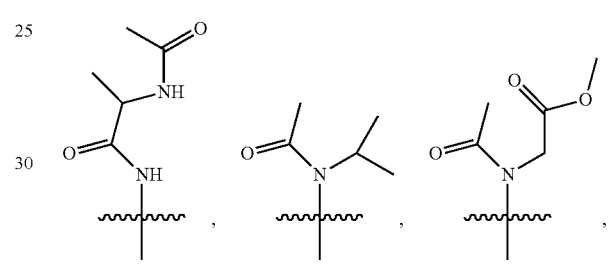
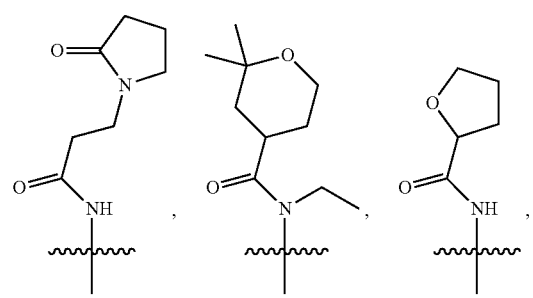
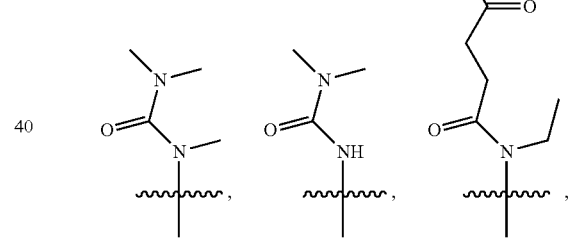
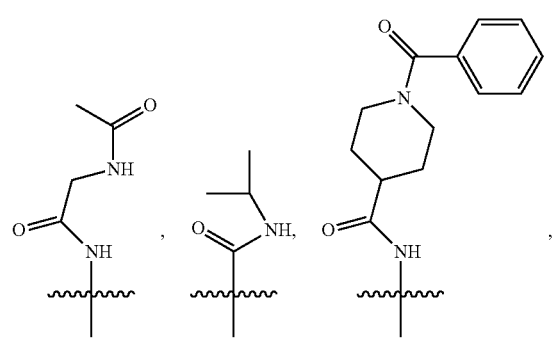
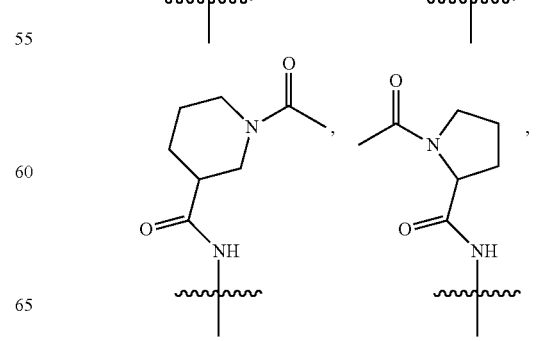

-continued
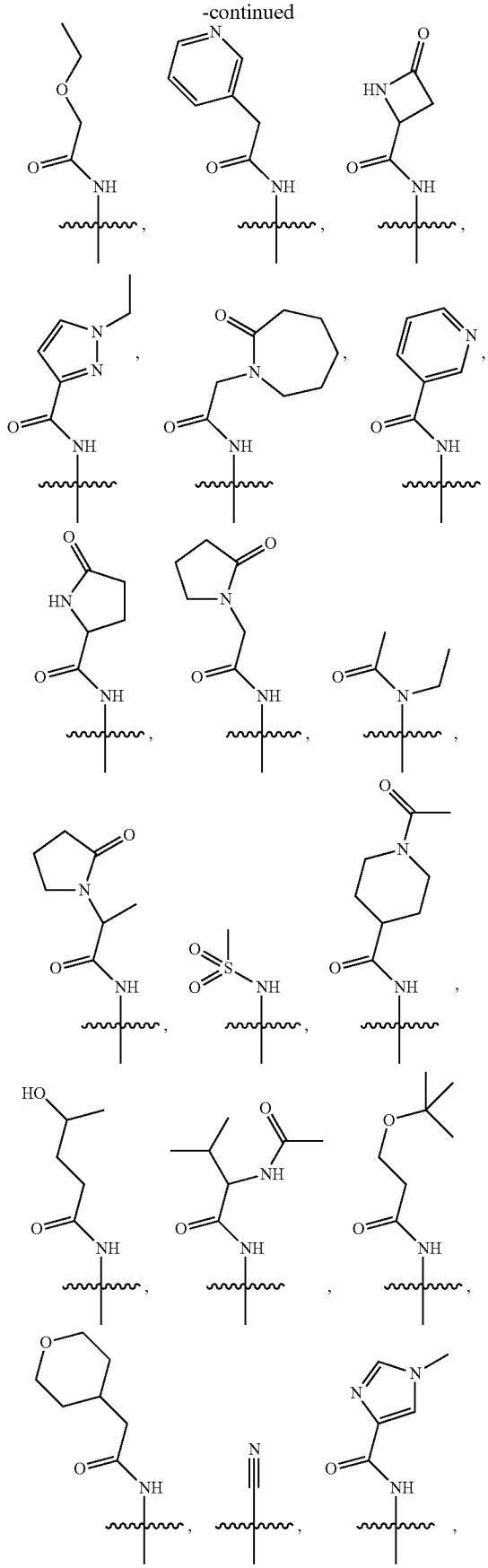
-continued
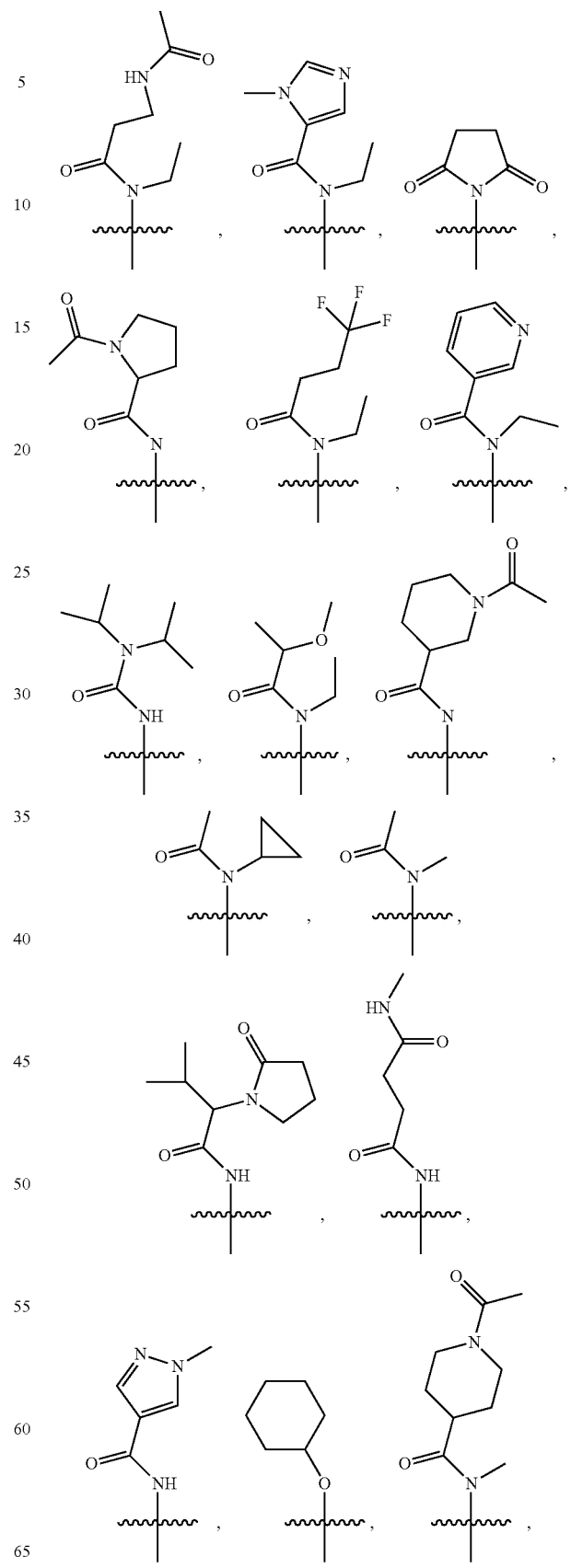

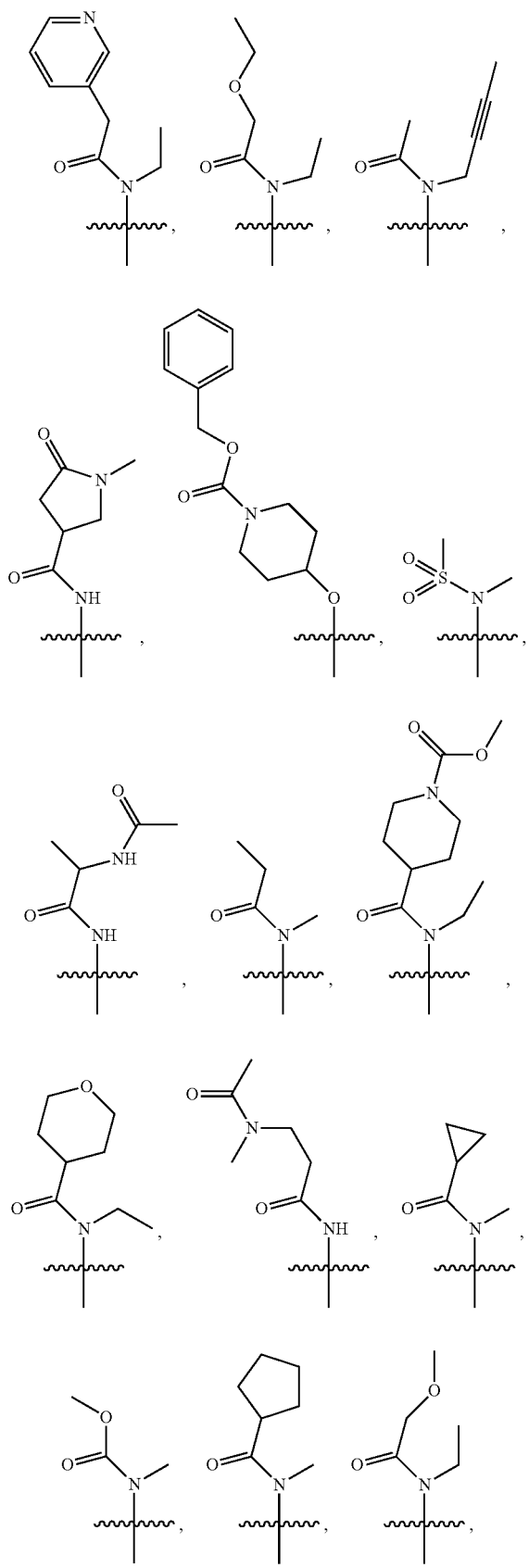

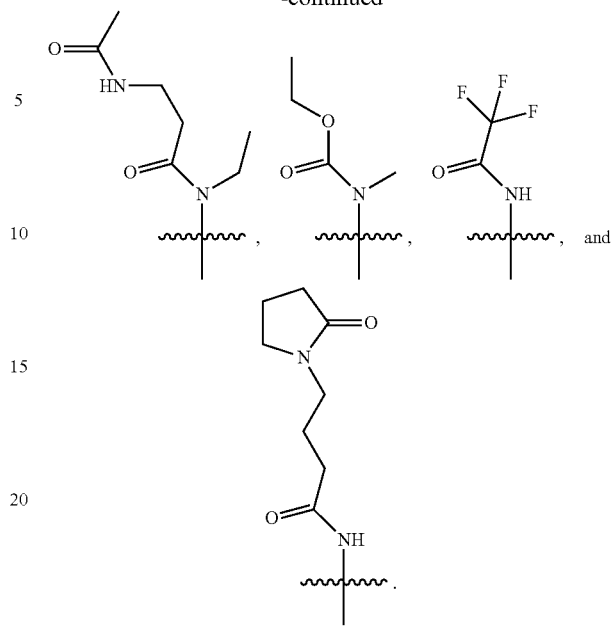

4. Substituents $R_4$ and $R'_4$:

$R_4$ and $R'_4$ together form an oxo group, or each is $-Z^D R_7$, wherein each $Z^D$ is independently a bond or an optionally substituted branched or straight $C_{1-4}$ aliphatic chain wherein up to two carbon units of $Z^D$ are optionally and independently replaced by $-CO-$, $-CS-$, $-CONR^D-$, $-CONR^D-NR^D-$, $-CO_2-$, $-OCO-$, $-NR^D CO_2-$, $-O-$, $-NR^D CONR^D-$, $-OCONR^D-$, $-NR^D NR^D-$, $-NR^D CO-$, $-S-$, $-S(O)-$, $-S(O)_2-$, $-NR^D-$, $-S(O)_2 NR^D-$, $-NR^D S(O)_2-$, or $-NR^D S(O)_2 NR^D-$; each $R_7$ is $R^D$, halo, $-OH$, $-NH_2$, $-NO_2$, $-CN$, or $-OCF_3$; and each $R^D$ is independently hydrogen, an optionally substituted $C_{1-8}$ aliphatic group; an optionally substituted cycloaliphatic, an optionally substited heterocycloaliphatic, an optionally substituted aryl, or an optionally substituted heteroaryl.

In several embodiments, $R_4$ and $R'_4$ are each independently hydrogen.

In several embodiments, $R_4$ and $R'_4$ are each independently optionally substituted $C_{1-4}$ aliphatic. For example, $R_4$ and $R'_4$ are each independently hydrogen methyl, ethyl, propyl, or butyl, each of which is optionally substituted.

In several embodiments, $R_4$ and $R'_4$ are both hydrogen. In other embodiments, $R_4$ and $R'_4$ are both fluoro.

5. Variables n, m, p, and q:

m and p are each independently 0-3; however, m+p is 3, 4, 5, or 6.

In several embodiments, m and p are both 2.

Each n is 0-2.

Each q is 0-3.

In several embodiments, m and p are each 0, 1, or 2. In other embodiments, n is 0 or 1. In several embodiments, q is 0, 1, 2, 3, or 4.

B. Sub-Generic Compounds

Another aspect of the present invention provides compounds of formula Ia:

Ia

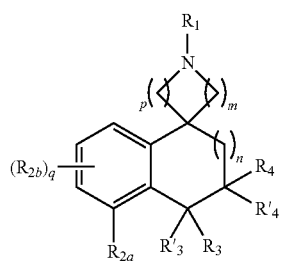

or a pharmaceutically acceptable salt thereof, wherein $R_1$, $R_{2a}$, $R_{2b}$, $R_4$, $R'_4$, m, n, p, and q are defined in formula I.

$R'_3$ is $-Z^F R_{10}$, wherein each $Z^F$ is independently a bond or an optionally substituted branched or straight $C_{1-4}$ aliphatic chain wherein up to two carbon units of $Z^F$ are optionally and independently replaced by —CO—, —CS—, —CONR$^E$—, —CONR$^E$NR$^E$—CO$_2$—, —OCO—, —NR$^E$CO$_2$—, —O—, —NR$^E$CONR$^E$—, —OCONR$^E$—, —NR$^E$NR$^E$—, —NR$^E$CO—, —S—, —S(O)—, —S(O)$_2$—, —S(O)$_2$NR$^E$—, —NR$^E$S(O)$_2$—, or —NR$^E$S(O)$_2$NR$^E$—. Each $R_{10}$ is independently $R^E$, halo, —OH, —NH$_2$, —NO$_2$, —CN, or —OCF$_3$. Each $R^E$ is independently an optionally substituted $C_{1-8}$ aliphatic group; an optionally substituted cycloaliphatic, an optionally substituted heterocycloaliphatic, an optionally substituted aryl, or an optionally substituted heteroaryl.

$R_3$ is independently $-Z^C R_6$, wherein each $Z^C$ is independently a bond or an optionally substituted branched or straight $C_{1-4}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—; each $R_6$ is independently $R^C$, halo, —OH, —NH$_2$, —NO$_2$, —CN, or —OCF$_3$; each $R^C$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

Another aspect of the present invention provides compounds of formula Ib:

Ib

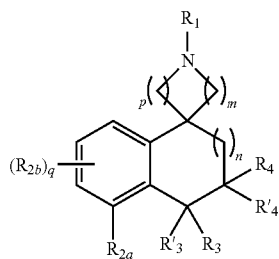

or a pharmaceutically acceptable salt thereof, wherein $R_{2a}$, $R_{2b}$, $R_3$, $R'_3$, $R_4$, $R'_4$, m, n, p, and q are defined in formula I.

$R_1$ is a branched or straight $C_{1-12}$ aliphatic optionally substituted with 1-3 of $R^A$, wherein up to 2 carbon units of $R_1$ are optionally and independently replaced by —CS—, —CONR$^F$—, —CONR$^F$NR$^F$—, —CO$_2$—, —OCO—, —NR$^F$CO$_2$—, —O—, NR$^F$CONR$^F$—, —OCONR$^F$—, —NR$^F$NR$^F$—, —NR$^F$CO—, —S—, —S(O)—, —S(O)$_2$—, —NR$^F$—, —S(O)$_2$NR$^F$—, —NR$^F$S(O)$_2$—, or —NR$^F$S(O)$_2$NR$^F$—. Each $R^A$ is halo, —OH, —NH$_2$, —NO$_2$, —CN, or —OCF$_3$. $R^F$ has been defined in formula I.

Another aspect of the present invention provides compounds of formula Ic:

Ic

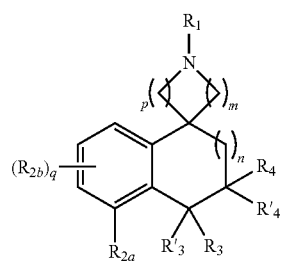

or a pharmaceutically acceptable salt thereof, wherein $R_{2a}$, $R_{2b}$, $R_4$, $R'_4$, m, n, p, and q are defined in formula I.

$R_1$ is a branched or straight $C_{1-12}$ aliphatic optionally substituted with 1-3 of $R^A$, wherein up to 2 carbon units of $R_1$ are optionally and independently replaced by —CS—, —CONR$^F$—, —CONR$^F$NR$^F$—, —CO$_2$—, —OCO—, —NR$^F$CO$_2$—, —O—, —NR$^F$CONR$^F$—, —OCONR$^F$—, —NR$^F$NR$^F$—, —NR$^F$CO—, S—, —S(O)—, —S(O)$_2$—, —NR$^F$—, —S(O)$_2$NR$^F$—, —NR$^F$S(O)$_2$—, or —NR$^F$S(O)$_2$NR$^F$—; and each $R^A$ is halo, —OH, —NH$_2$, —NO$_2$, —CN, or —OCF$_3$. $R^F$ has been defined in formula I.

$R_3$ is independently $-Z^C R_6$, wherein each $Z^C$ is independently a bond or an optionally substituted branched or straight $C_{1-4}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—; each $R_6$ is independently $R^C$, halo, —OH, —NH$_2$, —NO$_2$, —CN, or —OCF$_3$; each $R^C$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

$R'_3$ is $-Z^C R_6$, wherein each $Z^C$ is independently a bond or an optionally substituted branched or straight $C_{1-4}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—, or $R_3$ and $R'_3$ together form an oxo group. Each $R^C$ is independently an optionally substituted $C_{1-8}$ aliphatic group; an optionally substituted cycloaliphatic, an optionally substituted heterocycloaliphatic, an optionally substituted aryl, or an optionally substituted heteroaryl.

Alternatively, $R_3$ and $R'_3$ together form an oxo group.

Another aspect of the present invention provides compounds of formula Id:

Id

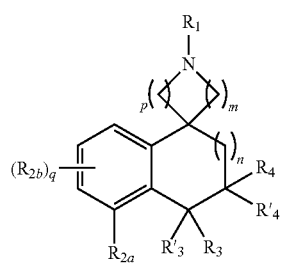

or a pharmaceutically acceptable salt thereof, wherein $R_{2a}$, $R_{2b}$, $R_4$, $R'_4$, m, n, p, and q are defined above.

$R_1$ is a branched or straight $C_{1-12}$ aliphatic optionally substituted with 1-3 of $R^A$, wherein up to 2 carbon units of $R_1$ are optionally and independently replaced by —CS—, —CONR$^F$—, —CONR$^F$NR$^F$—, —CO$_2$—, —OCO—, —NR$^F$CO$_2$—, —O—, —NR$^F$CONR$^F$—, —OCONR$^F$—, —NR$^F$NR$^F$—, —NR$^F$CO—, —S—, —S(O)—, —S(O)$_2$—, —NR$^F$—, —S(O)$_2$NR$^F$—, —NR$^F$S(O)$_2$—, or —NR$^F$S(O)$_2$NR$^F$—; each R$^A$ is halo, —OH, —NH$_2$, —NO$_2$, —CN, or —OCF$_3$; and R$^F$ has been defined in formula I.

R$_3$ is independently —Z$^C$R$_6$, wherein each Z$^C$ is independently a bond or an optionally substituted branched or straight C$_{1-4}$ aliphatic chain wherein up to two carbon units of Z$^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—; each R$_6$ is independently R$^C$, halo, —OH, —NH$_2$, —NO$_2$, —CN, or —OCF$_3$; each R$^C$ is independently hydrogen, an optionally substituted C$_{1-8}$ aliphatic group; an optionally substituted cycloaliphatic, an optionally substituted heterocycloaliphatic, an optionally substituted aryl, or an optionally substituted heteroaryl.

R'$_3$ is —Z$^C$R$_6$, wherein each Z$^C$ is independently a bond or an optionally substituted branched or straight C$_{1-4}$ aliphatic chain wherein up to two carbon units of Z$^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—. Each R$^C$ is independently an optionally substituted C$_{1-8}$ aliphatic group; an optionally substituted cycloaliphatic, an optionally substituted heterocycloaliphatic, an optionally substituted aryl, or an optionally substituted heteroaryl.

Alternatively, R$_3$ and R$_4$ together with the atoms to which they are attached form a 5-6 membered optionally substituted heterocycloaliphatic.

Another aspect of the present invention provides compounds of formula Ie:

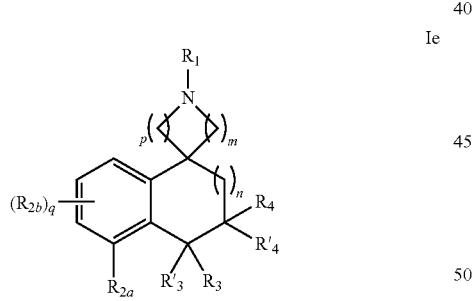

Ie or a pharmaceutically acceptable salt thereof, wherein R$_{2a}$, R$_{2b}$, R$_4$, R'$_4$, m, n, p, and q are define in formula I.

R$_1$ is a branched or straight C$_{1-12}$ aliphatic optionally substituted with 1-3 of R$^A$, wherein up to 2 carbon units of R$_1$ are optionally and independently replaced by —CS—, —CONR$^F$—, —CONR$^F$NR$^F$—, —CO$_2$—, —OCO—, —NR$^F$CO$_2$—, —O—, —NR$^F$CONR$^F$—, —OCONR$^F$—, —NR$^F$NR$^F$—, —NR$^F$CO—, —S—, —S(O)—, —S(O)$_2$—, —NR$^F$—, —S(O)$_2$NR$^F$—, —NR$^F$S(O)$_2$—, or —NR$^F$S(O)$_2$NR$^F$—. Each R$^A$ is halo, —OH, —NH$_2$, —NO$_2$, —CN, or —OCF$_3$. R$^F$ has been defined in formula I.

Each R$_3$ and R'$_3$ is independently —Z$^C$R$_6$, wherein each Z$^C$ is independently a bond or an optionally substituted branched or straight C$_{1-4}$ aliphatic chain wherein up to two carbon units of Z$^C$ are optionally and independently replaced by —CO—, —CS—, —CONR$^C$—, —CONR$^C$NR$^C$—, —CO$_2$—, —OCO—, —NR$^C$—, —NR$^C$CO$_2$—, —O—, —NR$^C$CO-NR$^C$—, —OCONR$^C$—, —NR$^C$NR$^C$—, —NR$^C$CO—, —S—, —S(O)—, —S(O)$_2$—, —S(O)$_2$NR$^C$—, —NR$^C$S(O)$_2$—, or —NR$^C$S(O)$_2$NR$^C$—. Each R$_6$ is independently R$^C$, halo, —OH, —NH$_2$, —NO$_2$, —CN, or —OCF$_3$. Each R$^C$ is independently hydrogen, an optionally substituted C$_{1-8}$ aliphatic group; an optionally substituted cycloaliphatic, an optionally substituted heterocycloaliphatic, an optionally substituted aryl, or an optionally substituted heteroaryl.

Alternatively, R$_3$ and R$_4$ together with the atoms to which they are attached form a 5-6 membered optionally substituted heterocycloaliphatic.

Alternatively, R$_3$ and R'$_3$ together form an oxo group.

Provided that when R$_1$ is —CH$_3$ or hydrogen, neither R$_3$ nor R'$_3$ are 1-(2,3-dichlorophenyl)tetrazol-5-yl-amino.

C. Exemplary Compounds

Exemplary compounds of the present invention include, but are not limited to, those illustrated in Table 1 below.

TABLE 1

Exemplary compounds of formulae I, Ia, Ib, Ic, Id, and Ie.

1

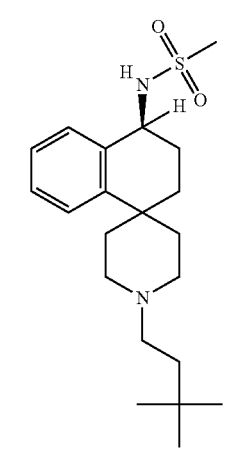

2

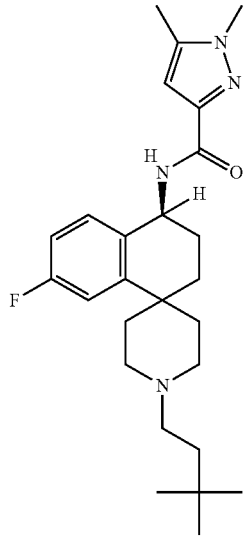

TABLE 1-continued
Exemplary compounds of formulae I, Ia, Ib, Ic, Id, and Ie.
3
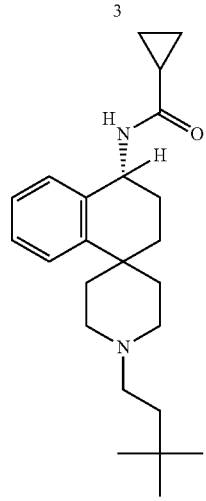
4
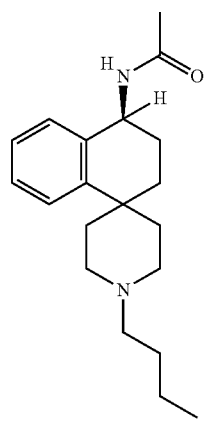
5
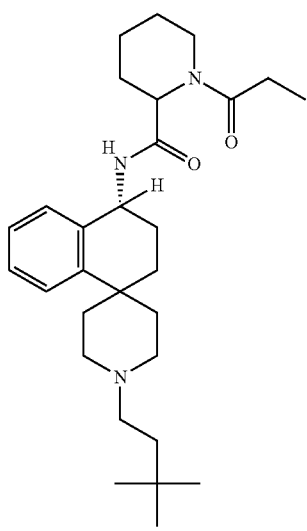
TABLE 1-continued
Exemplary compounds of formulae I, Ia, Ib, Ic, Id, and Ie.
6
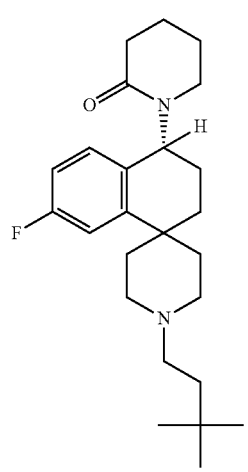
7
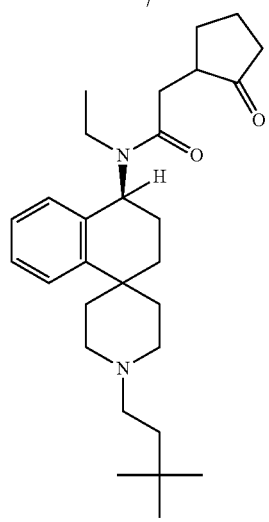
8
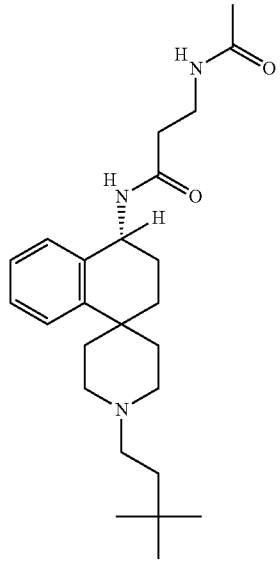

TABLE 1-continued
Exemplary compounds of formulae I, Ia, Ib, Ic, Id, and Ie.
9
10
11
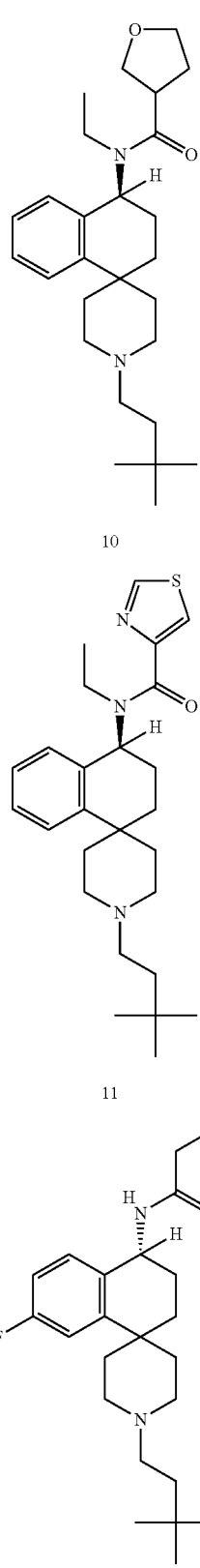
12
13
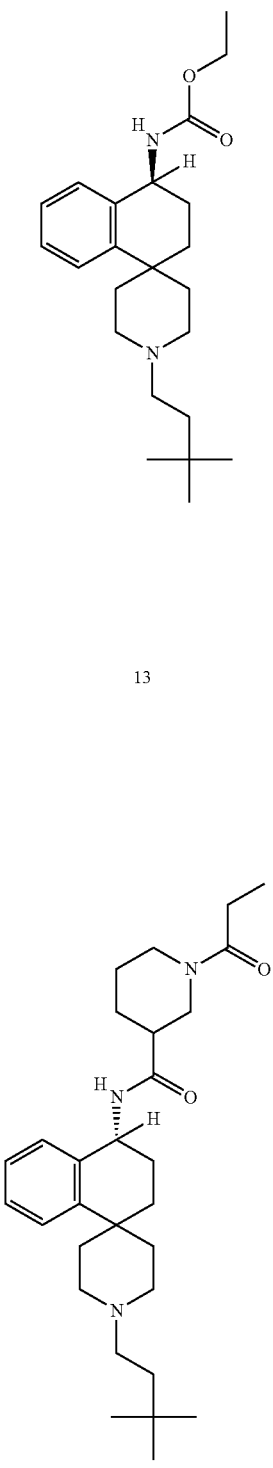

TABLE 1-continued
Exemplary compounds of formulae I, Ia, Ib, Ic, Id, and Ie.
14
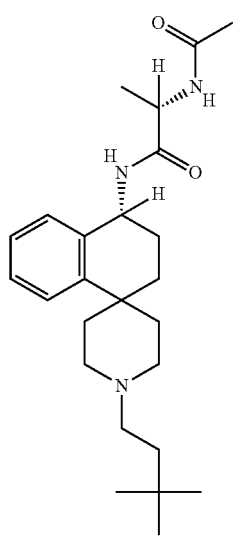
15
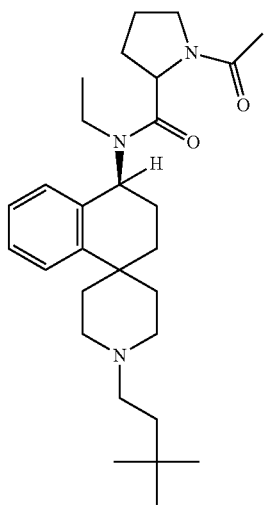
16
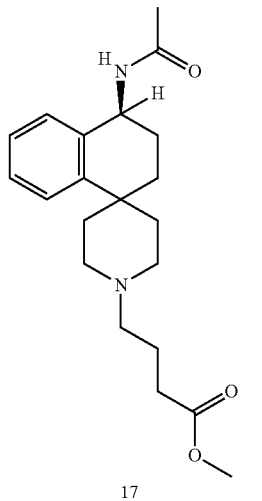
17
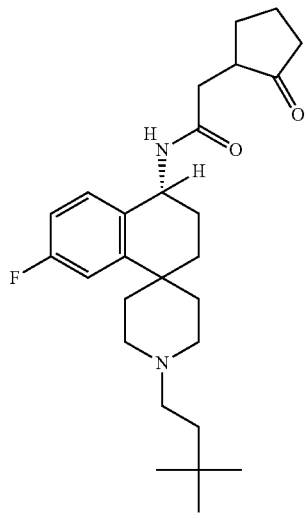
18
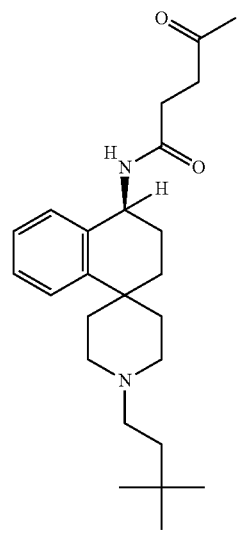

TABLE 1-continued
Exemplary compounds of formulae I, Ia, Ib, Ic, Id, and Ie.
19
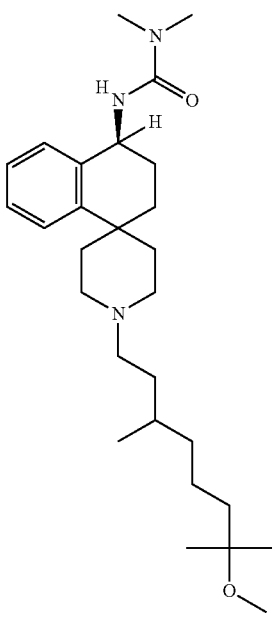
20
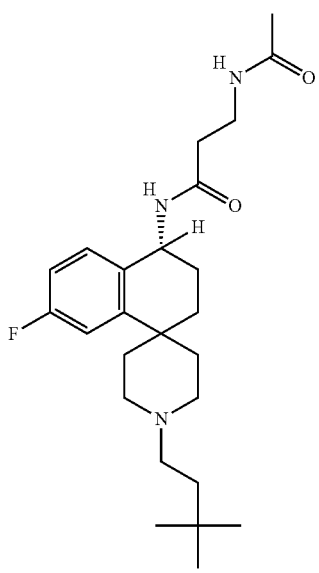
21
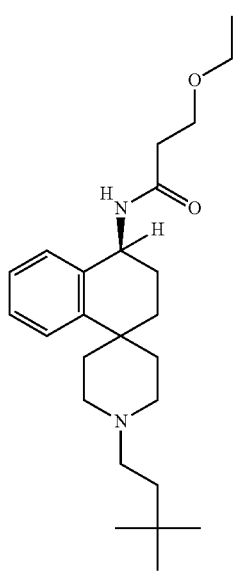
22
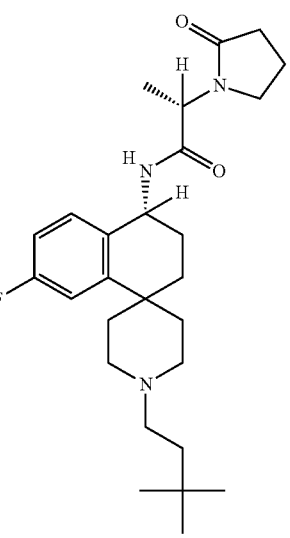

TABLE 1-continued
Exemplary compounds of formulae I, Ia, Ib, Ic, Id, and Ie.
23
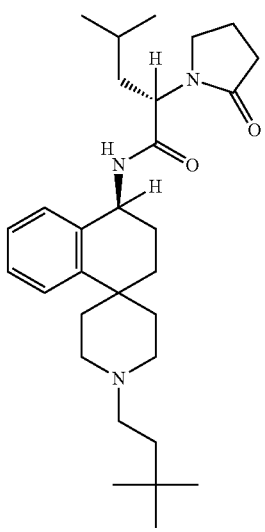
24
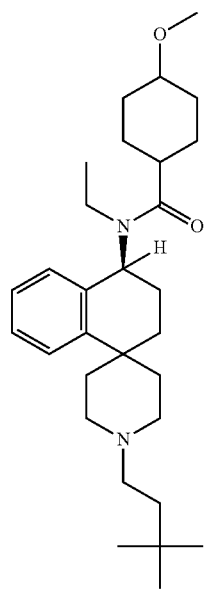
TABLE 1-continued
Exemplary compounds of formulae I, Ia, Ib, Ic, Id, and Ie.
25
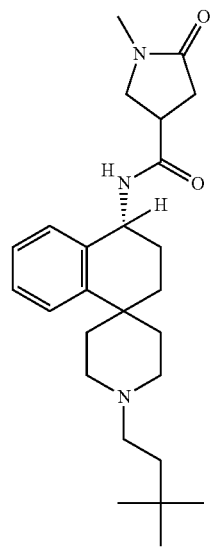
26
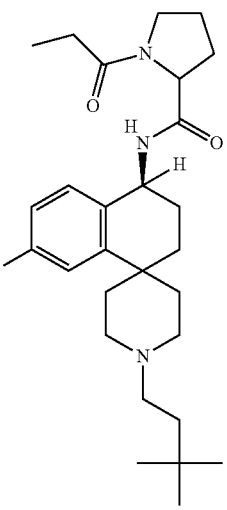

TABLE 1-continued
Exemplary compounds of formulae I, Ia, Ib, Ic, Id, and Ie.
27
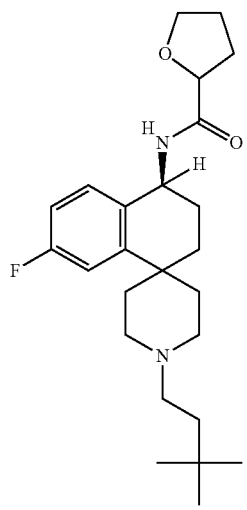
28
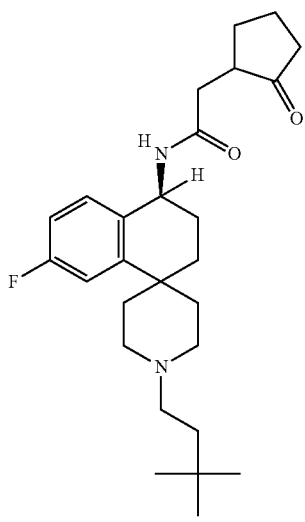
TABLE 1-continued
Exemplary compounds of formulae I, Ia, Ib, Ic, Id, and Ie.
29
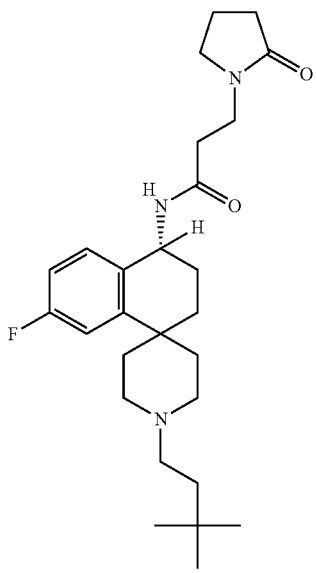
30
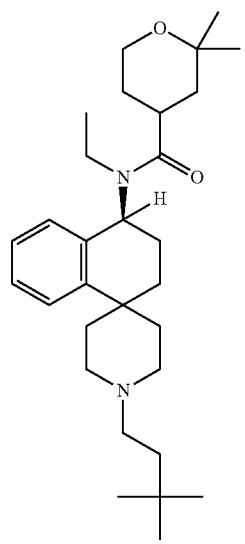

TABLE 1-continued
Exemplary compounds of formulae I, Ia, Ib, Ic, Id, and Ie.
31
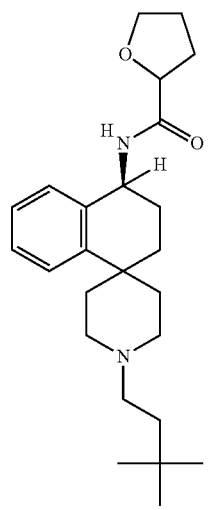
32
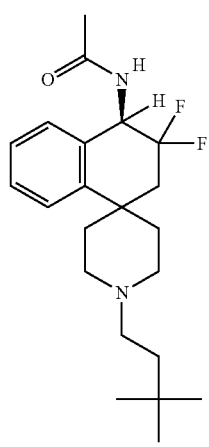
33
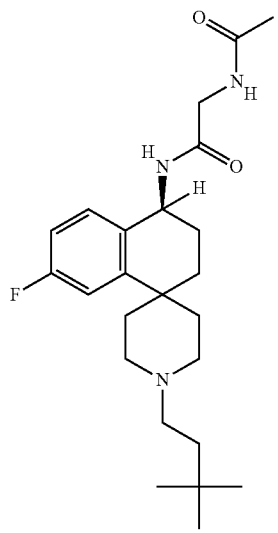
TABLE 1-continued
Exemplary compounds of formulae I, Ia, Ib, Ic, Id, and Ie.
34
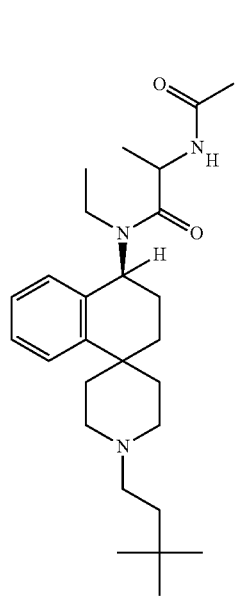
35
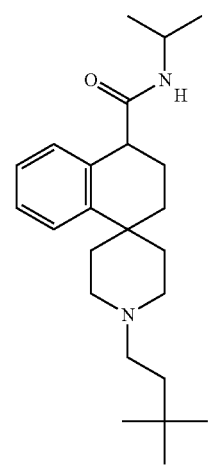

TABLE 1-continued
Exemplary compounds of formulae I, Ia, Ib, Ic, Id, and Ie.
36
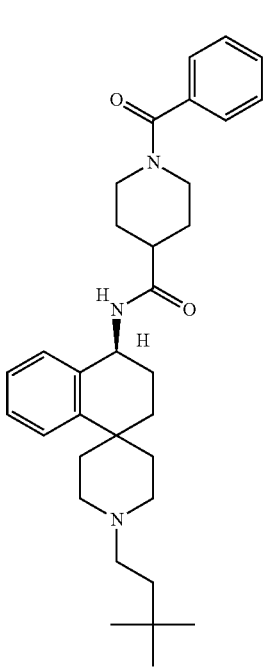
37
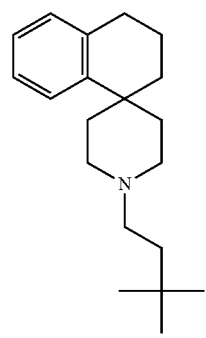
TABLE 1-continued
Exemplary compounds of formulae I, Ia, Ib, Ic, Id, and Ie.
38
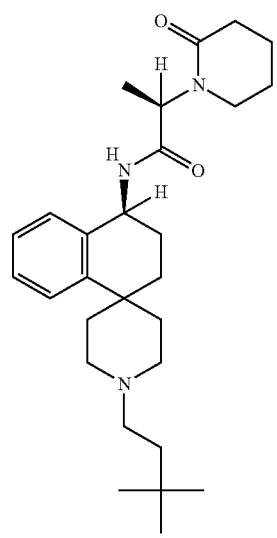
39
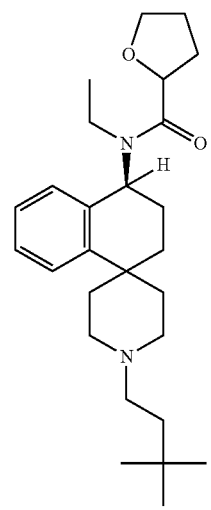

TABLE 1-continued
Exemplary compounds of formulae I, Ia, Ib, Ic, Id, and Ie.
40
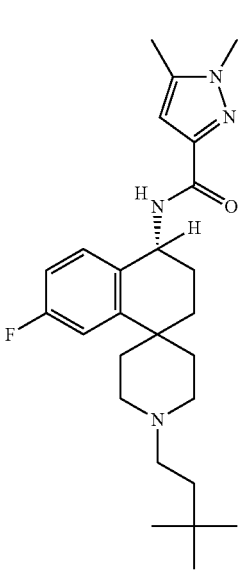
41
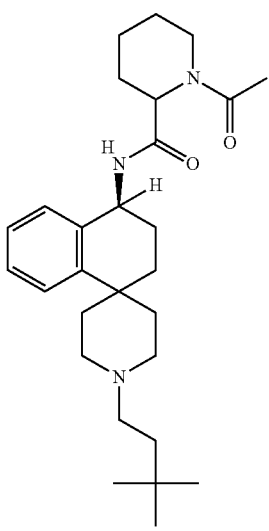
42
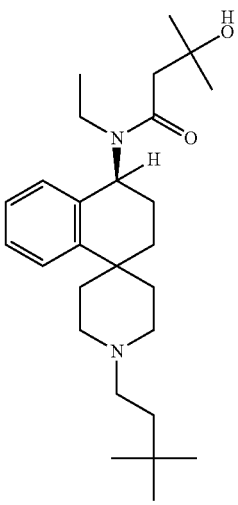
43
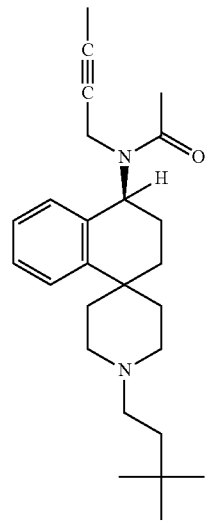

TABLE 1-continued
Exemplary compounds of formulae I, Ia, Ib, Ic, Id, and Ie.
44
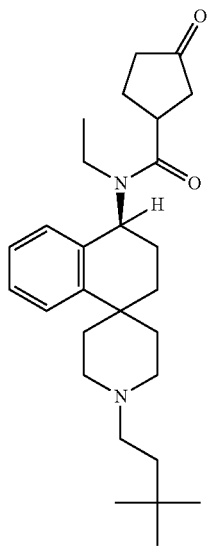
45
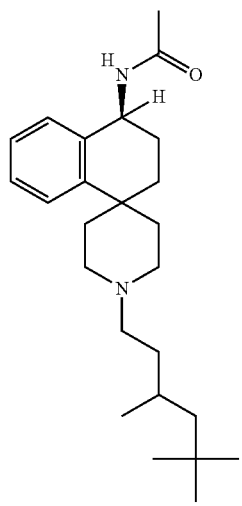
TABLE 1-continued
Exemplary compounds of formulae I, Ia, Ib, Ic, Id, and Ie.
46
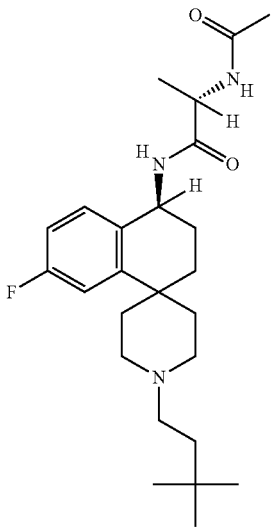
47
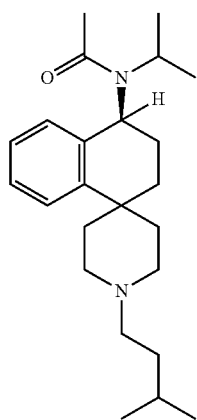
48
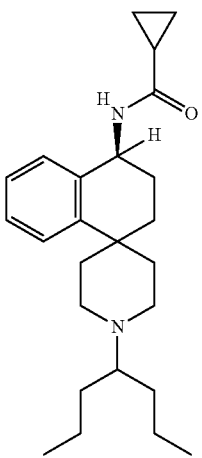

TABLE 1-continued
Exemplary compounds of formulae I, Ia, Ib, Ic, Id, and Ie.
49
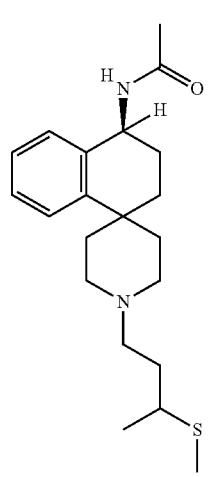
50
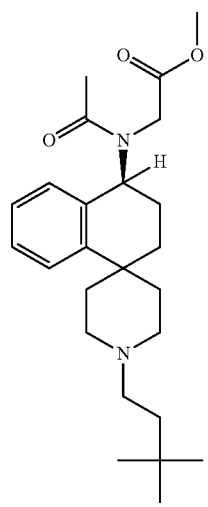
51
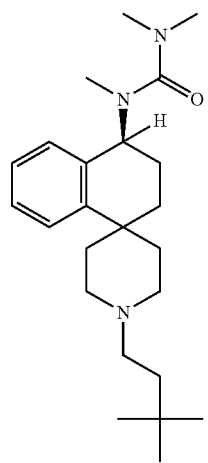
TABLE 1-continued
Exemplary compounds of formulae I, Ia, Ib, Ic, Id, and Ie.
52
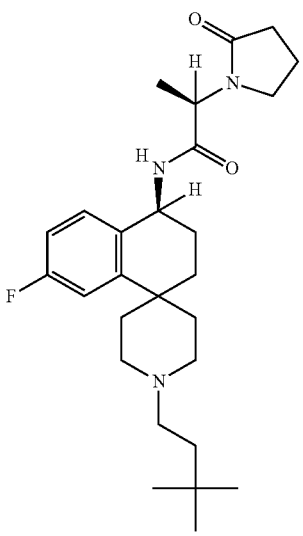
53
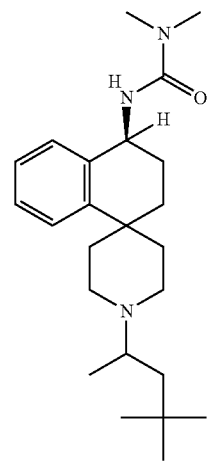
54
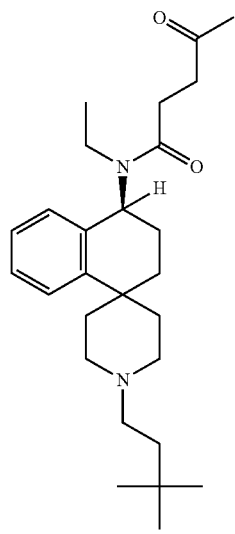

TABLE 1-continued
Exemplary compounds of formulae I, Ia, Ib, Ic, Id, and Ie.
55
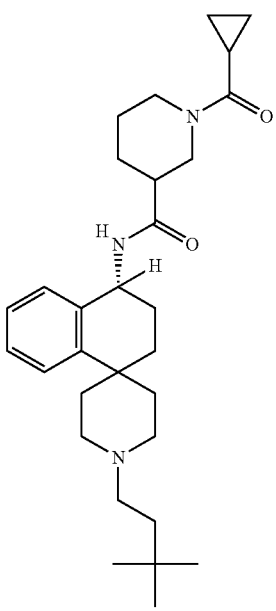
56
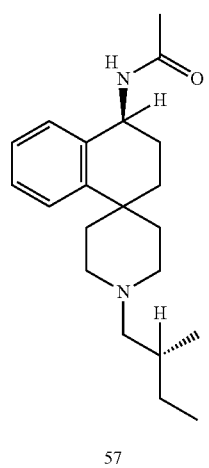
57
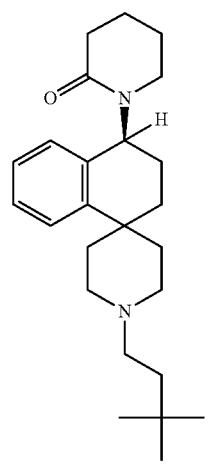
58
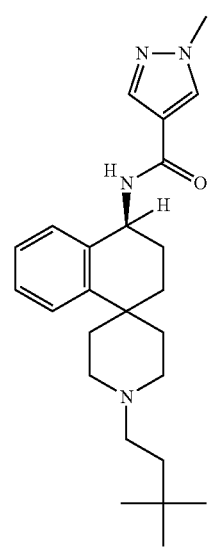
59
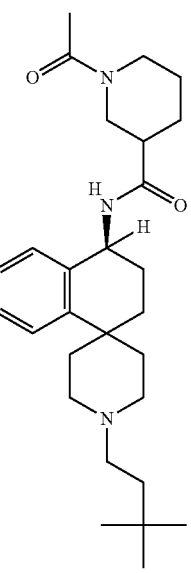

TABLE 1-continued
Exemplary compounds of formulae I, Ia, Ib, Ic, Id, and Ie.
60
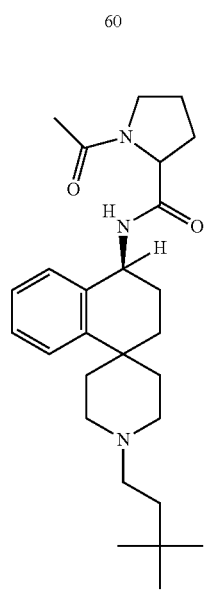
61
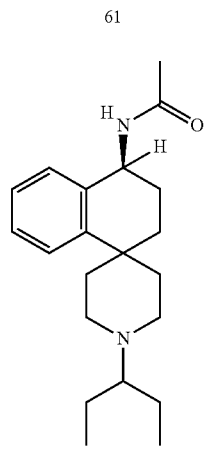
62
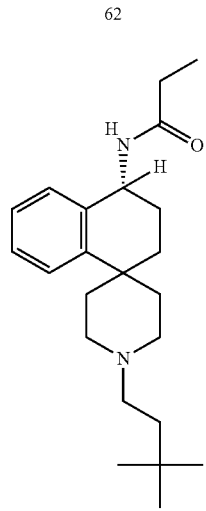
TABLE 1-continued
Exemplary compounds of formulae I, Ia, Ib, Ic, Id, and Ie.
63
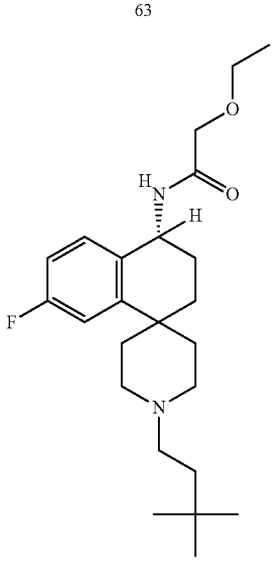
64
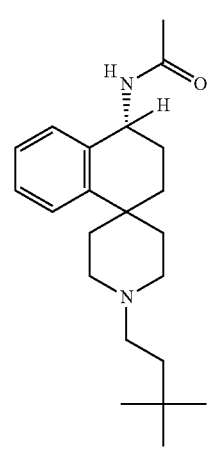
65
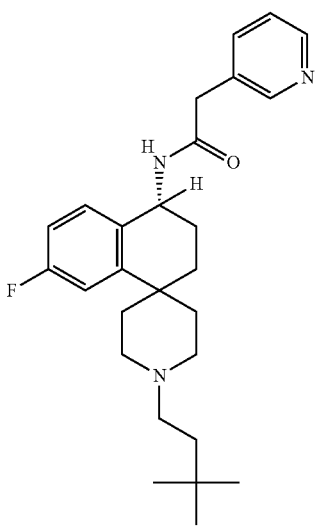

TABLE 1-continued
Exemplary compounds of formulae I, Ia, Ib, Ic, Id, and Ie.
66
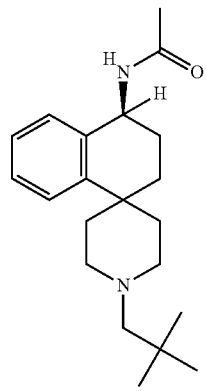
67
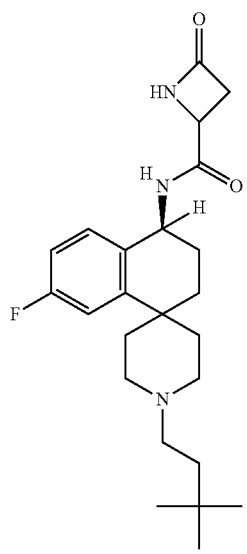
68
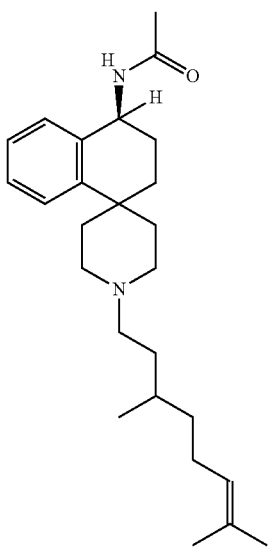
TABLE 1-continued
Exemplary compounds of formulae I, Ia, Ib, Ic, Id, and Ie.
69
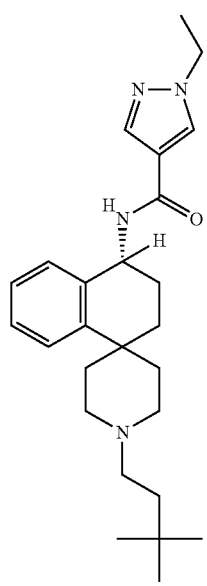
70
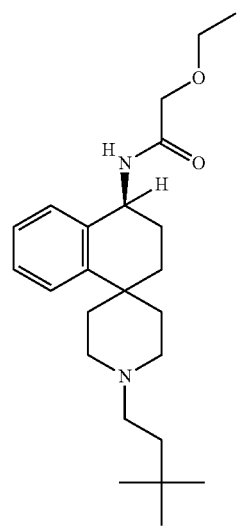

TABLE 1-continued
Exemplary compounds of formulae I, Ia, Ib, Ic, Id, and Ie.
71
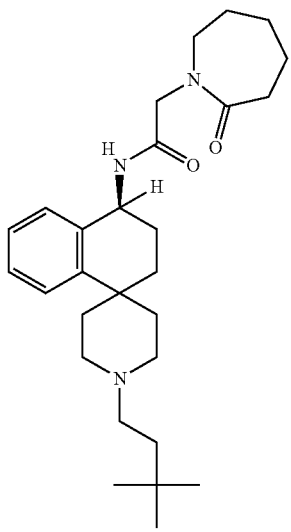
72
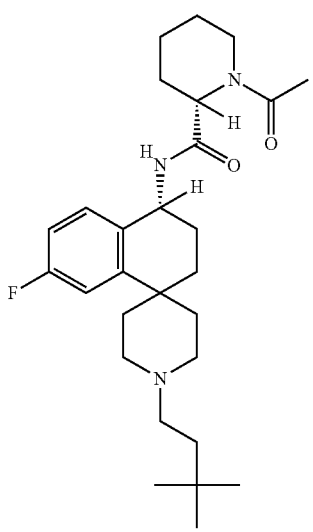
73
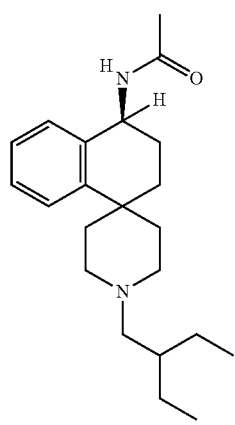
74
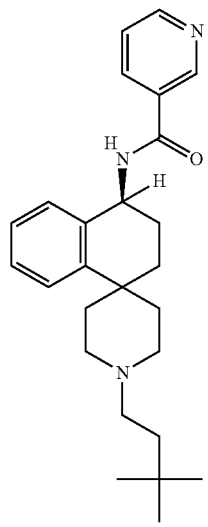
75
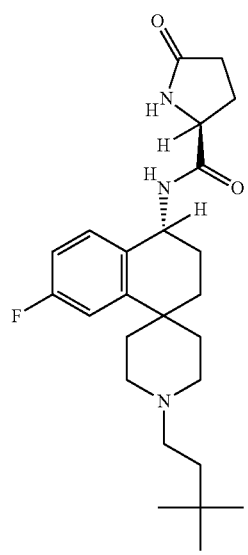

TABLE 1-continued
Exemplary compounds of formulae I, Ia, Ib, Ic, Id, and Ie.
76
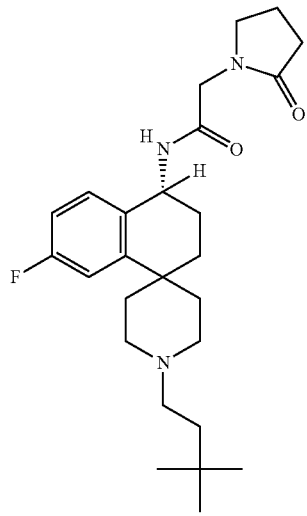
77
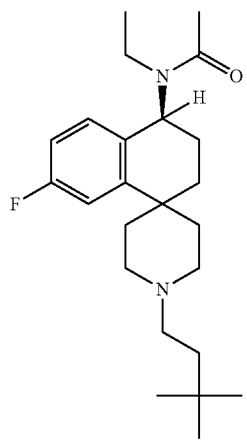
78
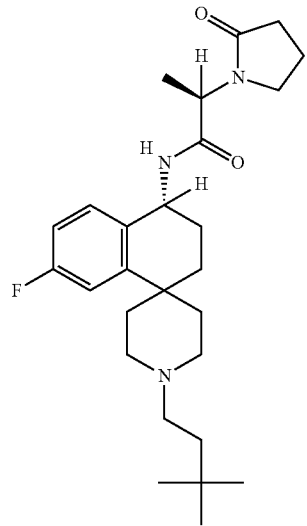
79
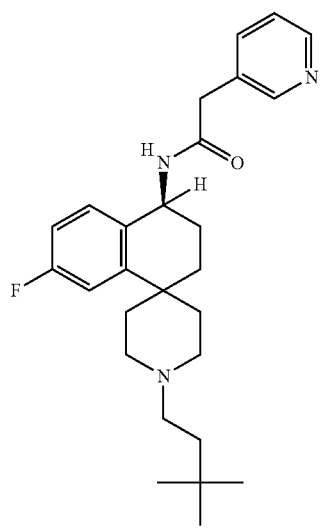
80
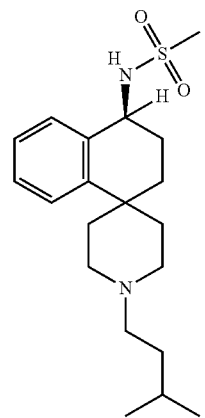

TABLE 1-continued
Exemplary compounds of formulae I, Ia, Ib, Ic, Id, and Ie.
81
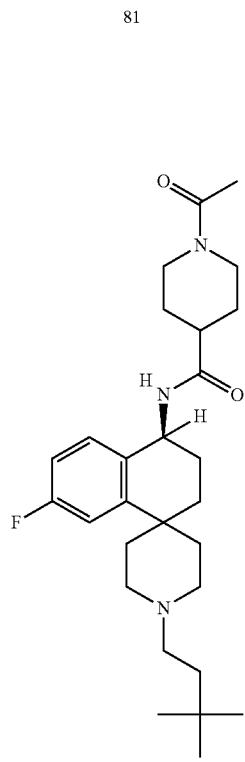
82
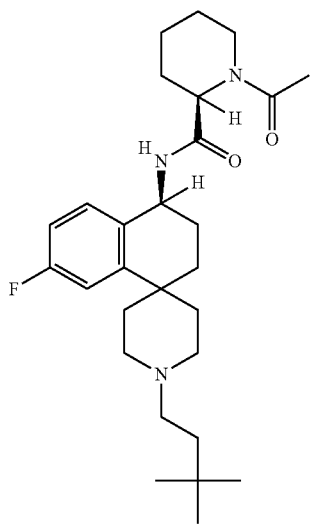
83
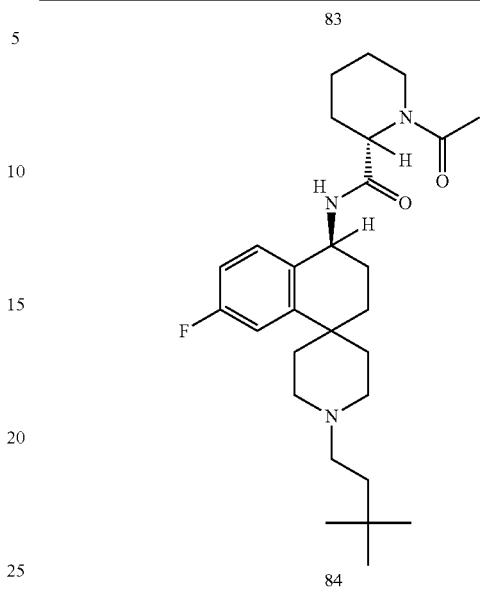
84
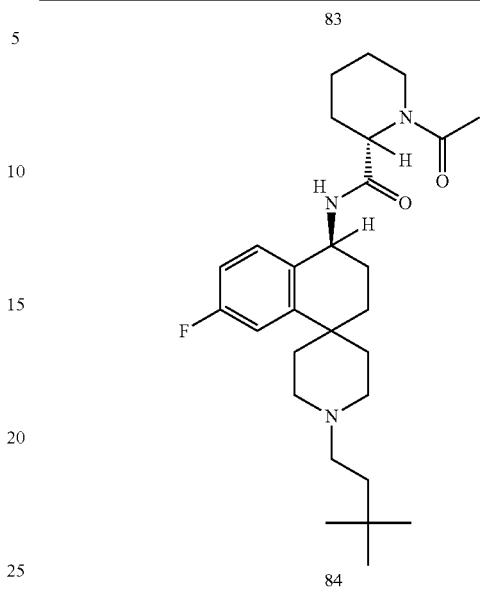
85
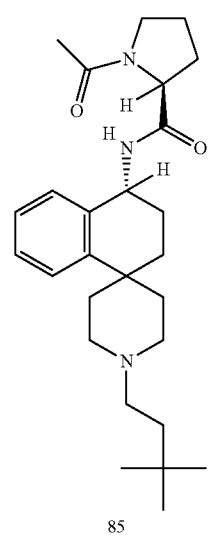

TABLE 1-continued
Exemplary compounds of formulae I, Ia, Ib, Ic, Id, and Ie.
86
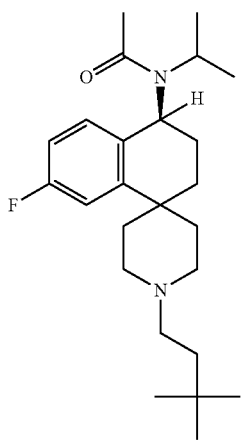
87
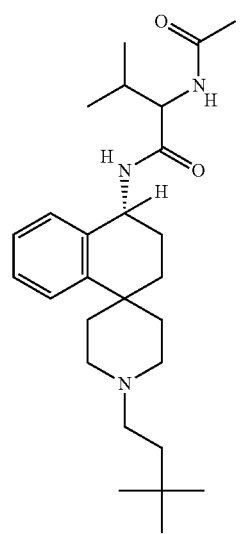
TABLE 1-continued
Exemplary compounds of formulae I, Ia, Ib, Ic, Id, and Ie.
88
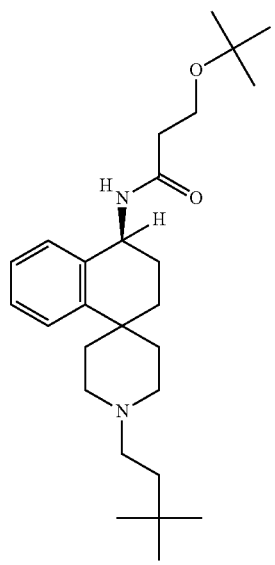
89
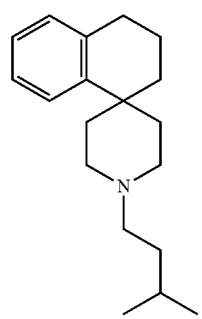
90
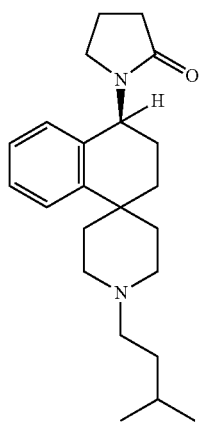

TABLE 1-continued
Exemplary compounds of formulae I, Ia, Ib, Ic, Id, and Ie.
91
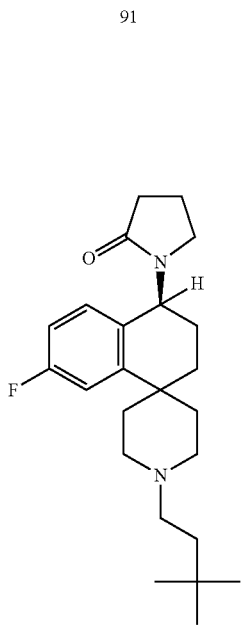
92
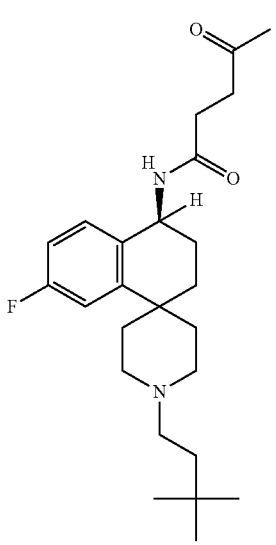
TABLE 1-continued
Exemplary compounds of formulae I, Ia, Ib, Ic, Id, and Ie.
93
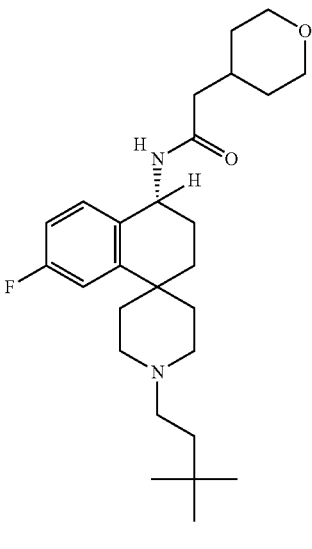
94
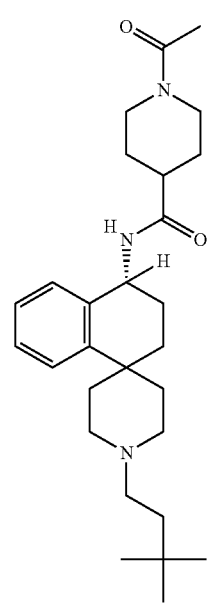
95
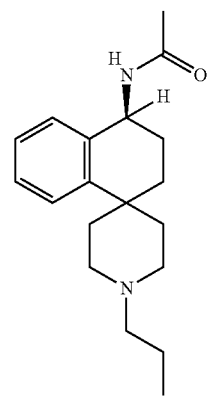

TABLE 1-continued
Exemplary compounds of formulae I, Ia, Ib, Ic, Id, and Ie.
96
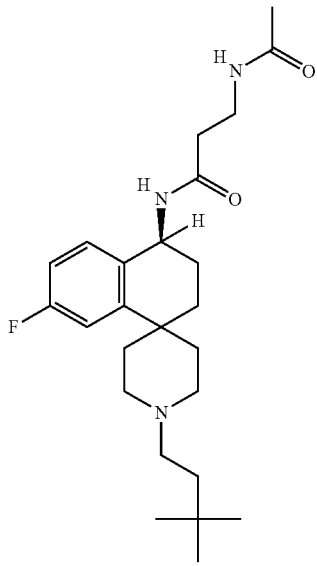
97
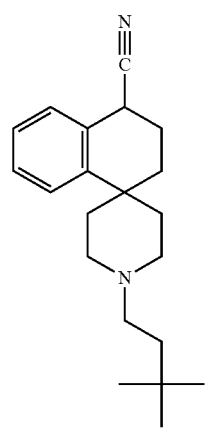
TABLE 1-continued
Exemplary compounds of formulae I, Ia, Ib, Ic, Id, and Ie.
98
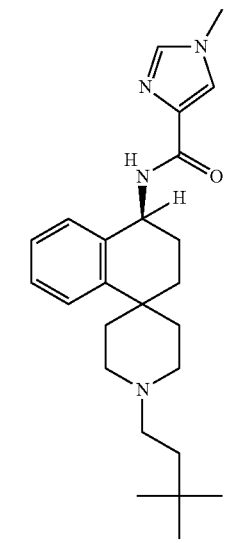
99
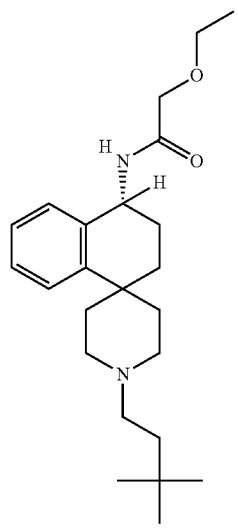

TABLE 1-continued
Exemplary compounds of formulae I, Ia, Ib, Ic, Id, and Ie.
100
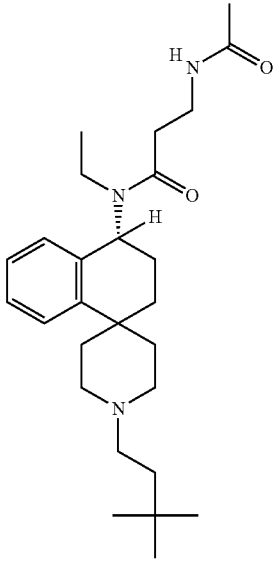
101
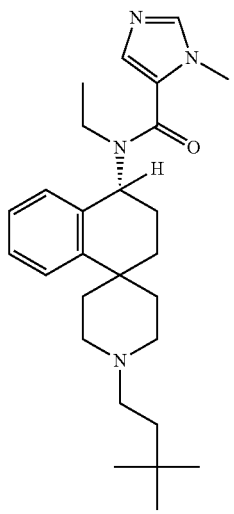
TABLE 1-continued
Exemplary compounds of formulae I, Ia, Ib, Ic, Id, and Ie.
102
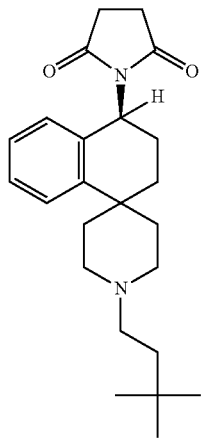
103
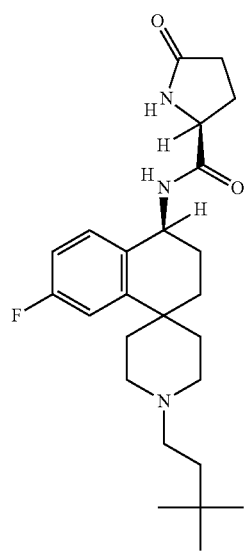
104
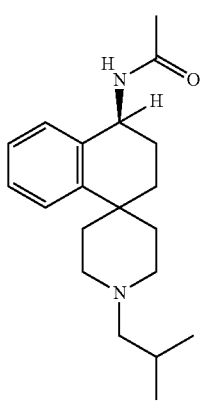

TABLE 1-continued
Exemplary compounds of formulae I, Ia, Ib, Ic, Id, and Ie.
105
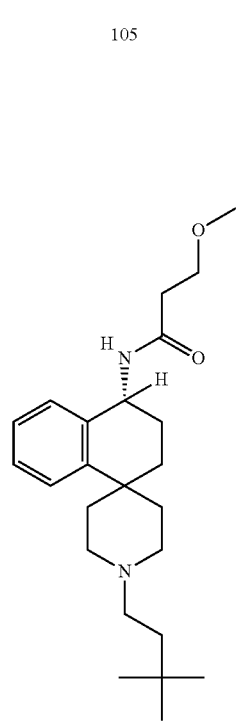
106
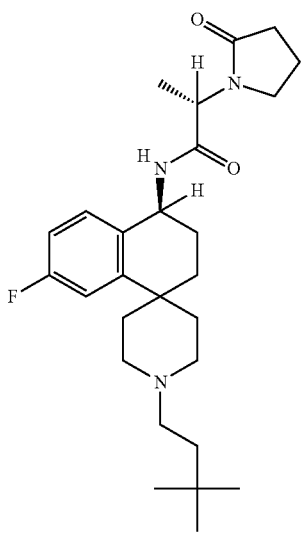
TABLE 1-continued
Exemplary compounds of formulae I, Ia, Ib, Ic, Id, and Ie.
107
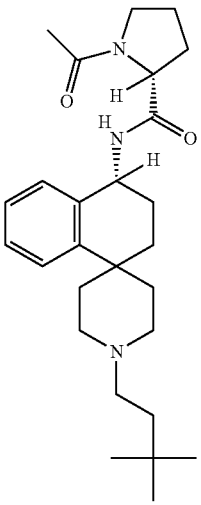
108
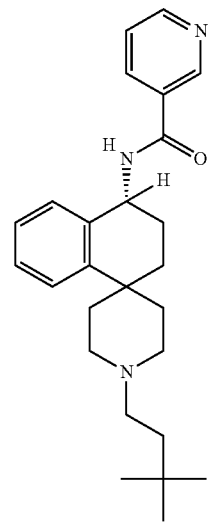
109
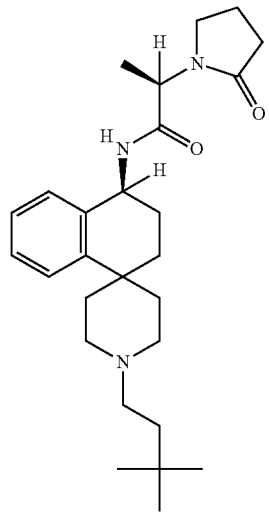

TABLE 1-continued
Exemplary compounds of formulae I, Ia, Ib, Ic, Id, and Ie.
110
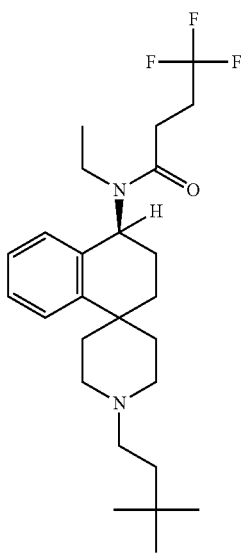
111
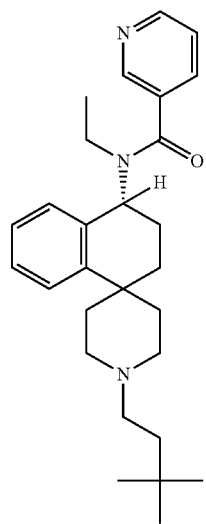
TABLE 1-continued
Exemplary compounds of formulae I, Ia, Ib, Ic, Id, and Ie.
112
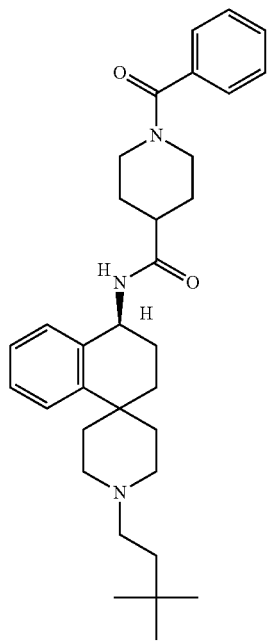
113
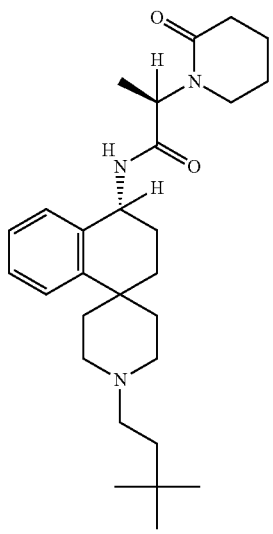

TABLE 1-continued
Exemplary compounds of formulae I, Ia, Ib, Ic, Id, and Ie.
114
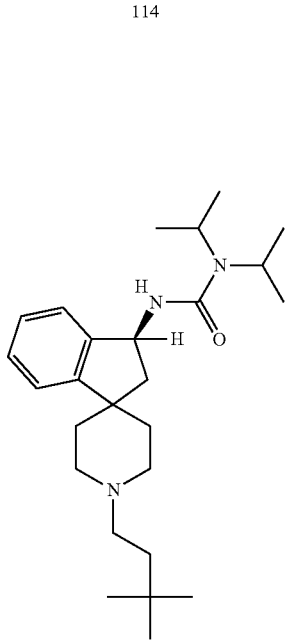
115
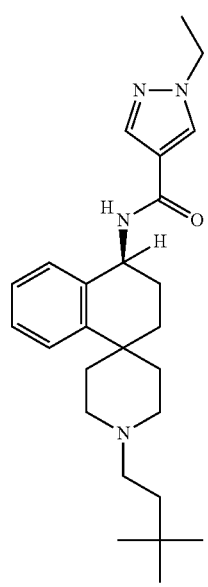
TABLE 1-continued
Exemplary compounds of formulae I, Ia, Ib, Ic, Id, and Ie.
116
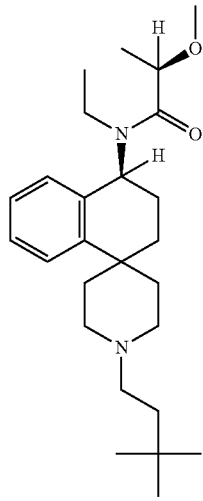
117
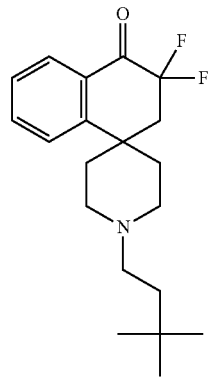
118
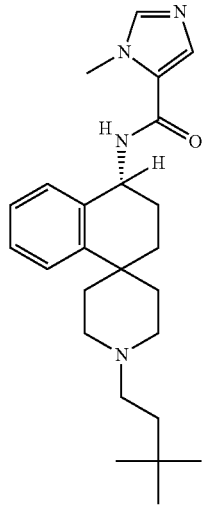

TABLE 1-continued
Exemplary compounds of formulae I, Ia, Ib, Ic, Id, and Ie.
119
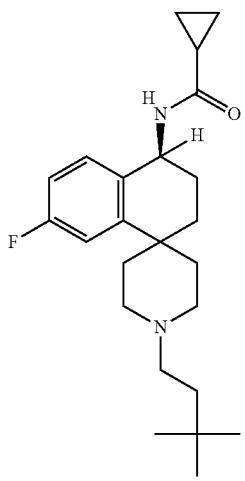
120
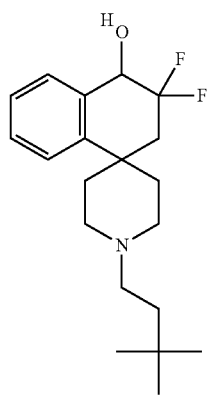
121
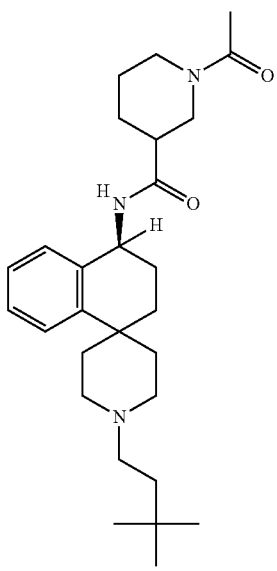
TABLE 1-continued
Exemplary compounds of formulae I, Ia, Ib, Ic, Id, and Ie.
122
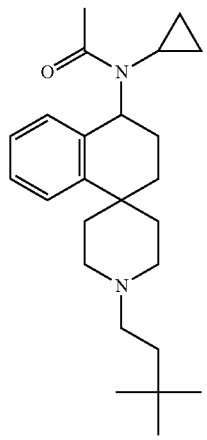
123
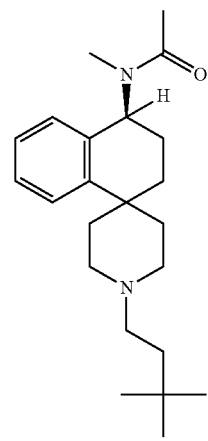
124
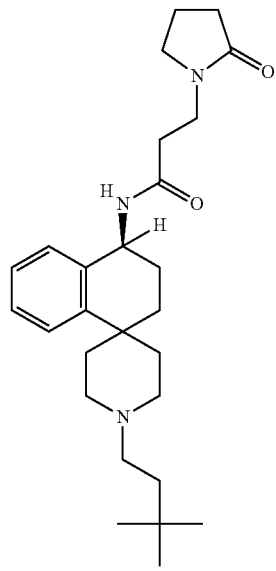

TABLE 1-continued
Exemplary compounds of formulae I, Ia, Ib, Ic, Id, and Ie.
125
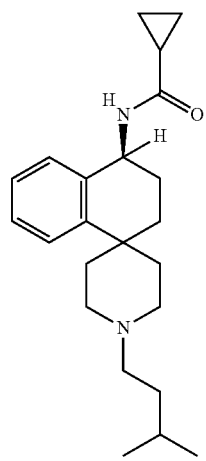
126
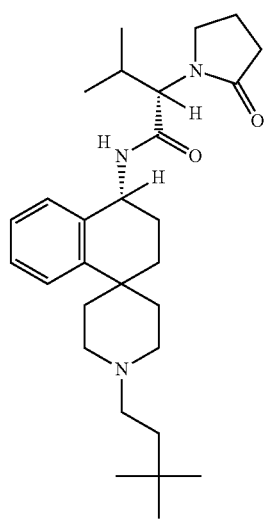
TABLE 1-continued
Exemplary compounds of formulae I, Ia, Ib, Ic, Id, and Ie.
127
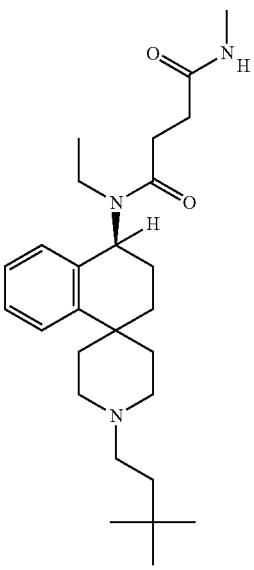
128
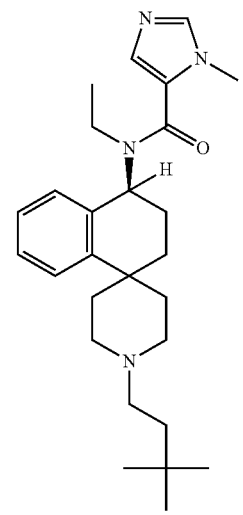

TABLE 1-continued
Exemplary compounds of formulae I, Ia, Ib, Ic, Id, and Ie.
129
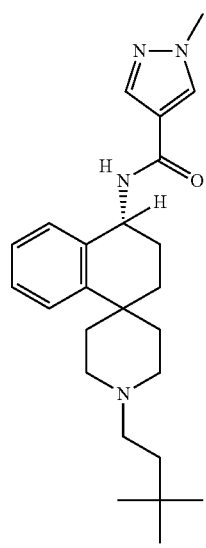
130
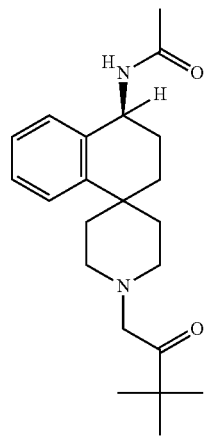
131
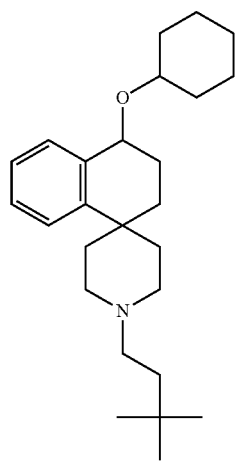
TABLE 1-continued
Exemplary compounds of formulae I, Ia, Ib, Ic, Id, and Ie.
132
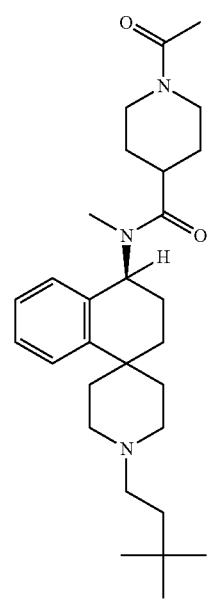
133
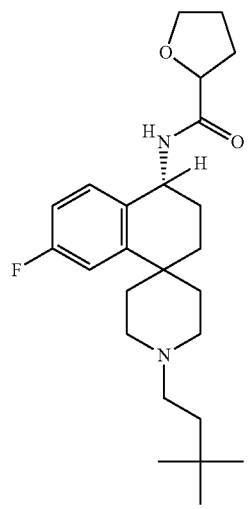

TABLE 1-continued
Exemplary compounds of formulae I, Ia, Ib, Ic, Id, and Ie.
134
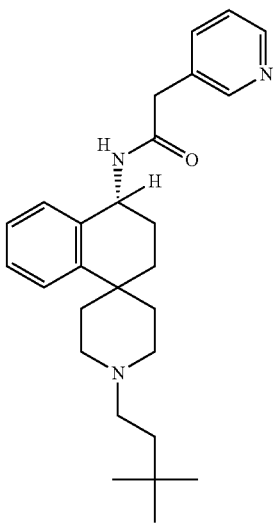
135
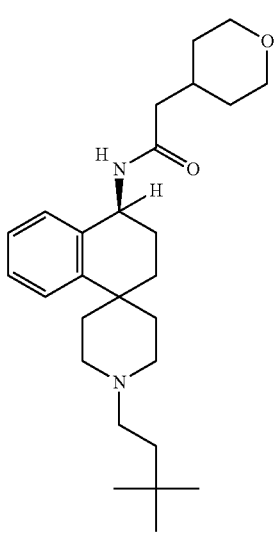
TABLE 1-continued
Exemplary compounds of formulae I, Ia, Ib, Ic, Id, and Ie.
136
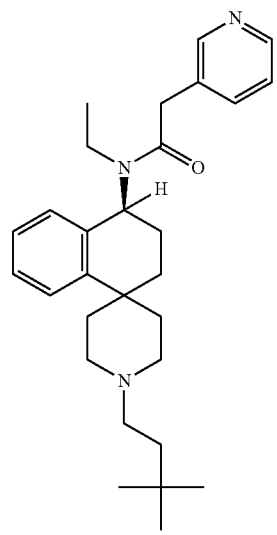
137
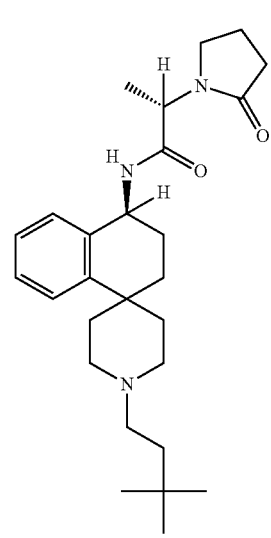

TABLE 1-continued
Exemplary compounds of formulae I, Ia, Ib, Ic, Id, and Ie.
138
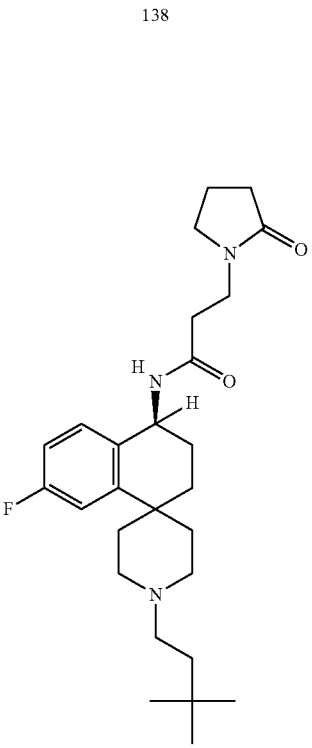
139
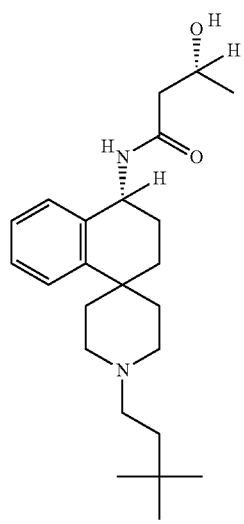
140
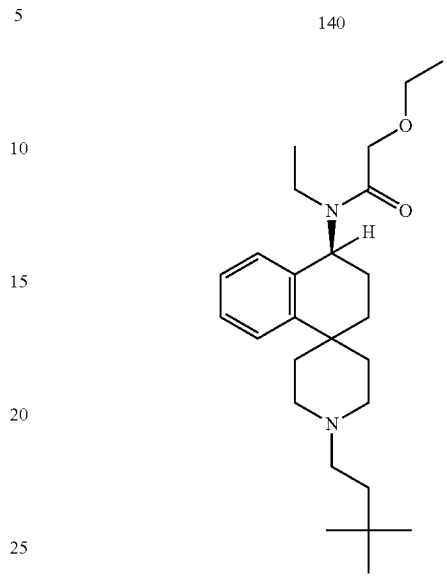
141
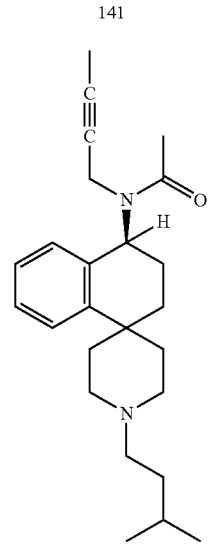
142
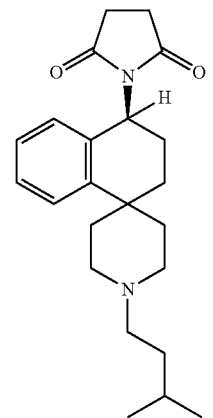

TABLE 1-continued
Exemplary compounds of formulae I, Ia, Ib, Ic, Id, and Ie.
143
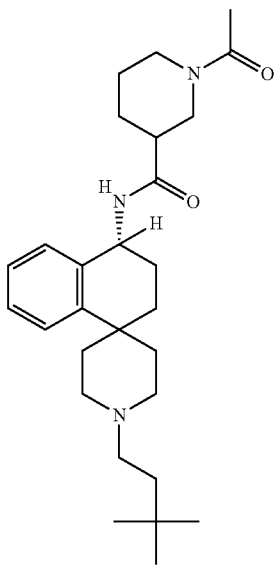
144
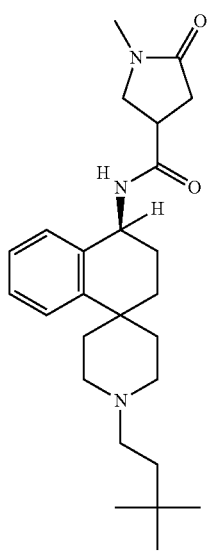
TABLE 1-continued
Exemplary compounds of formulae I, Ia, Ib, Ic, Id, and Ie.
145
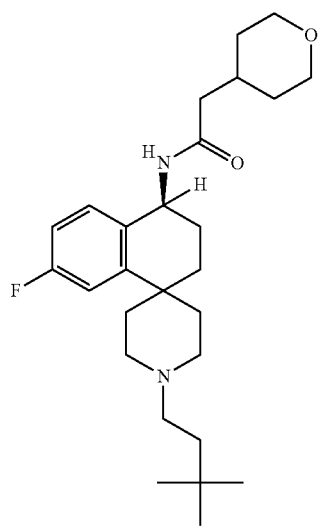
146
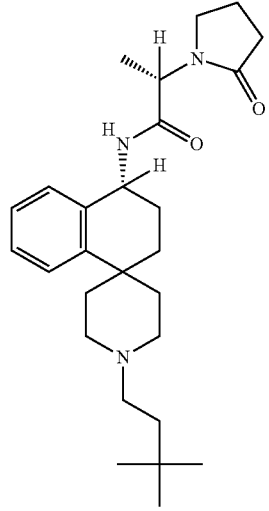

TABLE 1-continued
Exemplary compounds of formulae I, Ia, Ib, Ic, Id, and Ie.
147
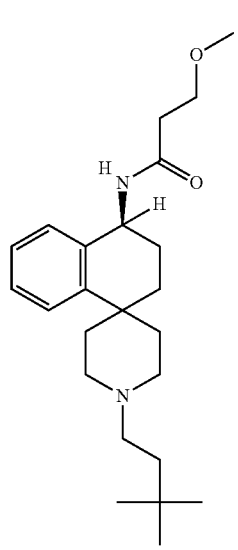
148
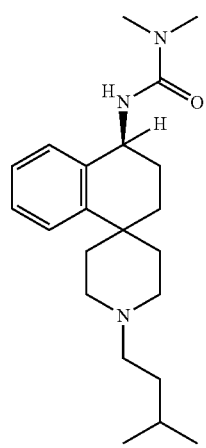
149
150
151
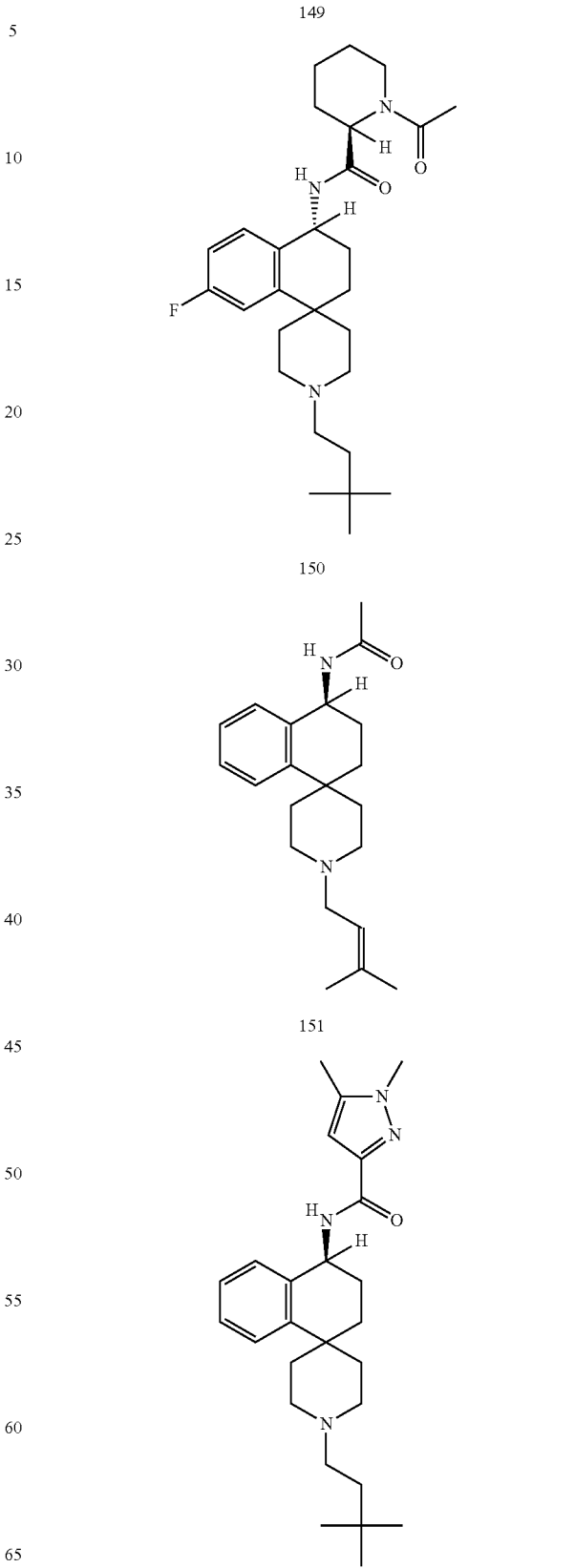

TABLE 1-continued
Exemplary compounds of formulae I, Ia, Ib, Ic, Id, and Ie.
152
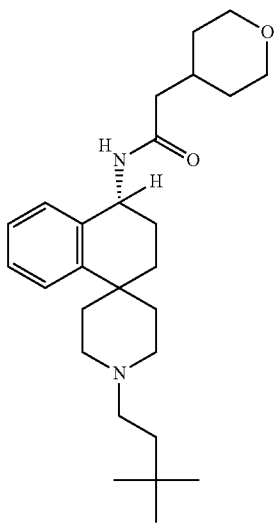
153
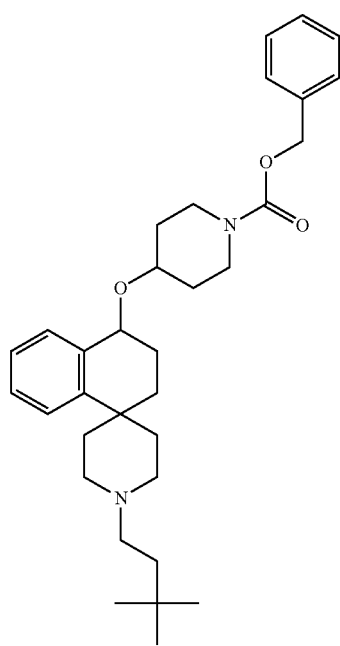
TABLE 1-continued
Exemplary compounds of formulae I, Ia, Ib, Ic, Id, and Ie.
154
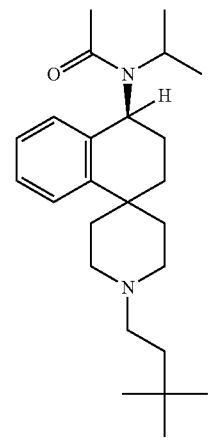
155
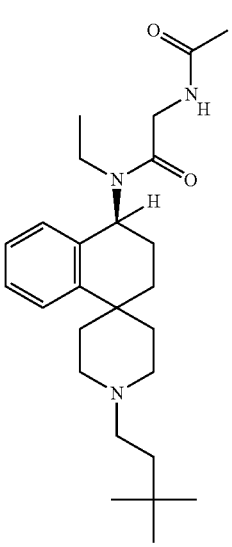
156
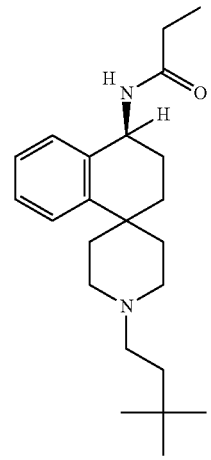

TABLE 1-continued
Exemplary compounds of formulae I, Ia, Ib, Ic, Id, and Ie.
157
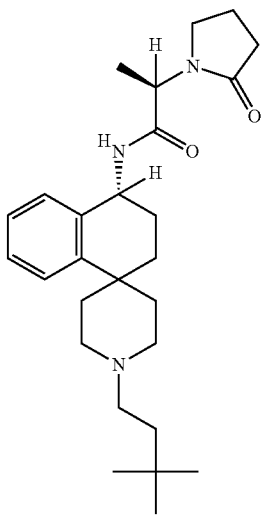
158
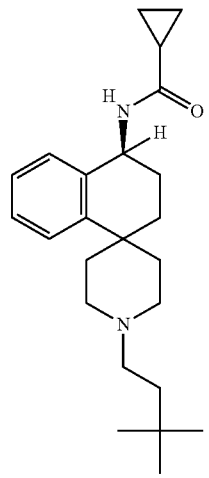
159
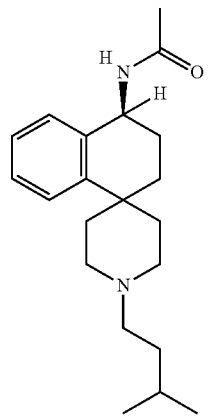
TABLE 1-continued
Exemplary compounds of formulae I, Ia, Ib, Ic, Id, and Ie.
160
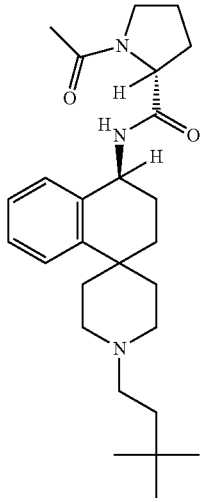
161
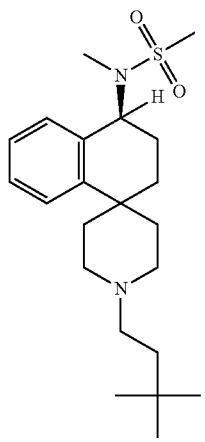
162
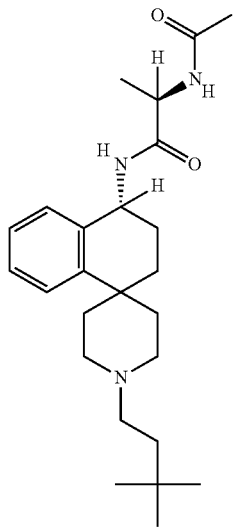

TABLE 1-continued
Exemplary compounds of formulae I, Ia, Ib, Ic, Id, and Ie.
163
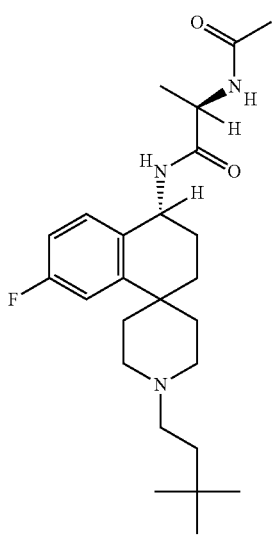
164
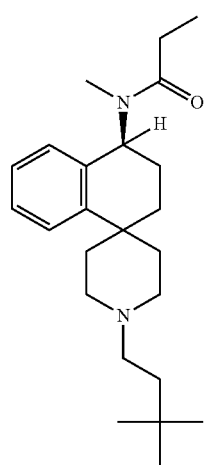
TABLE 1-continued
Exemplary compounds of formulae I, Ia, Ib, Ic, Id, and Ie.
165
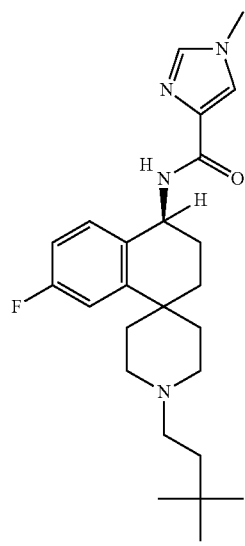
166
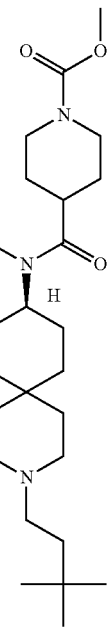

TABLE 1-continued
Exemplary compounds of formulae I, Ia, Ib, Ic, Id, and Ie.
167
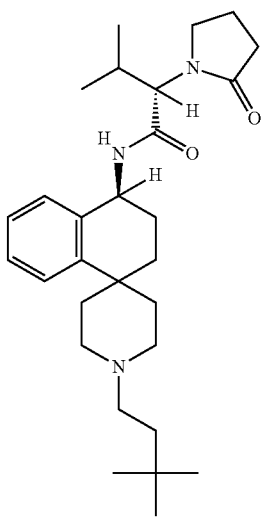
168
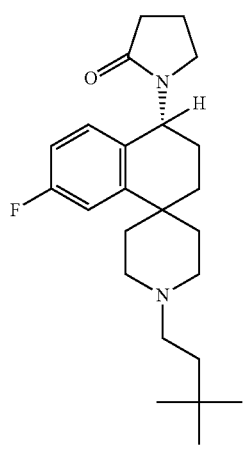
169
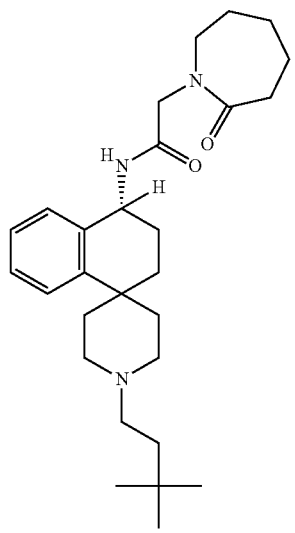
TABLE 1-continued
Exemplary compounds of formulae I, Ia, Ib, Ic, Id, and Ie.
170
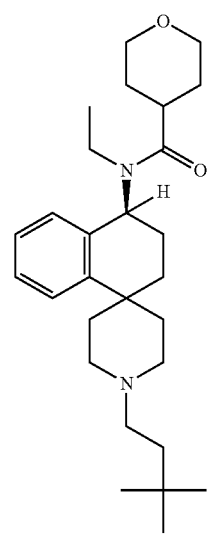
171
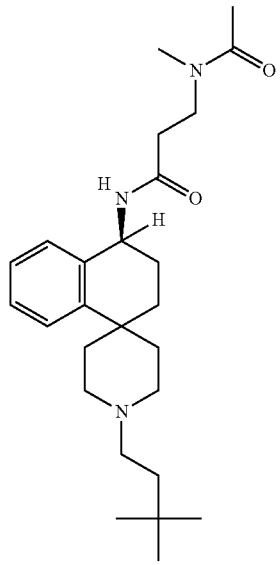

TABLE 1-continued
Exemplary compounds of formulae I, Ia, Ib, Ic, Id, and Ie.
172
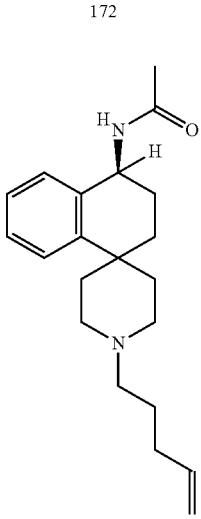
173
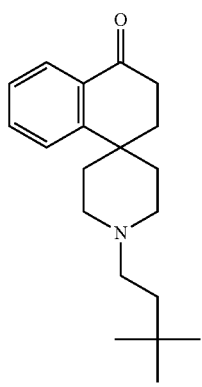
174
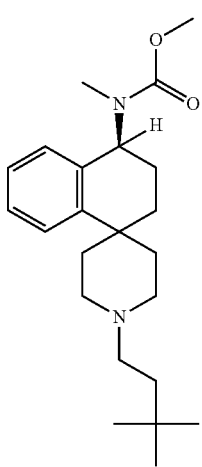
TABLE 1-continued
Exemplary compounds of formulae I, Ia, Ib, Ic, Id, and Ie.
175
176
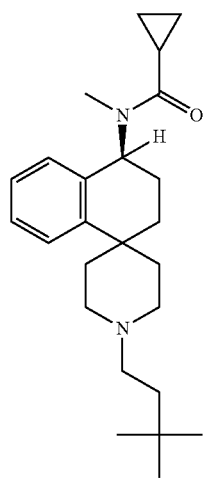
177
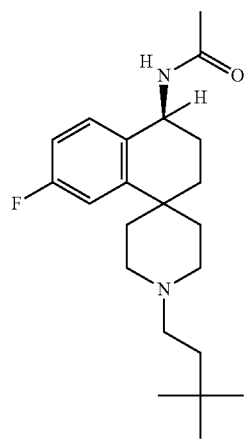

TABLE 1-continued
Exemplary compounds of formulae I, Ia, Ib, Ic, Id, and Ie.
178
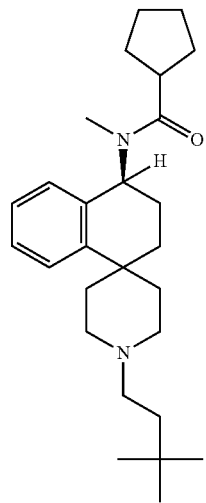
179
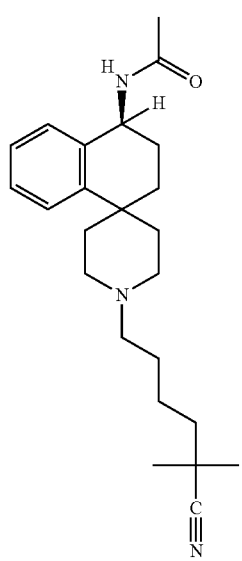
TABLE 1-continued
Exemplary compounds of formulae I, Ia, Ib, Ic, Id, and Ie.
180
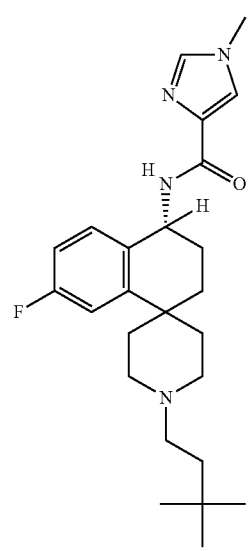
181
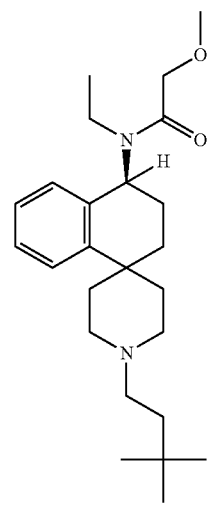

TABLE 1-continued
Exemplary compounds of formulae I, Ia, Ib, Ic, Id, and Ie.
182
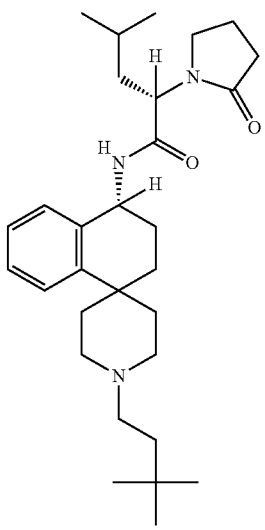
183
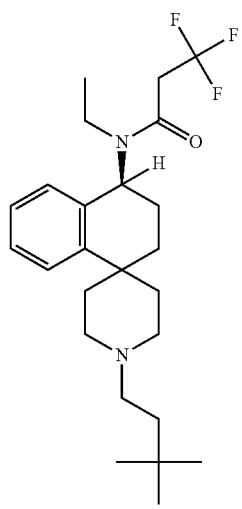
184
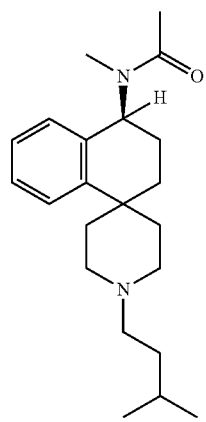
TABLE 1-continued
Exemplary compounds of formulae I, Ia, Ib, Ic, Id, and Ie.
185
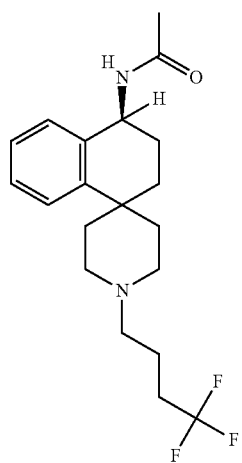
186
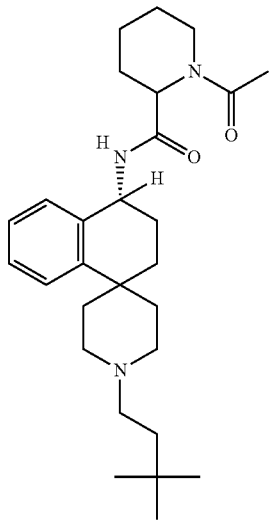

TABLE 1-continued
Exemplary compounds of formulae I, Ia, Ib, Ic, Id, and Ie.
187
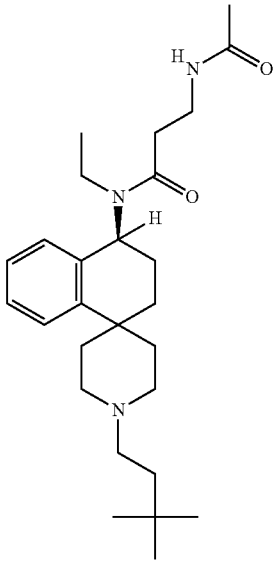
188
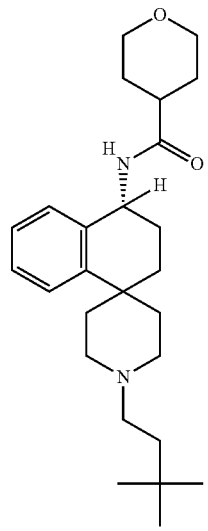
TABLE 1-continued
Exemplary compounds of formulae I, Ia, Ib, Ic, Id, and Ie.
189
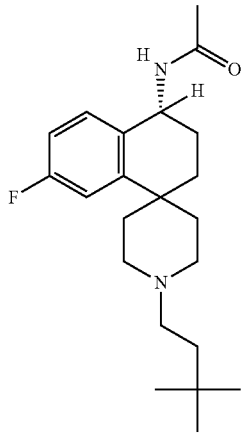
190
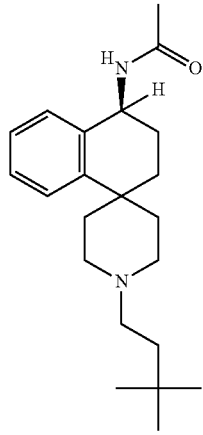
191
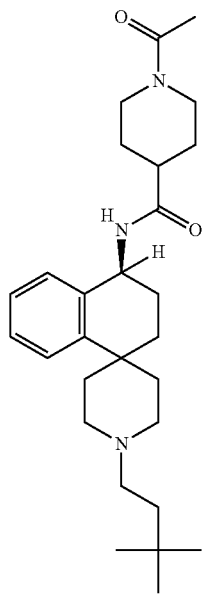

TABLE 1-continued
Exemplary compounds of formulae I, Ia, Ib, Ic, Id, and Ie.
192
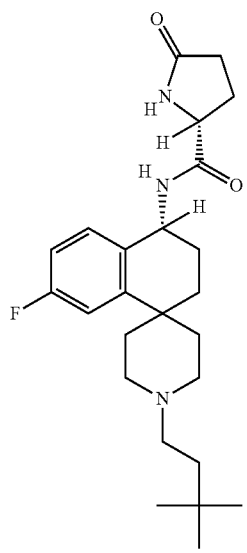
193
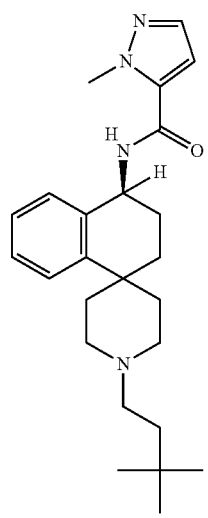
TABLE 1-continued
Exemplary compounds of formulae I, Ia, Ib, Ic, Id, and Ie.
194
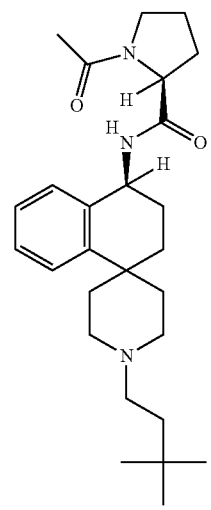
195
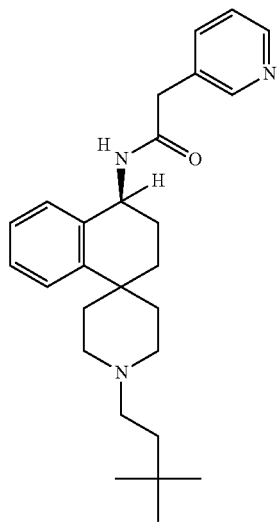

TABLE 1-continued
Exemplary compounds of formulae I, Ia, Ib, Ic, Id, and Ie.
196
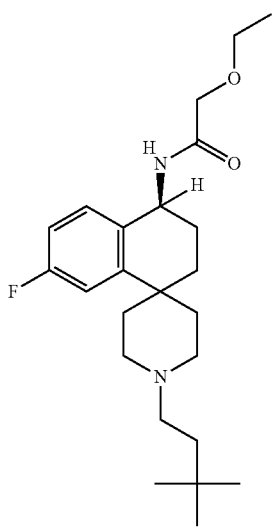
197
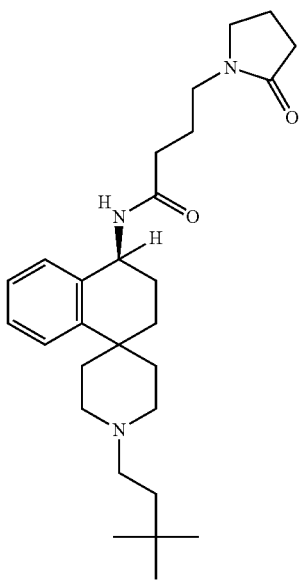
TABLE 1-continued
Exemplary compounds of formulae I, Ia, Ib, Ic, Id, and Ie.
198
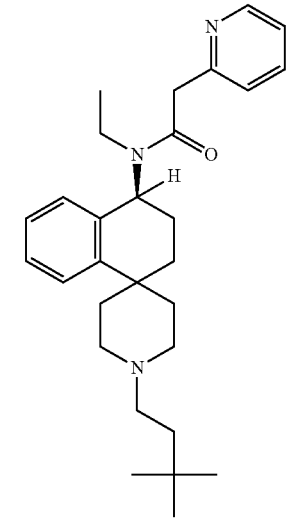
199
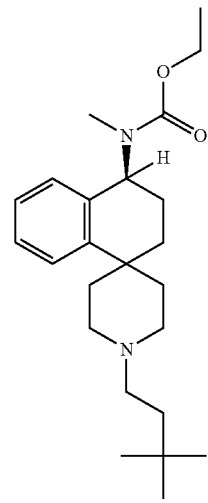

TABLE 1-continued
Exemplary compounds of formulae I, Ia, Ib, Ic, Id, and Ie.
200
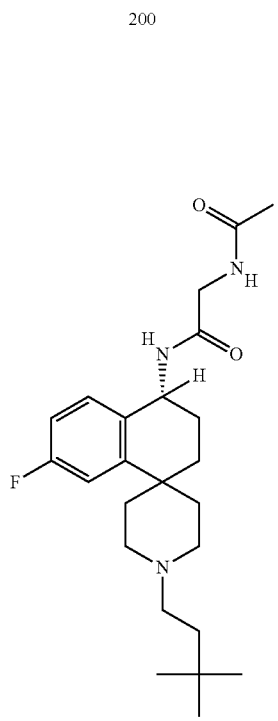
201
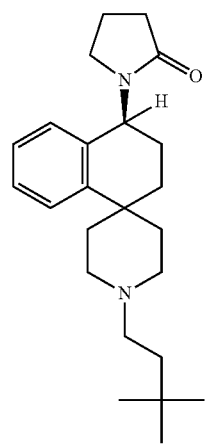
202
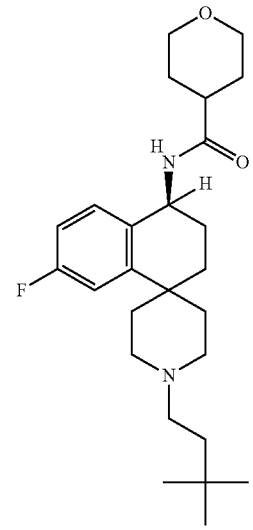
203
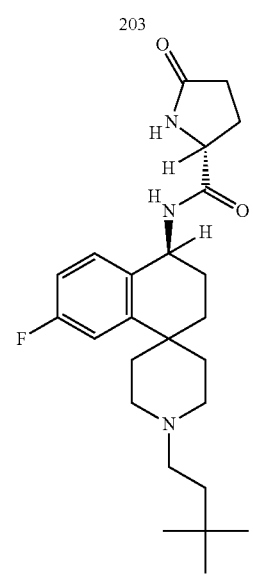
204
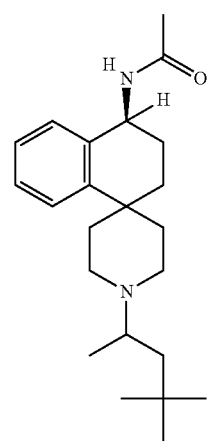

TABLE 1-continued
Exemplary compounds of formulae I, Ia, Ib, Ic, Id, and Ie.
205
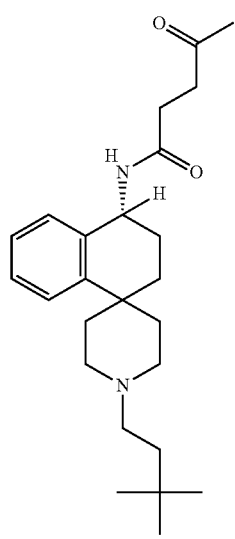
206
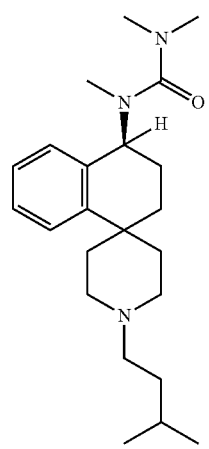
207
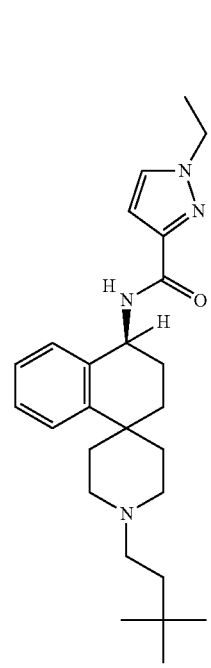
208
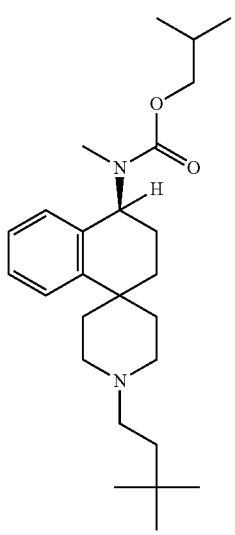

TABLE 1-continued
Exemplary compounds of formulae I, Ia, Ib, Ic, Id, and Ie.
209
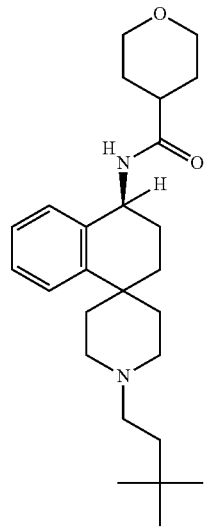
210
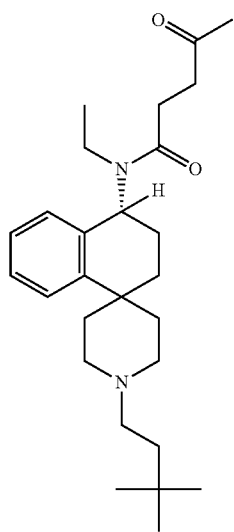
TABLE 1-continued
Exemplary compounds of formulae I, Ia, Ib, Ic, Id, and Ie.
211
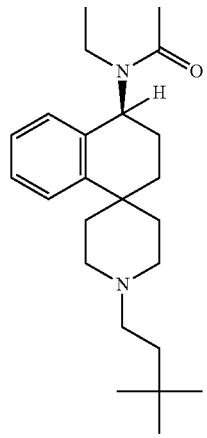
212
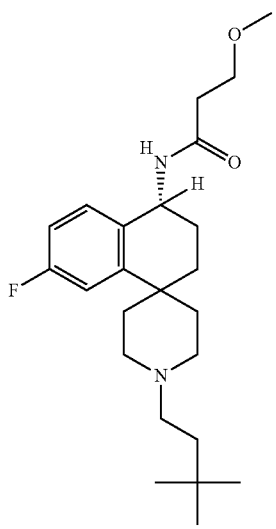
213
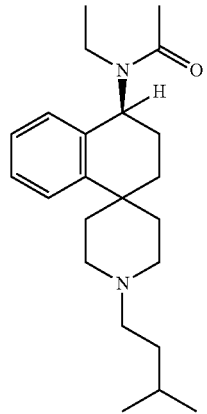

TABLE 1-continued
Exemplary compounds of formulae I, Ia, Ib, Ic, Id, and Ie.
214
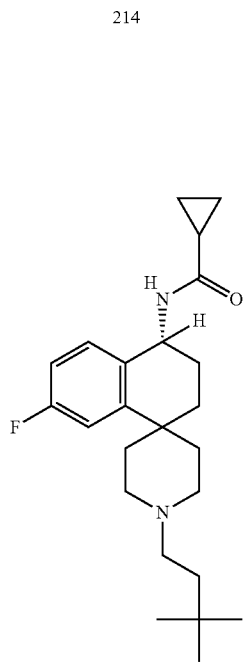
215
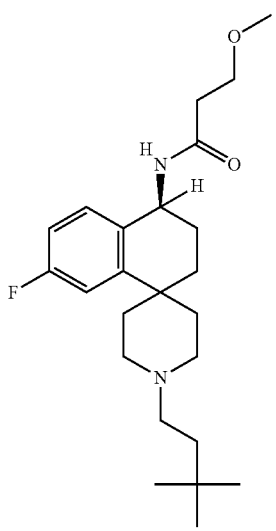
216
217
218
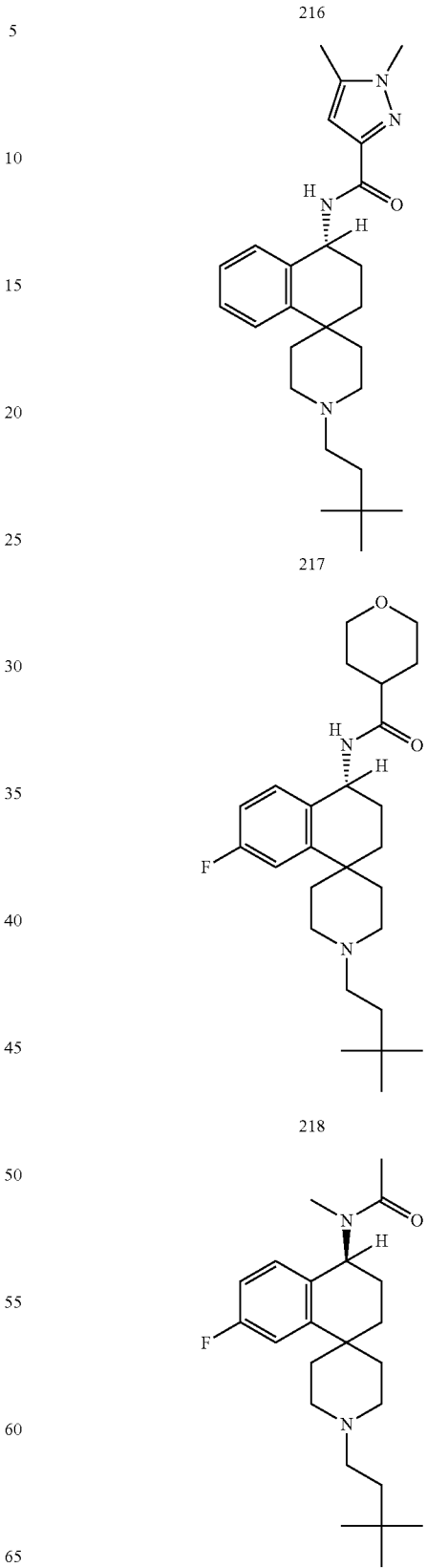

TABLE 1-continued
Exemplary compounds of formulae I, Ia, Ib, Ic, Id, and Ie.
219
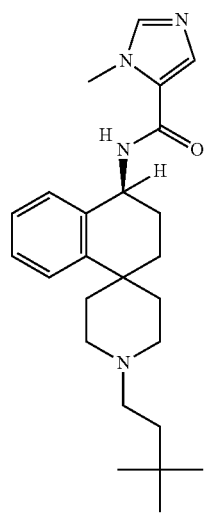
220
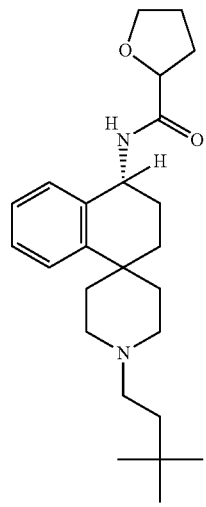
TABLE 1-continued
Exemplary compounds of formulae I, Ia, Ib, Ic, Id, and Ie.
221
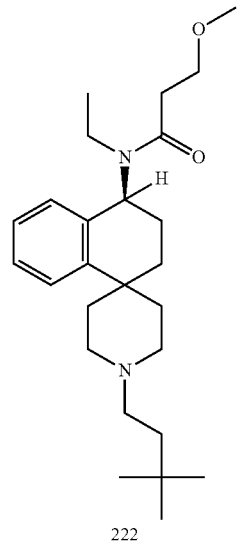
222
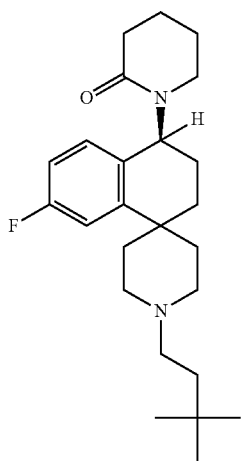
223
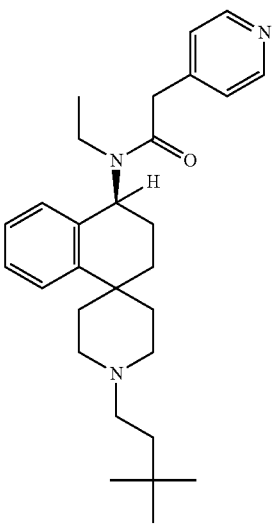

TABLE 1-continued
Exemplary compounds of formulae I, Ia, Ib, Ic, Id, and Ie.
224
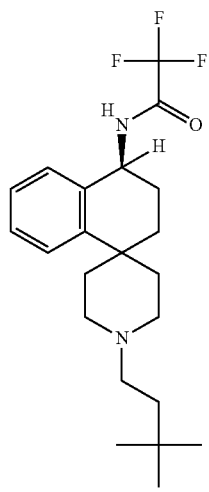
225
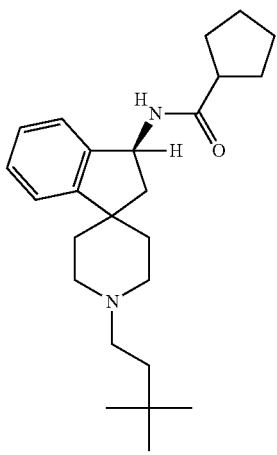
226
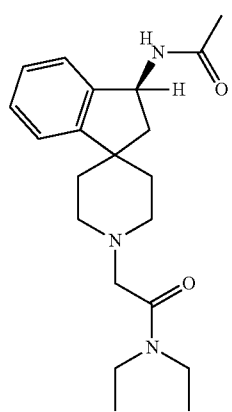
TABLE 1-continued
Exemplary compounds of formulae I, Ia, Ib, Ic, Id, and Ie.
227
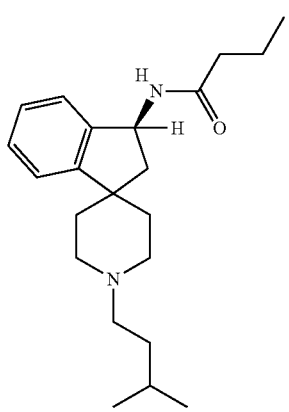
228
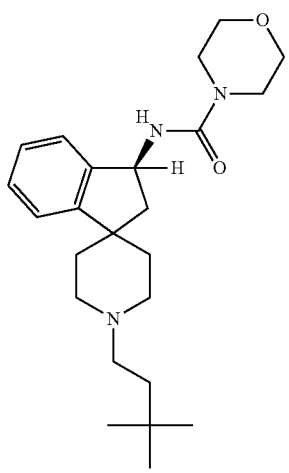
229
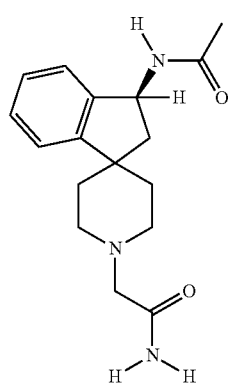

TABLE 1-continued
Exemplary compounds of formulae I, Ia, Ib, Ic, Id, and Ie.
230
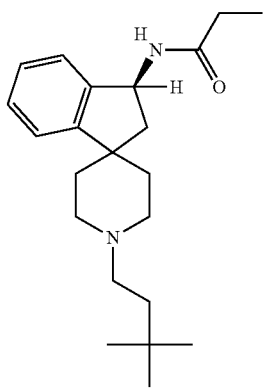
231
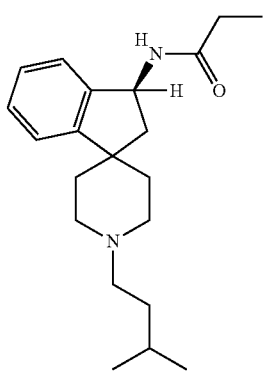
232
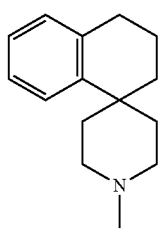
233
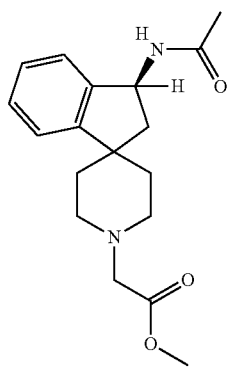
TABLE 1-continued
Exemplary compounds of formulae I, Ia, Ib, Ic, Id, and Ie.
234
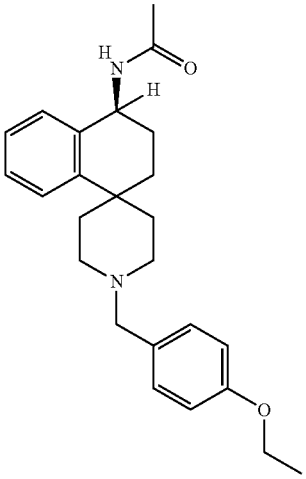
235
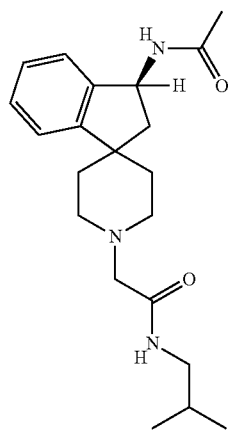
236
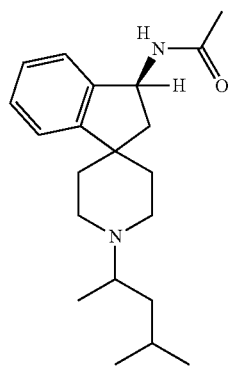

TABLE 1-continued
Exemplary compounds of formulae I, Ia, Ib, Ic, Id, and Ie.
237
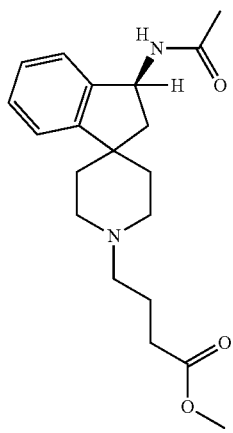
238
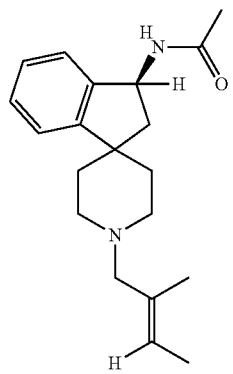
239
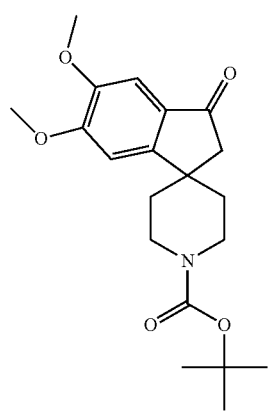
TABLE 1-continued
Exemplary compounds of formulae I, Ia, Ib, Ic, Id, and Ie.
241
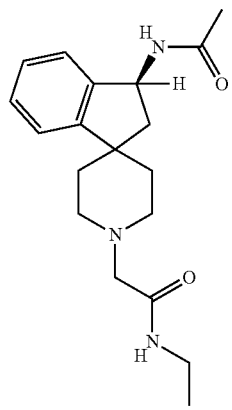
242
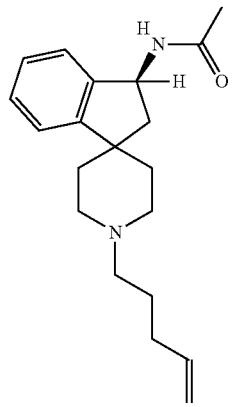
243
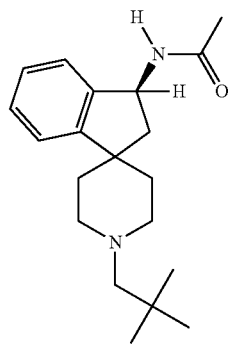

TABLE 1-continued
Exemplary compounds of formulae I, Ia, Ib, Ic, Id, and Ie.
244
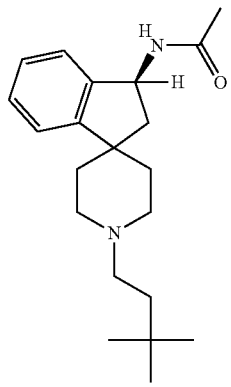
245
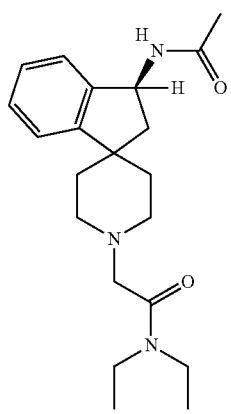
246
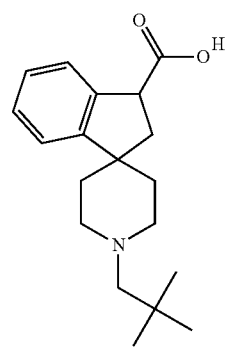
TABLE 1-continued
Exemplary compounds of formulae I, Ia, Ib, Ic, Id, and Ie.
247
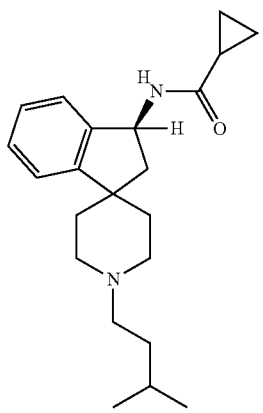
248
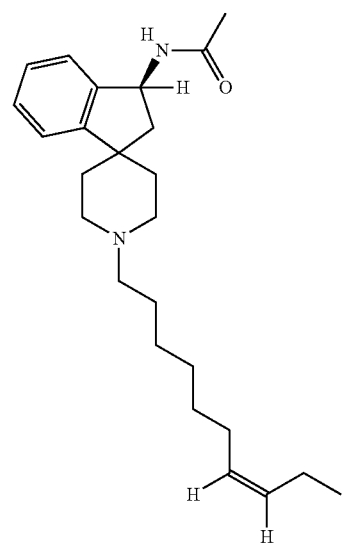
249
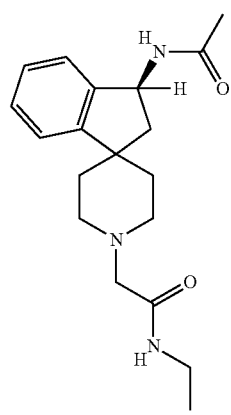

TABLE 1-continued
Exemplary compounds of formulae I, Ia, Ib, Ic, Id, and Ie.
250
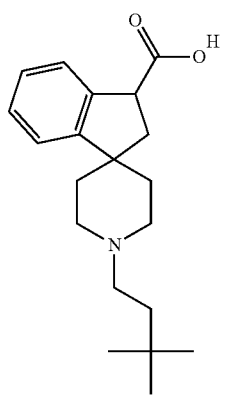
251
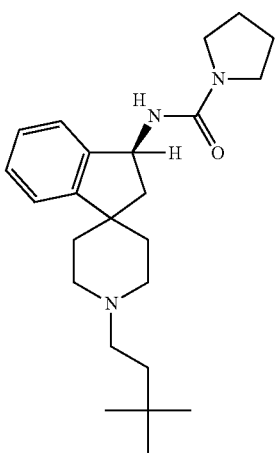
252
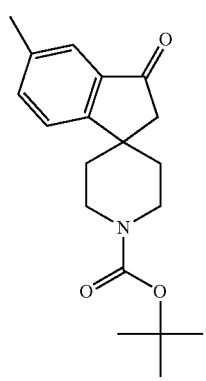
TABLE 1-continued
Exemplary compounds of formulae I, Ia, Ib, Ic, Id, and Ie.
253
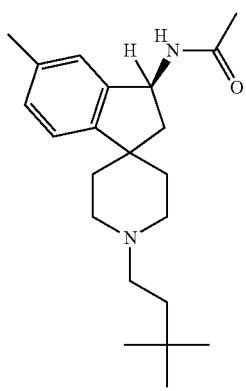
254
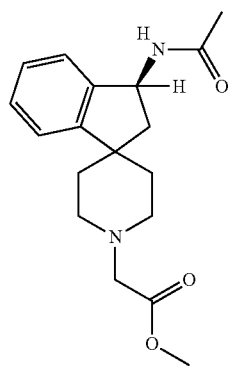
255
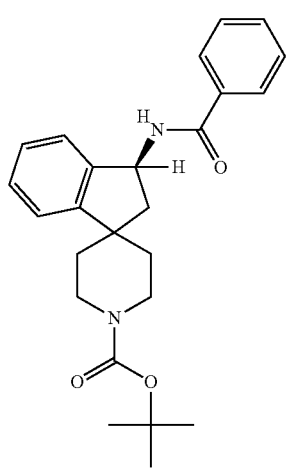

TABLE 1-continued
Exemplary compounds of formulae I, Ia, Ib, Ic, Id, and Ie.
256
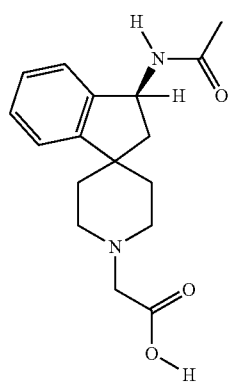
257
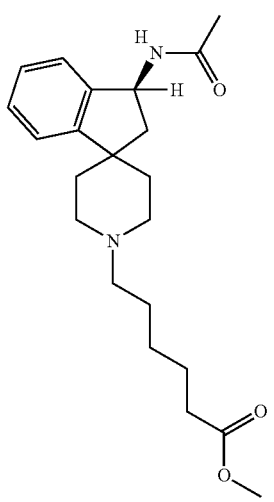
258
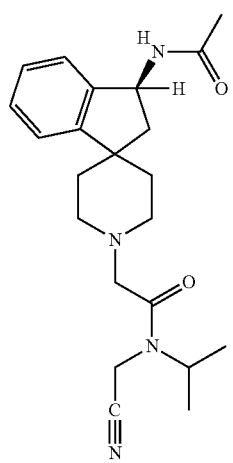
TABLE 1-continued
Exemplary compounds of formulae I, Ia, Ib, Ic, Id, and Ie.
259
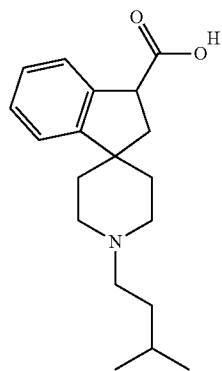
260
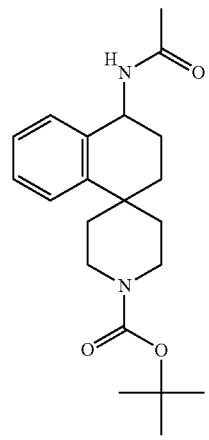
261
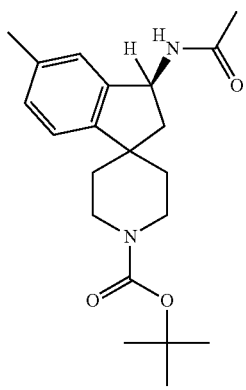

TABLE 1-continued
Exemplary compounds of formulae I, Ia, Ib, Ic, Id, and Ie.
262
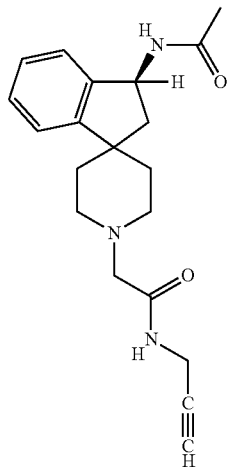
263
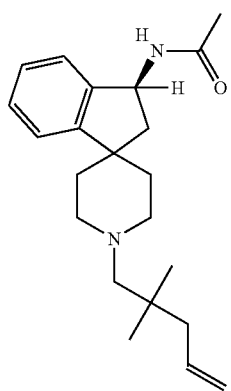
264
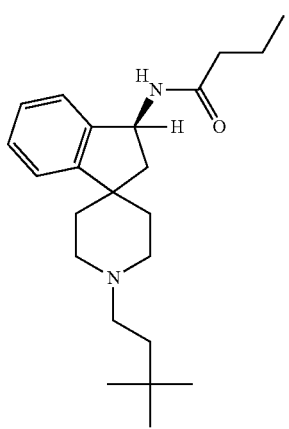
TABLE 1-continued
Exemplary compounds of formulae I, Ia, Ib, Ic, Id, and Ie.
267
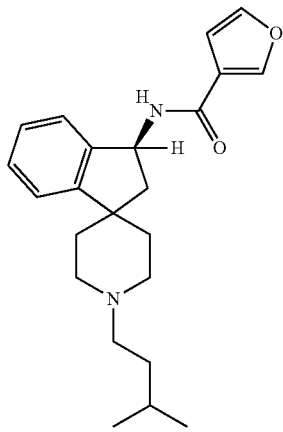
269
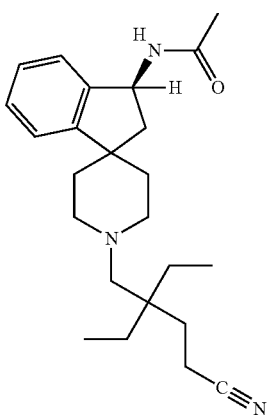
271
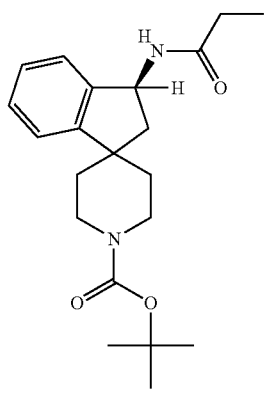

TABLE 1-continued
Exemplary compounds of formulae I, Ia, Ib, Ic, Id, and Ie.
272
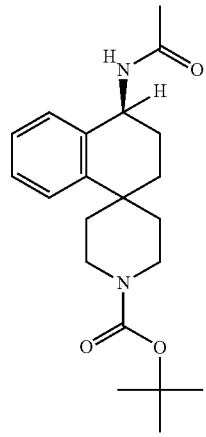
273
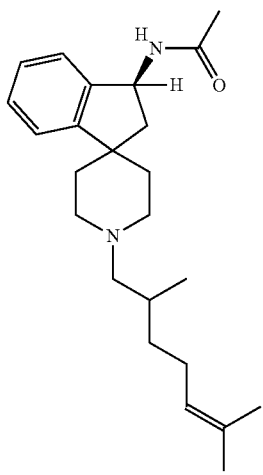
275
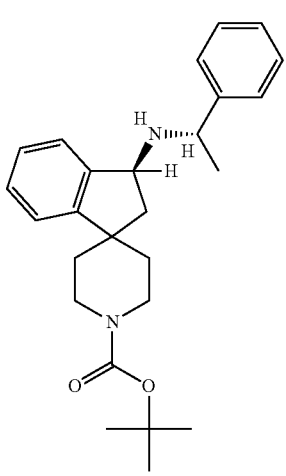
TABLE 1-continued
Exemplary compounds of formulae I, Ia, Ib, Ic, Id, and Ie.
276
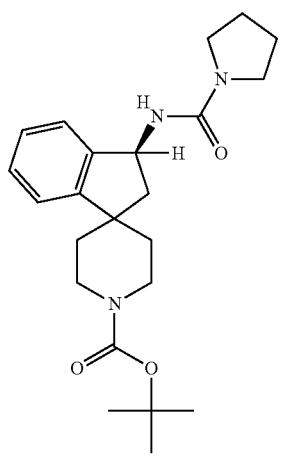
277
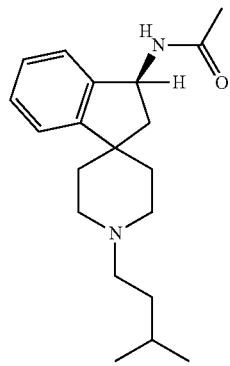
279
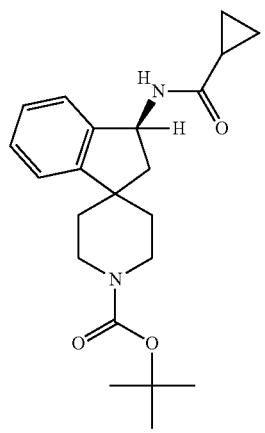

TABLE 1-continued
Exemplary compounds of formulae I, Ia, Ib, Ic, Id, and Ie.
280
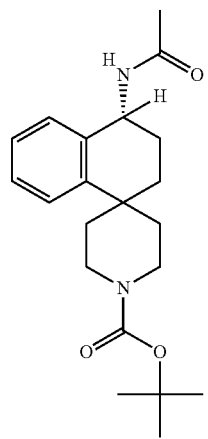
282
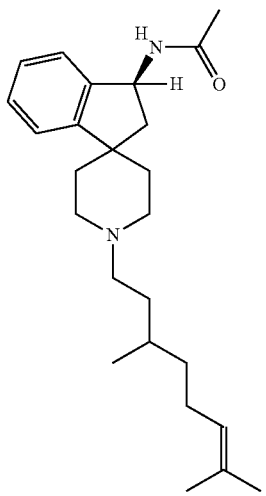
287
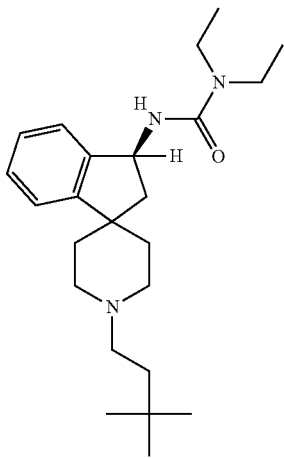
TABLE 1-continued
Exemplary compounds of formulae I, Ia, Ib, Ic, Id, and Ie.
288
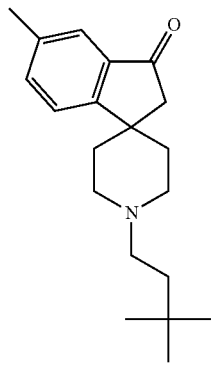
289
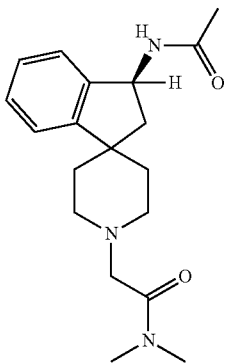
290
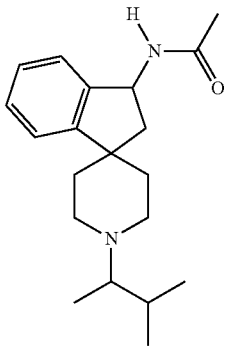
291
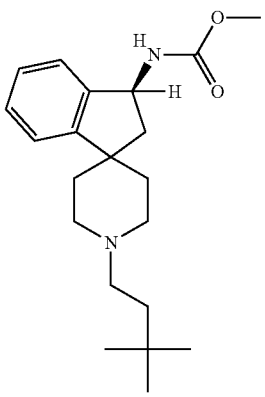

TABLE 1-continued
Exemplary compounds of formulae I, Ia, Ib, Ic, Id, and Ie.
292
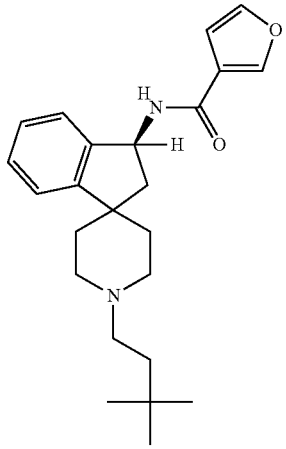
293
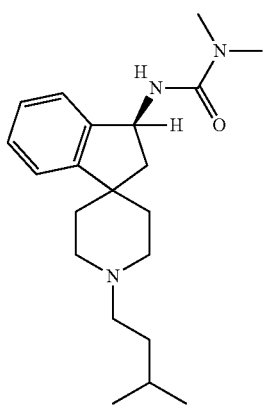
294
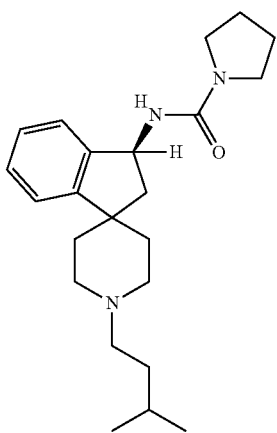
TABLE 1-continued
Exemplary compounds of formulae I, Ia, Ib, Ic, Id, and Ie.
295
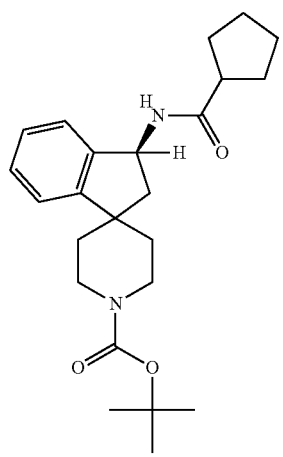
297
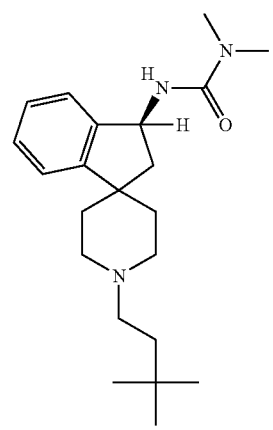
298
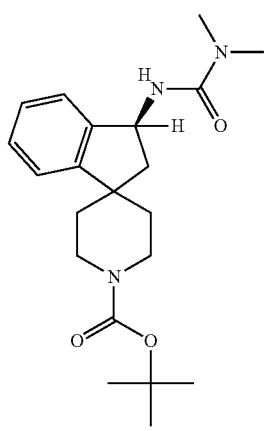

TABLE 1-continued

Exemplary compounds of formulae I, Ia, Ib, Ic, Id, and Ie.

299

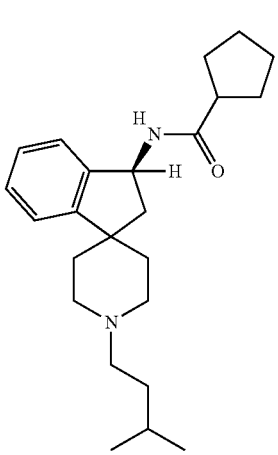

300

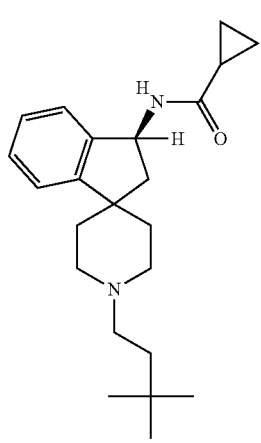

301

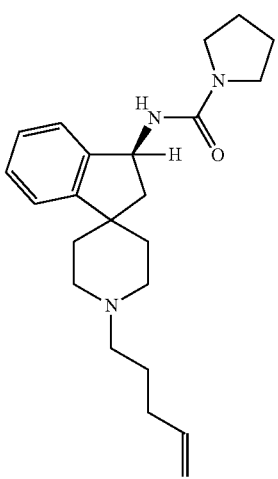

TABLE 1-continued

Exemplary compounds of formulae I, Ia, Ib, Ic, Id, and Ie.

302

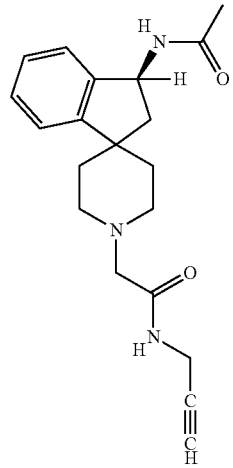

III. Synthetic Schemes

The compounds of formulae (I, Ia, Ib, Ic, Id, and Ie) may be readily synthesized from commercially available or known starting materials by known methods. Exemplary synthetic routes to produce compounds of formulae (I, Ia, Ib, Ic, Id, and Ie) are provided below in Schemes 1-3 below. In the following generic schemes, for simplicity a single formula is used wherein n is 1, p and m are both 2, and $R_4$ and $R'_4$ are both H. However, the generic schemes are not limiting and can be applied to preparation of other compounds having different variables.

Scheme 1 below depicts general conditions for the synthesis of compounds of formula I.

Scheme 1:

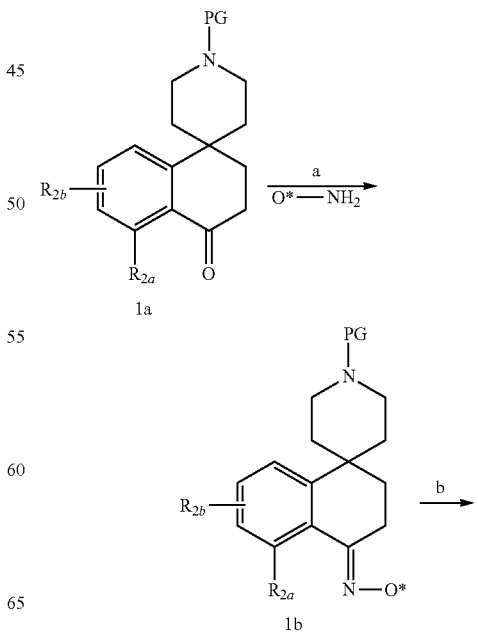

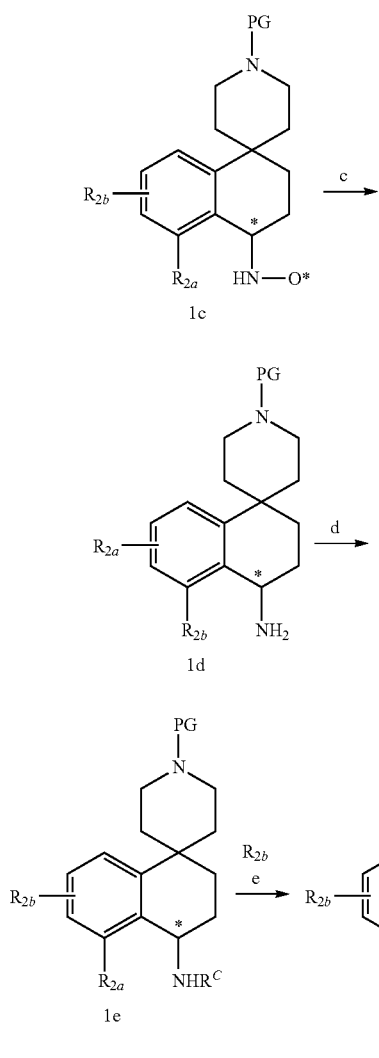

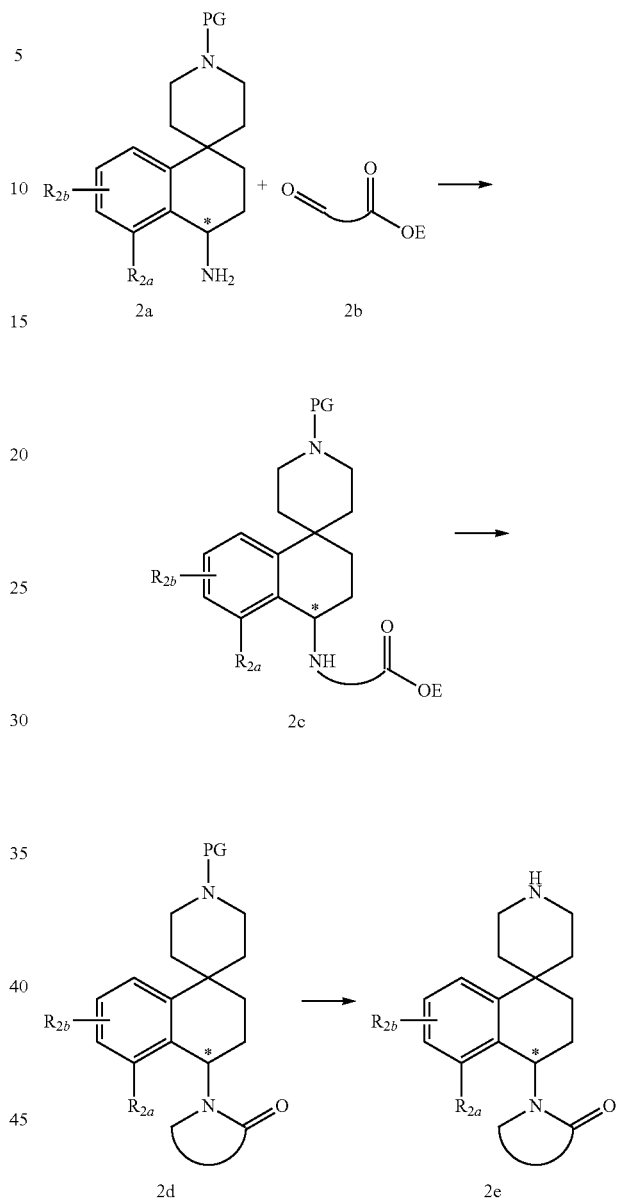

Scheme 2:

Referring to Scheme 1 the spirotetralone 1a is reacted with an optically active amine O*—NH$_2$ (step a) in the presence of a catalyst such as, for example, boron trifluoride etherate to provide the imine 1b as described in WO 2004/089307, hereby incorporated by reference. Suitable O*—NH$_2$ compounds are those wherein O* is an optically active amine protecting group, such as R or S (1-phenylethyl)amine, which may be subsequently removed. Reduction of the imine (step b) with, for example, sodium borohydride, provides the optically active amine 1c wherein * represents an optically active carbon. Removal of O* in (step c) can be achieved using know methods, for example, when O* is (1-phenylethyl)amine, hydrogenation in the presence of a palladium catalyst provides the amino compound 1d. Acylation of 1d using known methods (step d) provides acylamino compounds of formula 1e. Removal of the protecting group PG in 1e (step e) using known methods provides compounds of formula 1f. Compounds of formula 1f can be further modified to include R$_1$ functionalities.

In some embodiments, wherein R$^C$ represents a cycloaliphatic, lactam ring intermediates of formula 2e may be prepared as shown in Scheme 2.

Referring to Scheme 2, the alkylated spiroamine compound of formula 2c is prepared from 2a and the aldehyde ester 2b, where E is a C$_{1-4}$ aliphatic, by known reductive amination procedures such as reaction in the presence of sodium cyanoborohydride and acetic acid. In some instances, compounds of formula 2c may spontaneously cyclize to the lactam 2d. In other instances, the lactam 2d may be formed from 2c by heating in an inert solvent (e.g., toluene, NMP, or mixtures thereof) optionally in the presence of a catalyst such as, for example, potassium acetate. Removal of the protecting group from 2d provides the intermediates 2e.

Scheme 3 is another depiction of general conditions for the synthesis of compounds of formula I where R$_3$ and R'$_3$ are both hydrogen.

Scheme 3:

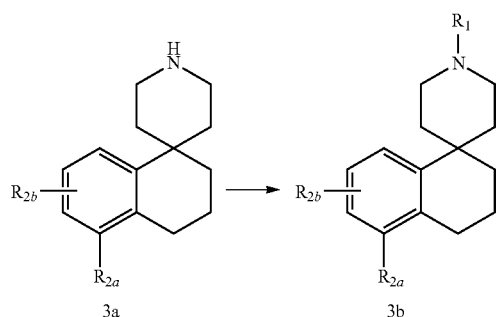

3a  3b

Referring to Scheme 3, the R$_1$-substituted 3,4-dihydro-2H-spiro[naphthalene-1,4'-piperidine] compound (3b) is prepared from the unsubstituted 3,4-dihydro-2H-spiro[naphthalene-1,4'-piperidine] compound (3a) using known alkylation procedures.

Further elaboration of intermediates 1f and 2e may be achieved using known methods and as illustrated in the examples.

IV. Formulations, Administrations, and Uses

A. Pharmaceutically Acceptable Compositions

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N$^+$(C$_{1-4}$ alkyl)$_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, infrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, Ia, Ib, Ic, Id, and Ie) are selective modulators of $M_1$, $M_2$ and $M_4$. More preferably, the compounds of formulae (I, Ia, Ib, Ic, Id, and Ie) are selective modulators of $M_1$ and/or $M_4$. Yet more preferably, certain compounds of formulae (I, Ia, Ib, Ic, Id, and Ie) are selective modulators of $M_1$. Or, preferably, certain compounds of formulae (I, Ia, Ib, Ic, Id, and Ie) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae (I, Ia, Ib, Ic, Id, and Ie), or an embodiment thereof as set forth herein.

According to another embodiment, the present invention provides a method of treating a disease mediated by a muscarinic receptor including the step of administering to said mammal a composition comprising a compound of formulae (I, Ia, Ib, Ic, Id, and Ie), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradhycardia, gastric acid secretion, asthma, or GI disturbances.

According to a preferred embodiment, the present invention is useful for treating or reducing the severity of psychosis, Alzheimer's disease, pain, or Parkinson's disease. All references cited within this document are incorporated herein by reference.

IV. Preparations and Examples

In order that the invention described therein may be more fully understood, the following examples are set forth. It should be understood that these examples are for illustrative purposes only and are not to be construed as limiting this invention in any manner.

$^1$H-NMR spectra were recorded at 500 MHz using a Bruker AMX 500 instrument. Mass spectroscopy samples were analyzed on a MicroMass ZQ or Quattro II mass spectrometer operated in single MS mode with electrospray ionization. Samples were introduced into the mass spectrometer using chromatography, using Zorbax SB C18 column, 3.0×150 mm. Flow rate: 1.0 mL/minute. Detection: 254 & 214 nm. Mobile phase for all mass spectroscopy analysis consisted of acetonitrile-water mixtures with 0.2% formic acid as a modifier using 10-90% acetonitrile and water gradient. As used herein, the term "$R_t$" refers to the HPLC retention time, in minutes, associated with the compound. HPLC purification refers to C-18 reverse phase using Gilson instrument, YMC combiprep ProC 18 column, 20×100 mm. Flow rate is 20 ml/minute. Mobile phase consisted of water with 0.1% TFA and acetonitrile with 0.1% TFA. Running time is 10 minutes.

Preparation A: Synthesis of tert-butyl 4-oxo-3,4-dihydro-2H-spiro[naphthalene-1,4'-piperidine]-1'-carboxylate

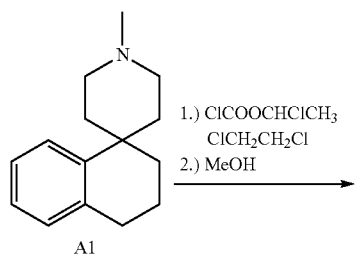

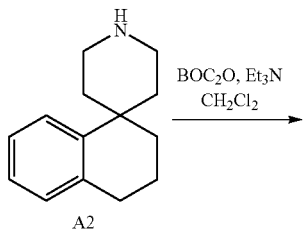

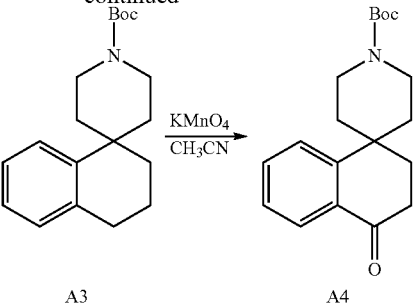

1'-Methyl-3,4-dihydro-2H-spiro[naphthalene-1,4'-piperidine] (A1) was prepared from commercially available 4-(3-phenylpropyl)pyridine as previously described. (Eberehard Reimann, Johann Speckbacher, Hermann Lotter, Arch Pharm. (Weinheim), 320 (1987), 385-393. Graham L. Patrick, J. Chem. Soc. Perkin Trans 1, (1995) 1273-1279).

To a solution of the N-methylpiperidine (A1) (37 g, 172 mmol) in 1,2-dichloroethane (250 ml) was added 1-chloroethyl chloroformate (20.7 ml, 190 mmol) at 0° C. The solution turned to a solid. After 0.5 hours at room temperature, the reaction mixture was heated under reflux for 15 hours. After concentration, the residue was dissolved in methanol (250 ml) and heated at 50° C. for 2 hours. The mixture was cooled to room temperature, the precipitate was filtered and washed with ether to produce 3,4-dihydro-2H-spiro[naphthalene-1,4'-piperidine] HCl salt (A2). The filtrate was concentrated, suspended in ether, filtered, and the solid washed with MeOH and ether to give additional 3,4-dihydro-2H-spiro[naphthalene-1,4'-piperidine] HCl salt (A2). LC-MS: m/e=202.1 (M+H). $R_t$=1.61 min. $^1$H-NMR (500 MHz, CDCl$_3$): 9.74 (s, 2H), 7.58 (d, J=7.9, 1H), 7.22 (t, J=7.8, 1H), 7.14 (t, J=7.9, 1H), 7.08 (d, J=8.0, 1H), 3.47 (d, J=12.4, 2H), 3.22-3.18 (m, 2H), 2.88 (t, J=4.9, 2H), 2.81 (t, J=6.2, H), 2.60 (td, 2H), 1.93-1.89 (m, 2H), 1.83-1.77 (m, 2H).

A solution of the piperidine salt (A2) (2.2 g, 9.2 mmol) in dichloromethane (100 ml) was treated with Et$_3$N (4 ml, 28.9 mmol) and di-tert-butyldicarbonate (2.5 g, 11.4 mmol) at room temperature for 2 hours. The reaction mixture was washed with dilute aqueous HCl, and the organic phase was washed with aqueous sodium bicarbonate, dried (Na$_2$SO$_4$), and concentrated to give tert-butyl 3,4-dihydro-2H-spiro [naphthalene-1,4'-piperidine]-1'-carboxylate (A3) as a white solid. LC-MS: m/e=246.0 (M+H−tBu). $R_t$=4.16 min. $^1$H-NMR (500 MHz, CDCl$_3$): 7.27 (d, J=7.9, 1H), 7.10 (td, J=7.4, 1.6, 1H), 7.05 (td, J=7.3, 1.3, 1H), 7.00 (d, J=7.6, 1H), 3.93 (br.d, J=13.3, 2H), 2.92 (td, J=13.2, 2.8, 2H), 2.71 (t, J=6.3, H), 1.90 (td, J=13.4, 5.0, 2 H), 1.82-1.80 (m, 2H), 1.72-1.67 (m, 2H), 1.49-1.46 (m, 2H), 1.42 (s, 9H).

To a solution of the Boc-piperidine (602 mg, 2 mmol) in acetonitrile (10 ml) was added potassium permanganate (KMnO$_4$, 950 mg, 6 mmol). The reaction mixture was stirred at 70° C. for 15 hours, filtered through Celite, and the filter cake was washed with dichloromethane. The filtrate and washings were concentrated and the residue was dissolved in acetonitrile (10 ml) and reacted with KMnO$_4$ (950 mg, 6 mmol) at 70° C. for another 24 hours. After filtration, washing and concentrating, the residue was purified by flash column chromatography (CH$_2$Cl$_2$/CH$_3$CN: 1:0 to 9:1) to provide tert-butyl 4-oxo-3,4-dihydro-2H-spiro[naphthalene-1,4'-piperidine]-1'-carboxylate (A4). LC-MS: m/e=260.0 (M+H−tBu). $R_t$=3.46 min. $^1$H-NMR (500 MHz, CDCl$_3$): 8.07 (dd, J=1.5, 7.8, 1H), 7.60-7.57 (td, J=7.9, 1.2, 1H), 7.50 (d, J=7.9, 1H), 7.36 (t, J=7.6, 1.0, 1H), 4.10 (br.d, J=13.2, 2H), 3.08 (t, J=13.8, 2H), 2.71 (t, J=6.7, 2H), 2.27 (t, J=6.9, 2H), 2.05 (td, J=13.4, 4.7, 2H), 1.73 (br.d, J=13.2, 2H), 1.52 (s, 9H).

Preparation B: Synthesis of (S)—N-(3,4-dihydro-2H-spiro[naphthalene-1,4'-piperidine]-4-yl)acetamide

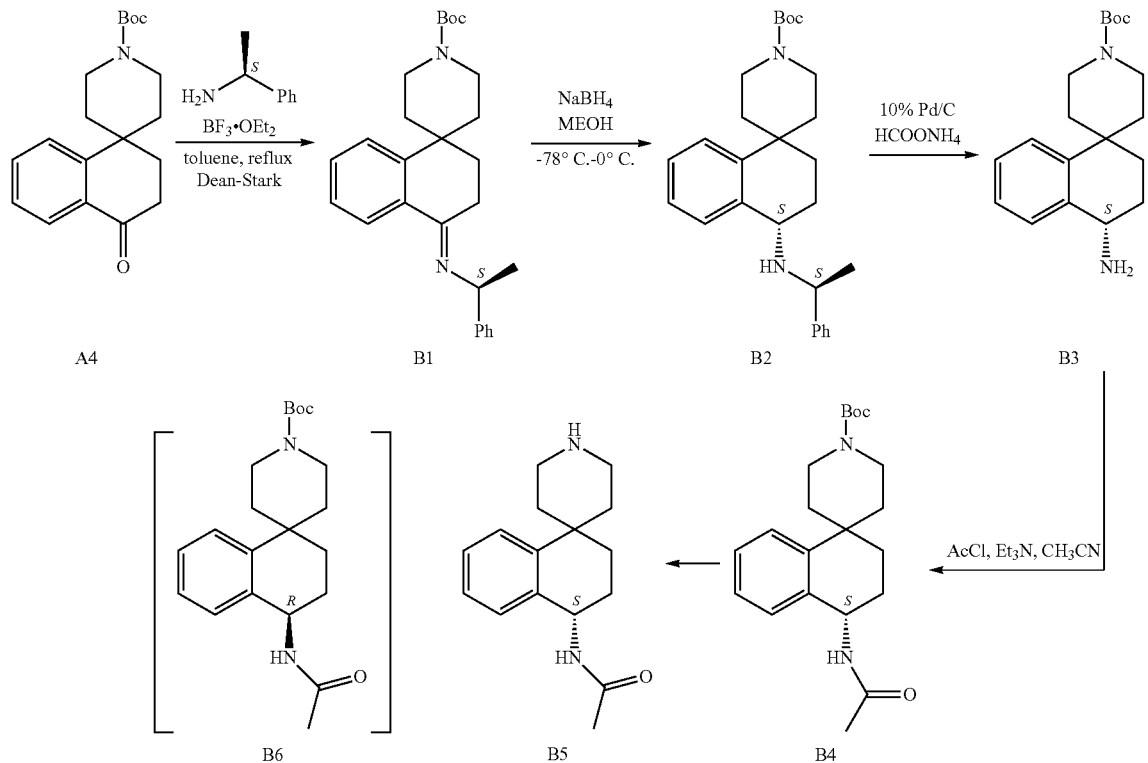

A solution of tert-butyl 4-oxo-3,4-dihydro-2H-spiro[naphthalene-1,4'-piperidine]-1'-carboxylate (A4) (5.0 g, 15.8 mmol), (S)-1-phenylethanamine (3.0 ml, 23.8 mmol) and boron trifluoride dimethyl etherate (0.5 ml, 5 mmol) in dry toluene (150 ml) was heated at 140° C. under a Dean-Stark trap for 24 hours. The solvent was distilled and the residue was cooled with an ice bath, dissolved in ethyl acetate, washed with saturated $NaHCO_3$, and water. The organic phase was dried over $Na_2SO_4$, filtered and concentrated to give (S)-tert-butyl 4-(1-phenylethylimino)-3,4-dihydro-2H-spiro[naphthalene-1,4'-piperidine]-1'-carboxylate (B1) as a gum. LC-MS analysis of the crude indicated that there is trace of starting material (A4). LC-MS: m/e=419.37 (M+H). $R_t$=2.24 min.

At −78° C., $NaBH_4$ (760 mg, 20 mmol) was added to a solution of the imine (B1) (7.82 g, 20 mmol) in methanol (100 ml). The reaction mixture was allowed to warm to 0° C. over 2-3 hours then treated with saturated $NaHCO_3$ (ca. 100 ml), concentrated under reduced pressure at <30° C. to remove the solvent. The residue was extracted with ethyl acetate. The organic phase was washed with water, dried over $Na_2SO_4$ and concentrated to give (S)-tert-butyl 4-((S)-1-phenylethylamino)-3,4-dihydro-2H-spiro[naphthalene-1,4'-piperidine]-1'-carboxylate (B2) as a solid. LC-MS: m/e=421.32 (M+H). $R_t$=2.20 min.

A suspension of the crude protected amine (B2) (7.55, 17.9 mmol), ammonium formate (10 g, 158 mmol) and 10% Pd/C (2.0 g) in methanol (150 ml) was stirred under $N_2$ for 24 hours. The reaction mixture was filtered through Celite and the filtrate was concentrated. The residue was dissolved in ethyl acetate, washed with saturated $NaHCO_3$, brine, dried over $Na_2SO_4$, and concentrated to give (S)-tert-butyl 4-amino-3,4-dihydro-2H-spiro[naphthalene-1,4'-piperidine]-1'-carboxylate (B3) as a syrup. LC-MS: m/e=317.21 (M+H), 244.2 (M+H−$Me_3CO$). $R_t$=1.81 min.

At −78° C., acetyl chloride (1 ml, 12 mmol) was added to a solution of the amine (B3) (3.2 g, 10 mmol) in dry acetonitrile (100 ml) followed by the dropswise addition of triethylamine. The reaction mixture was warmed to room temperature, stirred for 1 hour then concentrated. The residue was dissolved in ethyl acetate. The solution was washed with saturated $NaHCO_3$ and brine, dried and concentrated. The crude product was further purified by silica gel chromatography ($CH_2Cl_2/CH_3CN$ 9:1 to 7:3) to give (S)-tert-butyl 4-acetamido-3,4-dihydro-2H-spiro[naphthalene-1,4'-piperidine]-1'-carboxylate (B4). LC-MS: m/e=359.3 (M+H), 303.3 (M+H−$Me_3CO$). $R_t$=2.94 min. $^1$H-NMR (500 MHz, DMSO-$d_6$): 8.17 (d, 1H), 7.36 (d, 1H), 7.22 (ddd, 1H), 7.14 (m, 2H), 4.95 (m, 1H), 3.86 (m, 2H), 2.97 (m, 2H), 2.01 (m, 1H), 1.85 (s, 3H), 1.80 (m, 4H), 1.61 (m 2H), 1.48 (d, 1H), 1.42 (s, 9H).

Similarly, the enantiomer of (B4), compound (B6) or its racemate, Racemic (B6), was also synthesized applying the same synthetic route but replacing (S)-1-phenylethanamine with (R)-1-phenylethanamine or racemic mixture of 1-phenylethanamine.

The enantiomeric purity was confirmed using analytical chiral HPLC (CHIRALPAK AD column 250×4.6 mm, 1.5 mL/min, 7% 2-propanol/hexane, 15 minute run time). For Racemic (B6), there are two peaks at 12.18 min and 12.57 min, corresponding to (B4) and (B6), respectively. The enantiomeric purity was determined greater than 90% for both (B4) and (B6).

At 0° C., a solution of (B4) (2.2 g, 6.1 mmol) in dichloromethane (20 ml) was treated with TFA (10 ml) for 1 hour, concentrated, co-evaporated with acetonitrile and dissolved in dichloromethane. The resulting solution was washed with a mixture of brine (ca. 100 ml) and 6N NaOH (3 ml), dried over $Na_2SO_4$ and concentrated to give (S)—N-(3,4-dihydro-2H-spiro[naphthalene-1,4'-piperidine]-4-yl)acetamide (B5) as a white solid. LC-MS: m/e=258.9 (M+H). $R_t$=0.96 min. The crude was used directly for further reactions.

Preparation C: Synthesis of (S)-1-(3,4-dihydro-2H-spiro[naphthalene-1,4'-piperidine]-4-yl)pyrrolidin-2-one

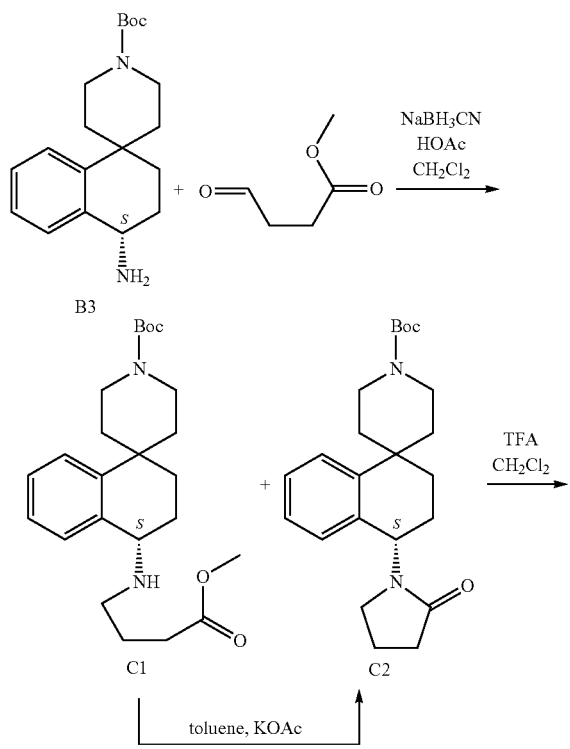

A solution of the amine (B3) (480 mg, 1.24 mmol) and methyl 3-formylpropanoate (232 mg, 2.00 mmol) in dichloromethane (5 ml) was stirred at room temperature for 1.5 hours. Then methanol (2 ml), sodium cyanoborohydride (200 mg, 3.10 mmol), and acetic acid (0.1 ml) were added, and the mixture was kept overnight. The reaction mixture was diluted with dichloromethane (ca. 100 ml), washed with a mixture of saturated sodium bicarbonate (2 ml), 6N sodium hydroxide (2 ml) and brine (ca. 50 ml). The organic phase was separated, dried over $Na_2SO_4$ and concentrated to give a crude mixture of (S)-tert-butyl 4-(4-methoxy-4-oxobutylamino)-3,4-dihydro-2H-spiro[naphthalene-1,4'-piperidine]-1'-carboxylate (C1) and (8)-tert-butyl 4-(2-oxopyrrolidin-1-yl)-3,4-dihydro-2H-spiro[naphthalene-1,4'-piperidine]-1'-carboxylate (C2) in 1.6:1 ratio based on analytical HPLC. LC-MS: m/e=417.36 ($M_{(S)-7}$+H), $R_t$=2.00 min; m/e=385.30 ($M_{(S)-8}$+H), $R_t$=3.25 min.

A solution of the above crude mixture (700 mg) in methanol (20 ml) was heated together with potassium acetate (1.2 g) at 50° C. for 4 hours. The analytical HPLC data indicated that there was little conversion of (C1) to (C2). The solvent was evaporated and the residue was suspended in toluene (50 ml) and 1-methyl-2-pyrrolidinone (NMP) (3 ml) and heated at 120° C. for 5 days. The mixture was concentrated, and the residue was suspended in ethyl acetate. The solution was washed with saturated sodium bicarbonate, dried and evaporated. The residue was passed through silica gel column to give a crude mixture of (C1) and (C2) with a ratio of 2:1.

A solution of the mixture of (C1) and (C2) (530 mg) in dichloromethane (10 ml) was treated with TFA (5 ml) at 0° C. for 2 hours. The reaction mixture was concentrated. The residue was co-evaporated with acetonitrile, dissolved in dichloromethane (ca. 100 ml), washed with a mixture of brine (ca. 20 ml) and 6N sodium hydroxide (2 ml). The organic phase was dried over sodium sulfate and concentrated to give a crude product (C3), which was further purified by silica gel chromatography ($CH_2Cl_2$/MeOH 9:1) to give (S)-9 as oil. LC-MS: m/e=285.22 (M+H). $R_t$=1.31 min. $^1$H-NMR (500 MHz, DMSO-$d_6$): 8.58 (br. s, 1H), 8.35 (br. s, 1H), 7.40 (d, 1H), 7.30 (t, 1H), 7.20 (t, 1H), 6.93 (d, 1H), 5.14 (dd, 1H), 3.25-3.05 (m, 5H), 2.87 (td, 1H), 2.40-2.29 (m, 4H), 1.98-1.85 (m, 4H), 1.80 (t, 1H), 1.74 (m, 1H), 1.63 (t, 1H), 1.58 (d, 1H).

Method 1: Coupling with Aldehydes

Example 1

Synthesis of (S)—N-(1'-(3,3-dimethylbutyl)-3,4-dihydro-2H-spiro[naphthalene-1,4'-piperidine]-4-yl)acetamide (Compound No. 190)

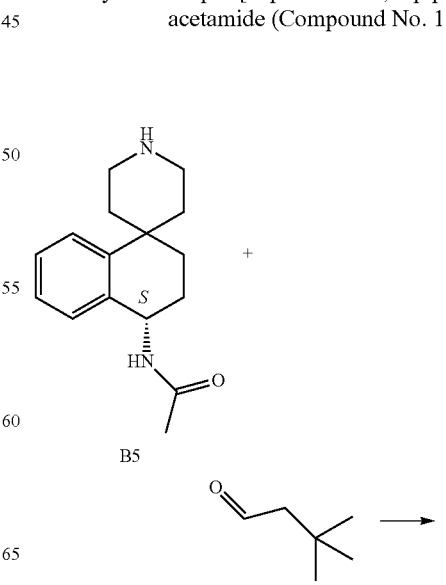

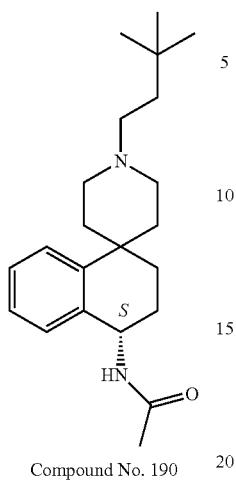

Compound No. 190

A solution of 3,3-dimethylbutyraldehyde (13 mg, 0.13 mmol) and the spiro-piperidine (B5) (25 mg, 0.10 mmol) in dry dichloromethane (2 ml) was stirred at room temperature for 30 min, cooled with ice-bath, and treated with sodium triacetoxyborohydride (44 mg, 0.2 mml), followed by acetic acid (1 drop) and methanol (1 ml). The reaction mixture was stirred for another 5 hours and concentrated under a stream of nitrogen. The residue was dissolved in methanol (1 ml) and purified by reverse phase HPLC to give the title compound no. 17 as a TFA salt. LC-MS: m/e=343.30 (M+H). $R_f$=1.63 min. $^1$H-NMR (500 MHz, DMSO-$d_6$): 9.28 (br.s, 1H), 8.18 (d, 1H), 7.35 (d, 1H), 7.30 (t, 1H), 7.19 (t, 1H), 7.16 (d, 1H), 4.92 (m, 1H), 3.45 (m, 2H), 3.14 (m, 4H), 2.19 (m, 2H), 2.05 (m, 1H), 1.87 (s, 3H), 1.82 (m, 2H), 1.73 (d, 1H), 1.60 (m, 3H), 0.93 (m, 9H).

Method 2: Coupling with Ketones

Example 2

Synthesis of (S)—N-(1'-(pentan-3-yl)-3,4-dihydro-2H-spiro[naphthalene-1,4'-piperidine]-4-yl)acetamide (Compound No. 61)

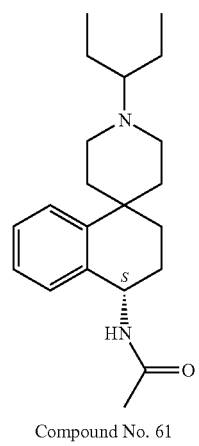

Compound No. 61

A solution of the piperidine (B5) (20 mg, 0.077 mmol) and 3-pentanone (27 mg, 0.31 mmol) in dichloromethane (2 ml) was stirred in a vial for 90 minutes and treated with titanium (IV) isopropoxide (60 µl, 0.21 mmol) for 24 hours. To the reaction mixture was added sodium borohydride (10 mg, 0.27 mmol) and stirred for 5 hours, then treated with methanol (1 ml) and acetic acid (1 drop) for 1 hour. The solvents were evaporated and the residue was dissolved in methanol (1 ml) and acidified with TFA and purified by HPLC to give the title compound no. 56. LC-MS: m/e=329.28 (M+H). $R_f$=1.42 min. $^1$H-NMR (500 MHz, DMSO-$d_6$): 8.65 (br.s, 1H), 8.18 (d, 1H), 7.42 (d, 1H), 7.31 (t, 1H), 7.20 (t, 1H), 7.16 (d, 1H), 4.92 (m, 1H), 3.45 (m, 1H), 3.35 (m, 1H), 3.28-3.17 (m, 2H), 3.10 (m, 1H), 2.28 (m, 2H), 2.05 (m, 1H), 1.86 (s, 3H), 1.84 (m, 4H), 1.72 (t, 1H), 1.68-1.59 (m, 2H), 1.51 (m, 1H), 1.37 (m, 1H), 0.99 (t, 5H), 0.91 (t, 1H).

Method 3: Coupling with Alkyl Bromides

Example 3

Synthesis of (S)—N-(1'-(3,3-dimethyl-2-oxobutyl)-3,4-dihydro-2H-spiro[naphthalene-1,4'-piperidine]-4-yl)acetamide (Compound No. 130)

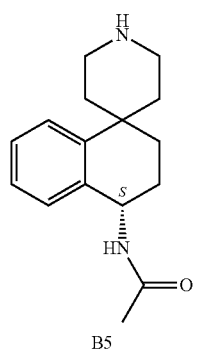

B5

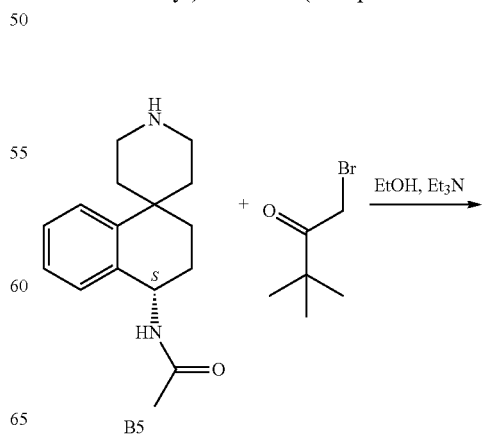

B5

-continued

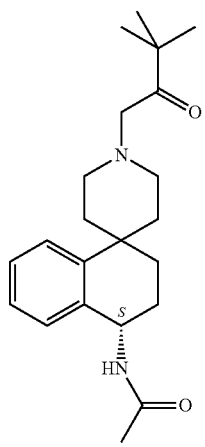

Compound No. 130

A suspension of the piperidine (B5) (24 mg, 0.09 mmol), 1-bromo-3,3-dimethylbutan-2-one (13.5 mg, 0.08 mmol) and sodium carbonate (32 mg, 0.3 mmol) in DMF (1 ml) was stirred at 50° C. in a sealed vial for 16 hours. The mixture was cooled and carefully neutralized with TFA and purified by reverse phase HPLC to give the title compound no. 19 as a TFA salt. LC-MS: m/e=357.30 (M+H). $R_t$=1.61 min. $^1$H-NMR (500 MHz, DMSO-$d_6$): 9.60 (br. s, 1H), 8.21 (d, 1H), 7.44 (d, 1H), 7.32 (t, 1H), 7.20 (t, 1H), 7.16 (d, 1H), 4.92 (q, 1H), 4.60 (d, 2H), 3.26 (m, 4H), 2.35 (m, 2H), 2.04 (dd, 1H), 1.87 (s, 3H), 1.80 (m, 3H), 1.71 (d, 1H), 1.63 (m, 1H), 1.16 (s, 9H).

A person skilled in the chemical arts can use the examples and schemes along with known synthetic methodologies to synthesize compounds of the present invention, including the compounds in Table 2 below.

TABLE 2

Physical data for exemplary compounds.

| Compound No. | LC/MS M + 1 | LC/RT min | NMR |
|---|---|---|---|
| 1 | 379.36 | 1.79 | DMSO (d6): 9.17 (br.s, 1H), 7.47 (d, 1H), 7.45 (d, 1H), 7.34 (t, 1H), 7.32 (t, 1H), 4.45 (q, 1H), 3.45 (m, 2H), 3.15 (m, 4H), 3.05 (s, 3H), 2.17 (m, 2H), 2.09 (t, 1H), 1.96 (m, 1H), 1.89-1.74 (m, 3H), 1.71 (d, 1H), 1.59 (m, 2H), 0.93 (s, 9H). |
| 2 | 441.4 | 1.21 | |
| 3 | 369.3 | 2.1 | |
| 4 | 315.2 | 1.38 | DMSO (d6): 9.083 (m, 1H), 8.18 (d, 1H), 7.36 (d, 1H), 7.30 (t, 1H), 7.20 (t, 1H), 7.17 (d, 1H), 4.92 (m, 1H), 3.42 (m, 2H), 3.12 (m, 4H), 2.20 (m, 2H), 2.05 (m, 1H), 1.87 (s, 3H), 1.82 (m, 3H), 1.73 (d, 1H), 1.64 (m, 3H), 1.35 (m, 2H), 0.94 (t, 3H). |
| 5 | 468.3 | 2.1 | |
| 6 | 401.7 | 1.8 | (300 MZ, CDCl3) 7.15 (dd, 1H), 6.94 (m, 2H), 5.93 (m, 1H), 3.64 (m, 2H), 2.80-3.05 (m, 6H), 2.80 (m, 1H), 2.60 (t, 2H), 2.30 (m, 1H), 1.64-1.92 (m, 12H), 0.95 (s, 9H) |
| 7 | 453.3 | 2.6 | |
| 8 | 414.3 | 1.7 | |
| 9 | 427.7 | 1.8 | |
| 10 | 440.6 | 1.9 | |
| 11 | 375.4 | 1.01 | |
| 12 | 373.6 | 2.88 | |
| 13 | 468.3 | 1.9 | |
| 14 | 414.3 | 2.75 | |
| 15 | 468.3 | 1.9 | |
| 16 | 359.3 | 1.3 | DMSO (d6): 9.15 (m, 1H), 8.18 (d, 1H), 7.35 (d, 1H), 7.30 (t, 1H), 7.20 (t, 1H), 7.17 (d, 1H), 4.92 (ddd, 1H), 3.63 (s, 3H), 3.43 (m, 2H), 3.15 (m, 4H), 2.47 (m, 2H), 2.20 (m, 2H), 2.05 (dd, 1H), 1.95 (m, 2H), 1.87 (s, 3H), 1.82 (m, 3H), 1.73 (d, 1H), 1.62 (m, 1H). |
| 17 | 443.4 | 1.09 | |
| 18 | 399.3 | 1.9 | |
| 19 | 458.3 | 2.17 | |
| 20 | 432.4 | 0.86 | |
| 21 | 401.6 | 1.7 | |
| 22 | 458.4 | 1.01 | |
| 23 | 482.4 | 2.2 | |
| 24 | 469.8 | 2 | |
| 25 | 426.3 | 1.8 | |
| 26 | 472.6 | 1.1 | |
| 27 | 417.6 | 1.13 | |
| 28 | 443.4 | 1.14 | |
| 29 | 458.4 | 0.94 | |
| 30 | 469.3 | 2.2 | |
| 31 | 399.3 | 2.1 | |
| 32 | 379.6 | 2.1 | |
| 33 | 418.6 | 0.92 | |
| 34 | 442.7 | 1.7 | |
| 35 | 371.2 | 1.79 | |
| 36 | 516.3 | 2.1 | |
| 37 | 286.6 | 2.01 | 1H NMR (500 MHz, DMSO (d6)): 9.02 (d, 1H), 7.33 (d, 1H), 7.21 (t, 1H), 7.13 (t, 1H), 7.06 (d, 1H), 3.44 (d, 2H), 3.19-3.10 (m, 4H), 2.72 (t, 2H), 2.20 (td, 2H), 1.90-1.84 (m, 2H), 1.76-1.64 (m, 4H), 1.59 (dd, 2H), 0.94 (s, 9H). |
| 38 | 454.3 | 2 | |
| 39 | 427.2 | 2.4 | |
| 40 | 441.4 | 1.16 | |
| 41 | 454.7 | 1.8 | |
| 42 | 429.7 | 1.9 | |
| 43 | 395.3 | 2.1 | |
| 44 | 439.8 | 1.9 | |
| 45 | 385.49 | 2 | DMSO (d6): 9.43 (br. s), 8.18 (d, 1H), 7.38 (d, 1H), 7.30 (t, 1H), 7.19 (t, 1H), 7.16 (d, 1H), 4.92 (q, 1H), 3.5 (m, 2H), 3.14 (m, 4H), 2.25 (m, 2H), 2.05 (dd, 1H), 1.87 (s, 3H), 1.81 (m, 3H), 1.72 (d, 1H), |

TABLE 2-continued

Physical data for exemplary compounds.

| Compound No. | LC/MS M + 1 | LC/RT min | NMR |
|---|---|---|---|
| | | | 1.69-1.51 (m, 4H), 1.25 (dd, 1H), 1.09 (dd, 1H), 0.95 (d, 3H), 0.90 (s, 9H). |
| 46 | 432.6 | 0.95 | |
| 47 | 371.4 | 2.04 | |
| 48 | 383.38 | 1.9 | |
| 49 | 361.2 | 1.54 | DMSO (d6): 9.28 (m, 1H), 8.18 (d, 1H), 7.35 (d, 1H), 7.30 (t, 1H), 7.20 (t, 1H), 7.17 (d, 1H), 4.92 (m, 1H), 3.44 (m, 2H), 3.21 (m, 4H), 2.80 (m, 1H), 2.20 (m, 2H), 2.06 (m, 1H), 2.05 (s, 3H), 1.91 (q, 2H), 1.87 (s, 3H), 1.83 (m, 3H), 1.74 (d, 1H), 1.63 (m, 1H), 1.27 (d, 3H). |
| 50 | 415.7 | 1.78 | |
| 51 | 386.3 | 2.02 | (500 MHz, DMSO-d6): 9.07 (m, 1H), 7.36 (d, 1H), 7.29 (t, 1H), 7.21 (t, 1H), 7.13 (d, 1H), 4.94 (t, 1H), 3.44 (dd, 2H), 3.21-3.11 (m, 4H), 2.78 (s, 6H), 2.46 (s, 3H), 2.45 (m, 2H), 2.01 (m, 1H), 1.98 (q, 1H), 1.81 (m, 2H), 1.63-1.55 (m, 4H), 0.93 (s, 9H). |
| 52 | 458.6 | 1.09 | |
| 53 | 386.2 | 2.04 | |
| 54 | 427.7 | 1.8 | |
| 55 | 480.3 | 2 | |
| 56 | 329.29 | 1.49 | DMSO (d6): 8.90 (br. s), 8.18 (d, 1H), 7.45 (d, 1H), 7.31 (t, 1H), 7.20 (t, 1H), 7.16 (d, 1H), 4.92 (q, 1H), 3.5 (m, 2H), 3.21-3.06 (m, 3H), 2.95 (m, 1H), 2.35 (m, 2H), 2.06 (dd, 1H), 1.87 (s, 3H), 192-1.77 (m, 4H), 1.69 (d, 1H), 1.62 (m, 1H), 1.43 (m, 1H), 1.21 (m, 1H), 0.99 (d, 3H), 0.91 (t, 3H). |
| 57 | 383.6 | 1.74 | |
| 58 | 409.3 | 1.9 | |
| 59 | 472.6 | 1.07 | |
| 60 | 440.3 | 1.8 | |
| 62 | 356.3 | 2.1 | |
| 63 | 405.4 | 1.11 | |
| 64 | 343.3 | 1.55 | DMSO (d6): 9.23 (br. s, 1H), 8.18 (d, 1H), 7.35 (d, 1H), 7.30 (t, 1H), 7.20 (t, 1H), 7.16 (d, 1H), 4.92 (q, 1H), 3.45 (m, 2H), 3.21-3.11 (m, 4H), 2.24-2.14 (m, 2H), 2.06 (dd, 1H), 1.87 (s, 3H), 1.82 (m, 3H), 1.73 (d, 1H), 1.67-1.55 (m, 3H), 0.93 (s, 9H). |
| 65 | 438.4 | 0.82 | |
| 66 | 329.2 | 1.5 | DMSO (d6): 8.20 (m, 1H), 8.17 (d, 1H), 7.48 (d, 1H), 7.32 (t, 1H), 7.20 (t, 1H), 7.16 (d, 1H), 4.92 (m, 1H), 3.43 (br. t, 3H), 3.32 (m, 2H), 3.05 (d, 2H), 2.42 (ddd, 2H), 2.06 (dd, 1H), 1.87 (s, 3H), 1.83 (m, 2H), 1.75 (d, 1H), 1.65 (m, 1H), 1.09 (s, 9H). |
| 67 | 416.4 | 0.95 | |
| 68 | 397.3 | 2.11 | DMSO (d6): 9.07 (m, 1H), 8.18 (d, 1H), 7.35 (d, 1H), 7.30 (t, 1H), 7.20 (t, 1H), 7.17 (d, 1H), 5.10 (t, 1H), 4.92 (ddd, 1H), 3.41 (m, 2H), 3.15 (m, 4H), 2.19 (m, 2H), 2.05 (dd, 2H), 1.98 (m, 2H), 1.87 (s, 3H), 1.83 (m, 3H), 1.73 (d, 1H), 1.67 (m, 2H), 1.66 (s, 3H), 1.59 (s, 3H), 1.50 (m, 2H), 1.32 (m, 1H), 1.19 (m, 1H), 0.91 (d, 3H). |
| 69 | 423.3 | 1.9 | |
| 70 | 387.3 | 2 | |
| 71 | 454.3 | 1.9 | |
| 72 | 472.4 | 1.09 | |
| 73 | 343.3 | 1.59 | DMSO (d6): 8.67 (br. s, 1H), 8.18 (d, 1H), 7.41 (d, 1H), 7.31 (t, 1H), 7.20 (t, 1H), 7.17 (d, 1H), 4.93 (q, 1H), 3.42 (m, 2H), 3.16 (t, 2H), 3.05 (t, 2H), 2.30 (qd, 2H), 2.07 (dd, 1H), 1.87 (s, 3H), 1.85-1.67 (m, 5H), 1.62 (m, 1H), 1.38 (m, 4H), 0.87 (t, 6H). |
| 74 | 406.3 | 1.9 | |
| 75 | 430.4 | 0.87 | |
| 76 | 444.4 | 0.94 | |
| 77 | 389.4 | 1.21 | |
| 78 | 458.4 | 1.03 | |
| 79 | 438.4 | 0.83 | |
| 80 | 365.33 | 1.68 | DMSO (d6): 9.19 (br.s, 1H), 7.47 (d, 1H), 7.45 (d, 1H), 7.35 (t, 1H), 7.23 (t, 1H), 4.45 (q, 1H), 3.43 (m, 2H), 3.14 (m, 4H), 3.05 (s, 3H), 2.18 (m, 2H), 2.08 (dd, 1H), 1.95 (m, 1H), 1.88-1.74 (m, 3H), 1.71 (d, 1H), 1.65-1.53 (m, 3H), 0.93 (d, 6H). |
| 81 | 472.6 | 1.04 | |
| 82 | 472.6 | 1.16 | |
| 83 | 472.6 | 1.14 | |
| 84 | 440.3 | 1.8 | |
| 85 | 387.3 | 1.7 | |
| 86 | 403.6 | 1.26 | |
| 87 | 441.3 | 1.8 | |
| 88 | 429.7 | 2.3 | |
| 89 | 272.5 | 1.94 | 1H NMR (500 MHz, DMSO (d6)): 9.02 (s, 1H), 7.33 (d, 1H), 7.21 (t, 1H), 7.13 (t, 1H), 7.06 (d, 1H), 3.42 (d, 2H), 3.18-3.12 (m, 4H), 2.72 (t, 2H), 2.20 (td, 2H), 1.90-1.86 (m, 2H), 1.76-1.66 (m, 4H), 1.66-1.63 (m, 1H), 1.63-1.55 (m, 2H), 0.95 (d, 6H). |
| 90 | 355.35 | 1.67 | DMSO-d6: 9.44 (s, 1H), 7.43 (d, 1H), 7.31 (t, 1H), 7.20 (t, 1H), 6.93 (d, 1H), 5.14 (dd, 1H), |

TABLE 2-continued

Physical data for exemplary compounds.

| Compound No. | LC/MS M + 1 | LC/RT min | NMR |
|---|---|---|---|
| | | | 3.42 (dd, 2H), 3.24-3.09 (m, 5H), 2.87 (ddd, 1H), 2.41-2.29 (m, 4H), 2.07 (td, 1H), 1.92 (m, 3H), 1.87 (t, 1H), 1.74 (m, 1H), 1.66-1.56 (m, 5H), 0.93 (d, 6H). |
| 91 | 387.6 | 1.8 | |
| 92 | 417.6 | 1.05 | |
| 93 | 445.4 | 1.04 | |
| 94 | 453.3 | 1.9 | |
| 95 | 301.2 | 1.27 | DMSO (d6): 9.15 (m, 1H), 8.18 (d, 1H), 7.36 (d, 1H), 7.30 (t, 1H), 7.20 (t, 1H), 7.16 (d, 1H), 4.92 (m, 1H), 3.42 (m, 2H), 3.15 (m, 2H), 3.08 (m, 2H), 2.21 (ddd, 2H), 2.05 (dd, 1H), 1.87 (s, 3H), 1.81 (m, 3H), 1.76-1.58 (m, 4H), 0.94 (t, 3H). |
| 96 | 432.6 | 0.93 | |
| 97 | 311.1 | 1.83 | DMSO (d6): 9.17 (br. s, 1H), 7.43 (d, 1H), 7.40 (t, 1H), 7.36 (d, 1H), 7.28 (td, 1H), 4.35 (t, 1H), 3.45 (t, 2H), 3.21-3.12 (m, 4H), 2.24 (td, 1H), 2.16 (td, 1H), 2.10-1.96 (m, 4H), 1.77 (dd, 2H), 1.61-1.57 (m, 2H), 0.93 (s, 9H). |
| 98 | 409.3 | 1.8 | |
| 99 | 387.3 | 2.3 | |
| 100 | 442.7 | 1.7 | |
| 101 | 437.7 | 1.4 | |
| 102 | 383.3 | 1.82 | |
| 103 | 430.4 | 0.91 | |
| 104 | 315.2 | 1.35 | DMSO (d6): 8.78 (m, 1H), 8.18 (d, 1H), 7.41 (d, 1H), 7.31 (t, 1H), 7.20 (t, 1H), 7.16 (d, 1H), 4.92 (m, 1H), 3.41 (br. t, 2H), 3.15 (m, 2H), 3.00 (t, 2H), 2.30 (m, 2H), 2.12 (m 1H), 2.05 (dd, 1H), 1.87 (s, 3H), 1.80 (m, 3H), 1.70 (d, 1H), 1.63 (m, 1H), 0.99 (d, 6H). |
| 105 | — | — | |
| 106 | 458.6 | 1.09 | |
| 107 | — | — | |
| 108 | 406.3 | 2.1 | |
| 109 | 440.3 | 1.7 | |
| 110 | 453.6 | 2.1 | |
| 111 | 434.7 | 1.7 | |
| 112 | 515.4 | 2.3 | |
| 113 | 454.4 | 1.9 | |
| 114 | 414.3 | 2.4 | |
| 115 | 423.3 | 2 | |
| 116 | 415.7 | 1.8 | |
| 117 | 336.6 | 2 | 1H NMR (300 MHz, DMSO) 8.04 (dd, J = 1.4, 7.9 Hz, 1H), 7.93-7.87 (m, 1H), 7.65-7.55 (m, 2H), 3.6 (m, 2H), 3.32 (m, 2H), 3.22-3.15 (m, 2H), 3.09-2.98 (t, 2H), 2.50 (qn, J = 1.8 Hz, DMSO-d6), 2.38 (m, 2H), 1.98 (s, 1H), 1.93 (s, 1H), 1.61 (m, 2H), 0.96 (s, 9H) |
| 118 | 409.3 | 2 | |
| 119 | 387.2 | 1.14 | |
| 120 | 338.5 | 1.7 | |
| 121 | 454.7 | 1.8 | |
| 122 | 383.7 | 1.82 | |
| 123 | 357.2 | 1.72 | (500 MHz, DMSO-d6): 9.14 (br.s, 1H), 7.40 and 7.38 (2d, 1H), 7.33 and 7.29 (2t, 1H), 7.24 and 7.20 (2t, 1H), 6.99 and 6.93 (2d, 1H), 5.67 (dd, 0.65 H), 5.03 (t, 0.33H), 3.43 (dd, 2H), 3.23-3.14 (m, 4H), 2.61 (s, 2H) and 2.43 (s, 1H, CH3), 2.45 (m, 2H), 2.17 (s, 1H) and 2.12 (s, 2H, CH3), 2.03-1.54 (m, 8H), 0.93 (s, 9H). |
| 124 | 440.6 | 2 | |
| 125 | 355.39 | 1.72 | DMSO (d6): 9.11 (br.s, 1H), 8.40 (d, 1H), 7.36 (d, 1H), 7.31 (t, 1H), 7.21 (t, 1H), 7.16 (d, 1H), 4.95 (q, 1H), 3.43 (m, 2H), 3.16 (m, 4H), 2.20 (ddd, 2H), 2.08 (m, 1H), 1.83 (m, 3H), 1.73 (d, 1H), 1.68-1.54 (m, 5H), 0.93 (d, 6H), 0.78-0.63 (m, 4H). |
| 126 | 468.4 | 1.7 | |
| 127 | 442.3 | 1.8 | |
| 128 | 437.7 | 1.4 | |
| 129 | 409.2 | 1.9 | |
| 131 | 384.6 | 2.34 | 300 MHz, DMSO-d6: 9.35 (m, 1H), 7.36-7.27 (m, 3H), 7.20 (td, 1H), 4.45 (m, 1H), 3.45 (m, 1H), 3.44 (d, 2H), 3.21-3.10 (m, 4H), 2.28-1.46 (m, 15H), 1.36-1.17 (m, 5H), 0.93 (s, 9H). |
| 132 | 468.8 | 2.06 | |
| 133 | 417.4 | 1.06 | |
| 134 | — | — | |
| 135 | 427.3 | 1.9 | |
| 136 | 448.2 | 1.6 | |
| 137 | 440.3 | 1.9 | |
| 138 | 458.6 | 1 | |
| 139 | — | — | |
| 140 | 415.7 | 1.9 | |
| 141 | 381.3 | 2.2 | |
| 142 | 369.6 | 1.65 | 300 MHz, DMSO-d6: 9.03 (m, 1H), 7.37 (d, 1H), 7.27 (t, 1H), 7.12 (t, 1H), 6.94 (d, 1H), 5.19 (q, 1H), 3.44 (m, 2H), 3.22-3.10 (m, 4H), 2.69 (m, 4H), 2.29 (q, 1H), 2.25 (m, 2H), 2.08-1.92 (m, 2H), 1.65-1.55 (m, 6H), 0.94 (d, 6H). |
| 143 | 454.3 | 1.8 | |
| 144 | 426.3 | 1.7 | |
| 145 | 445.6 | 1.1 | |
| 146 | 440.4 | 1.9 | |
| 147 | 387.3 | 1.9 | |
| 148 | 358.3 | 1.87 | DMSO (d6): 9.01 (s, 1H), 7.32 (d, 1H), 7.27 (t, 1H), 7.24 (d, 1H), 7.18 (t, 1H), 6.48 (d, 1H), 4.82 (q, 1H), 3.43 (d, 2H), 3.20-3.12 (m, |

TABLE 2-continued

Physical data for exemplary compounds.

| Compound No. | LC/MS M + 1 | LC/RT min | NMR |
|---|---|---|---|
| | | | 4H), 2.82 (s, 6H), 2.30 (td, 1H), 2.22 (dd, 1H), 2.06 (td, 1H), 1.93 (d, 1H), 1.83-1.77 (m, 1H), 1.73-1.55 (m, 6H), 0.93 (d, 6H). |
| 149 | 472.4 | 1.11 | |
| 150 | 327.1 | 1.71 | DMSO (d6): 9.10 (s, 1H), 8.18 (d, 1H), 7.33 (t, 1H), 7.29 (d, 1H), 7.20 (t, 1H), 7.16 (d, 1H), 5.29 (t, 1H), 4.92 (q, 1H), 3.76 (m, 2H), 3.34 (m, 2H), 3.16 (ddd, 2H), 2.16 (ddd, 2H), 2.07 (m, 1H), 1.87 (s, 3H), 1.81 (s, 3H), 1.75 (s, 3H), 1.86-1.79 (m, 4H), 1.66-1.59 (m, 1H). |
| 151 | 423.3 | 2.1 | |
| 152 | 427.3 | 2.1 | |
| 153 | 519.7 | 2.34 | 300 MHz, DMSO-d6: 9.30 (m, 1H), 7.40-7.28 (m, 8H), 7.20 (td, 1H), 5.07 (s, 2H), 4.95 (t, 1H), 3.83-3.68 (m, 3H), 3.40 (m, 2H), 3.25-3.10 (m, 6H), 2.30-2.00 (m, 3H), 1.93-1.70 (m, 7H), 1.62-1.56 (m, 2H), 1.52-1.37 (m, 2H), 0.93 (s, 9H). |
| 154 | 385.5 | 2.13 | |
| 155 | 427.3 | 1.7 | |
| 156 | 357.3 | 1.9 | |
| 157 | 440.3 | 1.8 | |
| 158 | 369.43 | 1.79 | DMSO (d6): 9.09 (br.s, 1H), 8.39 (d, 1H), 7.35 (d, 1H), 7.31 (t, 1H), 7.21 (t, 1H), 7.16 (d, 1H), 4.95 (q, 1H), 3.46 (m, 2H), 3.23-3.11 (m, 4H), 2.19 (ddd, 2H), 2.08 (m, 1H), 1.84 (m, 3H), 1.74 (d, 1H), 1.65 (ddd, 1H), 1.59 (m, 3H), 0.93 (s, 9H), 0.78-0.62 (m, 4H). |
| 159 | 329.2 | 1.53 | DMSO (d6): 9.23 (m, 1H), 8.18 (d, 1H), 7.36 (d, 1H), 7.30 (t, 1H), 7.20 (t, 1H), 7.17 (d, 1H), 4.92 (m, 1H), 3.43 (m, 2H), 3.14 (m, 4H), 2.20 (m, 2H), 2.04 (m, 1H), 1.87 (s, 3H), 1.81 (m, 3H), 1.72 (d, 1H), 1.59 (m, 4H), 0.92 (d, 6H). |
| 160 | 440.3 | 1.8 | |
| 161 | 393.7 | 2.17 | |
| 162 | 414.3 | 2.76 | |
| 163 | 432.4 | 0.89 | |
| 164 | 371.8 | 2.17 | |
| 165 | 427.4 | 0.92 | |
| 166 | 498.3 | 2.1 | |
| 167 | 468.3 | 1.7 | |
| 168 | 387.6 | 1.8 | 7.14 (d, 1H), 6.94 (d, 2H), 5.35 (t, 1H), 3.68 (m, 2H), 2.90-3.30 (6H), 2.64 (mn, 2H), 2.45 (m1H), 2.30 (m, 1H), 1.80-2.05 (m, 4H), 1.63-1.75 (m, 6H), 0.94 (s, 9H). |
| 169 | 454.3 | 1.9 | |
| 170 | 441.3 | 2 | |
| 171 | 428.7 | 1.6 | |
| 172 | 327.2 | 1.49 | DMSO (d6): 9.19 (m, 1H), 8.18 (d, 1H), 7.36 (d, 1H), 7.30 (t, 1H), 7.20 (t, 1H), 7.16 (d, 1H), 5.84 (m, 1H), 5.11 (dq, 1H), 5.06 (dq, 1H), 4.92 (ddd, 1H), 3.43 (m, 2H), 3.14 (m, 4H), 2.20 (m, 2H), 2.11 (m, 2H), 2.03 (dd, 1H), 1.87 (s, 3H), 1.83 (m, 5H), 1.73 (d, 1H), 1.63 (m, 1H). |
| 173 | 300.2 | 1.02 | |
| 174 | 373.7 | 2.17 | |
| 175 | 372.3 | 1.95 | DMSO (d6): 9.01 (s, 1H), 7.32 (d, 1H), 7.27 (t, 1H), 7.24 (d, 1H), 7.18 (t, 1H), 6.47 (d, 1H), 4.82 (m, 1H), 3.45 (d, 2H), 3.21-3.12 (m, 4H), 2.82 (s, 6H), 2.30 (td, 1H), 2.23 (dd, 1H), 2.05 (td, 1H), 1.93 (d, 1H), 1.83-1.77 (m, 1H), 1.74-1.65 (m, 3H), 1.58 (t, 2H), 0.94 (s, 9H). |
| 176 | 383.8 | 2.43 | |
| 177 | 361.4 | 0.91 | |
| 178 | 411.8 | 2.34 | |
| 179 | 382.39 | 1.6 | DMSO (d6): 9.43 (br. s), 8.18 (d, 1H), 7.39 (d, 1H), 7.30 (t, 1H), 7.20 (t, 1H), 7.16 (d, 1H), 4.92 (q, 1H), 3.5 (m, 2H), 3.15 (m, 4H), 2.25 (m, 2H), 2.05 (dd, 1H), 1.87 (s, 3H), 1.82 (m, 3H), 1.73 (m, 3H), 1.66-1.55 (m, 3H), 1.46 (m, 2H), 1.31 (s, 6H). □ |
| 180 | 427.4 | 0.86 | |
| 181 | 401.7 | 1.8 | |
| 182 | 482.4 | 2.2 | |
| 183 | 439.6 | 2.1 | |
| 184 | 343.1 | 1.61 | (500 MHz, DMSO-d6): 9.13 (br.s, 1H), 7.41 and 7.38 (2d, 1H), 7.33 and 7.29 (2t, 1H), 7.24 and 7.20 (2t, 1H), 6.99 and 6.93 (2d, 1H), 5.67 (dd, 0.65 H), 5.02 (t, 0.33H), 3.42 (dd, 2H), 3.23-3.10 (m, 4H), 2.61 (s, 2H) and 2.43 (s, 1H, CH3), 2.46 (m, 2H), 2.16 (s, 1H) and 2.11 (s, 2H, CH3), 2.03-1.54 (m, 9H), 0.93 and 0.89 (2d, 6H). |
| 185 | 369.3 | 1.42 | DMSO (d6): 9.41 (br. s, 1H), 8.18 (d, 1H), 7.36 (d, 1H), 7.30 (t, 1H), 7.19 (t, 1H), 7.16 (d, 1H), 4.92 (q, 1H), 3.45 (m, 2H), 3.20 (t, 4H), 2.46-2.35 (m, 2H), 2.27-2.18 (m, 2H), 2.06 (dd, 1H), 1.95 (m, 2H), 1.87 (s, 3H), 1.83 (m, 3H), 1.74 (d, 1H), 1.62 (m, 1H). |
| 186 | 454.3 | 1.7 | |
| 187 | 442.8 | 1.7 | |

TABLE 2-continued

Physical data for exemplary compounds.

| Compound No. | LC/MS M + 1 | LC/RT min | NMR |
|---|---|---|---|
| 188 | 413.3 | 1.9 | |
| 189 | 361.4 | 0.91 | |
| 191 | 454.3 | 1.7 | |
| 192 | 430.4 | 0.87 | |
| 193 | 409.3 | 2 | |
| 194 | 440.3 | 1.8 | |
| 195 | 420.3 | 1.9 | |
| 196 | 405.4 | 1.17 | |
| 197 | 454.3 | 1.8 | |
| 198 | 448.3 | 1.7 | |
| 199 | 387.8 | 2.12 | |
| 200 | 418.4 | 0.84 | |
| 201 | 369.4 | 1.74 | DMSO-d6: 9.87 (s, 1H), 7.45 (d, 1H), 7.30 (t, 1H), 7.20 (t, 1H), 6.93 (d, 1H), 5.14 (dd, 1H), 3.42 (t, 2H), 3.24-3.07 (m, 5H), 2.88 (m, 1H), 2.54 (td, 1H), 2.42-2.29 (m, 3H), 2.13 (td, 1H), 1.95-1.70 (m, 5H), 1.63 (m, 4H), 0.93 (s, 9H). |
| 202 | 431.6 | 1.08 | |
| 203 | 430.4 | 0.91 | |
| 204 | 357.2 | 1.95 | |
| 205 | — | — | |
| 206 | 372.3 | 1.94 | (500 MHz, DMSO-d6): 9.00 (m, 1H), 7.37 (d, 1H), 7.29 (t, 1H), 7.21 (t, 1H), 7.13 (d, 1H), 4.94 (t, 1H), 3.44 (dd, 2H), 3.19-3.10 (m, 4H), 2.78 (s, 6H), 2.46 (s, 3H), 2.45 (m, 2H), 2.01 (d, 1H), 1.98 (q, 1H), 1.83 (m, 2H), 1.65-1.51 (m, 5H), 0.93 (d, 6H). |
| 207 | 423.3 | 2.1 | |
| 208 | 415.8 | 2.63 | |
| 209 | 413.3 | 1.9 | |
| 210 | 427.7 | 1.8 | |
| 211 | 371.8 | 2.39 | 300 MHz, DMSO-d6 |
| 212 | 405.4 | 0.99 | |
| 213 | 357.5 | 1.91 | |
| 214 | 387.4 | 1.08 | |
| 215 | 405.4 | 1.06 | |
| 216 | 423.3 | 2 | |
| 217 | 431.4 | 1.01 | |
| 218 | 375.2 | 1.09 | |
| 219 | 409.3 | 1.9 | |
| 220 | — | — | |
| 221 | 415.7 | 1.8 | |
| 222 | 401.6 | 1.8 | |
| 223 | 448.8 | 1.4 | |
| 224 | 397.6 | 1.91 | 300 MHz, DMSO-d6: |
| 225 | 383.5 | 2.3 | H NMR (500 MHz, DMSO) 9.02 (s, 1H), 8.12 (d, J = 8.3 Hz, 1H), 7.34-7.27 (m, 2H), 7.19-7.16 (m, 2H), 5.36 (dd, J = 7.8, 15.8 Hz, 1H), 3.67-3.02 (m, 4H), 2.70-2.58 (m, 2H), 2.42-2.28 (m, 2H), 1.83-1.51 (m, 15H), 0.93 (s, 9H), |
| 226 | 358.4 | 1.3 | |
| 227 | 343.4 | 1.9 | |
| 228 | 400.2 | 1.9 | |
| 229 | 302.1 | 1.67 | |
| 230 | 342.3 | 1.9 | |
| 231 | 329.2 | 1.8 | |
| 232 | 216.1 | 1.54 | 1H NMR (500 MHz, CDCl3): 7.41 (d, 1H), 7.10 (t, 1H), 7.00 (t, 1H), 6.95 (d, 1H), 2.70-2.66 (m, 4H), 2.28 (s, 3H), 2.20 (t, 2H), 2.11 (td, 2H), 1.76 (m, 2H), 1.71-1.64 (m, 2H), 1.53 (dd, 2H), |
| 233 | 317.09 | 2.16 | |
| 234 | 393.3 | 1.74 | DMSO (d6): 9.32 (br.s, 1H), 8.19 (d, 1H), 7.43 (d, 2H), 7.34 (d, 1H), 7.28 (t, 1H), 7.18 (t, 1H), 7.15 (d, 1H), 7.02 (d, 2H), 4.92 (m, 1H), 4.30 (m, 2H), 4.06 (q, 2H), 3.23 (m, 4H), 2.17 (m, 2H), 2.05 (m, 1H), 1.86 (s, 3H), 1.82 (m, 3H), 1.73 (d, 1H), 1.62 (m, 1H), 1.33 (t, 3H). |
| 235 | 358.3 | 1.5 | |
| 236 | 329.3 | 1.5 | |
| 237 | 345.4 | 1.5 | |
| 238 | 313.4 | 1.7 | |
| 239 | 362 | 3.02 | CDCl3: 7.15 (s, 1H), 6.85 (s, 1H), 4.25 (brm, 2H), 3.98 (s, 3H), 3.91 (s, 3H), 2.85 (brm, 2H), 2.59 (s, 2H), 1.89 (m, 2H), 1.50 (s, 9H), 1.47 (m, 2H) |
| 241 | 330.2 | 1.2 | |
| 242 | 313.4 | 1.6 | |
| 243 | 315.4 | 1.6 | |
| 244 | 329.4 | 1.8 | |
| 245 | 358.4 | 1.3 | |
| 246 | 302.2 | 1.59 | |
| 247 | 341.2 | 1.9 | |
| 248 | 383.5 | 2.3 | |
| 249 | 330.2 | 1.2 | |
| 250 | 316.2 | 1.73 | |
| 251 | 384.5 | 2.1 | |
| 252 | 316.2 | 3.47 | (CDCl3, ppm) 7.52 (s, 1H), 7.44 (d, J = 8 Hz, 1H), 7.35 (d, J = 8 Hz, 1H), 4.18 (br s, 2H), 2.83 (t, J = 13 Hz, 2H), 2.60 (s, 2H), 2.39 (s, 3H), 1.94 (td, J = 4 Hz, 13 Hz, 2H), 1.48 (s, 9H), 1.44 (m, 2H). |
| 253 | 343.2 | 1.92 | |
| 254 | 317.09 | 2.16 | |
| 255 | 407.3 | 3.5 | |
| 256 | 303.06 | 1.63 | |
| 257 | 373.5 | 1.6 | |
| 258 | 383.3 | 1.4 | |
| 259 | 302.2 | 1.56 | |
| 260 | 359.3 | 2.94 | DMS)(d6): 8.17 (d, 1H), 7.36 (d, 1H), 7.22 (ddd, 1H), 7.14 (m, 2H), 4.95 (m, 1H), 3.86 (m, 2H), 2.97 (m, 2H), 2.01 (m, 1H), 1.85 (s, 3H), 1.80 (m, 4H), 1.61 (m 2H), 1.48 (d, 1H), 1.42 (s, 9H). |
| 261 | 359.4 | 3.09 | CDCl3 (ppm): 7.06 (m, 3H), 5.58 (m, 1H), 5.46 (q, 1H, J = 8 Hz), 4.08 (br s, 2H), 3.72 (m, 1H), 2.85 (m, 2H), 2.74 (m, 1H), 2.33 (s, 3H), 2.03 (s, 3H), 1.98 (m, 1H), 1.82 (m, 1H), 1.60 (m, 2H), 1.48 (s. 9H). |

TABLE 2-continued

Physical data for exemplary compounds.

| Compound No. | LC/MS M + 1 | LC/RT min | NMR |
|---|---|---|---|
| 262 | 340.2 | 1.3 | |
| 263 | 341.4 | 1.8 | |
| 264 | 357.5 | 2 | H NMR (500 MHz, DMSO) 9.08 (s, 1H), 8.16 (d, J = 8.2 Hz, 1H), 7.34-7.27 (m, 2H), 7.18 (dd, J = 7.3, 15.3 Hz, 2H), 5.37 (q, J = 7.9 Hz, 1H), 3.57-3.42 (m, 2H), 3.19-3.02 (m, 4H), 2.68 (dd, J = 7.9, 13.1 Hz, 1H), 2.36-2.07 (m, 4H), 1.90-1.54 (m, 8 H), 1.06-0.77 (m, 11H) |
| 267 | 367.5 | 2 | |
| 269 | 382.5 | 1.8 | in DMSO-d6 |
| 271 | | | iH NMR (CD3OD) 1.74-1.50 (m, 4H), 7.30-7.20 (m, 1H), 5.44 (t, J = 7.9 Hz, 2H), 3.06-2.88 (m, 2H), 2.73 (dd, J = 7.8, 13.0 Hz, 1H), 2.32-2.21 (m, 2H), 2.08-2.00 (m, 1H), 1.74-1.50 (m, 4H), 1.48 (s, 9H), 1.18 (t, J = 7.6 Hz, 3H), |
| 272 | 359.3 | 2.94 | DMSO (d6): 8.17 (d, 1H), 7.36 (d, 1H), 7.22 (ddd, 1H), 7.14 (m, 2H), 4.95 (m, 1H), 3.86 (m, 2H), 2.97 (m, 2H), 2.01 (m, 1H), 1.85 (s, 3H), 1.80 (m, 4H), 1.61 (m 2H), 1.48 (d, 1H), 1.42 (s, 9H). |
| 273 | 369.5 | 2.1 | |
| 275 | 407.4 | 2.69 | |
| 276 | | | |
| 277 | 315.4 | 1.7 | performed in DMSO-d6 |
| 279 | 371.3 | 3.2 | |
| 280 | 359.19 | 3.02 | DMSO (d6): 8.17 (d, 1H), 7.36 (d, 1H), 7.22 (ddd, 1H), 7.13 (m, 2H), 4.91 (td, 1H), 3.86 (m, 2H), 2.98 (m, 2H), 2.01 (dd, 1H), 1.86 (s, 3H), 1.61 (m, 4H), 1.80 (m, 2H), 1.48 (d, 1H), 1.42 (s, 9H). |
| 282 | 383.5 | 2.3 | |
| 287 | 386.3 | 2.2 | performed |
| 288 | 300.2 | 2.04 | (DMSO-d6, ppm) 9.12 (br s, 1H), 7.59 (d, J = 8 Hz, 1H), 7.45 (m, 2H), 3.59 (d, J = 12 Hz, 2H), 3.14 (m, 2H), 3.07 (m, 2H), 2.73 (s, 2H), 2.39 (s, 3H), 2.15 (td, J = 3, 11 Hz, 2H), 1.75 (d, J = 14 Hz, 2H), 1.59 (m, 2H), 0.94 (s, 9H). |
| 289 | 330.2 | 1.1 | |
| 290 | 315.4 | 1.6 | |
| 291 | 345.2 | 2 | |
| 292 | 381.5 | 2.1 | |
| 293 | 344.4 | 1.8 | |
| 294 | 370.3 | 1.9 | |
| 295 | 399.3 | 3.53 | |
| 297 | 358.5 | 1.9 | H NMR (500 MHz, DMSO) 9.08 (s, 1H), 7.33-7.14 (m, 4H), 6.55-6.48 (m, 1H), 5.32-5.24 (m, 2H), 3.54 (t, J = 13.3 Hz, 2H), 3.20-3.02 (m, 3H), 2.83 (s, 6H), 2.70 (dd, J = 7.8, 12.9 Hz, 1H), 2.36-2.28 (m, 1H), 1.83-1.52 (m, 6H), 0.98-0.90 (s, 9H), |
| 298 | 374.3 | 3 | |
| 299 | 369.5 | 2.2 | |
| 300 | 355.3 | 2 | H NMR (500 MHz, DMSO) 9.04 (s, 1H), 8.44 (d, J = 8.2 Hz, 1H), 7.35-7.17 (m, 4H), 5.36 (q, J = 7.9 Hz, 1H), 4.10-3.27 (m, 2H partially obscured by solvent), 3.18-3.03 (m, 4H), 2.71-2.58 (m, 1H), 2.42-2.22 (m, 1H), 1.89-1.51 (m, 4H), 1.63-1.49 (m, 3H), 0.94 (s, 9H), 0.81-0.65 (m, 4H), |
| 301 | 368.5 | 1.9 | |
| 302 | 340.2 | 1.3 | H NMR (500 MHz, DMSO) 9.02 (s, 1H), 8.12 (d, J = 8.3 Hz, 1H), 7.34-7.27 (m, 2H), 7.19-7.16 (m, 2H), 5.36 (dd, J = 7.8, 15.8 Hz, 1H), 3.67-3.02 (m, 4H), 2.70-2.58 (m, 2H), 2.42-2.28 (m, 2H), 1.83-1.51 (m, 15H), 0.93 (s, 9H), |

V. Assays for Detecting and Measuring Inhibition Properties of Compounds

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat#12430-054), containing 25 mM Hepes and supplemented with Fetal Bovine Serum (Hyclone, cat# SH30071.03), 0.1 mM of MEM non-essential amino acids (GIBCO, Cat#11140-050), 1 mM MEM Sodium Pyruvate (GIBCO Cat#11360-070) and 100 units/ml of Penicillin G and 100 µg/ml of Streptomycin (GIBCO Cat#15140-122). The recombinant muscarinic receptor cell lines are grown under antibiotic pressure with media containing 25 µg/ml zeocin and 500 m/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Versene (GIBCO Cat#15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 µl/well of Fluo-3 AM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 mM. The fluorescent dye is removed using the plate washer with Bath 1 containing 1 mM Probenecid, leaving 25 µl/well of this solution after the wash. Alternatively, cells can be loaded with the calcium indicator from Molecular Devices (Calcium 3 Assay Reagents, Cat # R7181) adding 5 µl of a 5× solution dye in Bath 1 containing 1 mM Probenecid (10 ml per dye flask cat# R7182 to generate a solution 20×) to 20 µl of the same buffer. After loading for 60 min, the experiment can be run without having to remove the dye.

Compounds are prepared at a 2× fold concentration in a 96-well plate (round bottom, Costar Corning cat#3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 µl compound/well) to the cell assay plate (containing 25 µl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 µl compound/well) to the assay plate and pre-incubated for 15 min prior to adding 25 µl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on M4 receptors.

The compounds of the present invention were found to modulate the $M_1$ and/or $M_4$ muscarinic receptors selectively over the other receptor types.

Examples of activities and efficacies of the muscarinic compounds of formulae (I, Ia, Ib, Ic, Id, and Ie) on modulating $M_1$ and $M_4$ receptors are shown below in Table 3. The compound activity for the $M_1$, $M_2$, $M_3$ and $M_4$ is illustrated with "+++" if activity was measured to be less than 2.0 µM, "++" if activity was measured to be from 2.0 µM to 5.0 µM, "+" if activity was measured to be greater than 5.0 µM, and "−" if no data was available. The efficacy for $M_1$ and $M_4$ modulation is illustrated with "+++" if efficacy was calculated to be greater than 100%, "++" if efficacy was calculated to be from 100% to 25%, "+" if efficacy was calculated to be less than 25%, and "−" if no data was available. It should be noted that 100% efficacy is the maximum response obtained with the Carbachol control.

TABLE 3

Compound activities and efficacies for modulating $M_1$ and $M_4$ receptors.

| Compound No. | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 1 | +++ | ++ | ++ | + | + | + | +++ | ++ |
| 2 | +++ | ++ | +++ | ++ | + | + | +++ | ++ |
| 3 | + | + | + | + | + | + | +++ | ++ |
| 4 | ++ | ++ | + | + | + | + | ++ | ++ |
| 5 | ++ | + | ++ | + | + | + | +++ | ++ |
| 6 | + | + | + | + | + | + | +++ | ++ |
| 7 | ++ | ++ | + | + | + | + | +++ | ++ |
| 8 | +++ | ++ | ++ | + | + | + | +++ | ++ |
| 9 | + | ++ | + | + | + | + | +++ | ++ |
| 10 | + | + | + | + | + | + | +++ | ++ |
| 11 | +++ | ++ | + | + | + | + | +++ | ++ |
| 12 | +++ | ++ | +++ | ++ | + | + | +++ | ++ |
| 13 | + | + | + | + | + | + | +++ | ++ |
| 14 | + | ++ | ++ | + | + | + | +++ | ++ |
| 15 | +++ | ++ | + | + | + | + | +++ | ++ |
| 16 | ++ | ++ | + | + | + | + | + | ++ |
| 17 | +++ | ++ | + | + | + | + | +++ | ++ |
| 18 | +++ | ++ | +++ | ++ | + | + | +++ | ++ |
| 19 | + | + | + | + | + | + | + | + |
| 20 | +++ | ++ | +++ | ++ | + | + | +++ | ++ |
| 21 | +++ | ++ | +++ | ++ | + | + | +++ | ++ |
| 22 | ++ | ++ | ++ | + | + | + | +++ | ++ |
| 23 | ++ | + | + | + | + | + | +++ | ++ |
| 24 | + | + | +++ | ++ | + | + | +++ | ++ |
| 25 | + | + | + | + | + | + | +++ | ++ |
| 26 | +++ | ++ | + | + | + | + | +++ | ++ |
| 27 | +++ | ++ | +++ | + | + | + | +++ | ++ |
| 28 | +++ | ++ | ++ | + | + | + | +++ | ++ |
| 29 | +++ | ++ | +++ | ++ | + | + | +++ | ++ |
| 30 | + | + | + | + | + | + | ++ | ++ |
| 31 | +++ | ++ | +++ | + | + | + | +++ | ++ |
| 32 | +++ | ++ | +++ | ++ | + | + | +++ | ++ |
| 33 | +++ | ++ | +++ | ++ | + | + | +++ | ++ |
| 34 | +++ | ++ | ++ | + | + | + | +++ | ++ |
| 35 | + | + | + | + | + | + | +++ | ++ |
| 36 | +++ | ++ | + | + | + | + | +++ | ++ |
| 37 | ++ | ++ | ++ | ++ | + | + | +++ | ++ |
| 38 | +++ | ++ | + | + | + | + | +++ | ++ |

TABLE 3-continued

Compound activities and efficacies for modulating $M_1$ and $M_4$ receptors.

| Compound No. | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 39 | + | ++ | + | + | + | + | +++ | ++ |
| 40 | +++ | ++ | +++ | ++ | + | + | +++ | ++ |
| 41 | +++ | ++ | + | + | + | + | +++ | ++ |
| 42 | ++ | ++ | + | + | + | + | +++ | ++ |
| 43 | +++ | ++ | +++ | ++ | + | + | +++ | ++ |
| 44 | ++ | ++ | + | + | + | + | +++ | ++ |
| 45 | +++ | ++ | ++ | + | + | ++ | + | + |
| 46 | +++ | ++ | +++ | ++ | + | + | +++ | ++ |
| 47 | ++ | ++ | + | + | + | + | ++ | ++ |
| 48 | + | + | + | + | + | + | + | + |
| 49 | ++ | ++ | + | + | + | + | +++ | ++ |
| 50 | + | ++ | + | + | + | + | +++ | ++ |
| 51 | +++ | ++ | + | + | + | + | +++ | ++ |
| 52 | +++ | ++ | +++ | + | + | + | +++ | ++ |
| 53 | + | + | + | + | + | + | +++ | ++ |
| 54 | +++ | ++ | + | + | + | + | +++ | ++ |
| 55 | ++ | + | +++ | + | + | + | +++ | ++ |
| 56 | +++ | ++ | +++ | ++ | + | + | +++ | ++ |
| 57 | ++ | ++ | + | + | + | + | +++ | ++ |
| 58 | +++ | ++ | +++ | ++ | + | + | +++ | ++ |
| 59 | +++ | ++ | ++ | + | + | + | +++ | ++ |
| 60 | +++ | ++ | + | + | + | + | +++ | ++ |
| 61 | + | ++ | + | + | + | + | + | ++ |
| 62 | + | + | + | + | + | + | +++ | ++ |
| 63 | +++ | ++ | +++ | + | + | + | +++ | ++ |
| 64 | ++ | + | + | + | + | + | +++ | ++ |
| 65 | +++ | ++ | ++ | + | + | + | +++ | ++ |
| 66 | +++ | ++ | + | ++ | + | + | +++ | ++ |
| 67 | +++ | ++ | +++ | ++ | + | + | +++ | ++ |
| 68 | +++ | +++ | +++ | ++ | + | + | +++ | ++ |
| 69 | + | + | + | + | + | + | +++ | ++ |
| 70 | +++ | ++ | +++ | + | + | + | +++ | ++ |
| 71 | +++ | ++ | +++ | ++ | + | + | +++ | ++ |
| 72 | ++ | ++ | ++ | + | + | + | +++ | ++ |
| 73 | +++ | ++ | + | + | + | + | +++ | ++ |
| 74 | +++ | ++ | +++ | ++ | + | + | +++ | ++ |
| 75 | ++ | ++ | ++ | + | + | + | +++ | ++ |
| 76 | +++ | ++ | +++ | ++ | + | + | +++ | ++ |
| 77 | +++ | ++ | ++ | + | + | + | +++ | ++ |
| 78 | +++ | ++ | +++ | ++ | + | + | +++ | ++ |
| 79 | +++ | ++ | +++ | ++ | + | + | +++ | ++ |
| 80 | +++ | ++ | + | + | + | + | +++ | ++ |
| 81 | ++ | ++ | + | + | + | + | +++ | ++ |
| 82 | +++ | ++ | ++ | + | + | + | +++ | ++ |
| 83 | +++ | ++ | + | + | + | + | +++ | ++ |
| 84 | ++ | ++ | +++ | ++ | + | + | +++ | ++ |
| 85 | +++ | ++ | +++ | ++ | + | + | +++ | ++ |
| 86 | +++ | ++ | + | + | + | + | +++ | ++ |
| 87 | + | + | + | + | + | + | +++ | ++ |
| 88 | +++ | ++ | +++ | ++ | + | + | +++ | ++ |
| 89 | + | ++ | + | + | + | + | +++ | ++ |
| 90 | ++ | ++ | + | + | + | + | ++ | ++ |
| 91 | +++ | ++ | +++ | + | + | + | +++ | ++ |
| 92 | +++ | ++ | +++ | ++ | + | + | +++ | ++ |
| 93 | ++ | ++ | + | + | + | + | +++ | ++ |
| 94 | + | ++ | + | + | + | + | +++ | ++ |
| 95 | + | ++ | + | + | + | + | + | ++ |
| 96 | +++ | ++ | +++ | ++ | + | + | +++ | ++ |
| 97 | +++ | ++ | +++ | ++ | + | + | +++ | ++ |
| 98 | +++ | ++ | + | + | + | + | +++ | ++ |
| 99 | + | + | + | + | + | + | +++ | ++ |
| 100 | + | + | + | + | + | + | +++ | ++ |
| 101 | +++ | ++ | + | + | + | + | ++ | ++ |
| 102 | ++ | ++ | + | + | + | + | +++ | ++ |
| 103 | +++ | ++ | +++ | + | + | + | +++ | ++ |
| 104 | ++ | ++ | + | ++ | + | + | ++ | ++ |
| 105 | ++ | + | + | + | + | + | +++ | ++ |
| 106 | +++ | ++ | +++ | ++ | + | + | +++ | ++ |
| 107 | ++ | ++ | ++ | + | + | + | +++ | ++ |
| 108 | +++ | ++ | +++ | + | + | + | +++ | ++ |
| 109 | +++ | ++ | + | + | + | + | +++ | ++ |
| 110 | + | ++ | + | + | + | + | +++ | ++ |
| 111 | + | + | + | + | + | + | +++ | ++ |
| 112 | ++ | ++ | + | + | + | + | +++ | ++ |
| 113 | + | + | + | + | + | + | +++ | ++ |

TABLE 3-continued

Compound activities and efficacies for modulating M₁ and M₄ receptors.

| Compound No. | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 114 | − | − | − | − | − | − | − | − |
| 115 | +++ | ++ | +++ | ++ | + | + | +++ | ++ |
| 116 | + | ++ | + | + | + | + | +++ | ++ |
| 117 | +++ | ++ | +++ | ++ | + | + | +++ | ++ |
| 118 | ++ | ++ | + | + | + | + | +++ | ++ |
| 119 | +++ | ++ | +++ | ++ | + | + | +++ | ++ |
| 120 | +++ | ++ | +++ | ++ | + | + | +++ | ++ |
| 121 | +++ | ++ | + | + | + | + | +++ | ++ |
| 122 | +++ | ++ | + | + | + | + | +++ | ++ |
| 123 | +++ | ++ | + | + | + | + | +++ | ++ |
| 124 | +++ | ++ | +++ | ++ | + | + | +++ | ++ |
| 125 | +++ | ++ | ++ | + | + | + | +++ | ++ |
| 126 | + | + | + | + | + | + | +++ | ++ |
| 127 | +++ | ++ | ++ | + | + | + | +++ | ++ |
| 128 | ++ | ++ | + | + | + | + | +++ | ++ |
| 129 | + | + | + | + | + | + | +++ | ++ |
| 130 | ++ | ++ | + | + | + | + | +++ | ++ |
| 131 | − | − | − | − | − | − | − | − |
| 132 | ++ | ++ | + | + | + | + | +++ | ++ |
| 133 | +++ | ++ | +++ | ++ | + | + | +++ | ++ |
| 134 | + | + | + | + | + | + | +++ | ++ |
| 135 | +++ | ++ | + | + | + | + | +++ | ++ |
| 136 | ++ | ++ | ++ | + | + | + | +++ | ++ |
| 137 | +++ | ++ | + | + | + | + | +++ | ++ |
| 138 | +++ | ++ | +++ | ++ | + | + | +++ | ++ |
| 139 | ++ | + | + | + | + | + | +++ | ++ |
| 140 | ++ | ++ | + | + | + | + | +++ | ++ |
| 141 | +++ | ++ | + | + | + | + | +++ | ++ |
| 142 | ++ | ++ | + | + | + | + | + | + |
| 143 | ++ | ++ | + | + | + | + | +++ | ++ |
| 144 | +++ | ++ | +++ | ++ | + | + | +++ | ++ |
| 145 | +++ | ++ | +++ | + | + | + | +++ | ++ |
| 146 | + | ++ | + | + | + | + | +++ | ++ |
| 147 | +++ | ++ | +++ | ++ | + | + | +++ | ++ |
| 148 | + | + | + | + | + | + | ++ | ++ |
| 149 | ++ | ++ | ++ | ++ | + | + | +++ | ++ |
| 150 | + | ++ | + | + | + | + | ++ | ++ |
| 151 | +++ | ++ | + | + | + | + | +++ | ++ |
| 152 | + | + | + | + | + | + | +++ | ++ |
| 153 | − | − | − | − | − | − | − | − |
| 154 | +++ | ++ | + | + | + | + | +++ | ++ |
| 155 | +++ | ++ | ++ | ++ | + | + | +++ | ++ |
| 156 | +++ | ++ | +++ | ++ | + | + | +++ | ++ |
| 157 | ++ | ++ | +++ | + | + | + | +++ | ++ |
| 158 | +++ | ++ | +++ | ++ | + | + | +++ | ++ |
| 159 | +++ | ++ | + | + | + | + | +++ | ++ |
| 160 | +++ | ++ | + | + | + | + | +++ | ++ |
| 161 | +++ | ++ | + | + | + | + | +++ | ++ |
| 162 | + | ++ | + | + | + | + | +++ | ++ |
| 163 | +++ | ++ | +++ | ++ | + | + | +++ | ++ |
| 164 | +++ | ++ | + | + | + | + | +++ | ++ |
| 165 | +++ | ++ | +++ | ++ | + | + | +++ | ++ |
| 166 | + | ++ | + | + | + | + | +++ | ++ |
| 167 | +++ | ++ | + | + | + | + | +++ | ++ |
| 168 | ++ | + | + | + | + | + | +++ | ++ |
| 169 | +++ | ++ | +++ | + | + | + | +++ | ++ |
| 170 | + | + | + | + | + | + | +++ | ++ |
| 171 | +++ | ++ | +++ | ++ | + | + | +++ | ++ |
| 172 | +++ | ++ | ++ | ++ | + | + | +++ | ++ |
| 173 | +++ | ++ | +++ | ++ | + | + | +++ | ++ |
| 174 | ++ | ++ | + | + | + | + | +++ | ++ |
| 175 | + | + | + | + | + | + | +++ | ++ |
| 176 | ++ | + | + | + | + | + | +++ | ++ |
| 177 | +++ | ++ | +++ | ++ | + | + | +++ | ++ |
| 178 | + | + | + | + | + | + | +++ | ++ |
| 179 | +++ | ++ | + | + | + | + | + | + |
| 180 | +++ | ++ | +++ | ++ | + | + | +++ | ++ |
| 181 | ++ | ++ | + | + | + | + | +++ | ++ |
| 182 | ++ | ++ | + | + | + | + | +++ | ++ |
| 183 | ++ | ++ | + | + | + | + | +++ | ++ |
| 184 | +++ | ++ | + | + | + | + | +++ | ++ |
| 185 | ++ | ++ | + | + | + | ++ | ++ | ++ |
| 186 | ++ | ++ | + | + | + | + | +++ | ++ |
| 187 | +++ | ++ | + | + | + | + | +++ | ++ |
| 188 | + | + | + | + | + | + | +++ | ++ |

TABLE 3-continued

Compound activities and efficacies for modulating $M_1$ and $M_4$ receptors.

| Compound No. | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 189 | +++ | ++ | +++ | + | + | + | +++ | ++ |
| 190 | +++ | ++ | +++ | ++ | + | + | +++ | ++ |
| 191 | +++ | ++ | + | + | + | + | +++ | ++ |
| 192 | + | + | + | + | + | + | +++ | ++ |
| 193 | +++ | ++ | + | + | + | + | +++ | ++ |
| 194 | +++ | ++ | + | + | + | + | +++ | ++ |
| 195 | +++ | ++ | +++ | ++ | + | + | +++ | ++ |
| 196 | +++ | ++ | +++ | ++ | + | + | +++ | ++ |
| 197 | +++ | ++ | +++ | ++ | + | + | +++ | ++ |
| 198 | +++ | ++ | ++ | + | + | + | +++ | ++ |
| 199 | ++ | + | + | + | + | + | +++ | ++ |
| 200 | +++ | ++ | +++ | ++ | + | + | +++ | ++ |
| 201 | +++ | ++ | + | + | + | + | +++ | ++ |
| 202 | +++ | ++ | + | + | + | + | +++ | ++ |
| 203 | +++ | ++ | +++ | ++ | + | + | +++ | ++ |
| 204 | +++ | ++ | + | + | + | + | +++ | ++ |
| 205 | +++ | ++ | + | + | + | + | +++ | ++ |
| 206 | + | + | + | + | + | + | +++ | ++ |
| 207 | ++ | ++ | + | + | + | + | +++ | ++ |
| 208 | +++ | ++ | +++ | + | + | + | +++ | ++ |
| 209 | +++ | ++ | + | + | + | + | +++ | ++ |
| 210 | +++ | + | + | + | + | + | +++ | ++ |
| 211 | +++ | ++ | + | + | + | + | +++ | ++ |
| 212 | +++ | ++ | + | + | + | + | +++ | ++ |
| 213 | ++ | ++ | + | + | + | + | +++ | ++ |
| 214 | +++ | ++ | +++ | + | + | + | +++ | ++ |
| 215 | +++ | ++ | +++ | ++ | + | + | +++ | ++ |
| 216 | ++ | ++ | ++ | ++ | + | + | +++ | ++ |
| 217 | ++ | ++ | + | + | + | + | +++ | ++ |
| 218 | +++ | ++ | +++ | + | + | + | +++ | ++ |
| 219 | +++ | ++ | +++ | ++ | + | + | +++ | ++ |
| 220 | + | + | + | + | + | + | +++ | ++ |
| 221 | ++ | ++ | + | + | + | + | +++ | ++ |
| 222 | +++ | ++ | + | + | + | + | +++ | ++ |
| 223 | + | ++ | + | + | + | + | +++ | ++ |
| 224 | +++ | ++ | + | + | + | + | +++ | ++ |
| 225 | + | + | + | + | + | + | + | + |
| 226 | + | + | + | + | + | + | + | + |
| 227 | + | + | + | + | + | + | + | + |
| 228 | − | − | − | − | − | − | − | − |
| 229 | + | + | + | + | + | + | + | + |
| 230 | +++ | ++ | + | + | + | + | +++ | ++ |
| 231 | + | + | + | + | + | + | +++ | + |
| 232 | + | + | + | + | + | + | + | + |
| 233 | + | ++ | + | + | + | + | + | + |
| 234 | ++ | ++ | + | + | + | + | ++ | ++ |
| 235 | + | + | + | + | + | + | + | + |
| 236 | + | + | + | + | + | + | + | + |
| 237 | + | ++ | + | + | + | + | + | ++ |
| 238 | + | + | + | + | + | + | + | + |
| 239 | + | + | + | + | + | + | + | + |
| 241 | + | + | + | + | + | + | + | + |
| 242 | + | ++ | + | + | + | + | ++ | ++ |
| 243 | + | ++ | + | ++ | + | + | +++ | ++ |
| 244 | +++ | ++ | + | + | + | + | +++ | ++ |
| 245 | + | + | + | + | + | + | + | + |
| 246 | + | + | + | + | + | + | + | + |
| 247 | + | ++ | + | + | + | + | + | + |
| 248 | ++ | ++ | + | + | + | + | + | ++ |
| 249 | + | + | + | + | + | + | + | + |
| 250 | + | ++ | + | + | + | + | + | ++ |
| 251 | + | + | + | + | + | + | + | + |
| 252 | + | + | + | + | + | + | + | + |
| 253 | + | + | + | + | + | + | + | ++ |
| 254 | + | ++ | + | + | + | + | + | + |
| 255 | + | + | + | + | + | + | + | + |
| 256 | + | + | + | + | + | + | + | + |
| 257 | +++ | +++ | +++ | ++ | + | ++ | +++ | ++ |
| 258 | + | + | + | + | + | + | + | + |
| 259 | + | ++ | + | + | + | + | + | + |
| 260 | + | + | + | + | + | + | + | + |
| 261 | + | + | + | + | + | + | + | + |
| 262 | + | + | + | + | + | + | + | + |
| 263 | + | ++ | + | + | + | + | ++ | + |
| 264 | + | + | + | + | + | + | +++ | ++ |

TABLE 3-continued

Compound activities and efficacies for modulating $M_1$ and $M_4$ receptors.

| Compound No. | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 267 | + | + | + | + | + | + | + | + |
| 269 | + | ++ | + | + | + | + | ++ | ++ |
| 271 | + | + | + | + | + | + | + | + |
| 272 | + | + | + | + | + | + | + | + |
| 273 | +++ | ++ | + | + | + | + | +++ | ++ |
| 275 | + | + | + | + | − | − | + | + |
| 276 | + | + | + | + | + | + | + | + |
| 277 | ++ | ++ | + | + | + | + | +++ | ++ |
| 279 | + | + | + | + | + | + | + | + |
| 280 | + | + | + | + | + | + | + | + |
| 282 | +++ | ++ | + | + | + | + | + | + |
| 287 | − | − | − | − | − | − | − | − |
| 288 | + | ++ | + | + | + | + | ++ | ++ |
| 289 | + | + | + | + | + | + | + | + |
| 290 | + | ++ | + | + | + | + | + | ++ |
| 291 | − | − | − | − | − | − | − | − |
| 292 | + | + | + | + | + | + | + | + |
| 293 | + | + | + | + | + | + | + | + |
| 294 | + | + | + | + | + | + | + | + |
| 295 | + | + | + | + | + | + | + | + |
| 297 | + | + | + | + | + | + | + | + |
| 298 | + | + | + | + | + | + | + | + |
| 299 | + | + | + | + | + | + | + | + |
| 300 | +++ | ++ | + | + | + | + | +++ | + |
| 301 | + | + | + | + | + | + | + | + |
| 302 | + | + | + | + | + | + | + | + |

VIII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A method of modulating the activity of an $M_1$, $M_2$, or $M_4$ muscarinic receptor comprising the step of contacting said receptor with a compound of formula Ie:

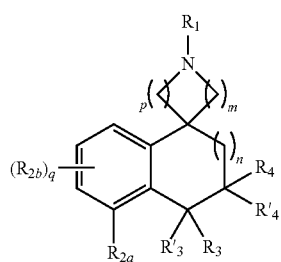

or a pharmaceutically acceptable salt thereof, wherein:
$R_1$ is a branched or straight $C_{1-12}$ aliphatic optionally substituted with 1-3 of $R^A$, wherein up to 3 carbon units of $R_1$ are optionally and independently replaced by —CONR$^F$—, —O—, —NR$^F$CO—, or —S—;
Each $R^A$ is halo, —OH, —NH$_2$, —NO$_2$, —CN, or —OCF$_3$;
Each $R^F$ is hydrogen, or a branched or straight $C_{1-8}$ aliphatic group optionally substituted with 1-3 of $R^A$;
$R_{2a}$ is —Z$^B$R$_5$, wherein each Z$^B$ is independently a bond or an optionally substituted branched or straight $C_{1-4}$ aliphatic chain wherein up to two carbon units of Z$^B$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—;
Each $R_5$ is independently R$^B$, halo, —OH, —CN, or —OCF$_3$;
Each R$^B$ is independently hydrogen, an optionally substituted $C_{1-8}$ aliphatic group, an optionally substituted cycloaliphatic, an optionally substituted heterocycloaliphatic, an optionally substituted aryl, an optionally substituted heteroaryl, or
$R_{2a}$ and $R_3$ together with the atoms to which they are attached form a 5-7 membered partially unsaturated optionally substituted cyclic group optionally having 1-2 heteroatoms independently selected from N, O, and S;
Each $R_{2b}$ is hydrogen, fluoro or methyl; or
$R_{2a}$ and one $R_{2b}$ together with the atoms to which they are attached form a 5-7 membered partially unsaturated optionally substituted cyclic group optionally having 1-2 heteroatoms independently selected from N, O, and S, wherein $R_{2b}$ is attached to a carbon atom vicinal to the carbon atom to which $R_{2a}$ is attached on the fused phenyl of formula I, or
Two of $R_{2b}$ together with the atoms to which they are attached form a 5-7 membered partially unsaturated optionally substituted cyclic group optionally having 1-2 heteroatoms independently selected from N, O, and S, wherein each $R_{2b}$ is attached to a vicinal carbon atom on the fused phenyl of formula Ie;
one of $R_3$ and $R'_3$ is hydrogen and the other of $R_3$ and $R'_3$ is independently —Z$^C$R$_6$, wherein each Z$^C$ is independently an optionally substituted branched or straight $C_{1-4}$ aliphatic chain wherein up to two carbon units of Z$^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —SO$_2$NR$^C$—, —NR$^C$SO$_2$—, or —NR$^C$SO$_2$NR$^C$—;

Each R$_6$ is independently R$^C$, halo, —OH, —NH$_2$, —NO$_2$, —CN, or —OCF$_3$;

Each R$^C$ is independently hydrogen, an optionally substituted C$_{1-8}$ aliphatic group; an optionally substituted cycloaliphatic, an optionally substituted heterocycloaliphatic, an optionally substituted aryl, or an optionally substituted heteroaryl having 1-3 heteroatoms;

R$_4$ and R'$_4$ are each independently hydrogen or fluoro;

m is 2, p is 2;

n is 0-2; and q is 0-3.

2. The method of claim 1, wherein R$_1$ is a straight C$_{1-10}$ alkyl, straight C$_{2-10}$ alkenyl, straight C$_{2-10}$ alkynyl, branched C$_{3-12}$ alkyl, branched C$_{3-12}$ alkenyl, or branched C$_{3-12}$ alkynyl, each of which is optionally substituted with 1-3 of R$^A$; and each R$^A$ is independently halo, —OH, —NH$_2$, —NO$_2$, —CN, or —OCF$_3$.

3. The method of claim 1, wherein R$_1$ is an optionally substituted straight or branched C$_{1-12}$ aliphatic wherein 1-2 of the carbon units have been optionally replaced with —S—.

4. The method of claim 1, wherein R$_1$ is one selected from:

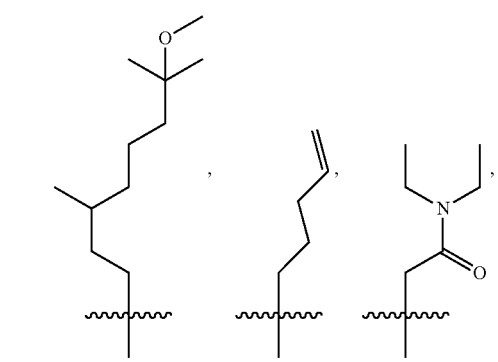

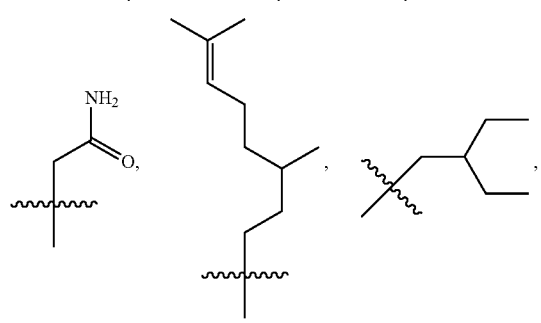

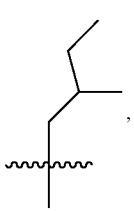

-continued

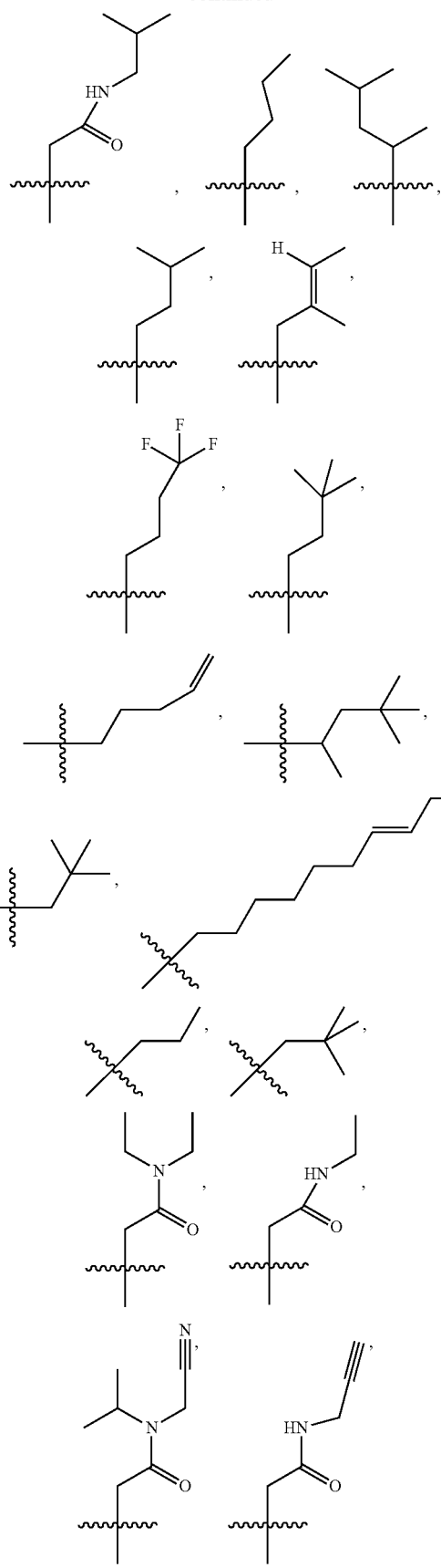

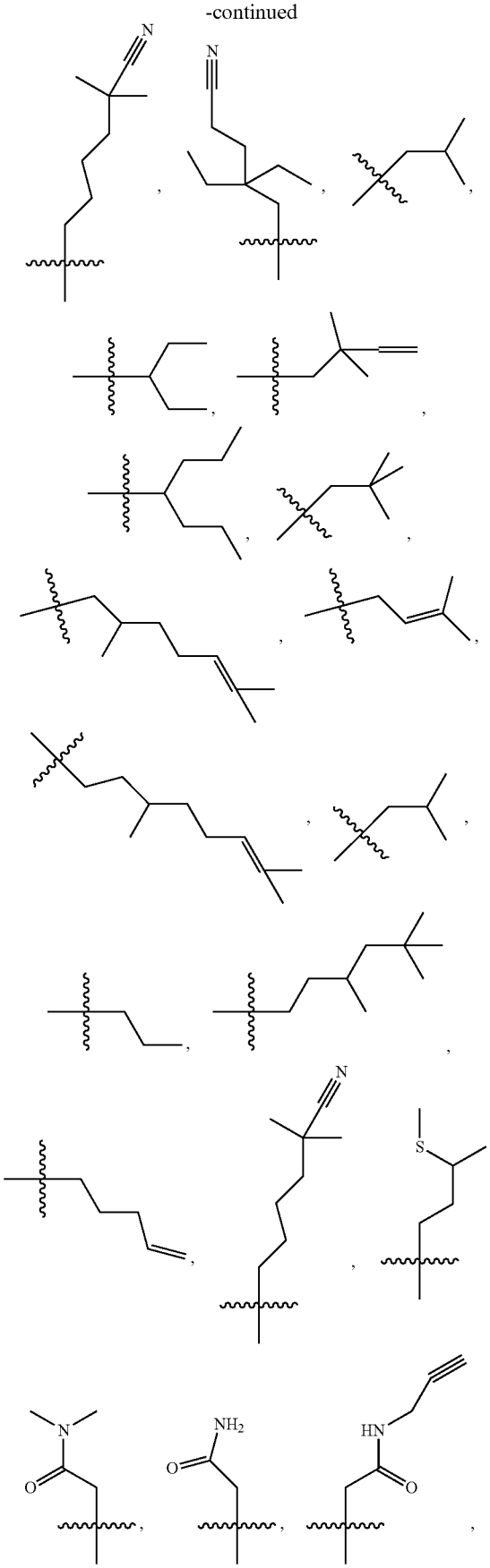

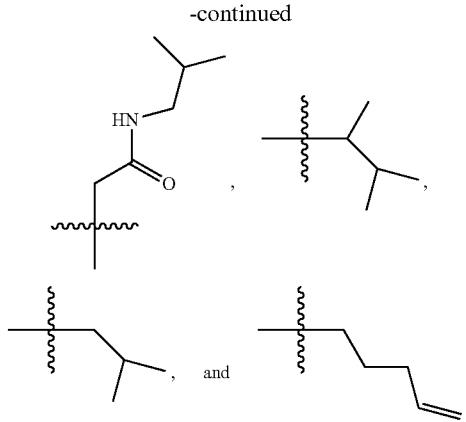

5. The method of claim 1, wherein q is 0 and $R_{2a}$ is hydrogen.

6. The method of claim 1, wherein one of $R_3$ and $R'_3$ is a branched or straight optionally substituted $C_{1-4}$ aliphatic wherein up to two carbon units of $R_3$ or $R'_3$ are optionally and independently replaced by —C(O)—, —CONH—, or —S(O)$_2$—, and the remaining $R_3$ or $R'_3$ is hydrogen.

7. The method of claim 6, wherein one of $R_3$ and $R'_3$ is straight optionally substituted $C_{2-4}$ aliphatic wherein a first carbon unit is optionally and independently replaced by —CONH—.

8. The method of claim 7, wherein one of $R_3$ and $R'_3$ is an optionally substituted (methylcarbonyl)amino, and the remaining $R_3$ or $R'_3$ is hydrogen.

9. The method of claim 1, wherein $R_3$ or $R'_3$ is independently selected from:

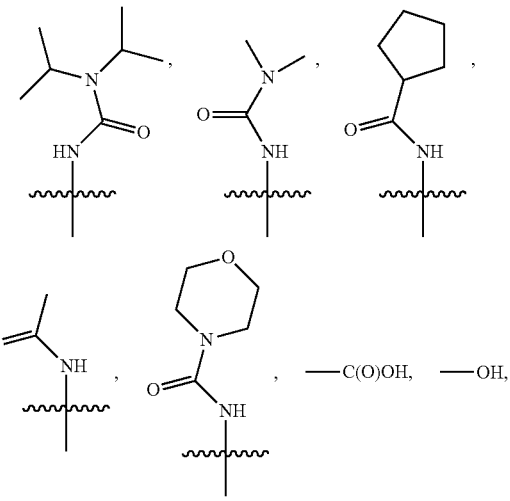

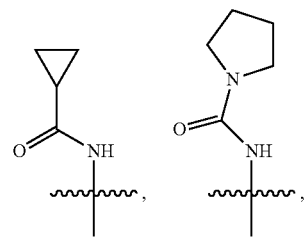

187
-continued
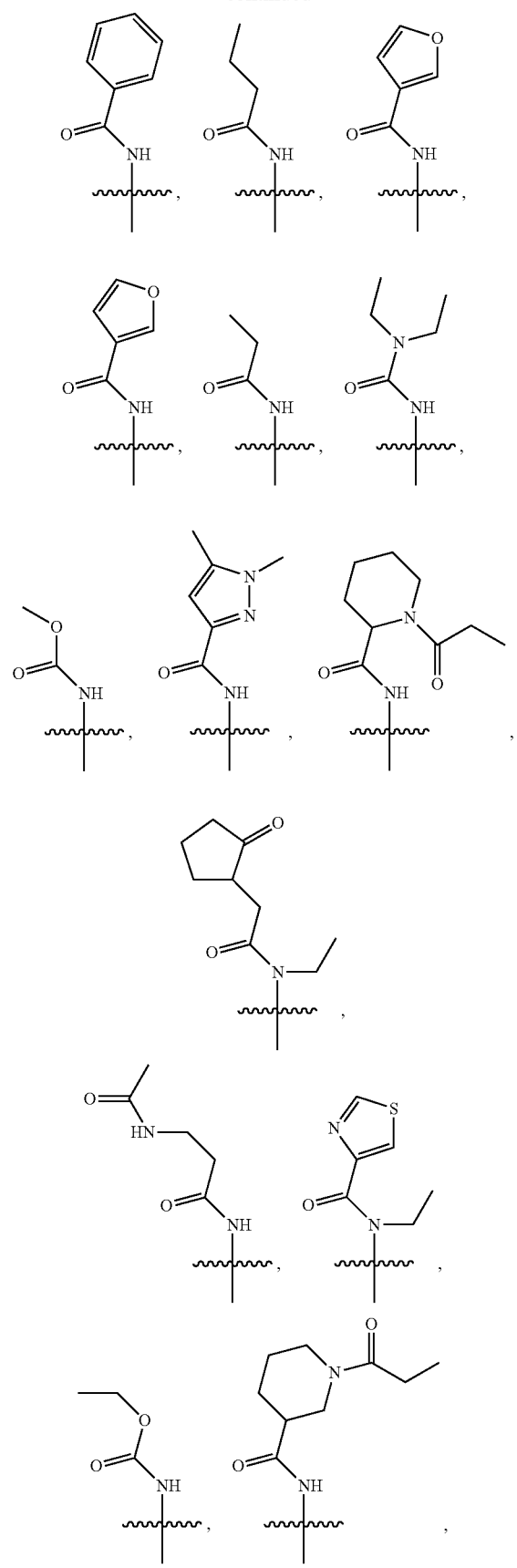
188
-continued
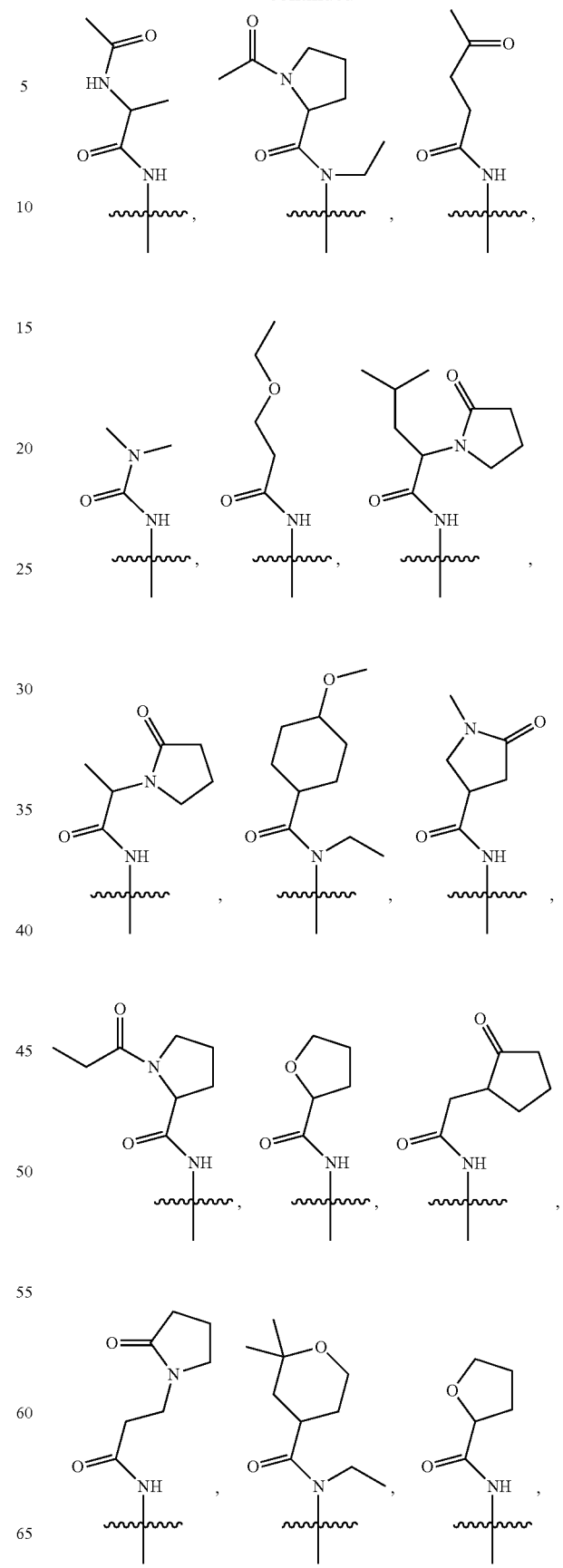

189
-continued
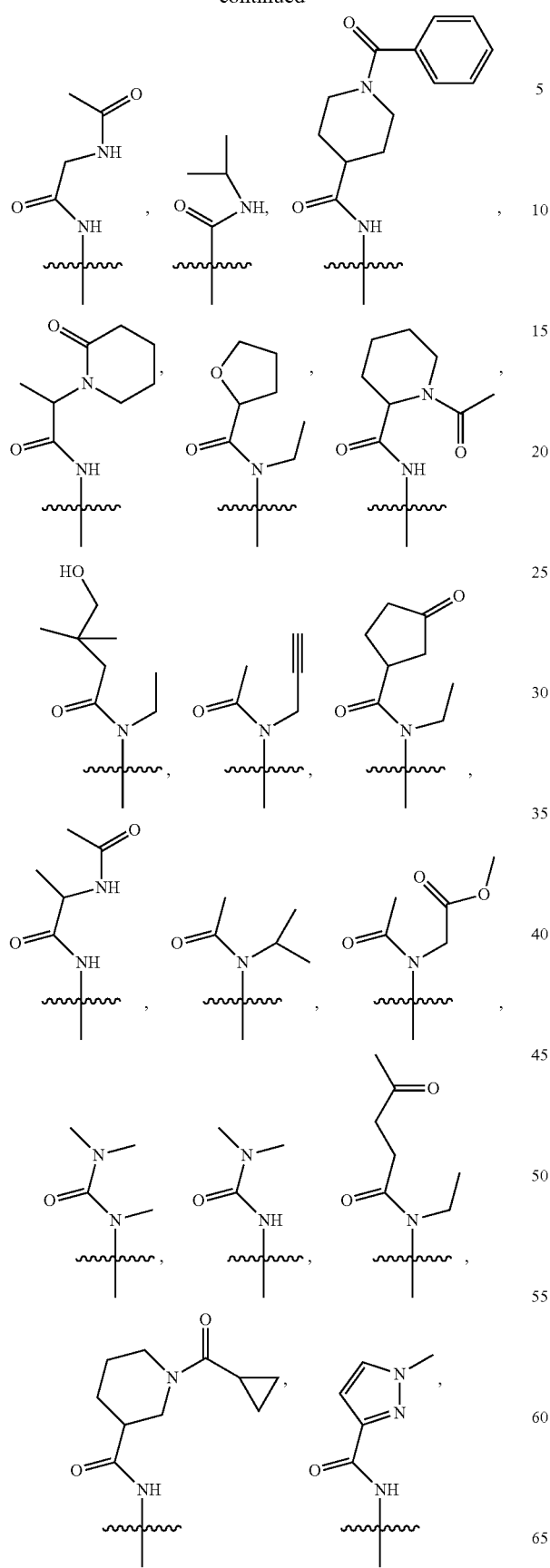
190
-continued
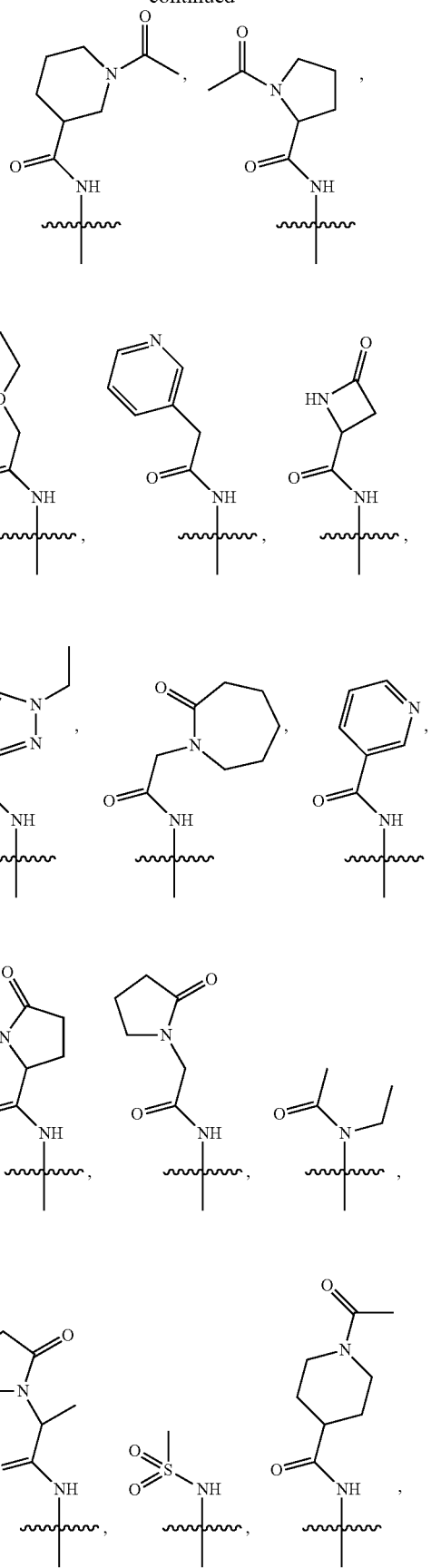

191
-continued
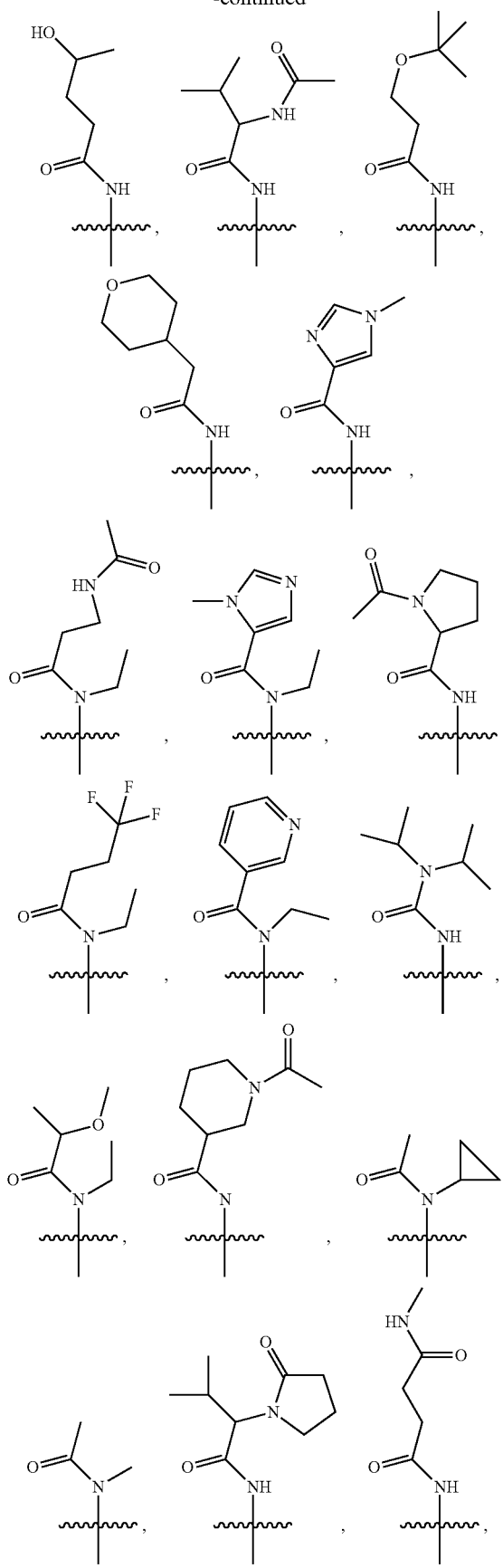
192
-continued
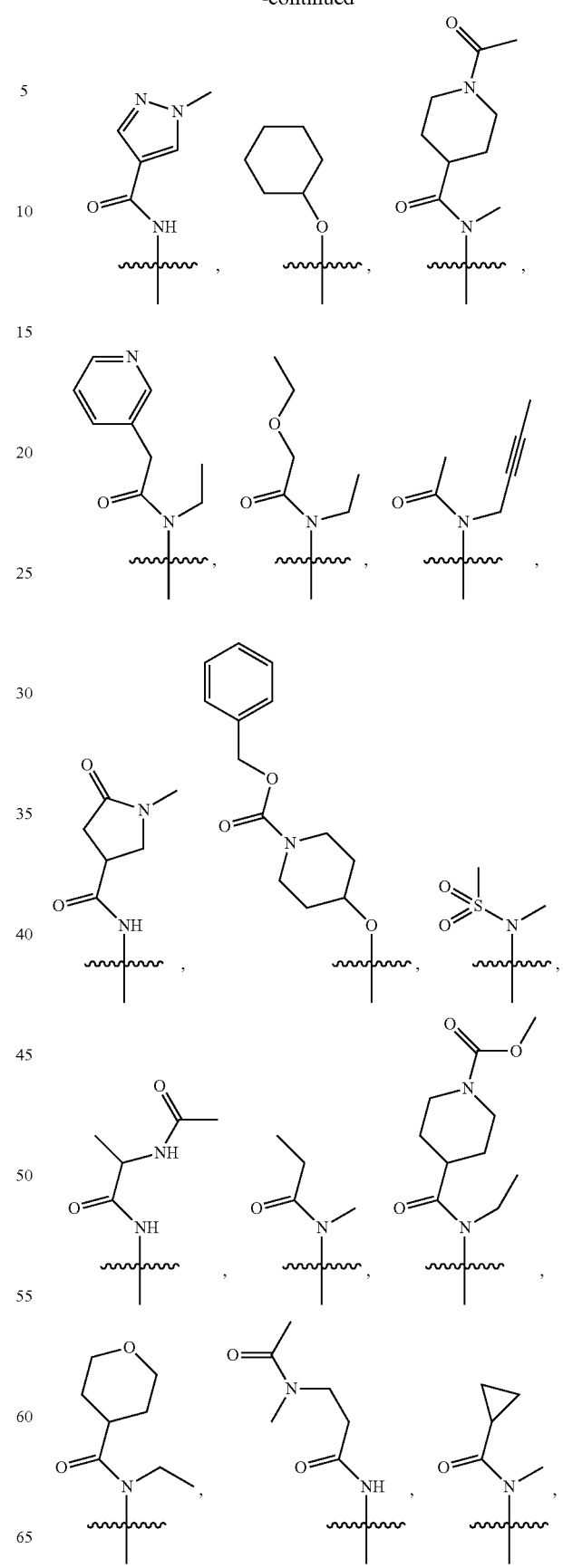

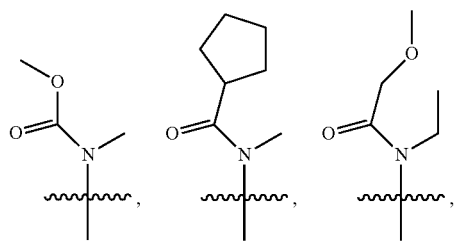
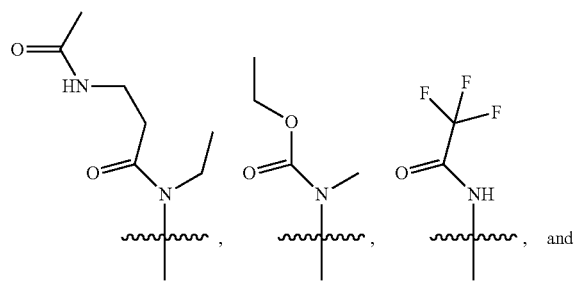
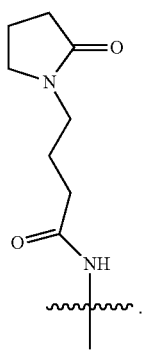
10. A method of modulating the activity of an $M_1$, $M_2$ or $M_4$ muscarinic receptor comprising the step of contacting said receptor with a compound selected from the group consisting of:
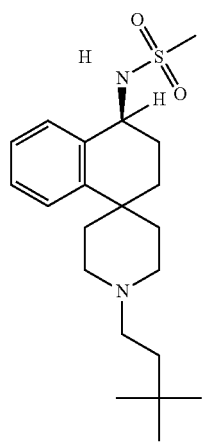
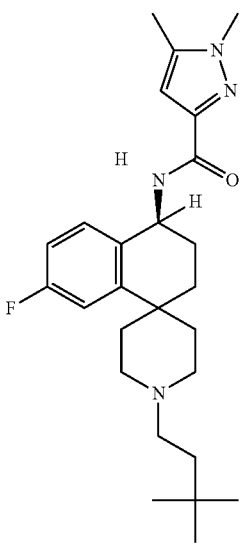
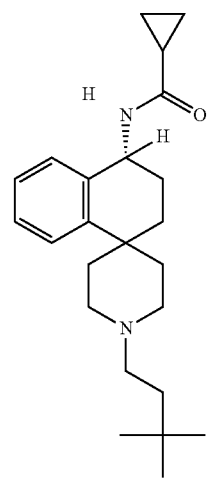
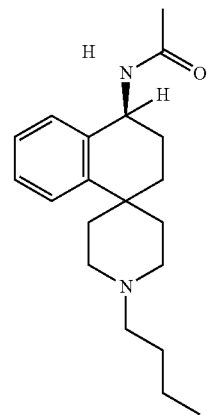

| 195 -continued | 196 -continued |
|---|---|
| 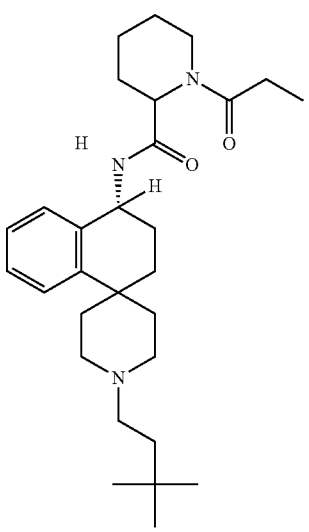 5 | 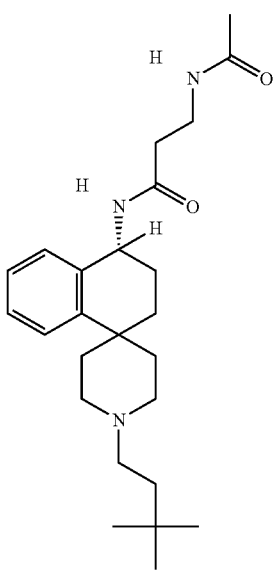 8 |
| 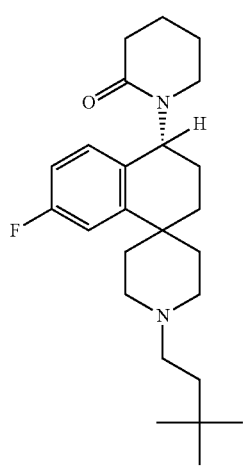 6 | 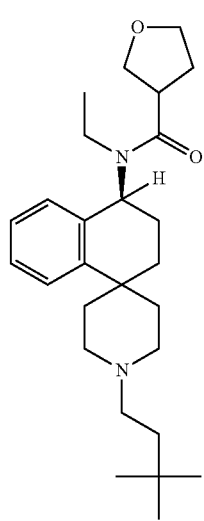 9 |
| 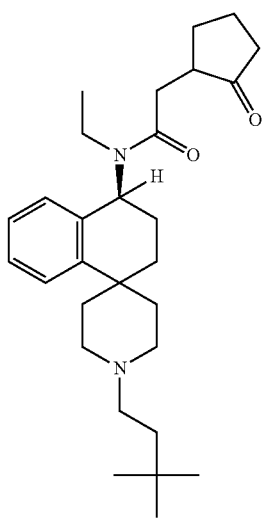 7 | 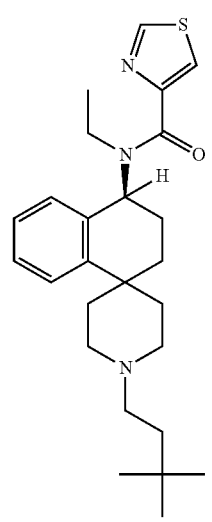 10 |

11
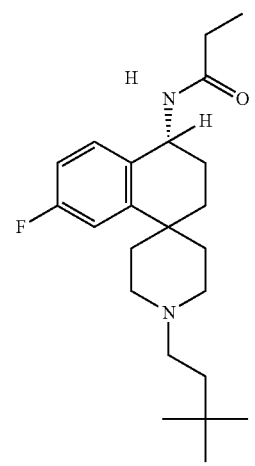
12
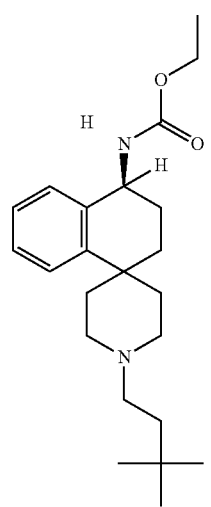
13
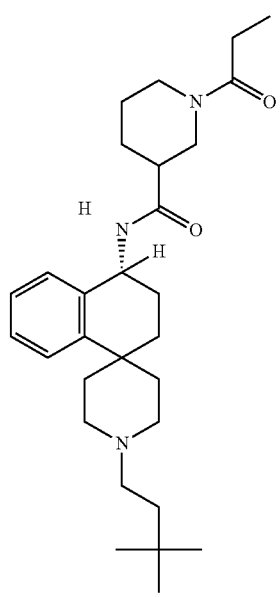
14
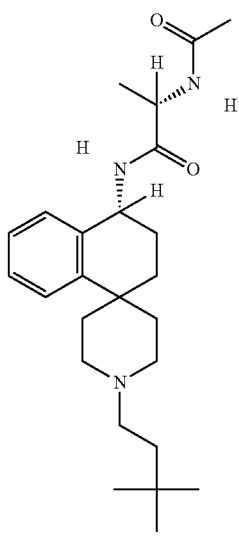
15
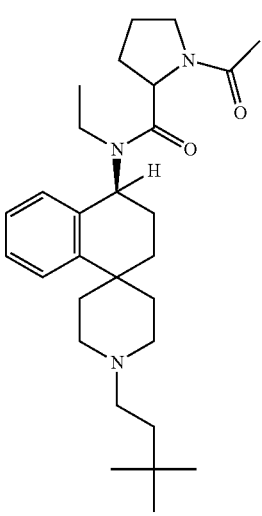
16
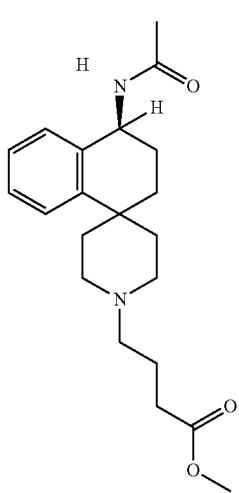

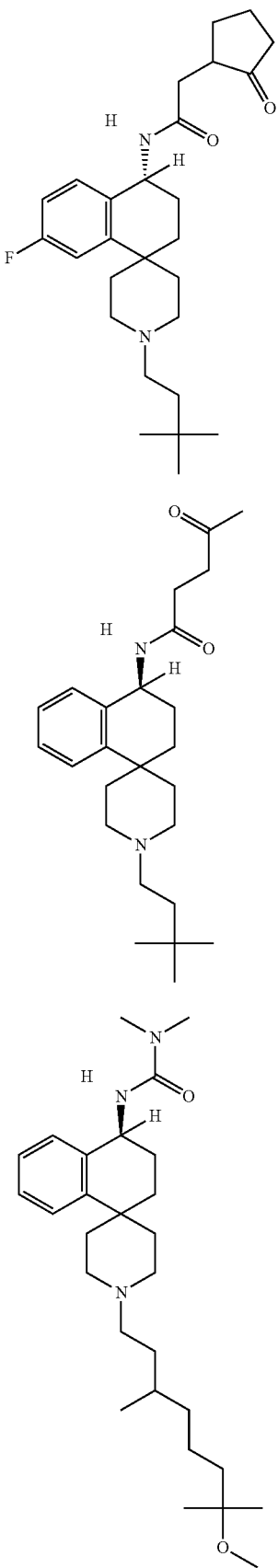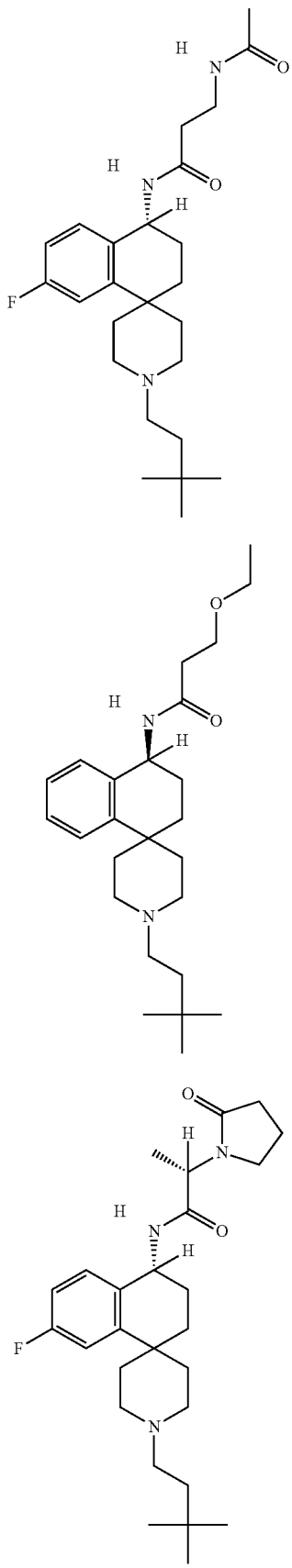

| 201 -continued | 202 -continued |
|---|---|
| 23 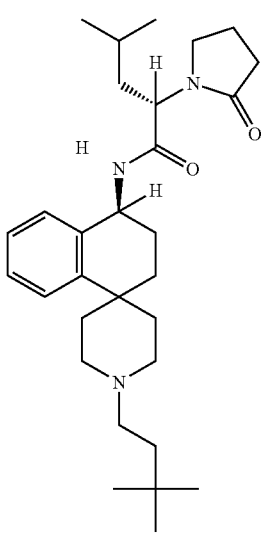 | 26 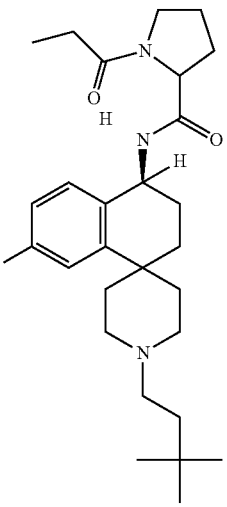 |
| 24 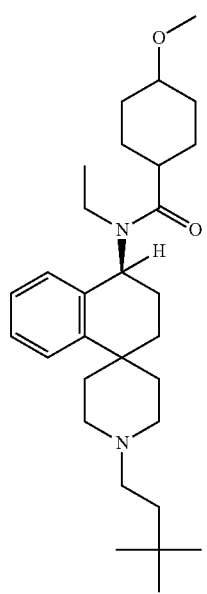 | 27 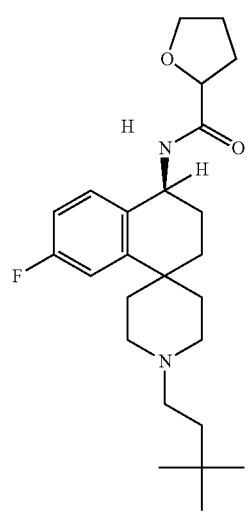 |
| 25 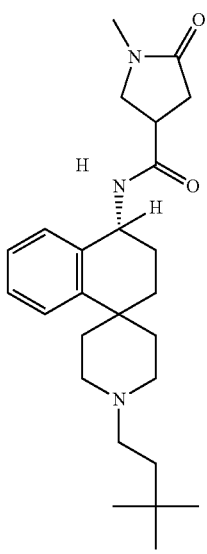 | 28 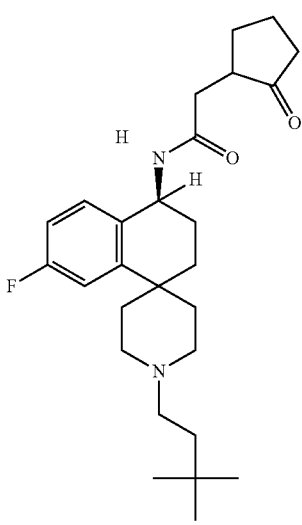 |

-continued
29
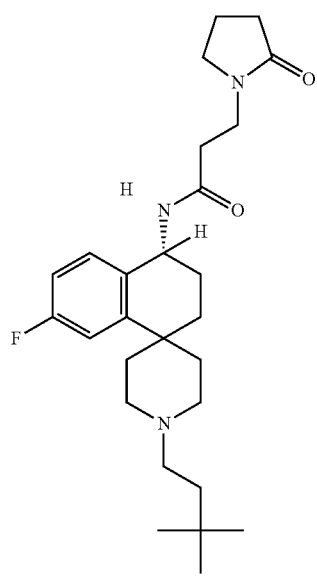
30
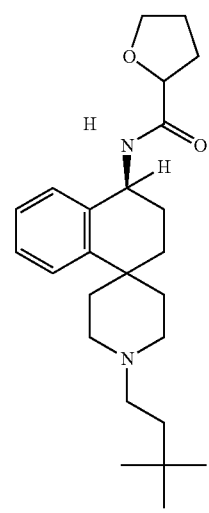
31
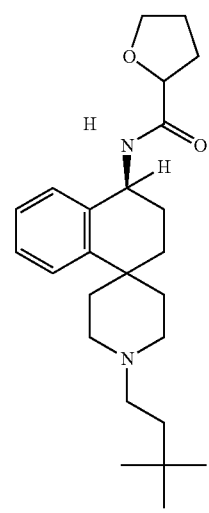
-continued
32
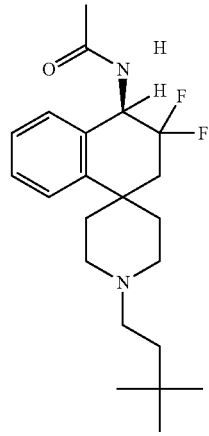
33
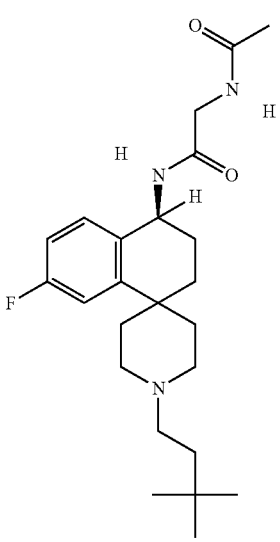
34
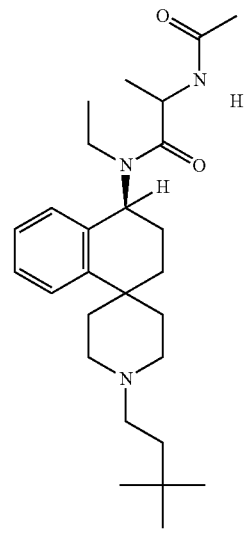

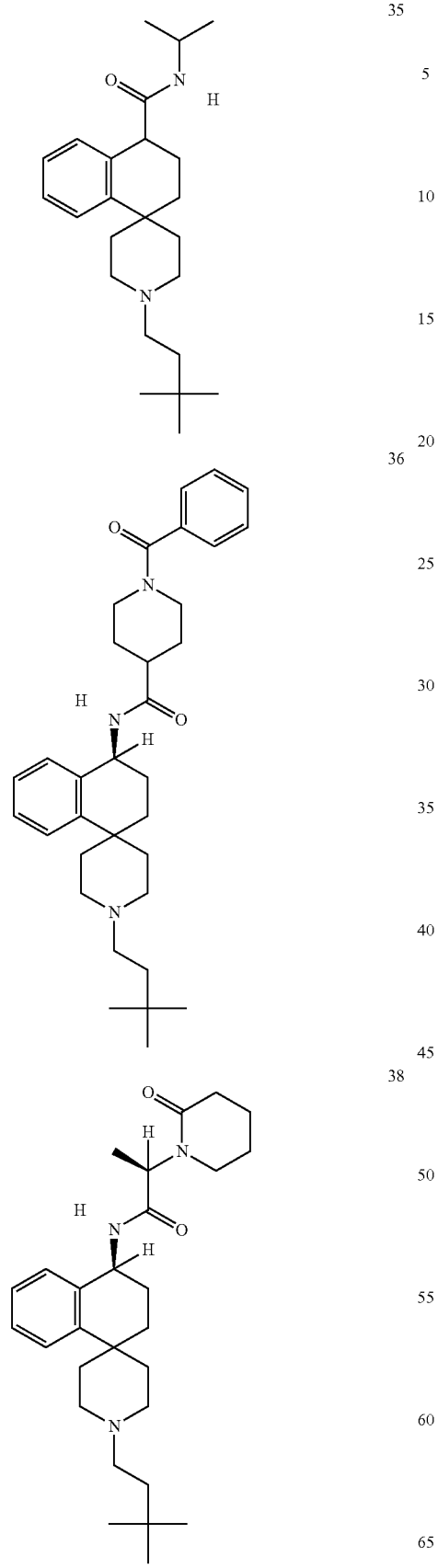
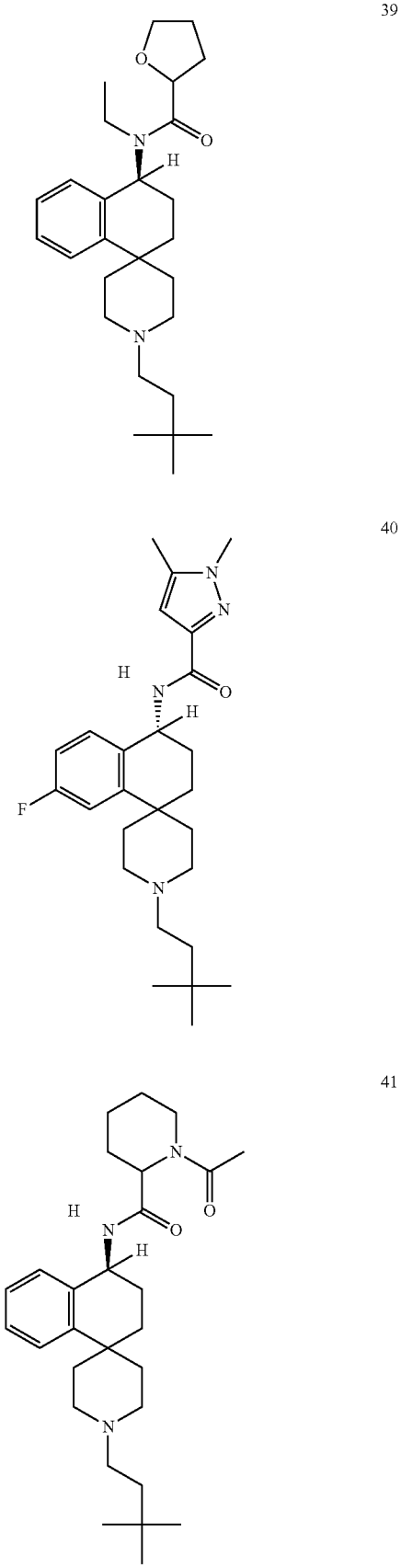

207
-continued
42
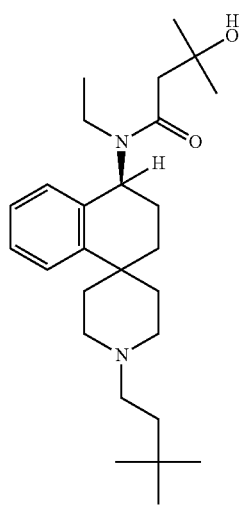
43
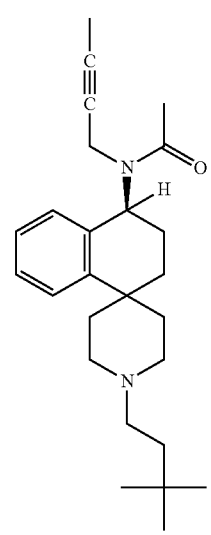
44
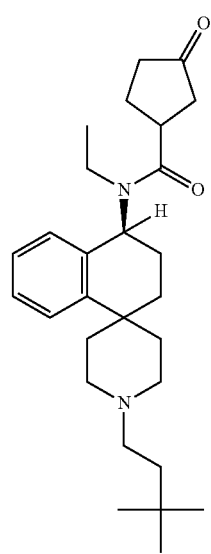
208
-continued
45
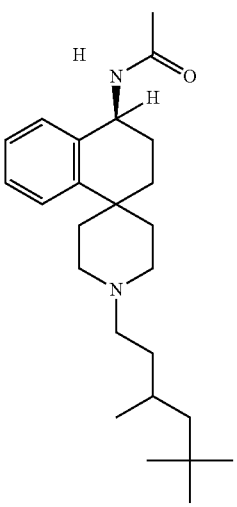
46
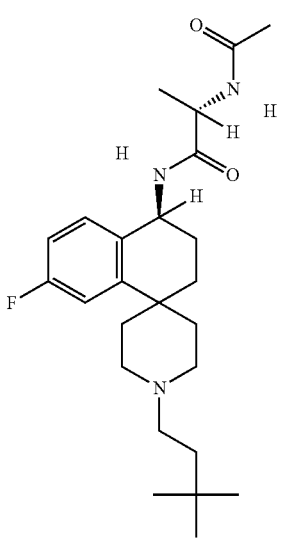
47
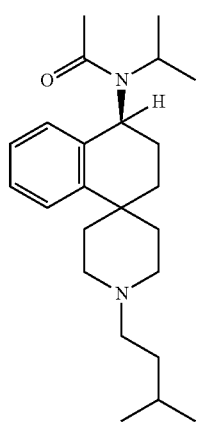

48
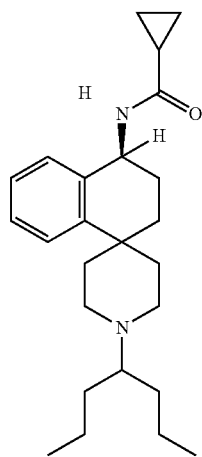
49
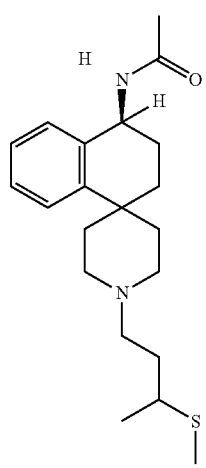
50
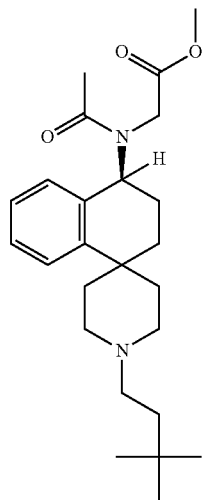
51
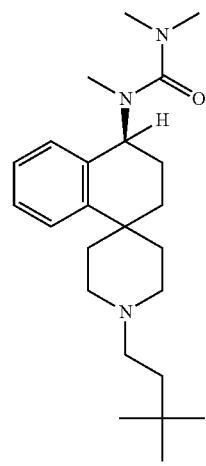
52
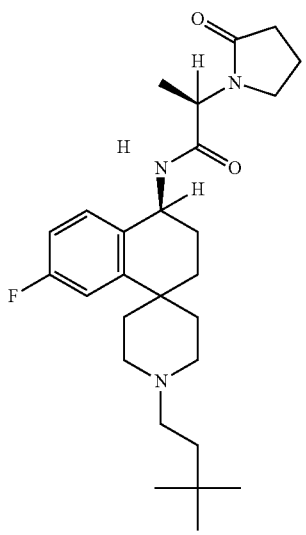
53
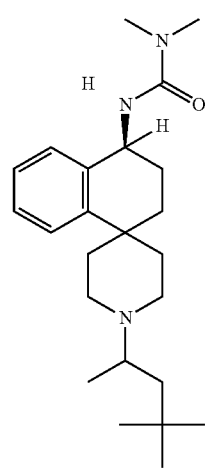

| 54 | 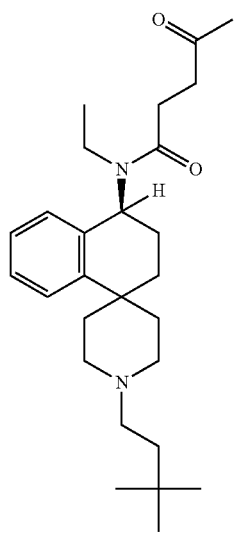 | 57 | 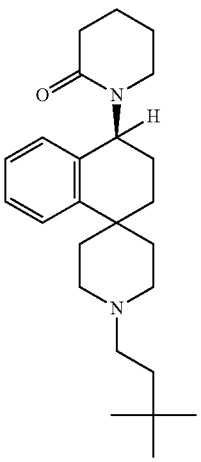 |
| --- | --- | --- | --- |
| 55 | 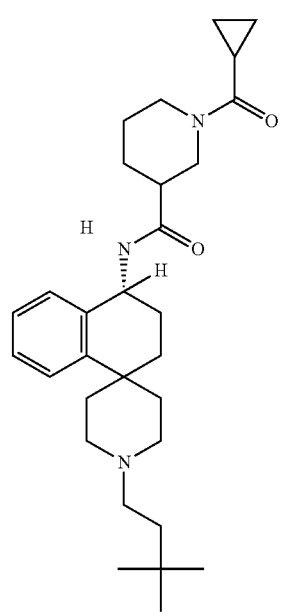 | 58 | 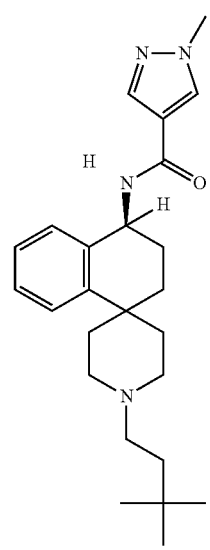 |
| 56 | 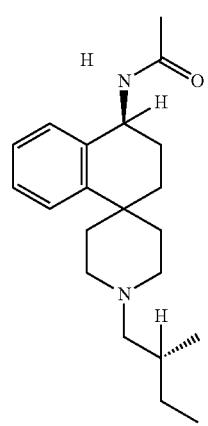 | 59 | 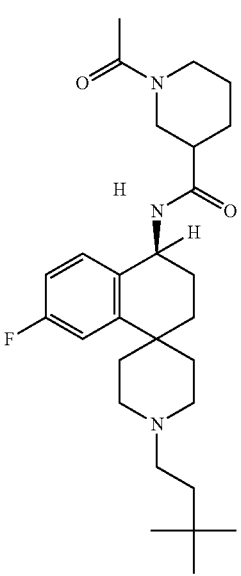 |

213
-continued
60
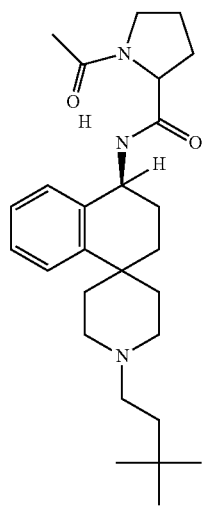
61
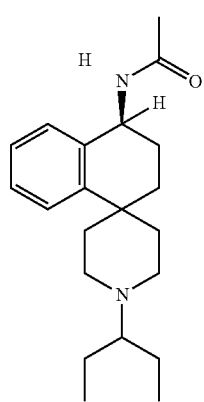
62
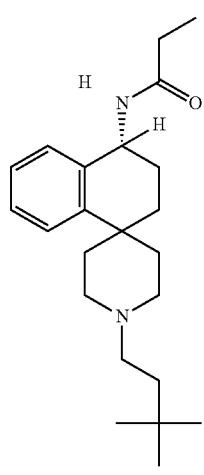
214
-continued
63
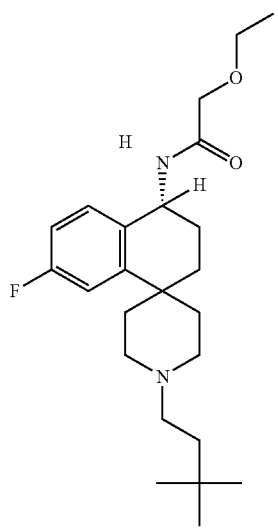
64
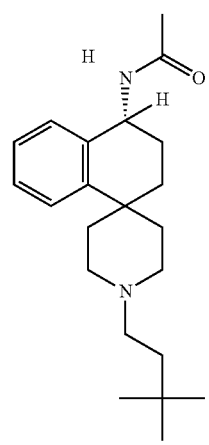
65
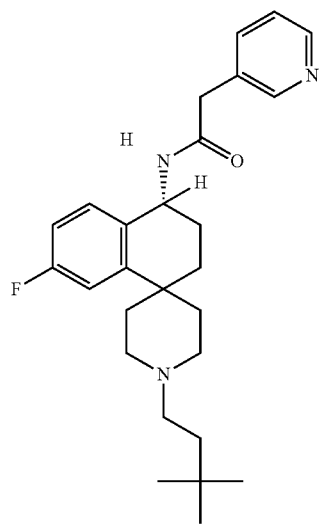

66
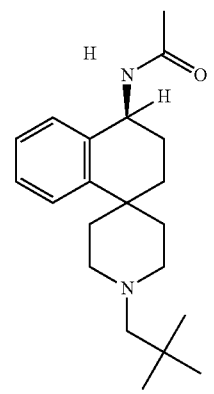
67
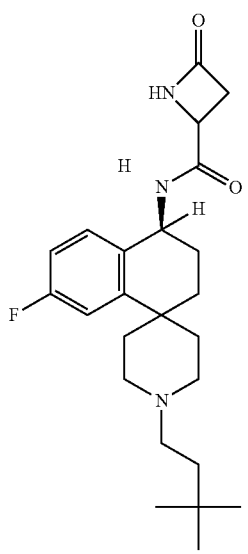
68
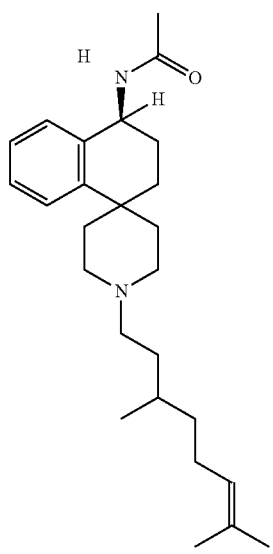
69
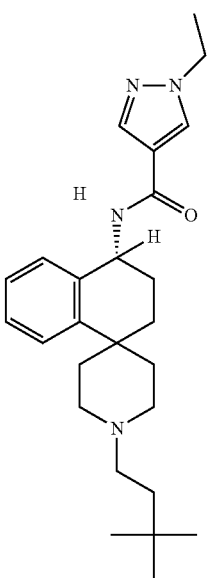
70
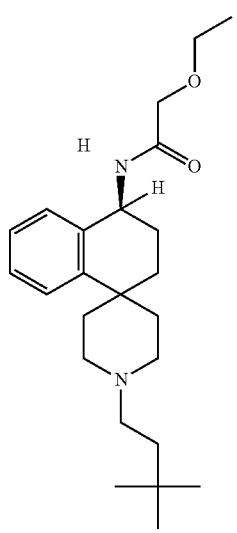
71

217
-continued
72
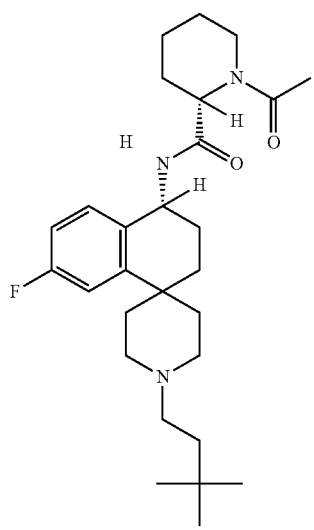
73
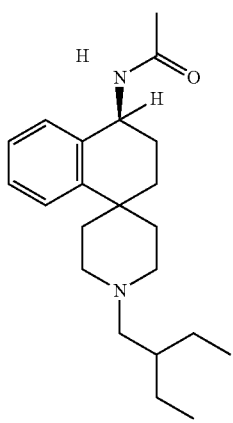
74
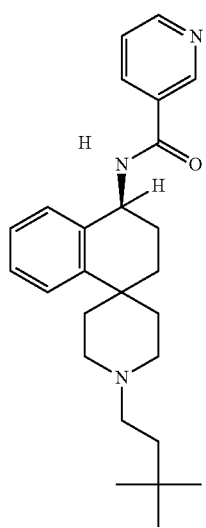
218
-continued
75
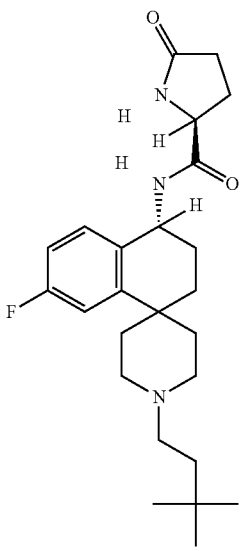
76
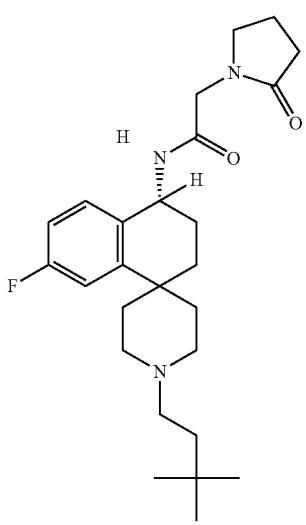
77
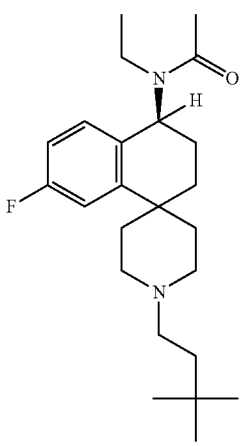

219
-continued
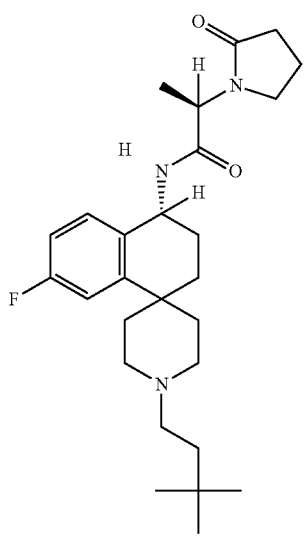
78
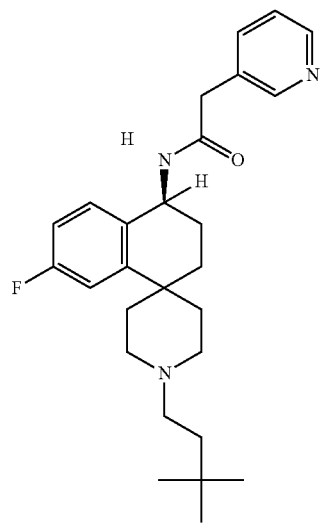
79
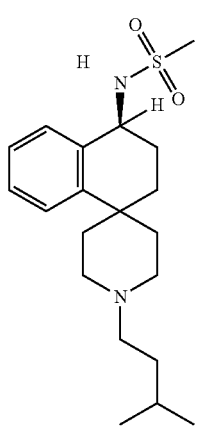
80
220
-continued
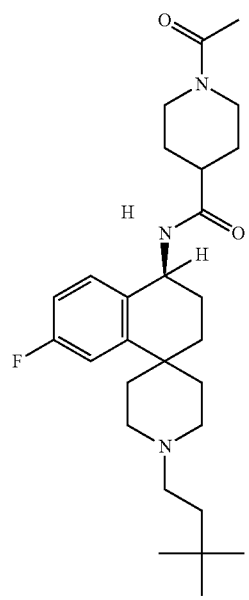
81
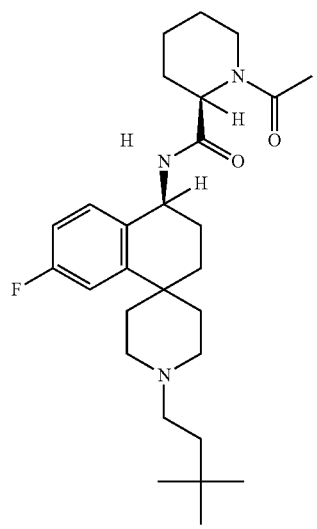
82
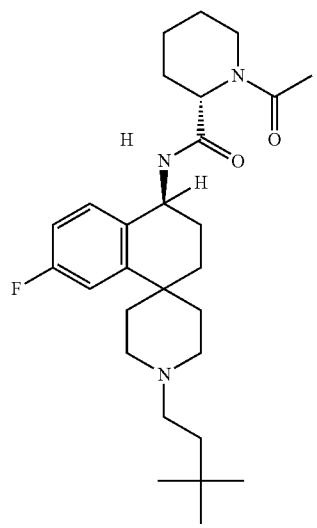
83

221
-continued
84
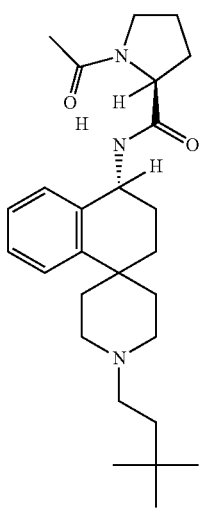
85
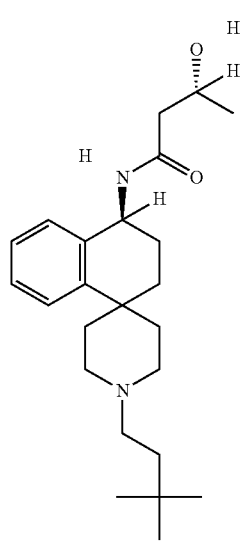
86
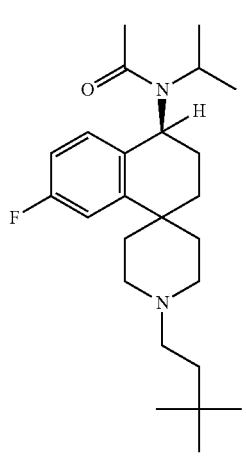
222
-continued
87
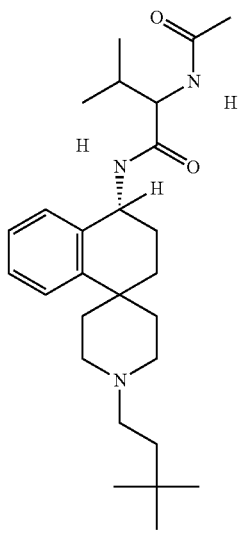
88
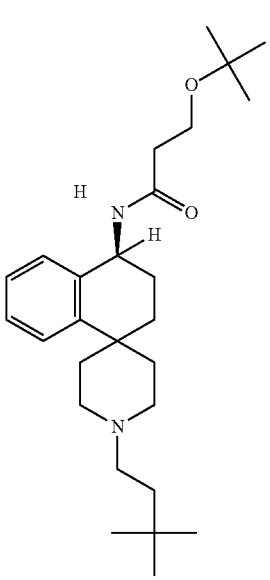
90
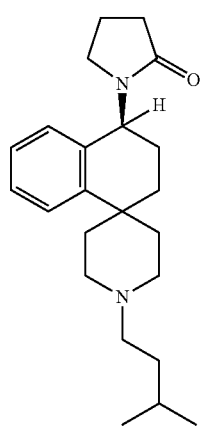

91 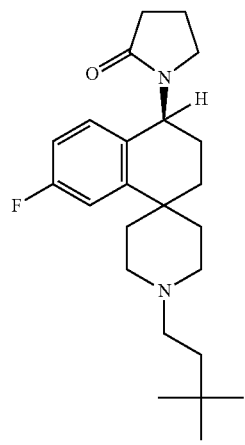
92 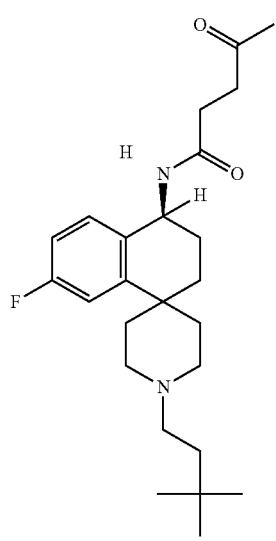
93 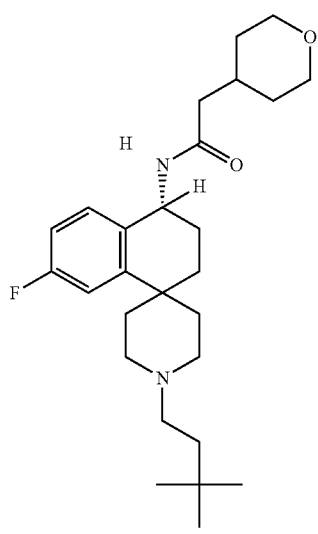
94 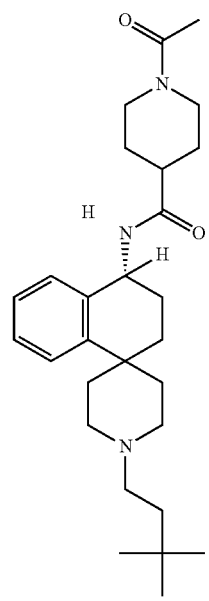
95 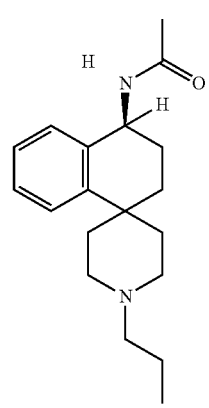
96 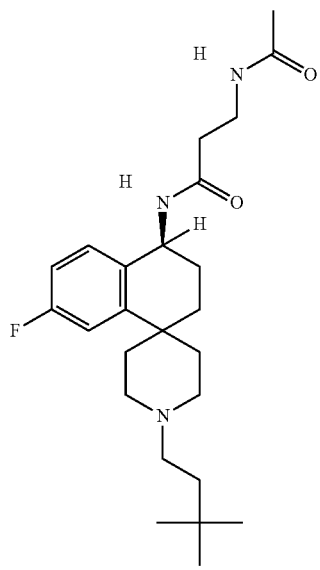

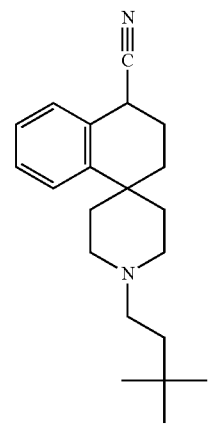
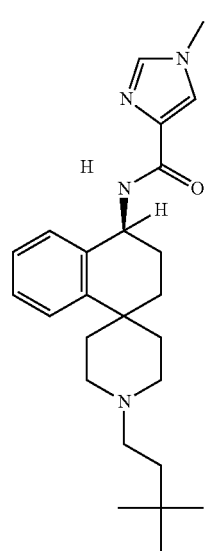
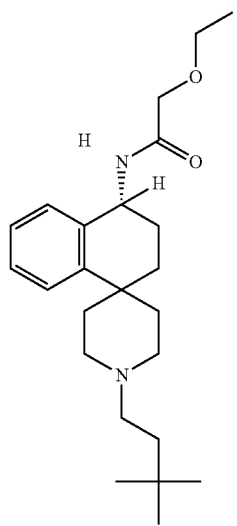
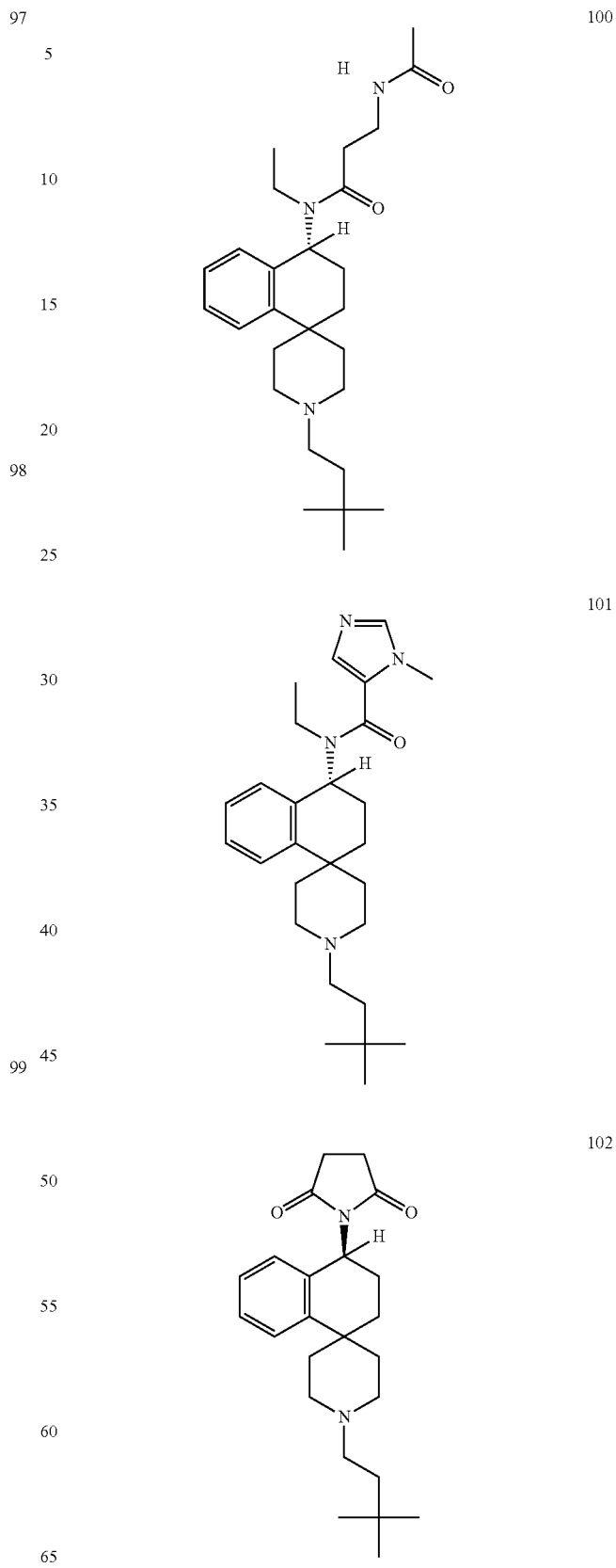

| 103 | 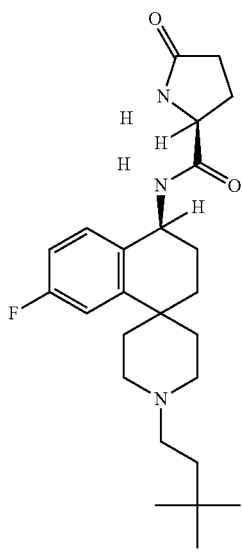 | 106 | 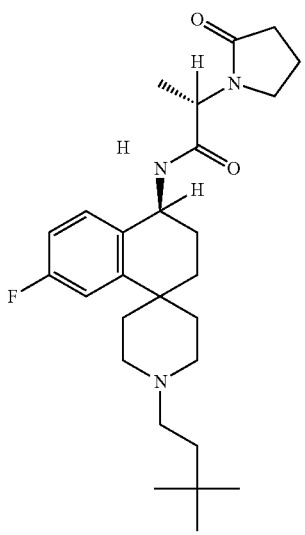 |
| --- | --- | --- | --- |
| 104 | 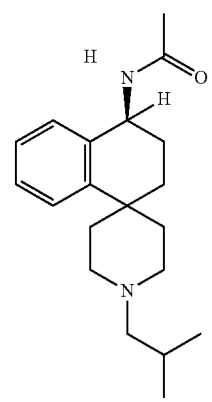 | 107 | 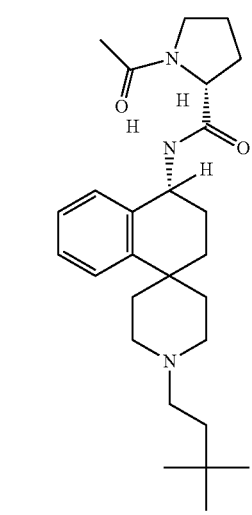 |
| 105 | 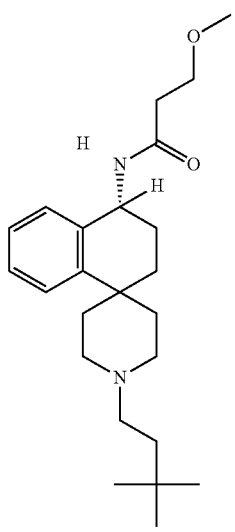 | 108 | 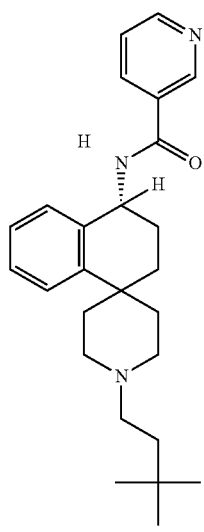 |

109
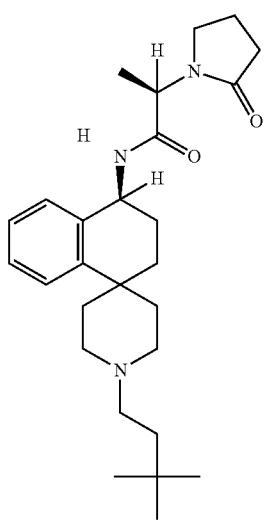
110
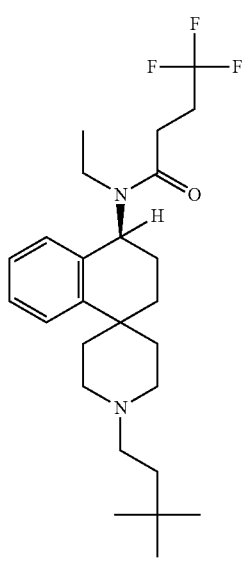
111
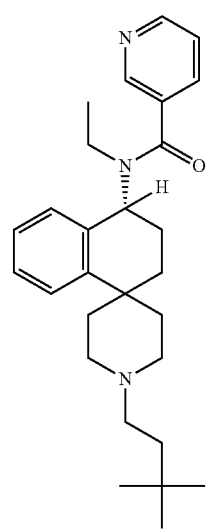
112
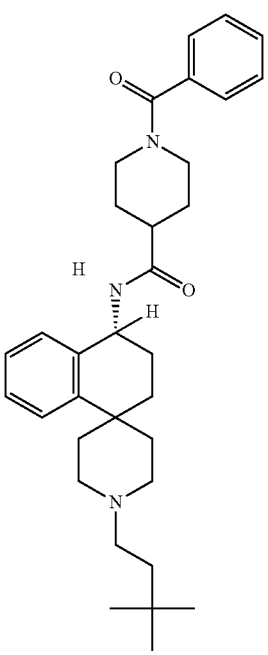
113
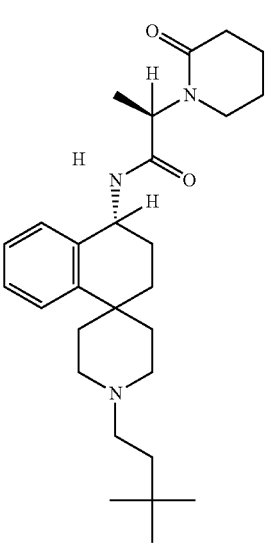
114
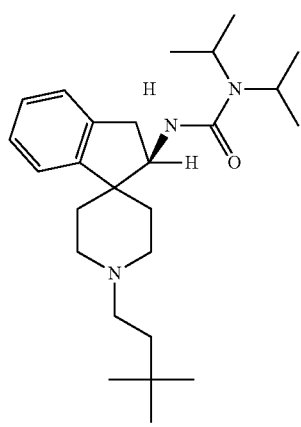

231
-continued
115
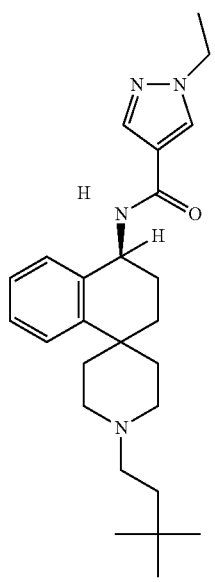
116
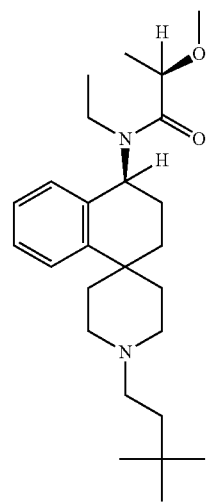
117
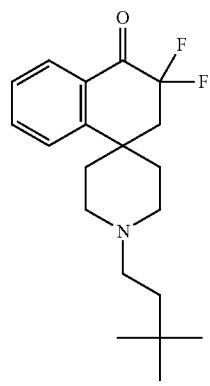
232
-continued
118
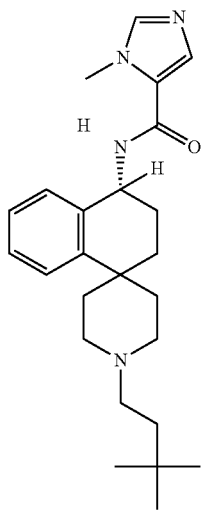
119
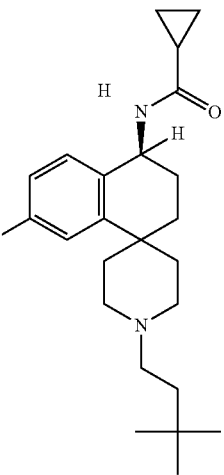
120
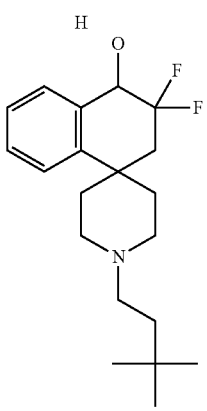

| 121 | 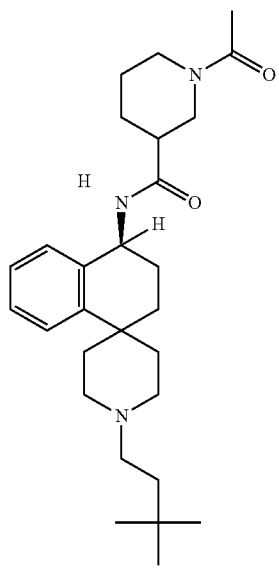 | 124 | 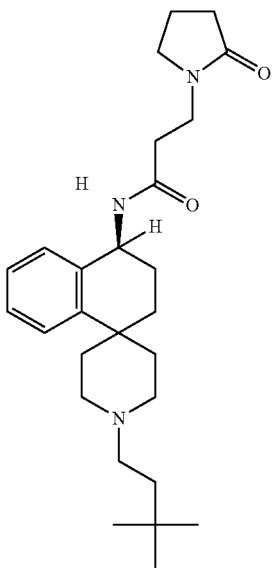 |
| 122 | 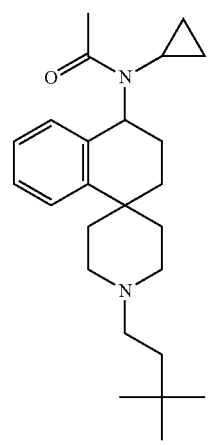 | 125 | 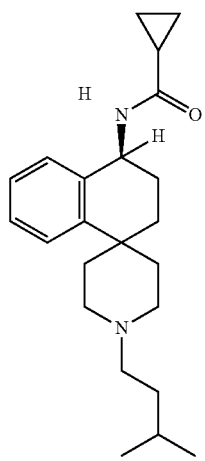 |
| 123 | 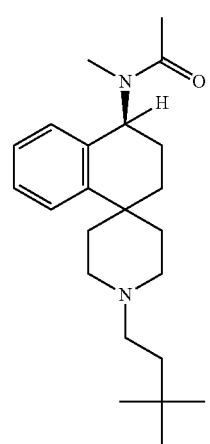 | 126 | 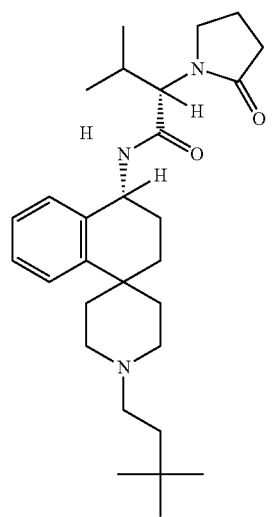 |

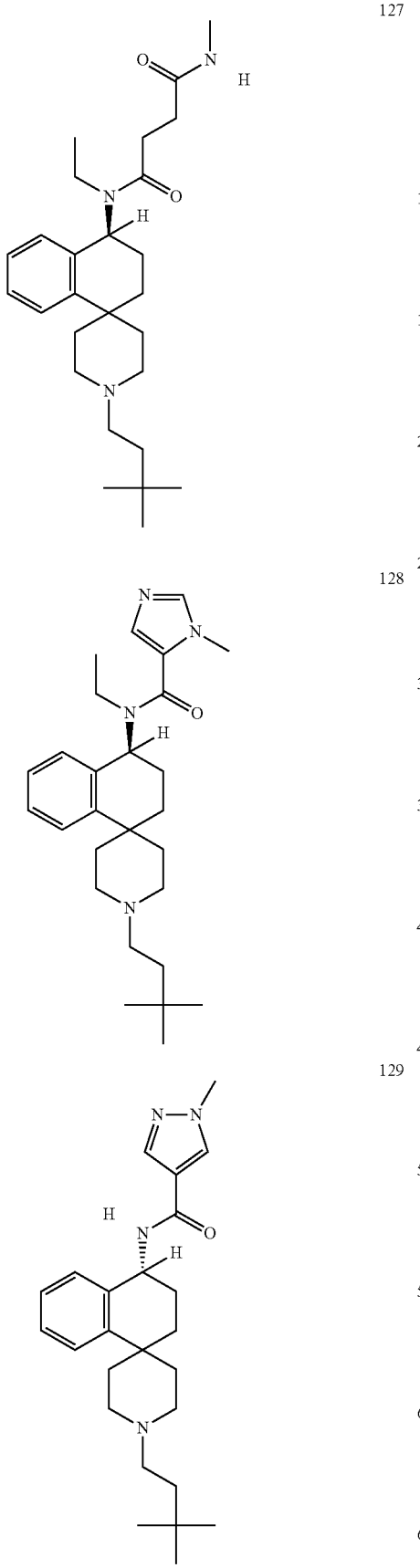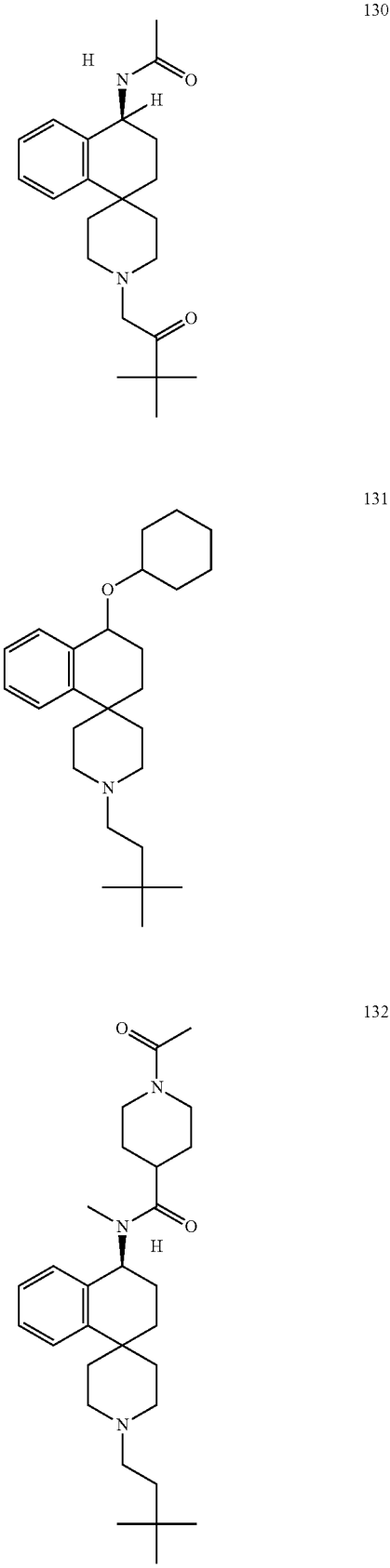

-continued
139
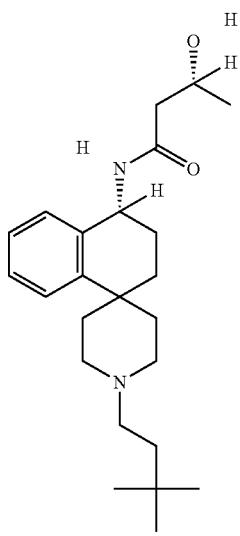
140
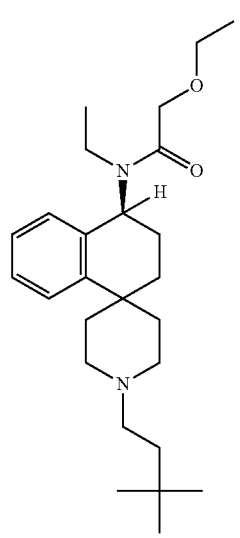
141
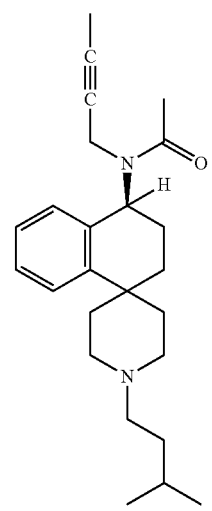
-continued
142
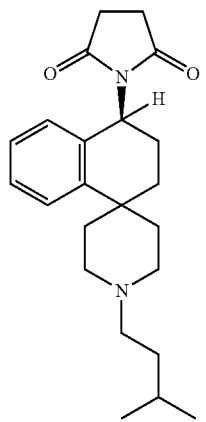
143
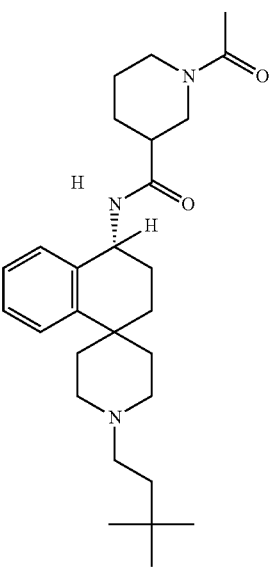
144
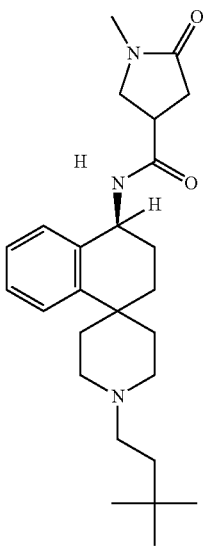

| 145 | 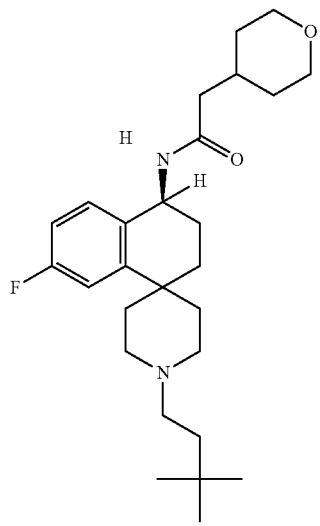 | 148 | 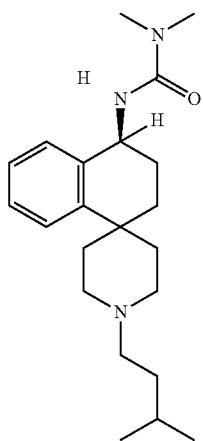 |
| 146 | 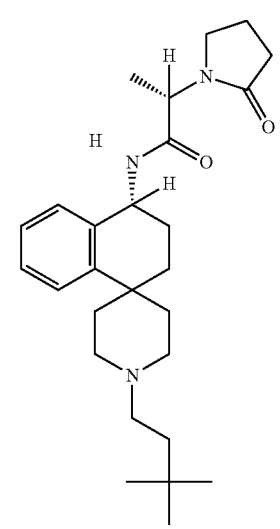 | 149 | 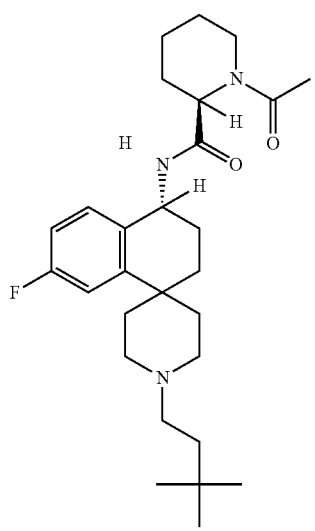 |
| 147 | 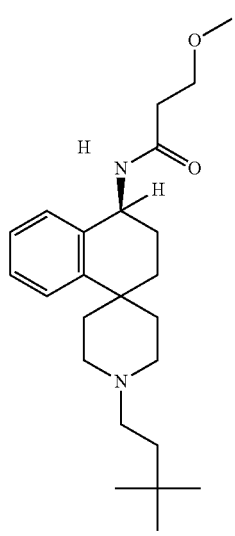 | 150 | 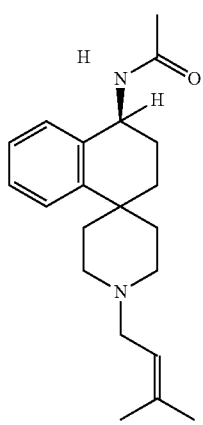 |

151 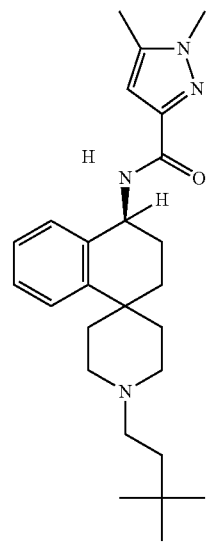
152 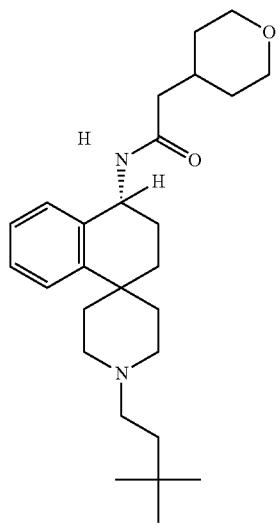
153 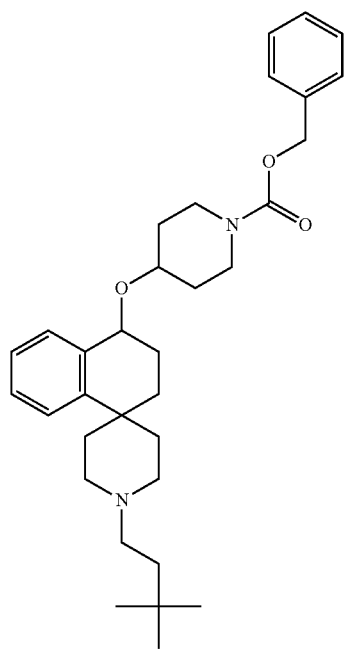
154 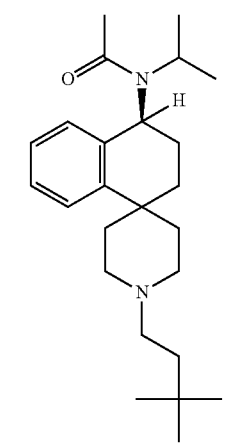
155 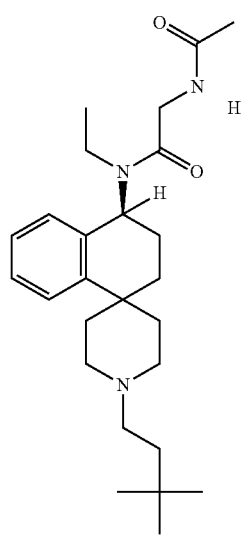

156 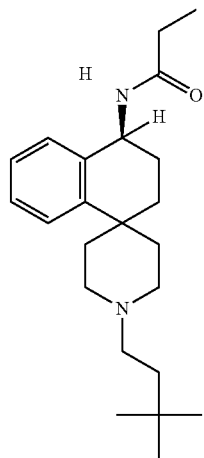
157 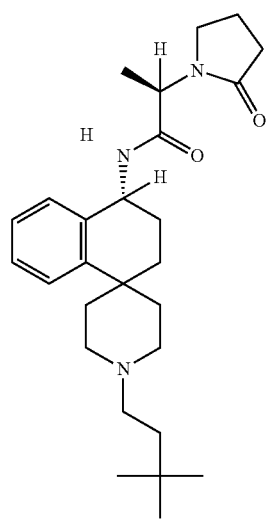
158 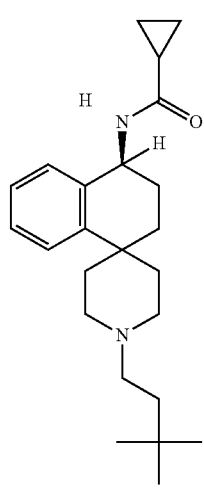
159 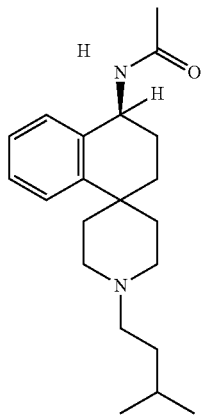
160 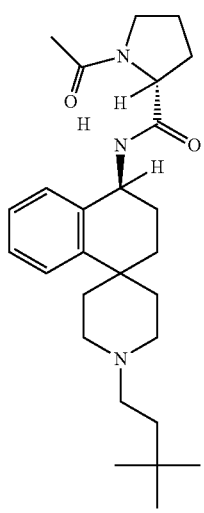
161 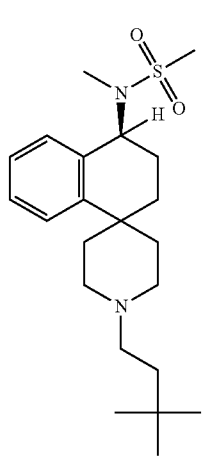

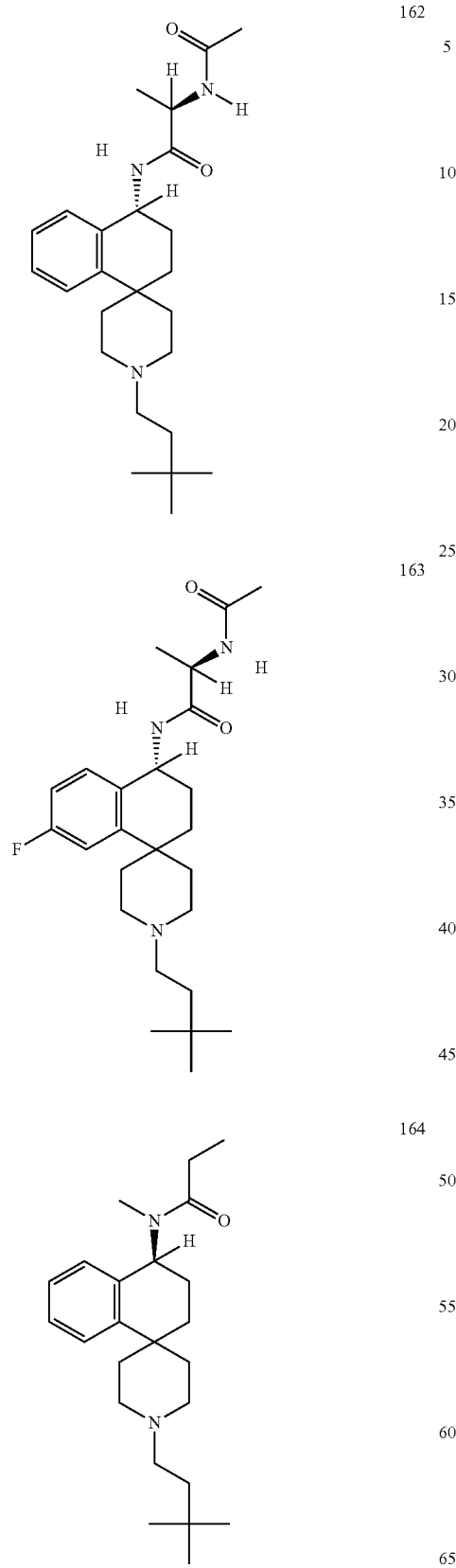
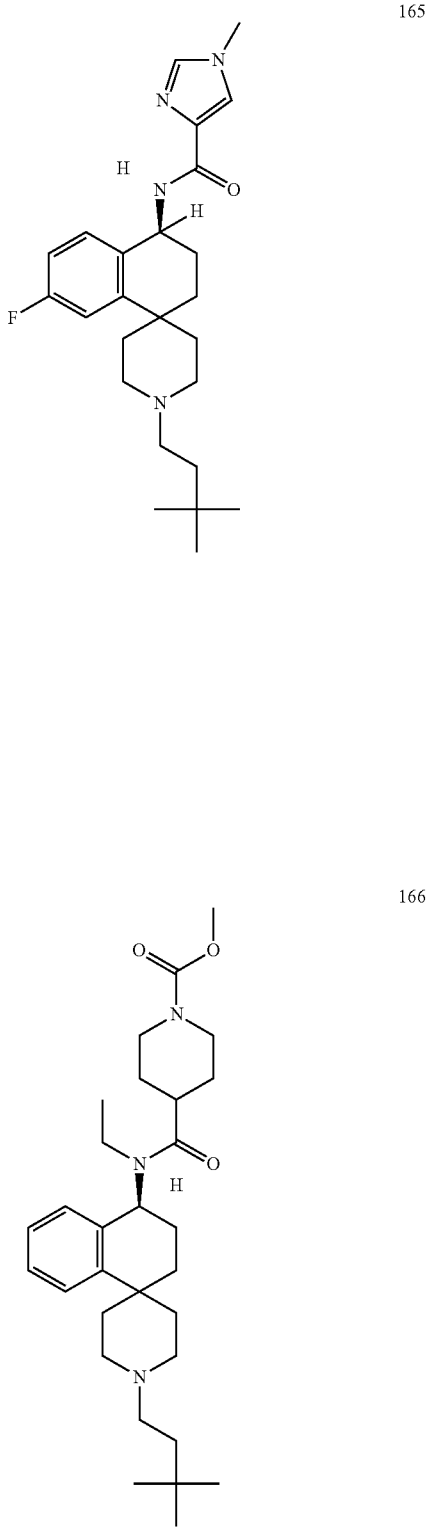

249
-continued
167
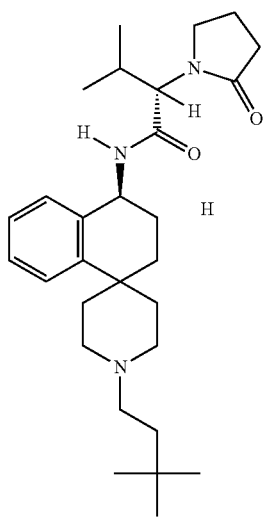
168
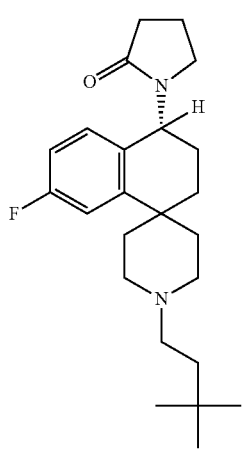
169
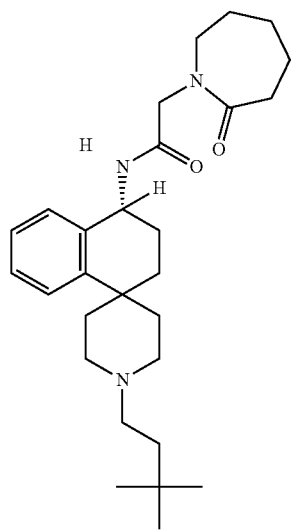
250
-continued
170
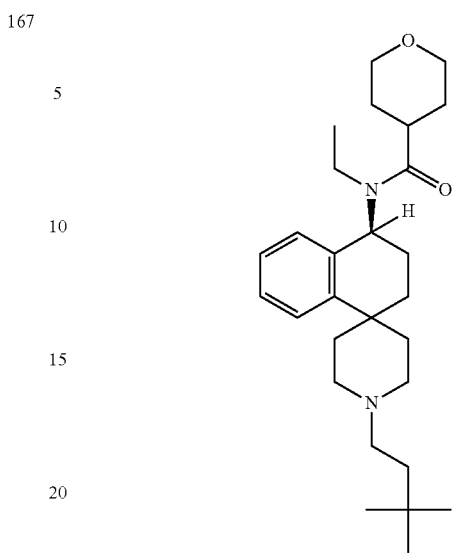
171
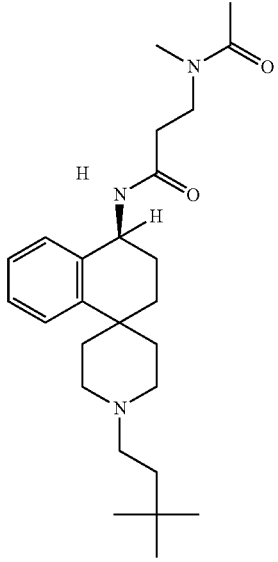
172
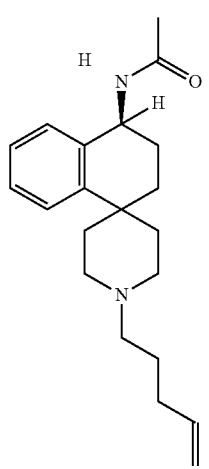

251 252
173 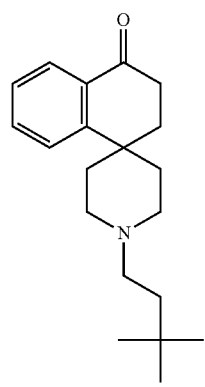
174 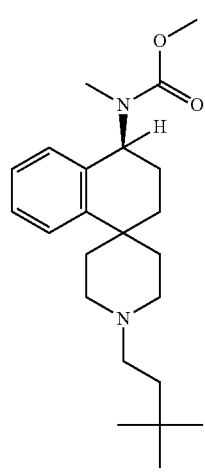
175 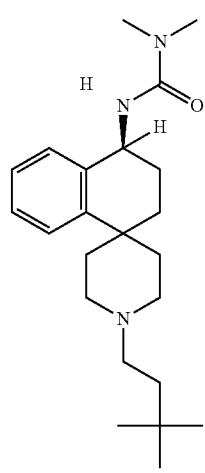
176 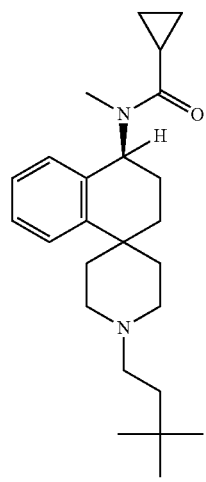
177 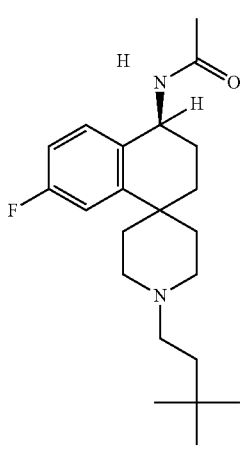
178 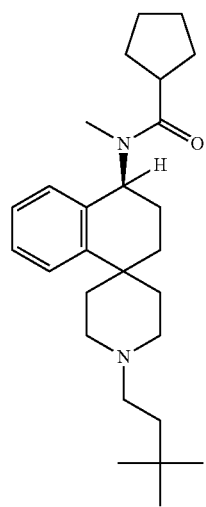

253
-continued
179
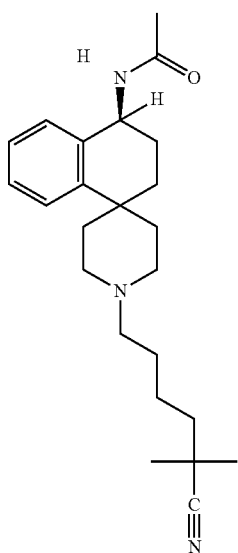
180
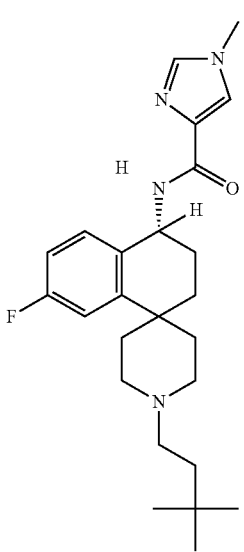
181
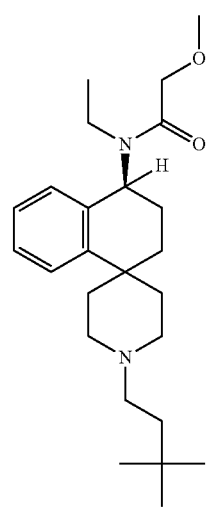
254
-continued
182
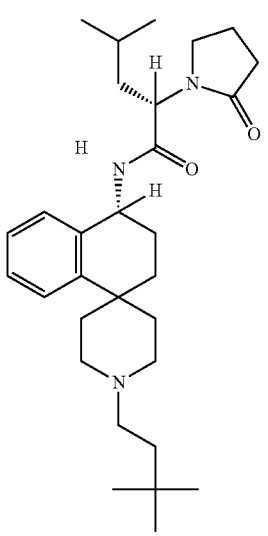
183
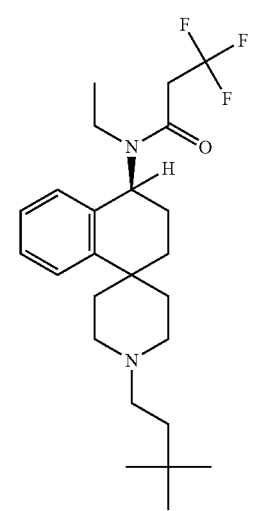
184
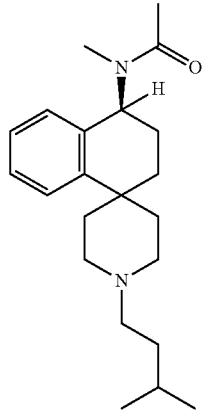

185
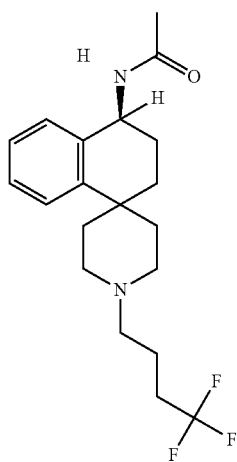
186
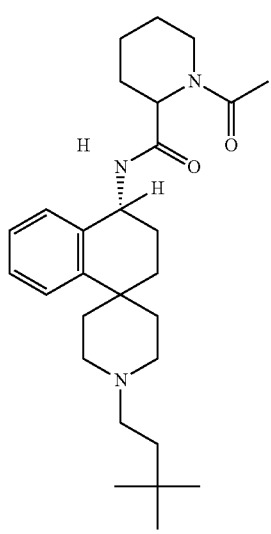
187
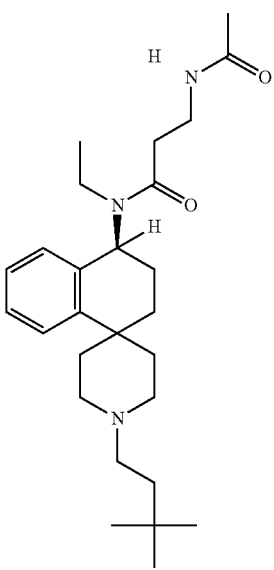
188
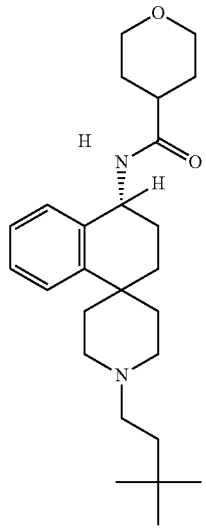
189
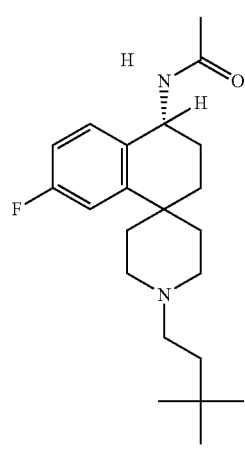
190
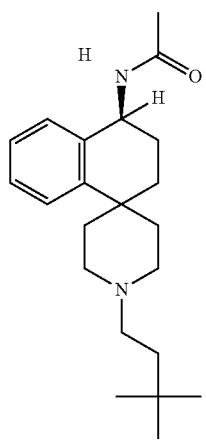

257
-continued
| | |
|---|---|
| 191 | 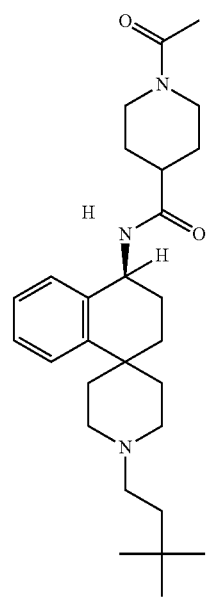 |
| 192 | 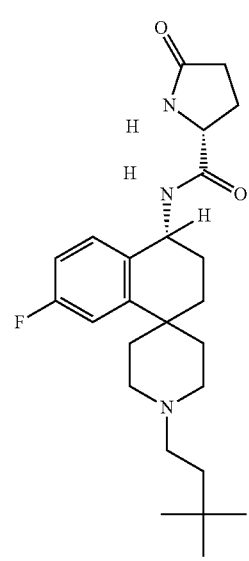 |
| 193 | 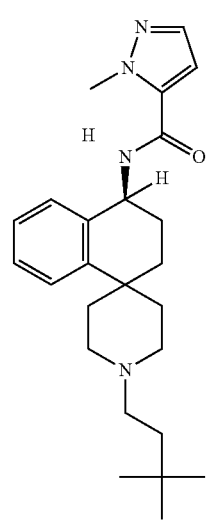 |
258
-continued
| | |
|---|---|
| 194 | 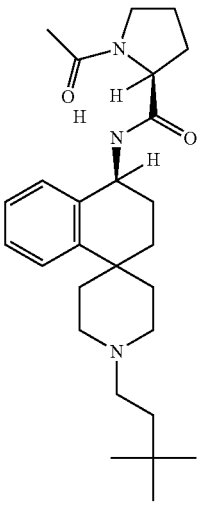 |
| 195 | 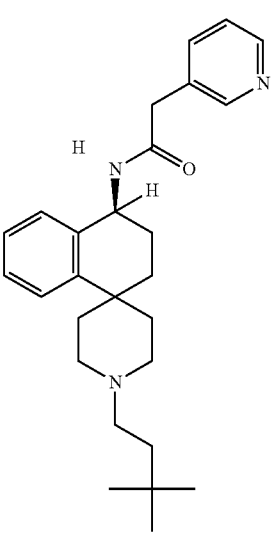 |
| 196 | 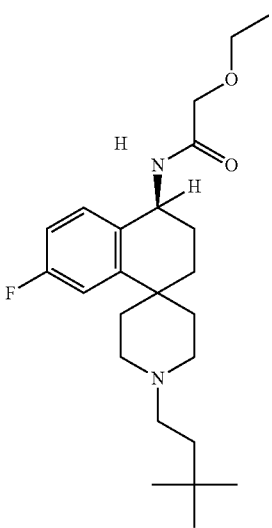 |

259
-continued
197
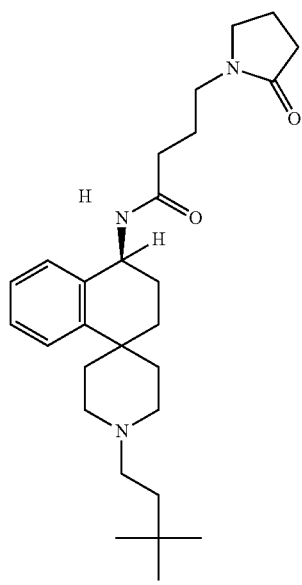
198
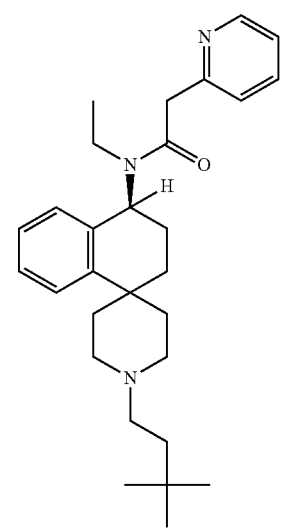
199
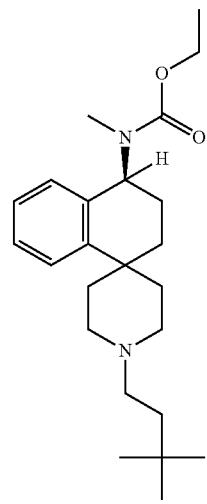
260
-continued
200
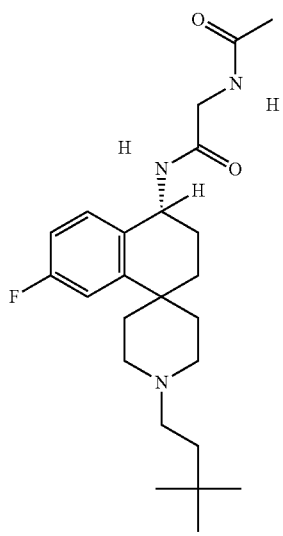
201
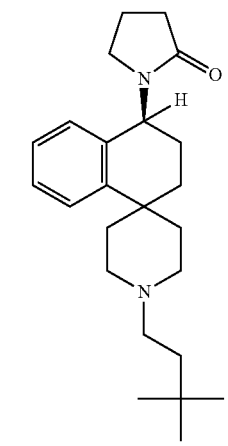
202
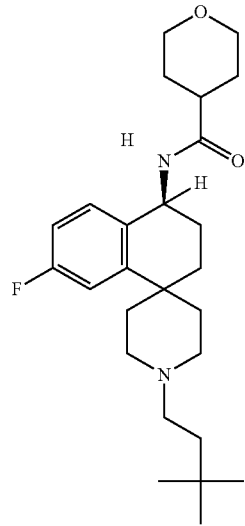

203
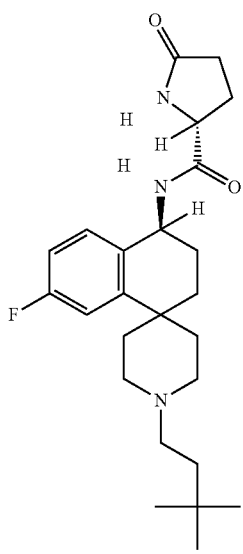
204
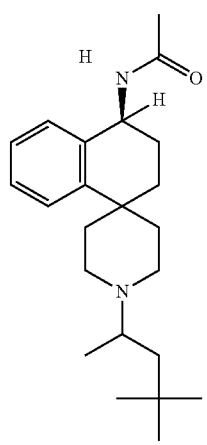
205
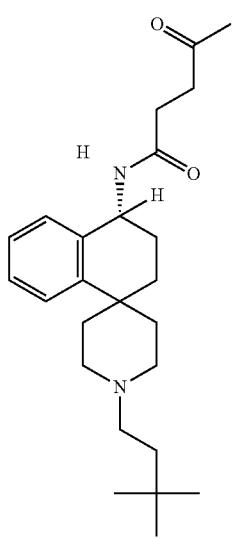
206
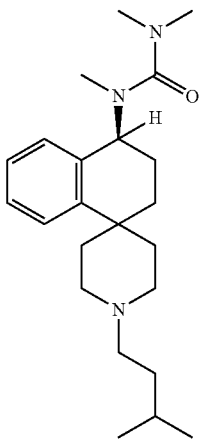
207
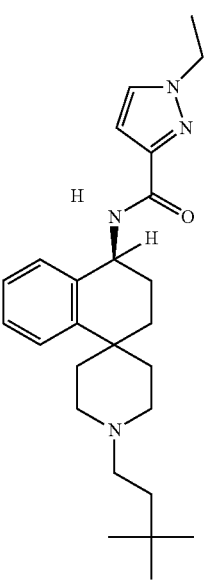
208

209
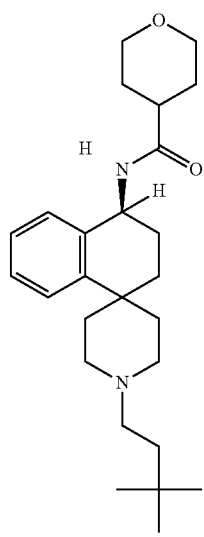
210
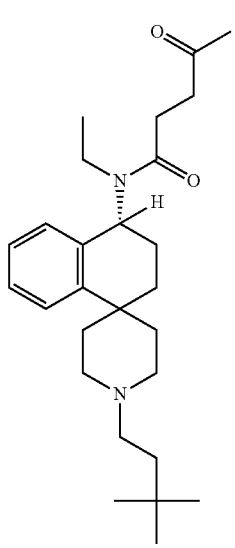
211
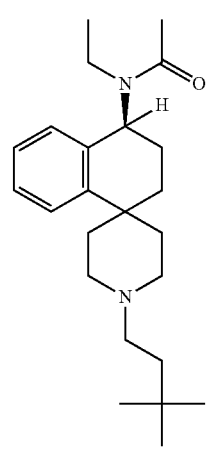
212
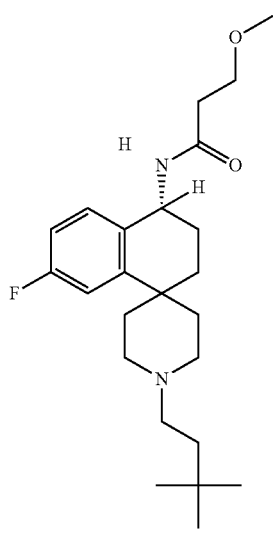
213
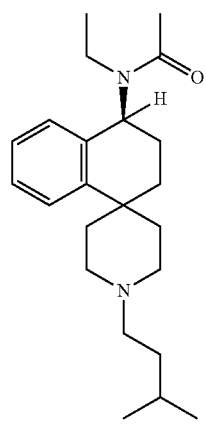
214
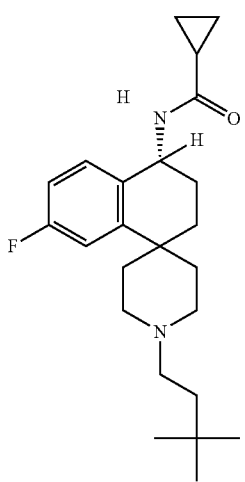

215
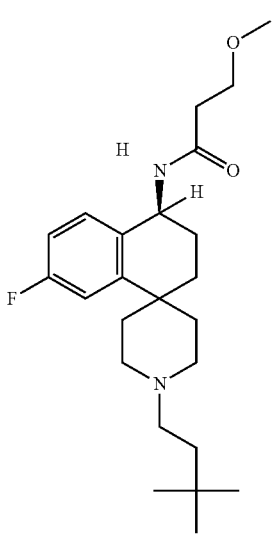
216
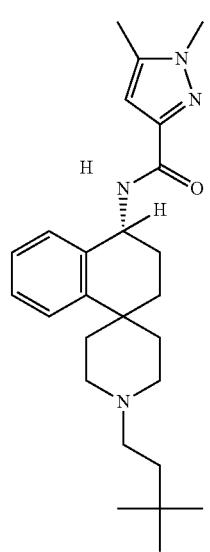
217
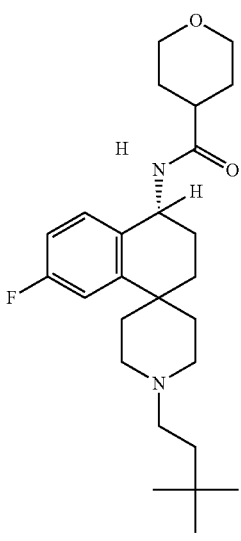
218
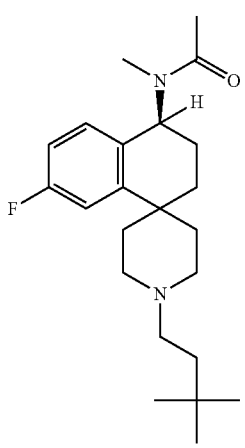
219
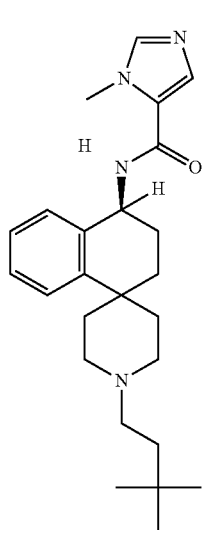
220
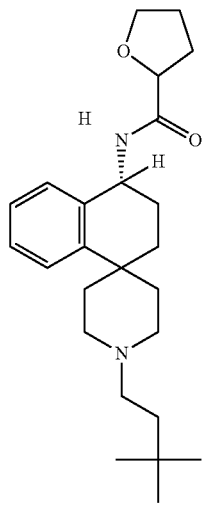

221 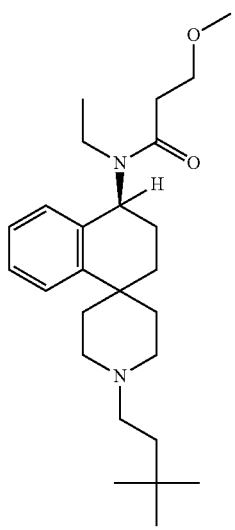
224 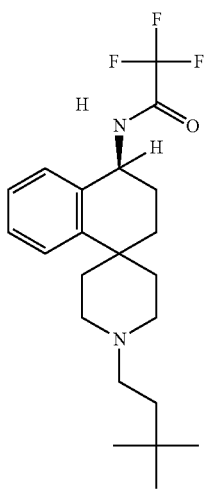
222 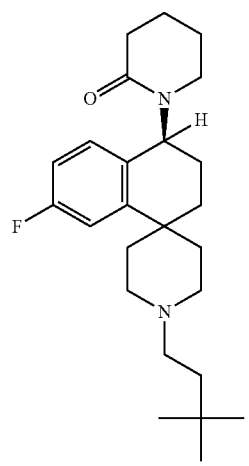
225 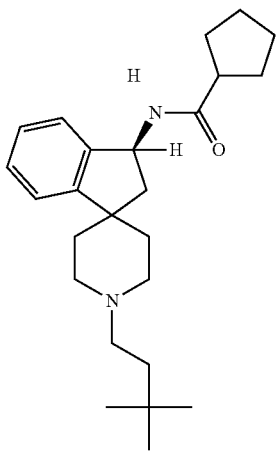
223 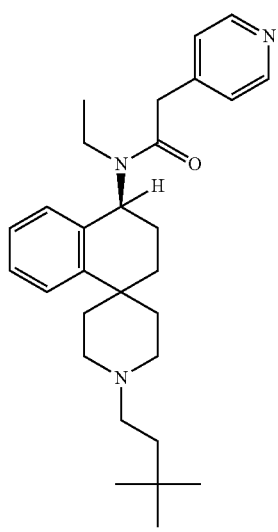
226

227 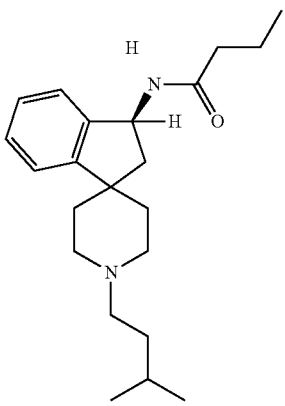
228 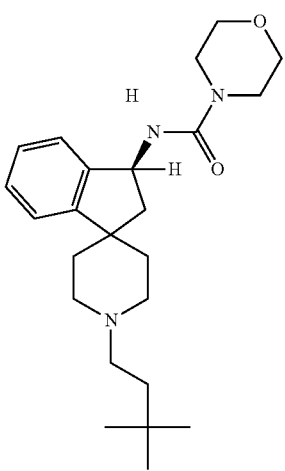
229 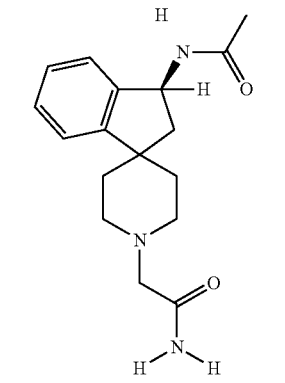
230 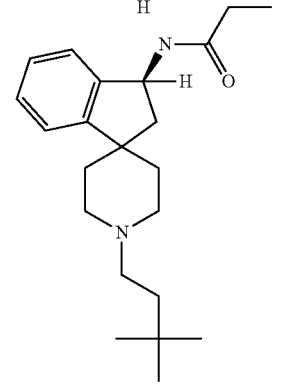
231 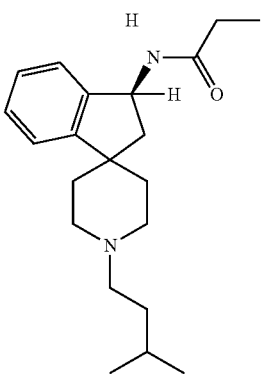
233 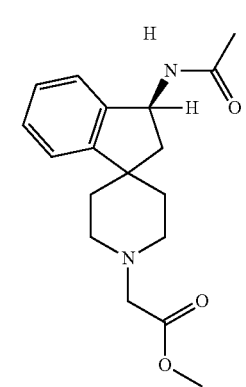
235 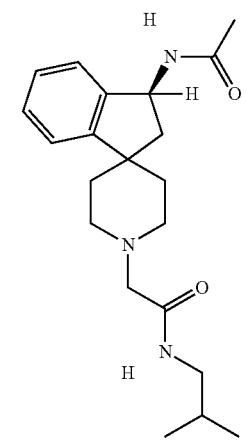
236 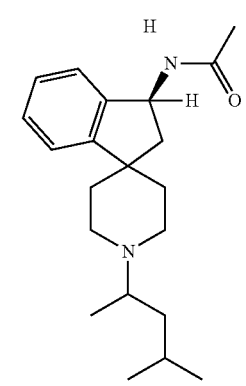

| 237 | 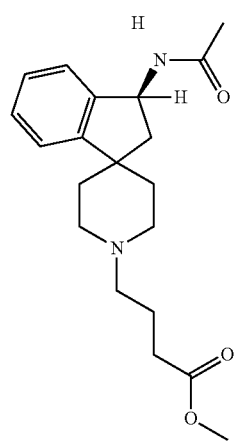 | 242 | 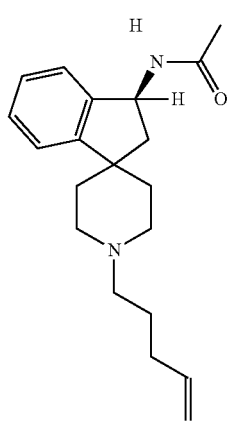 |
| 238 | 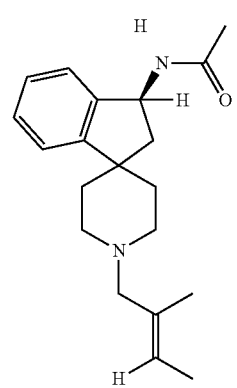 | 243 | 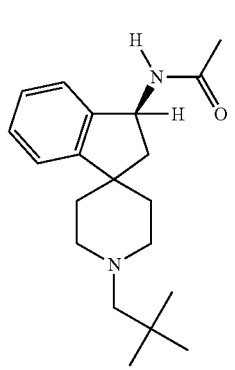 |
| 239 | 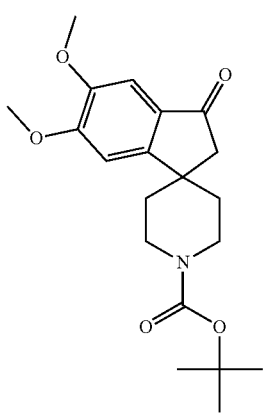 | 244 | 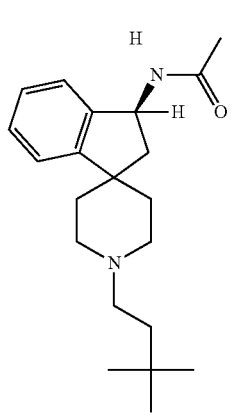 |
| 241 | 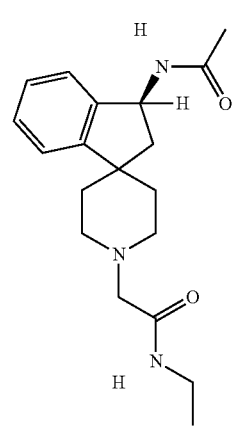 | 245 | 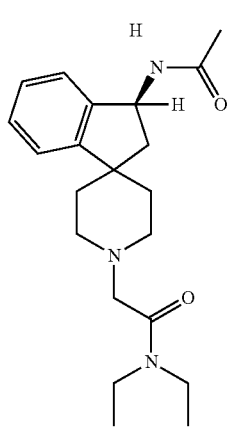 |

273
-continued
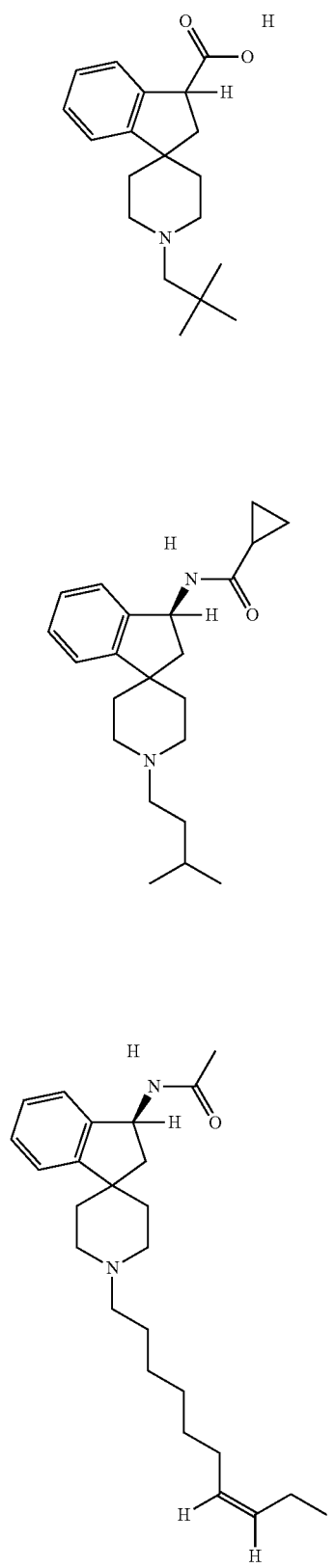
246
247
248
274
-continued
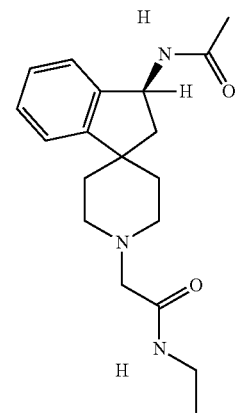
249
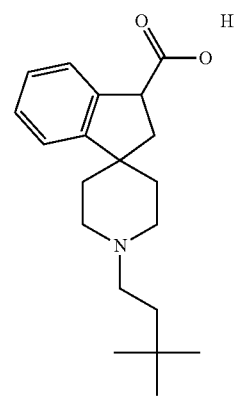
250
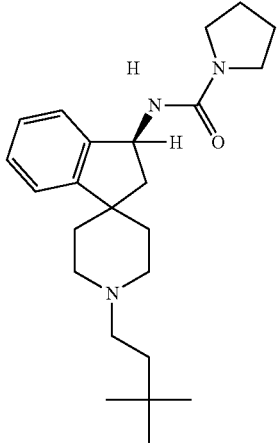
251
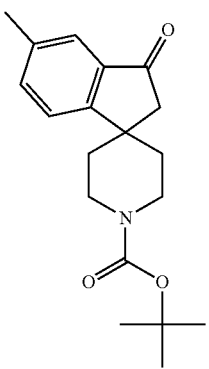
252

275
-continued
253
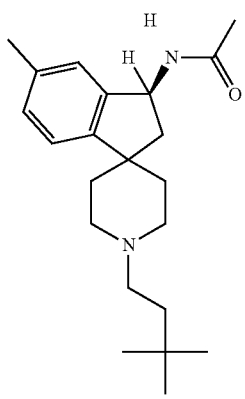
254
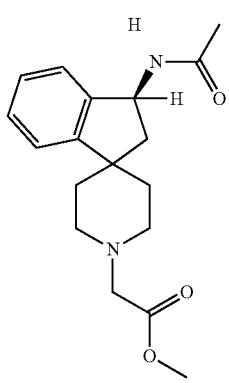
255
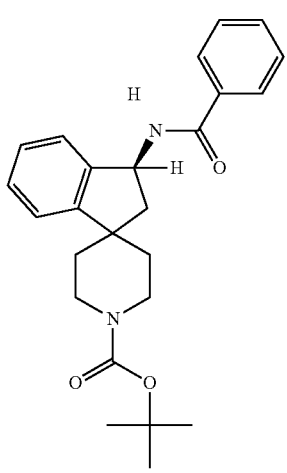
256
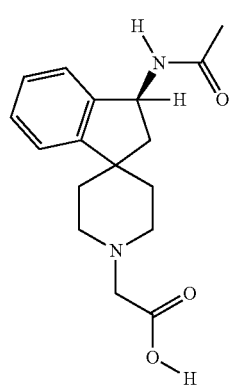
276
-continued
257
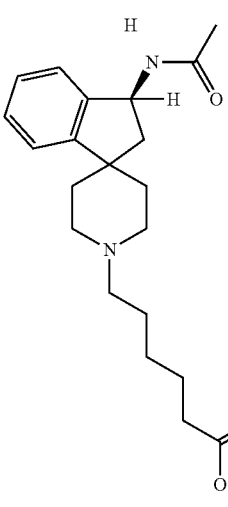
258
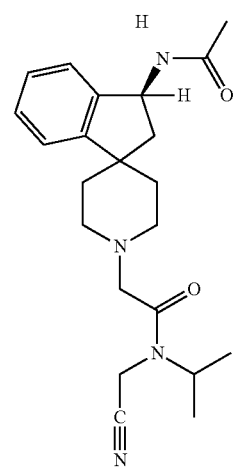
259
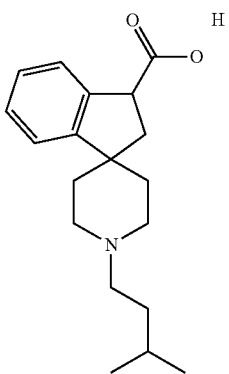

277
-continued
260 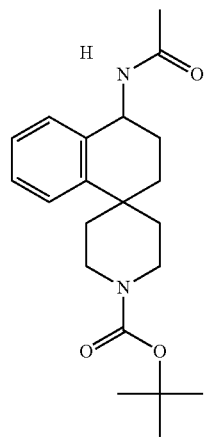
261 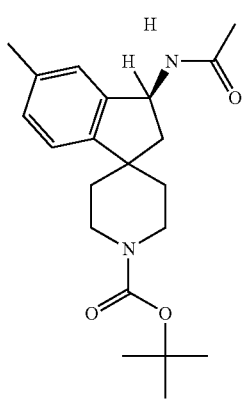
262 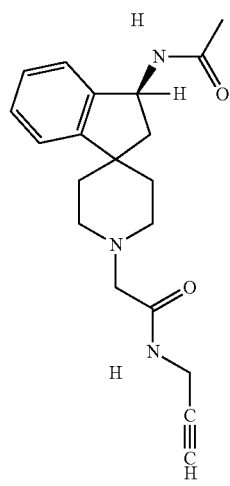
278
-continued
263 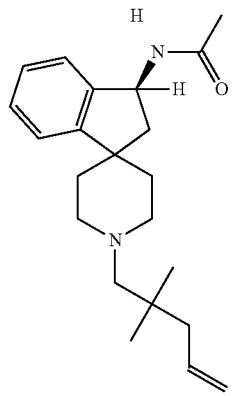
264 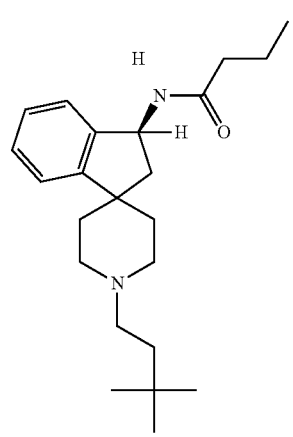
267 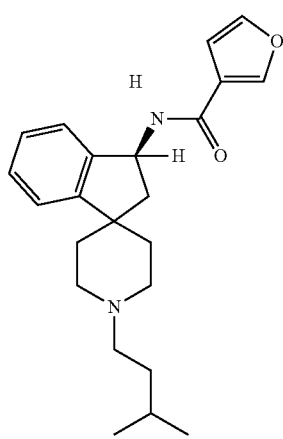

269 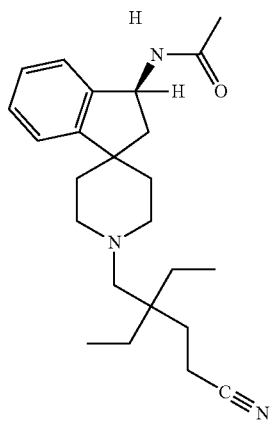
271 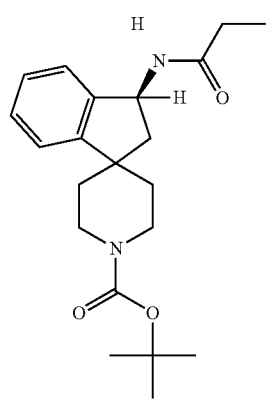
272 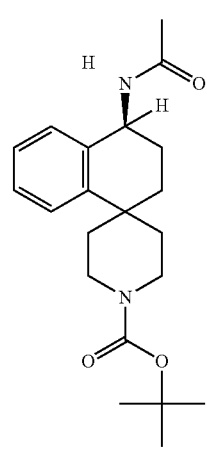
273 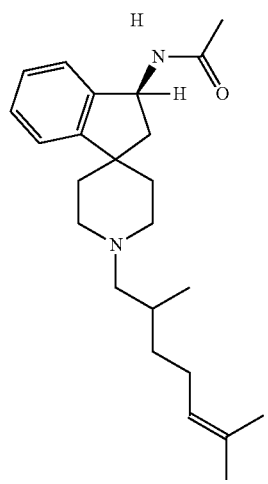
276 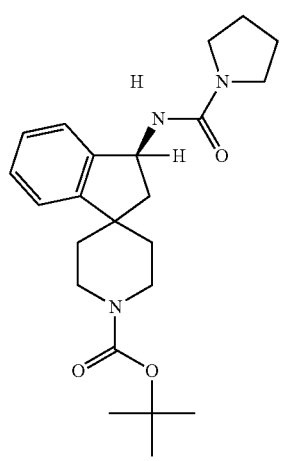
277 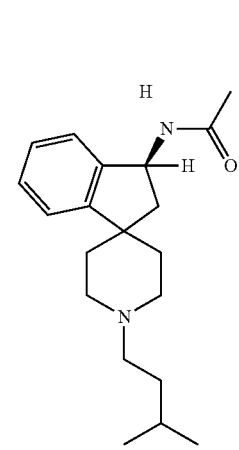

279
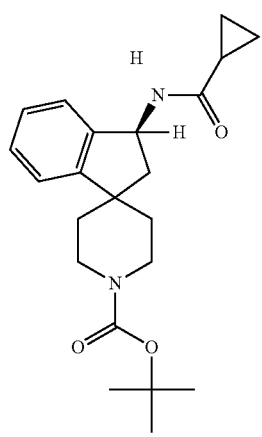
280
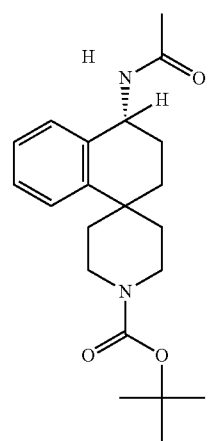
282
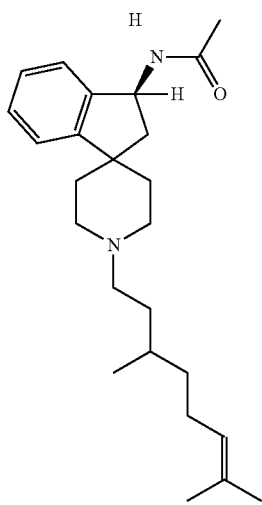
287
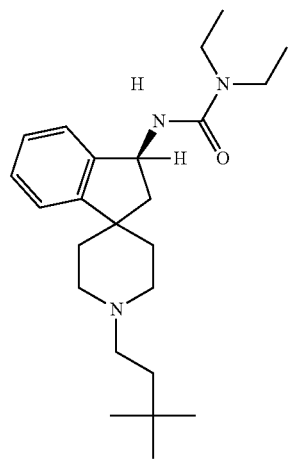
288
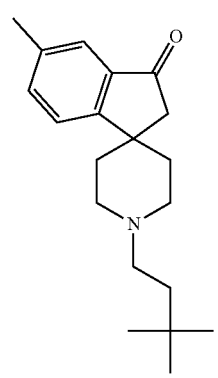
289
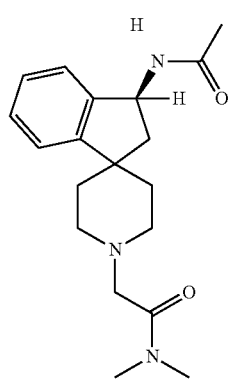
290
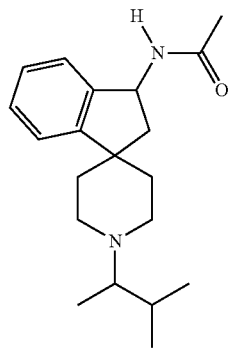

291 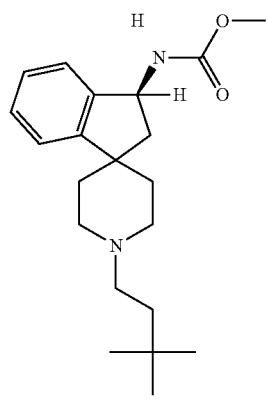
292 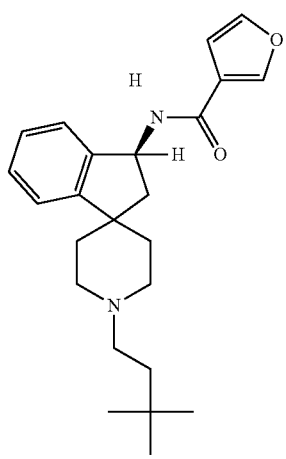
293 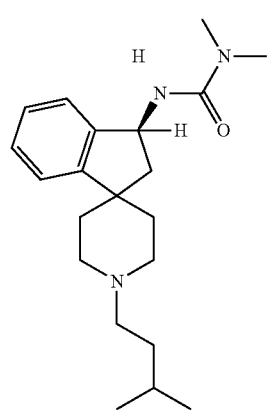
294 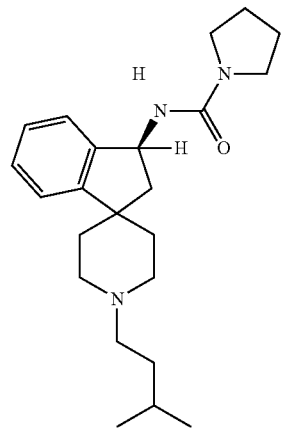
295 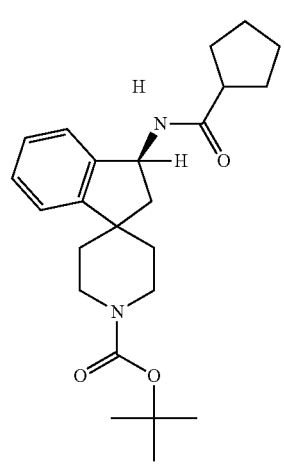
297 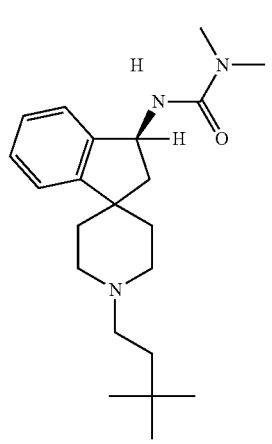

298
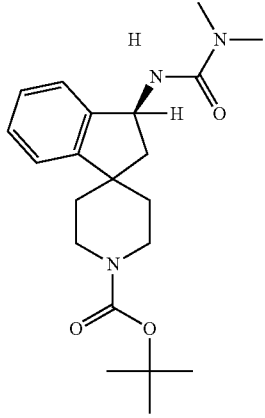
299
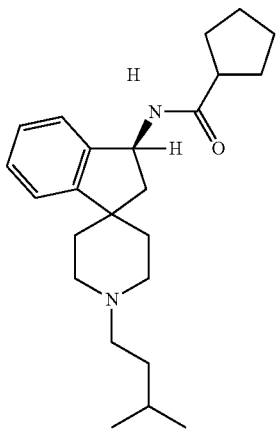
300
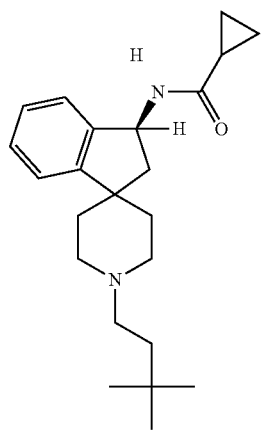
301
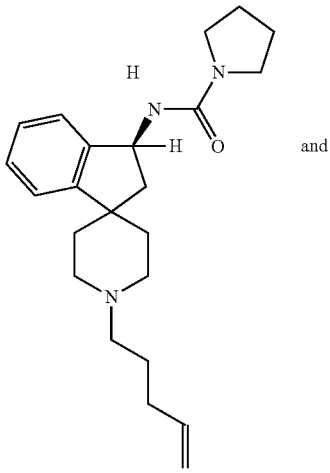
302
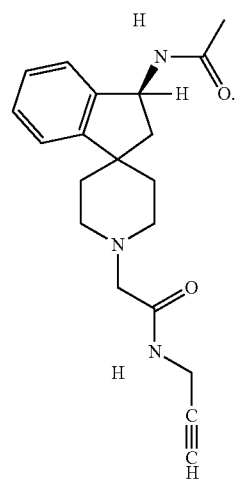
and
11. A method of modulating the activity of an $M_1$, $M_2$, or $M_4$ muscarinic receptor comprising the step of contacting said receptor with a compound selected from the group consisting of:
275
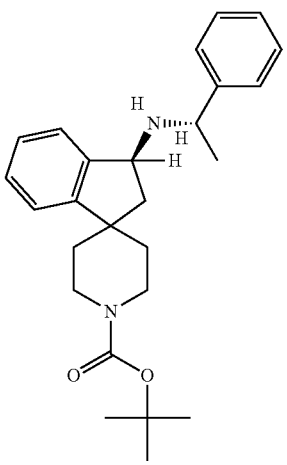

287
-continued
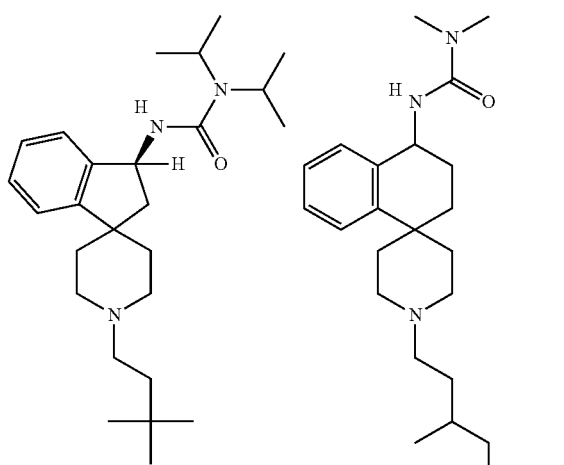
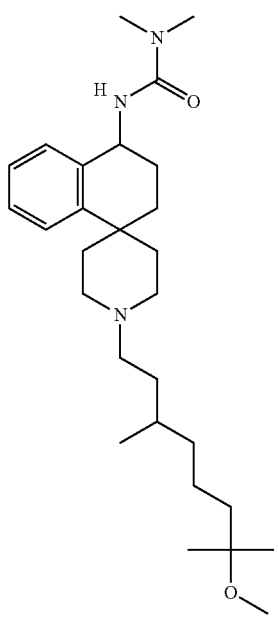
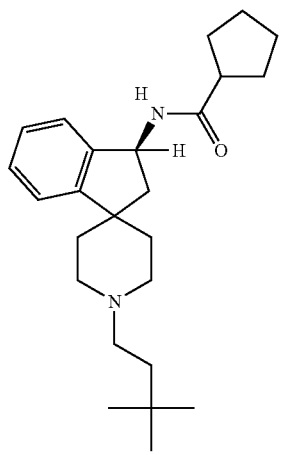
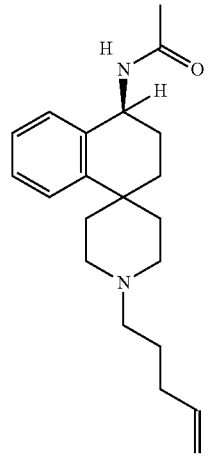
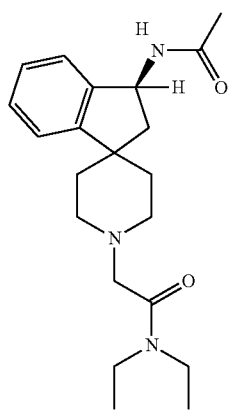
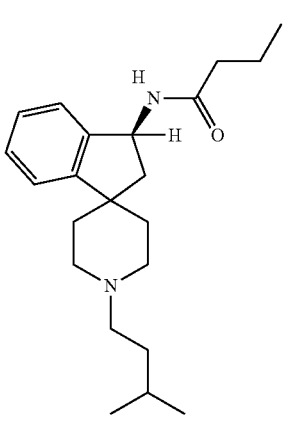
288
-continued
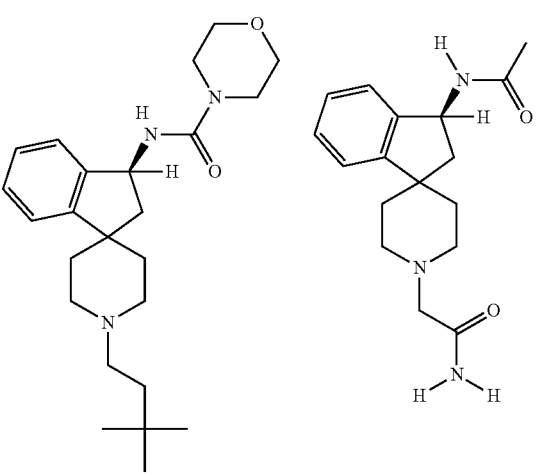
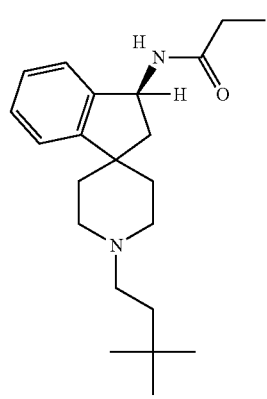
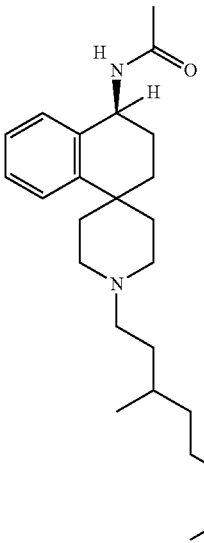
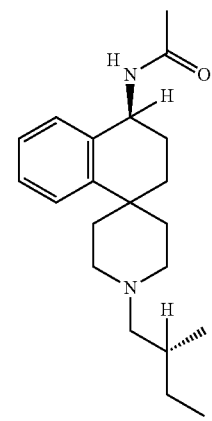
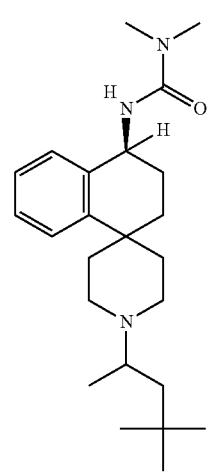

289
-continued
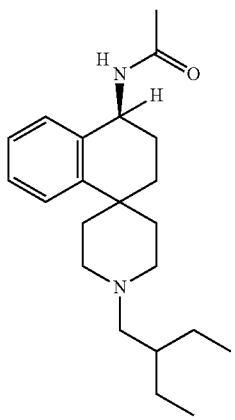 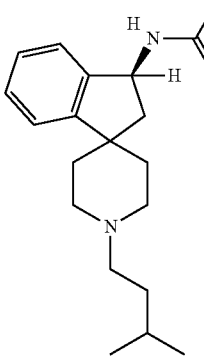
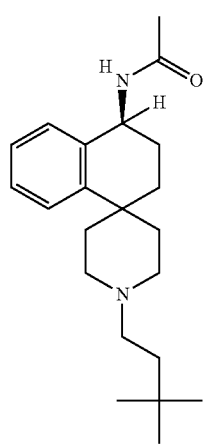 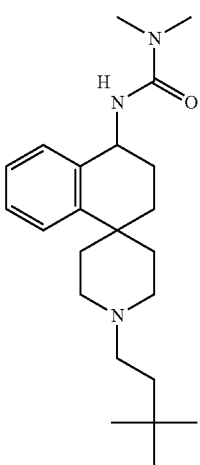
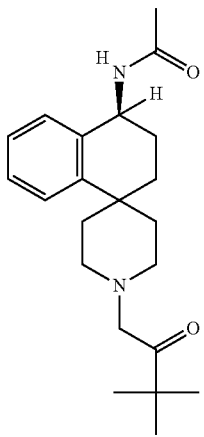 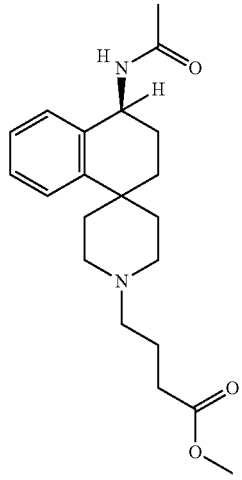
290
-continued
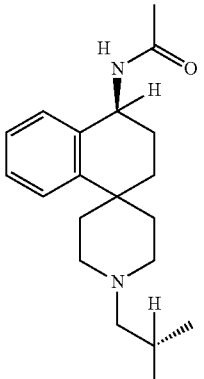 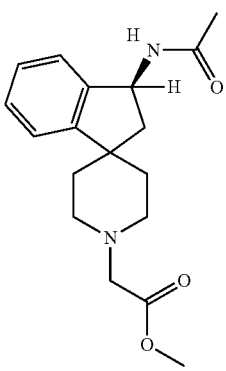
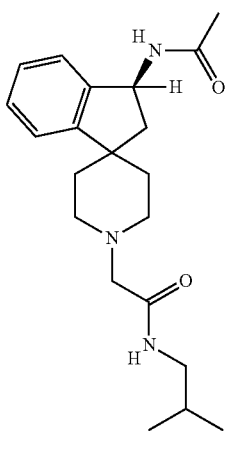 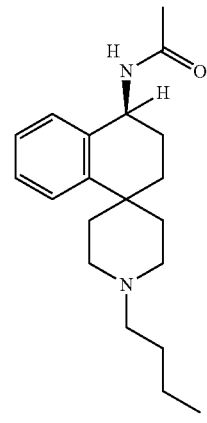
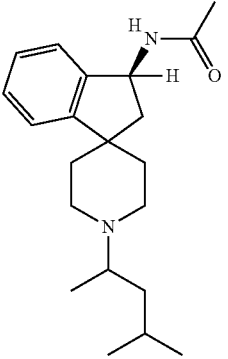 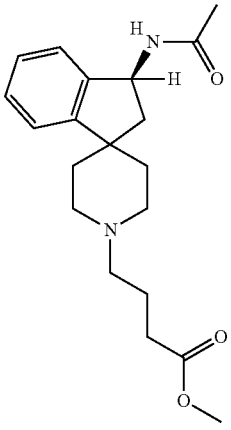
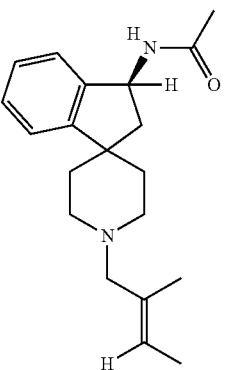 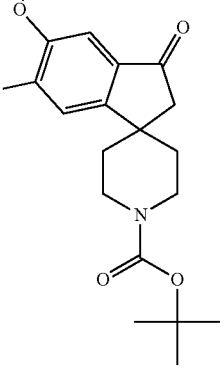

291
-continued
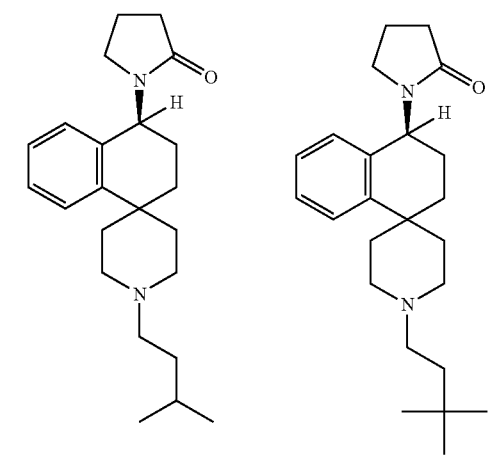
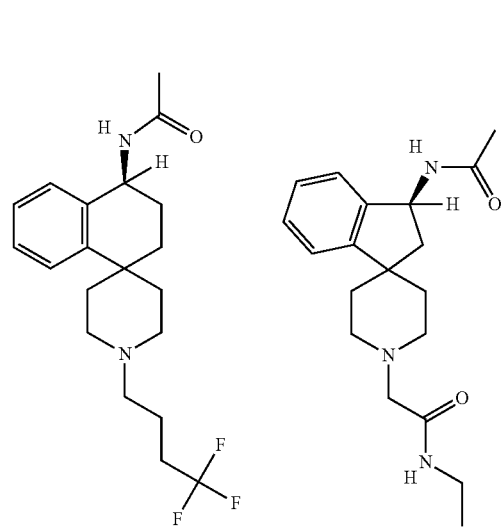
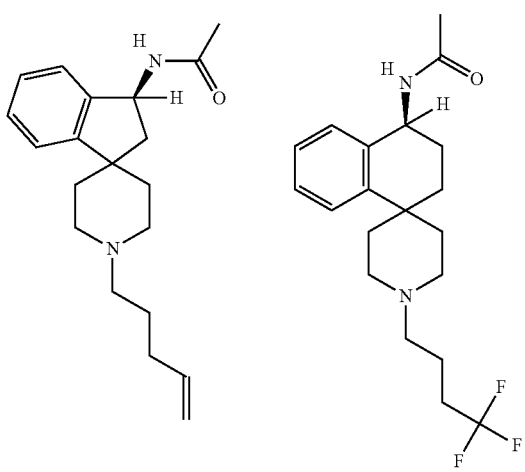
292
-continued
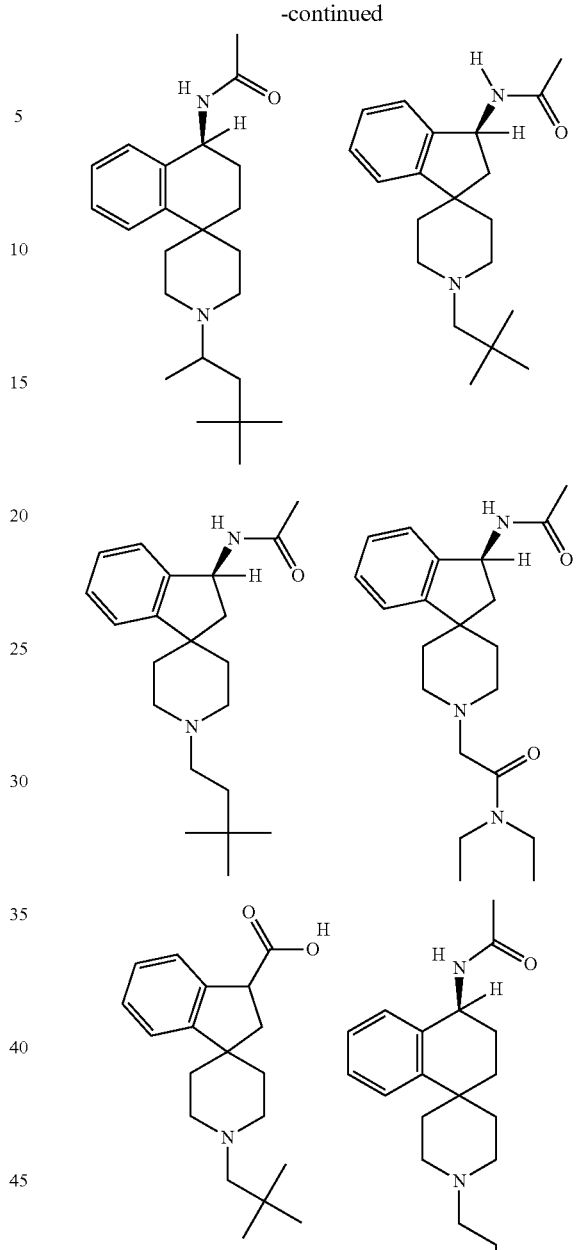
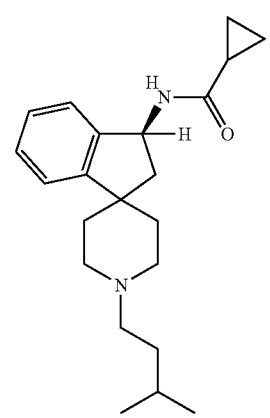

293
-continued
294
-continued
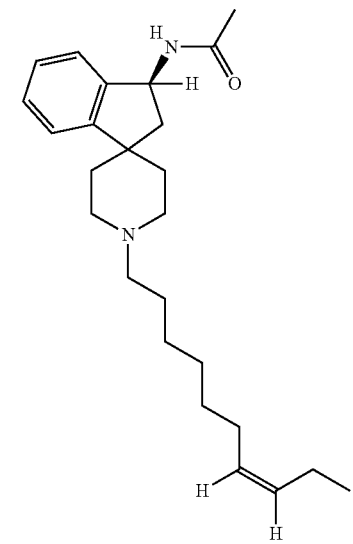
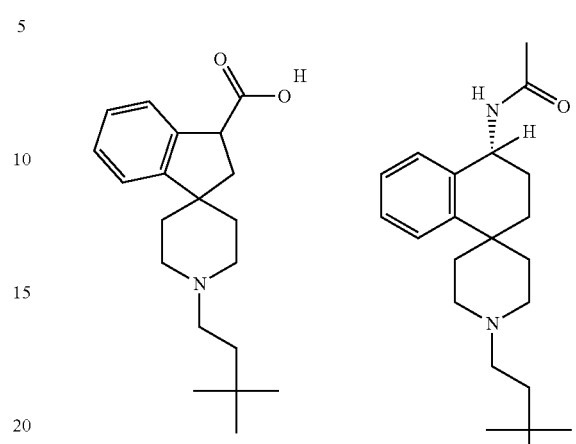
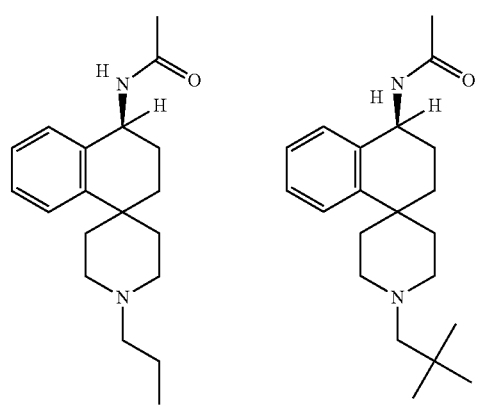
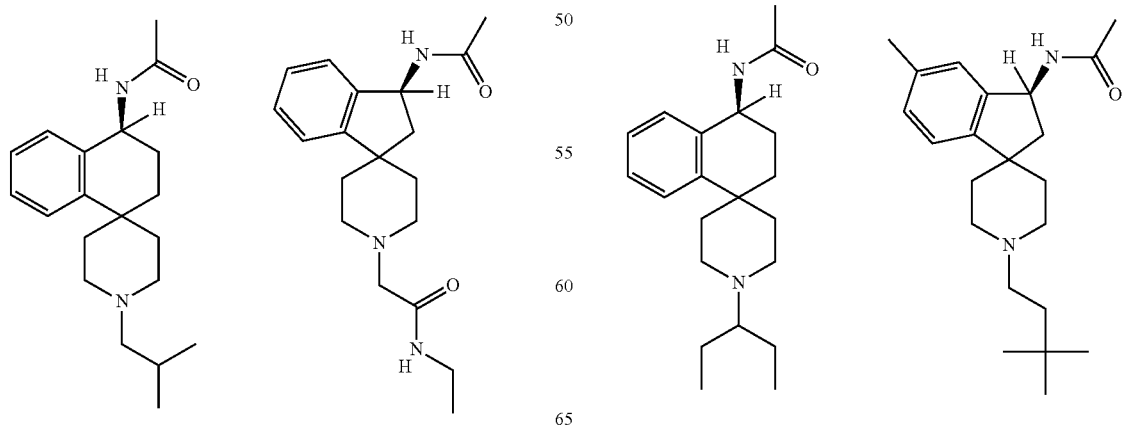

295
-continued
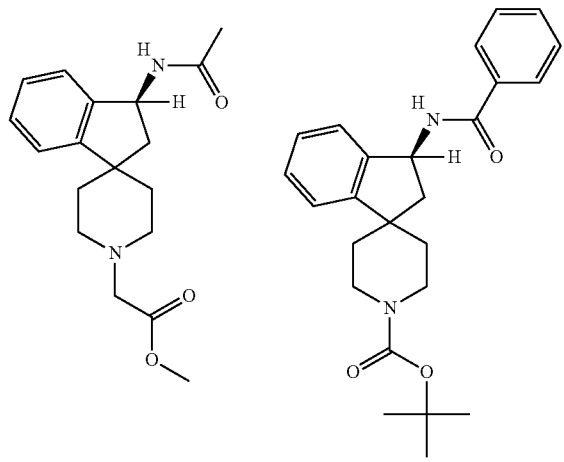
296
-continued
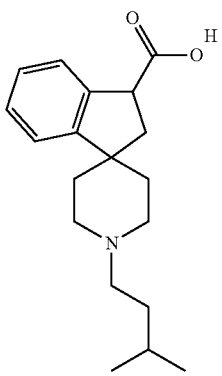
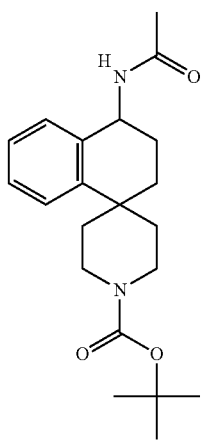
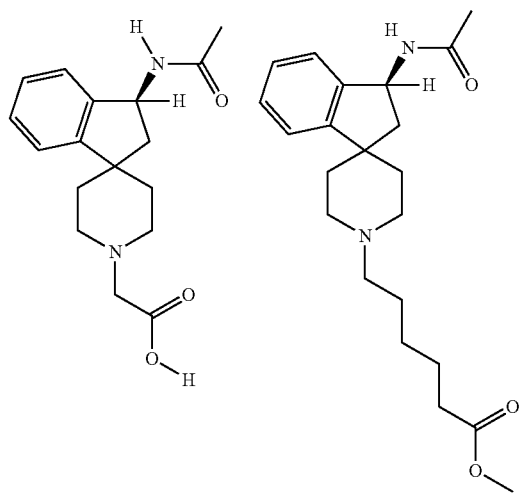
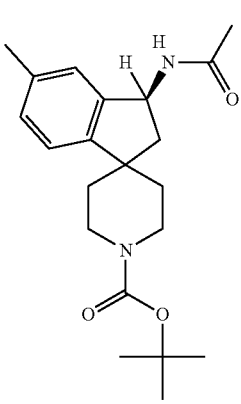
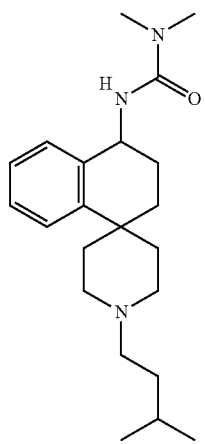
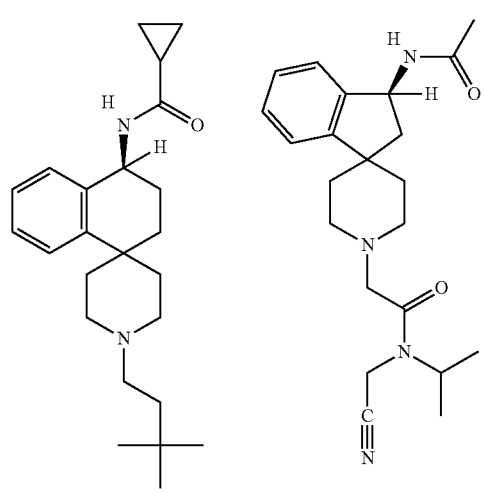
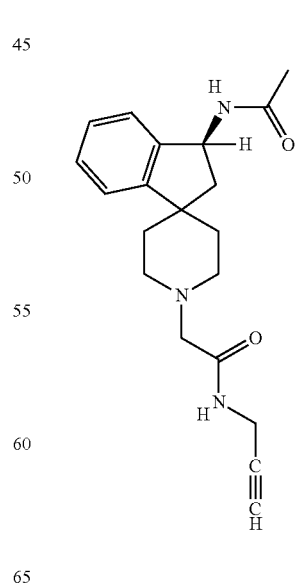
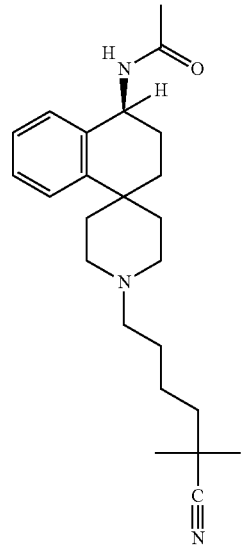

297
-continued
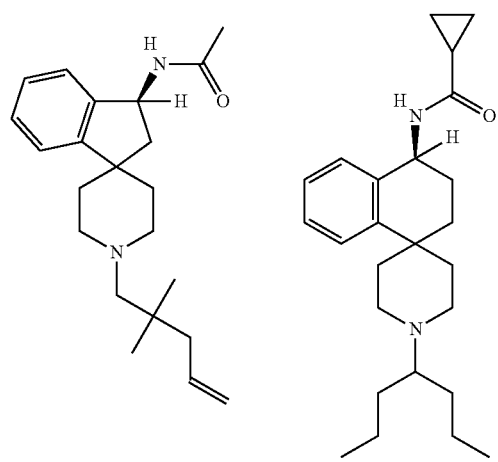
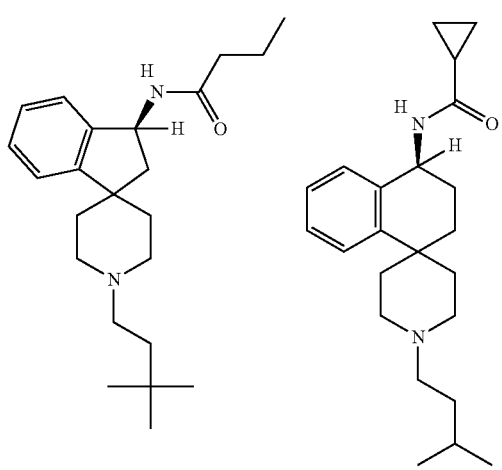
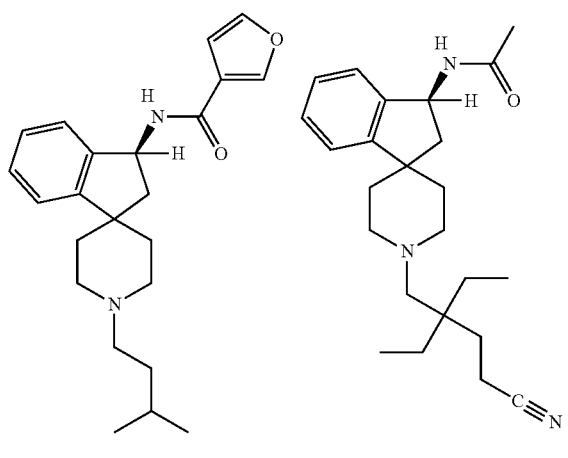
298
-continued
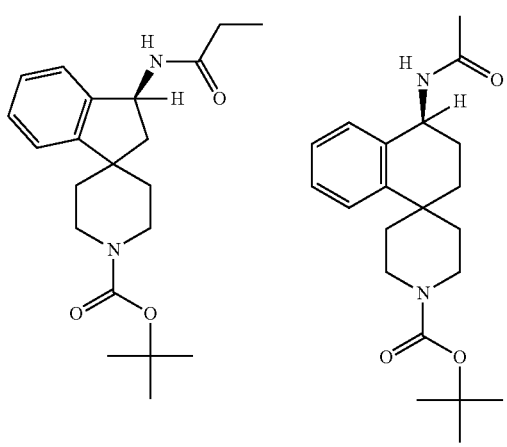
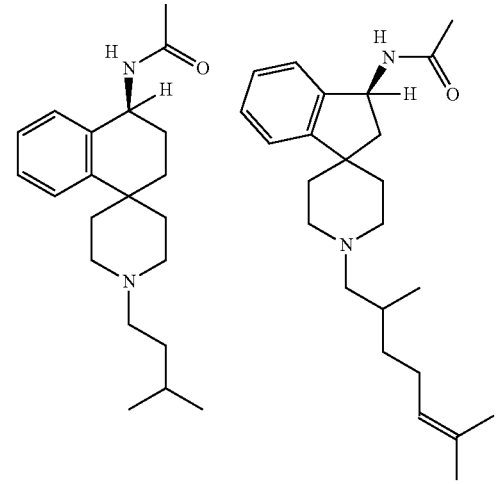
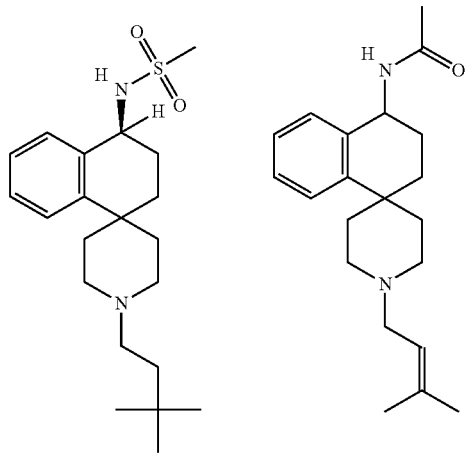

299 -continued
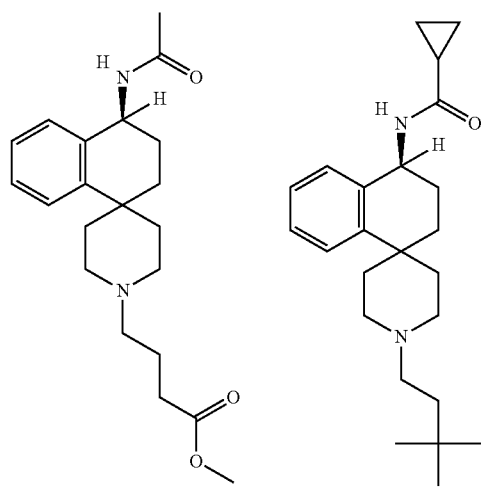
300 -continued
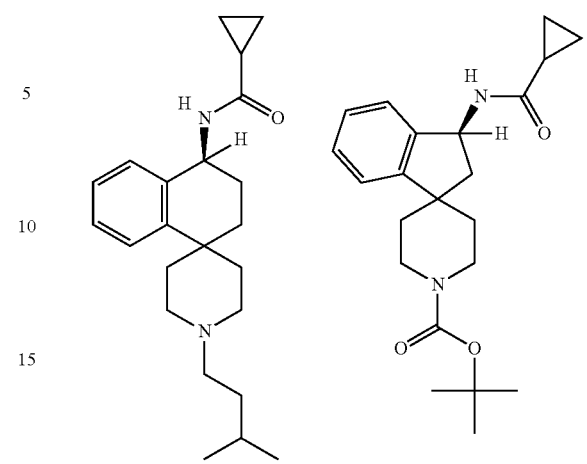
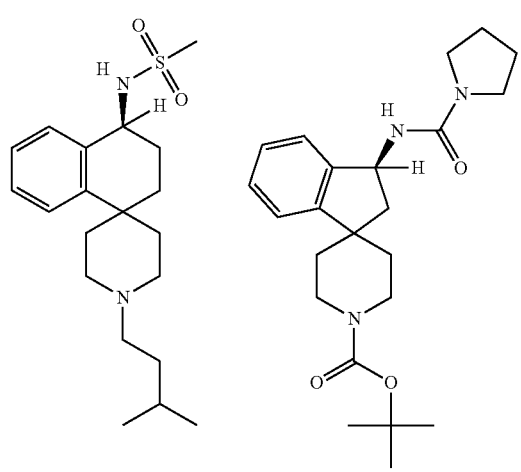
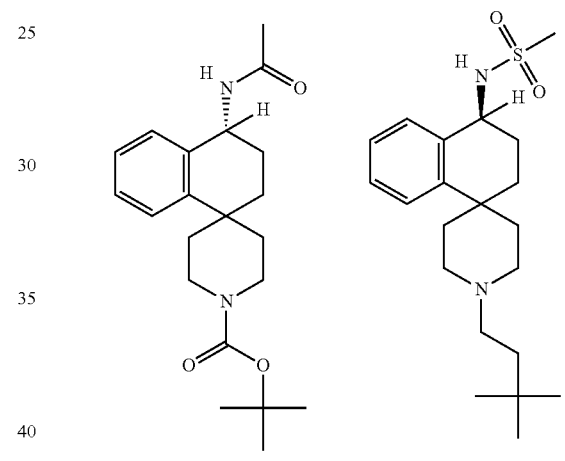
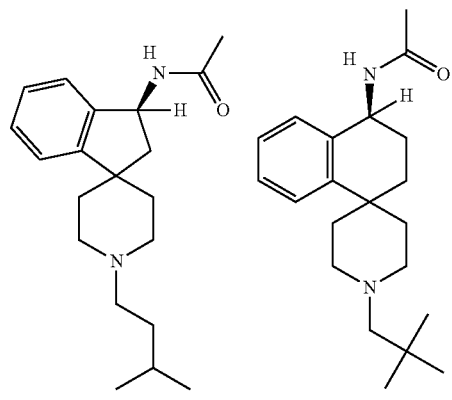
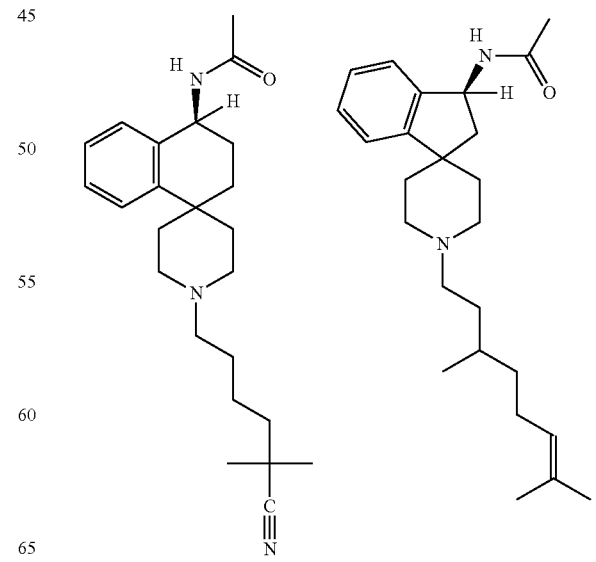

301
-continued
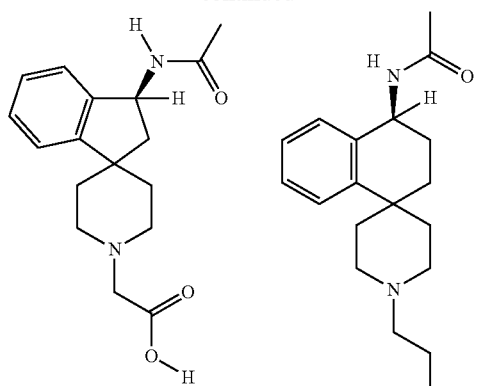
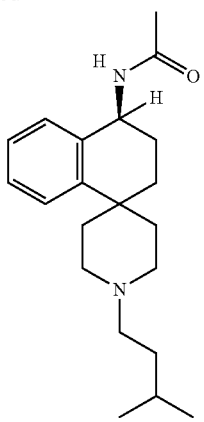
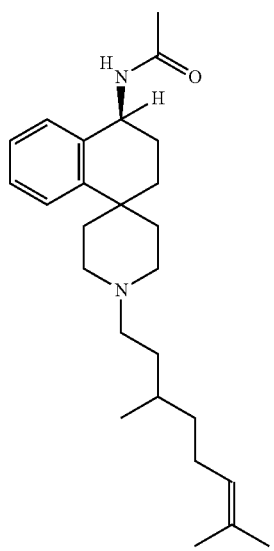
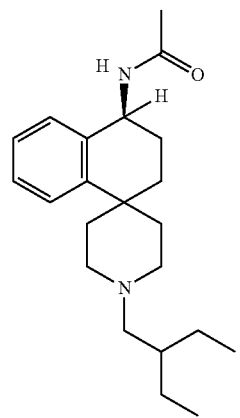
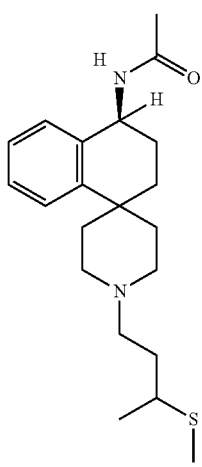
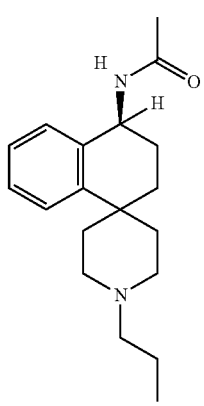
302
-continued
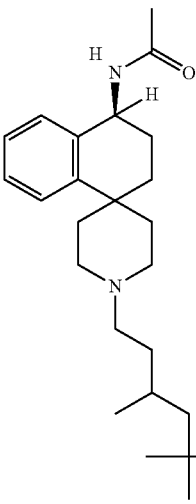
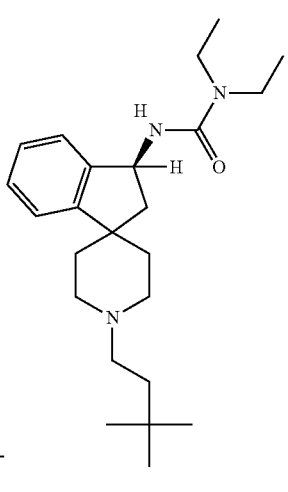
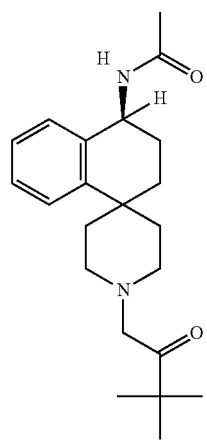
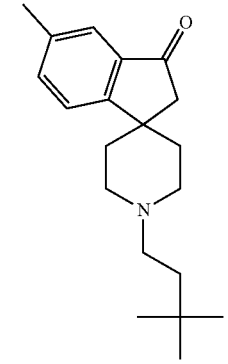
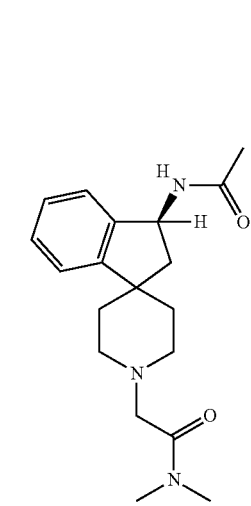
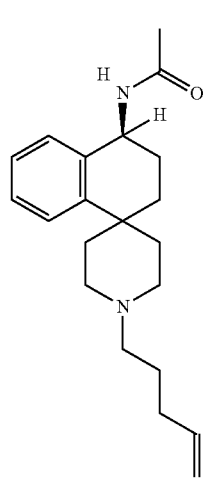

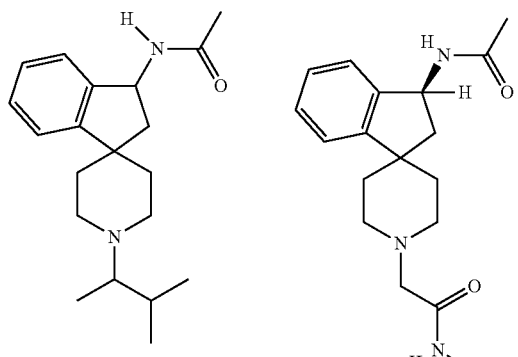
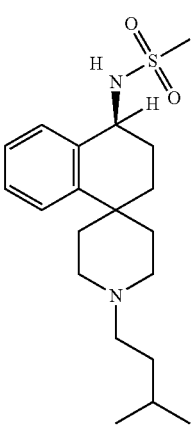
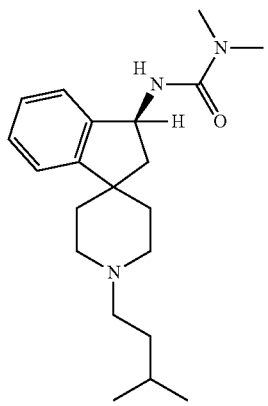
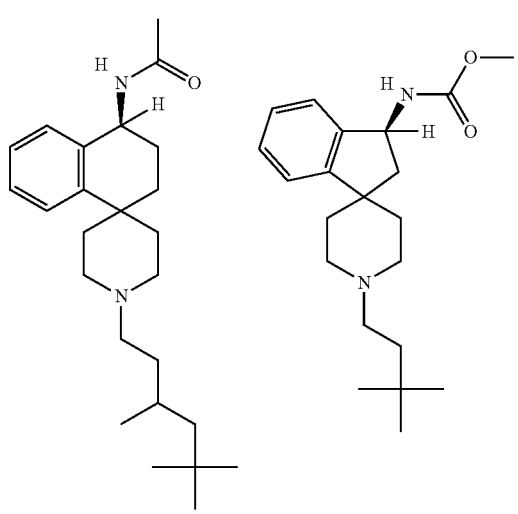
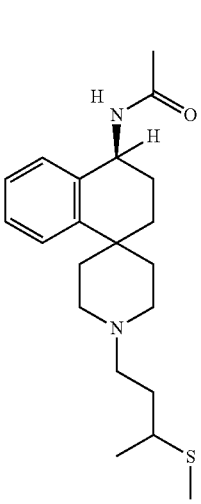
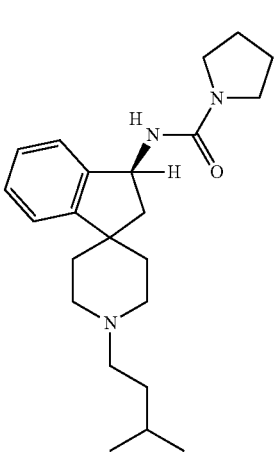
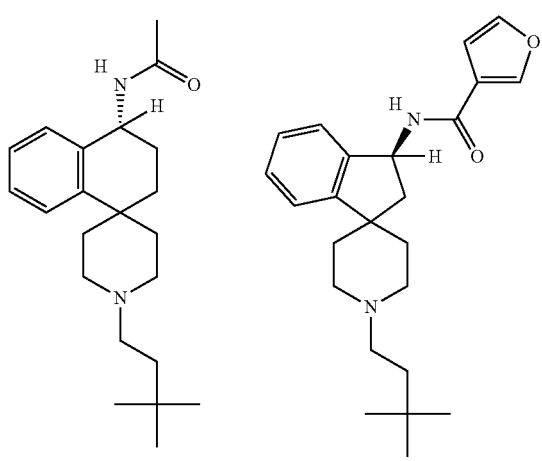
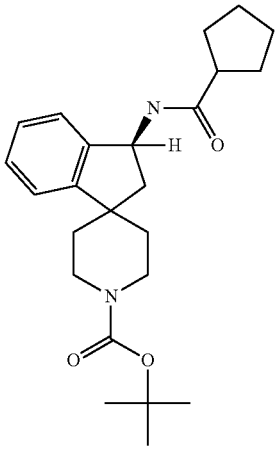
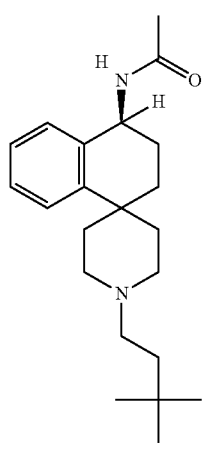

305
-continued

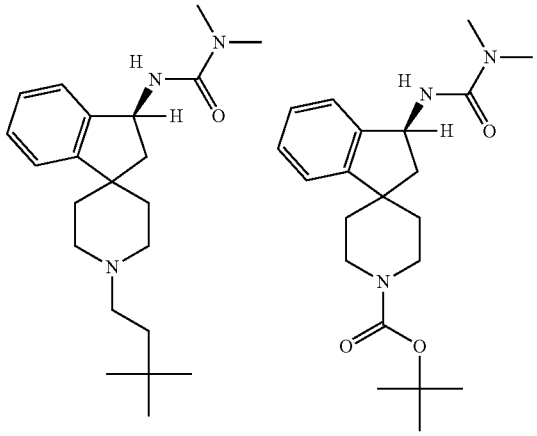

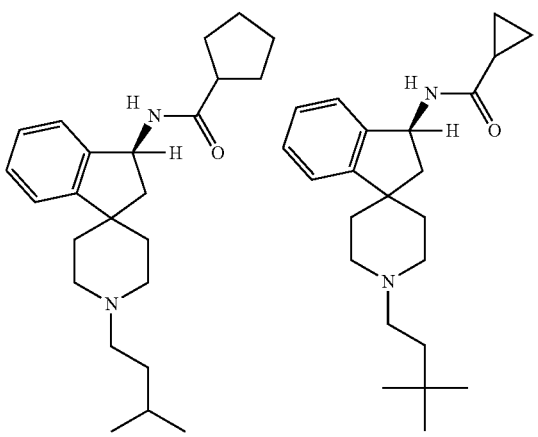

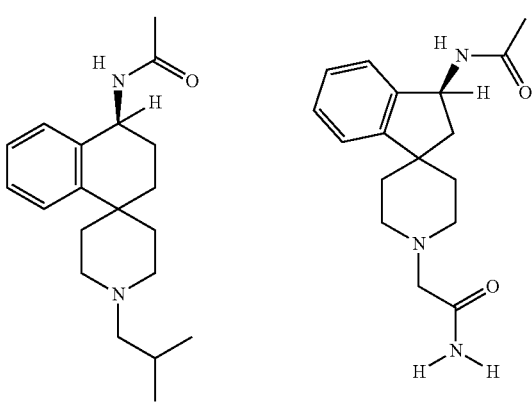

306
-continued

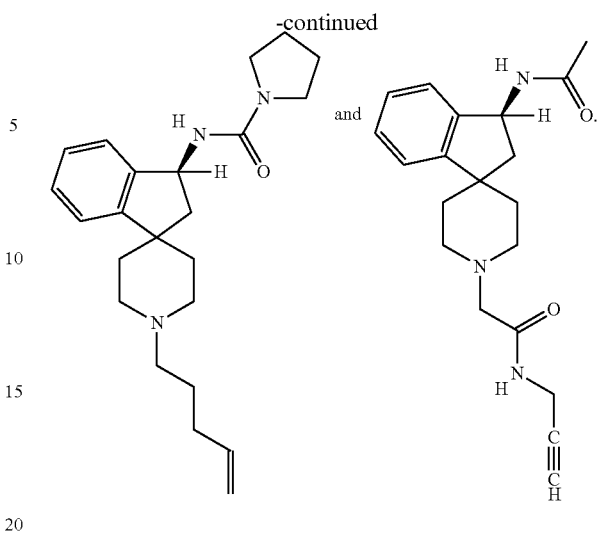

12. A method of treating or reducing the severity of a disease or condition in a patient, wherein said disease or condition is selected from Attention Deficit Hyperactivity Disorder (ADHD), obesity, Alzheimer's disease, dementia, schizophrenia, mania, bipolar disorder, acute or chronic pain conditions, Huntington's Chorea, Friederich's ataxia, Gilles de la Tourette's Syndrome, Downs Syndrome, Pick disease, clinical depression, Parkinson's disease, Glaucoma, dry eyes, dry mouth, Sjögren's Syndrome, bradycardia, gastric acid secretion, and asthma, wherein said method comprises the step of contacting said patient with a compound of formula Ie:

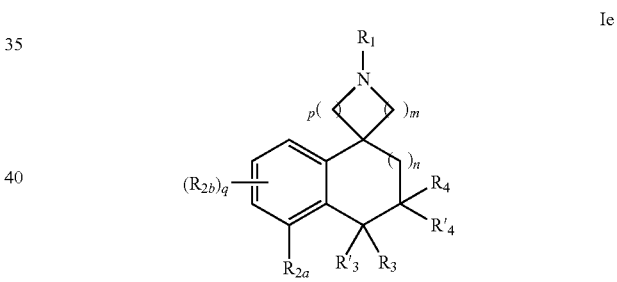

Ie or a pharmaceutically acceptable salt thereof, wherein:
$R_1$ is a branched or straight $C_{1-12}$ aliphatic optionally substituted with 1-3 of $R^A$ wherein u to 3 carbon units of $R_1$ are optionally and independently replaced by —$CONR^F$-, —O—, —$NR^FCO$—, or —S—;

Each $R^A$ is halo, —OH, —$NH_2$, —$NO_2$, —CN, or —$OCF_3$;

Each $R^F$ is hydrogen or a branched or straight $C_{1-8}$ aliphatic group optionally substituted with 1-3 of $R^A$;

$R_{2a}$ is —$Z^B R_5$, wherein each $Z^B$ is independently a bond or an optionally substituted branched or straight $C_{1-4}$ aliphatic chain wherein up to two carbon units of $Z^B$ are optionally and independently replaced by —CO— —CS— —$CONR^B$—, —$CONR^BNR^B$—, —$CO_2$—, —OCO—, —$NR^BCO_2$—O—, —$NR^BCONR^B$—, —$OCONR^B$—, —$NR^BNR^B$—, —$NR^BCO$—, —S—, —SO—, —$SO_2$—, —$NR^B$—, —$SO_2NR^B$—, —$NR^BSO_2$—, or —$NR^BSO_2NR^B$—;

Each $R_5$ is independently $R^B$ halo —OH —CN or —$OCF_3$;

Each $R^B$ is independently hydrogen an optionally substituted $C_{1-8}$ aliphatic group, an optionally substituted cycloaliphatic, an optionally substituted heterocycloaliphatic, an optionally substituted aryl, an optionally substituted heteroaryl, or $R_{2a}$ and $R_3$ to ether with the atoms to which the are attached form a 5-7 membered partially unsaturated optionally substituted cyclic group optionally having 1-2 heteroatoms independently selected from N, O, and S;

Each $R_{2b}$ is hydrogen, fluoro or methyl; or $R_{2a}$ and one $R_{2b}$ to ether with the atoms to which the are attached form a 5-7 membered partially unsaturated optionally substituted cyclic group optionally having 1-2 heteroatoms independently selected from N, O, and S, wherein $R_{2b}$ is attached to a carbon atom vicinal to the carbon atom to which $R_{2a}$ is attached on the fused phenyl of formula I, or Two of $R_{2b}$ to ether with the atoms to which the are attached form a 5-7 membered partially unsaturated optionally substituted cyclic group optionally having 1-2 heteroatoms independently selected from N, O, and S, wherein each $R_{2b}$ is attached to a vicinal carbon atom on the fused phenyl of formula Ie;

one of $R_3$ and $R'_3$ is hydrogen and the other of $R_3$ and $R'_3$ is independently $-Z^C R_6$, wherein each $Z^C$ is independently an optionally substituted branched or straight $C_{1-4}$ aliphatic chain wherein up to two carbon units of $Z^C$ are optionally and independently replaced by $-CO-$ $-CS-$, $-CONR^C-$, $-CONR^C NR^C-$, $-CO_2$, $-OCO-$, $-NR^C CO_2-$, $-O-$, $-NR^C CONR^C-$, $-OCONR^C-$, $-NR^C NR^C-$, $-NR^C CO-$, $-S-$, $-SO-$, $-SO_2-$, $-SO_2 NR^C-$, $-NR^C SO_2-$, or $-NR^C SO_2 NR^C-$;

Each $R_6$ is independently $R^C$, halo, $-OH$, $-NH_2-$, $-NO_2$, $-CN$, or $-OCF_3$;

Each $R^C$ is independently hydrogen an optionally substituted $C_{1-8}$ aliphatic group; an optionally substituted cycloaliphatic, an optionally substituted heterocycloaliphatic, an optionally substituted aryl, or an optionally substituted heteroaryl having 1-3 heteroatoms;

$R_4$ and $R'_4$ are each independently hydrogen or fluoro;

m is 2, p is 2;

n is 0-2; and q is 0-3.

13. The method of claim 12, wherein $R_1$ is a straight $C_{1-10}$ alkyl, straight $C_{2-10}$ alkenyl, straight $C_{2-10}$ alkynyl, branched $C_{3-12}$ alkyl, branched $C_{3-12}$ alkenyl, or branched $C_{3-12}$ alkynyl, each of which is optionally substituted with 1-3 of $R^A$; and each $R^A$ is independently halo, $-OH$, $-NH_2$, $-NO_2$, $-CN$, or $-OCF_3$.

14. The method of claim 12, wherein $R_1$ is an optionally substituted straight or branched $C_{1-12}$ aliphatic wherein 1-2 of the carbon units have been optionally replaced with $-S-$.

15. The method of claim 12, wherein $R_1$ is one selected from:

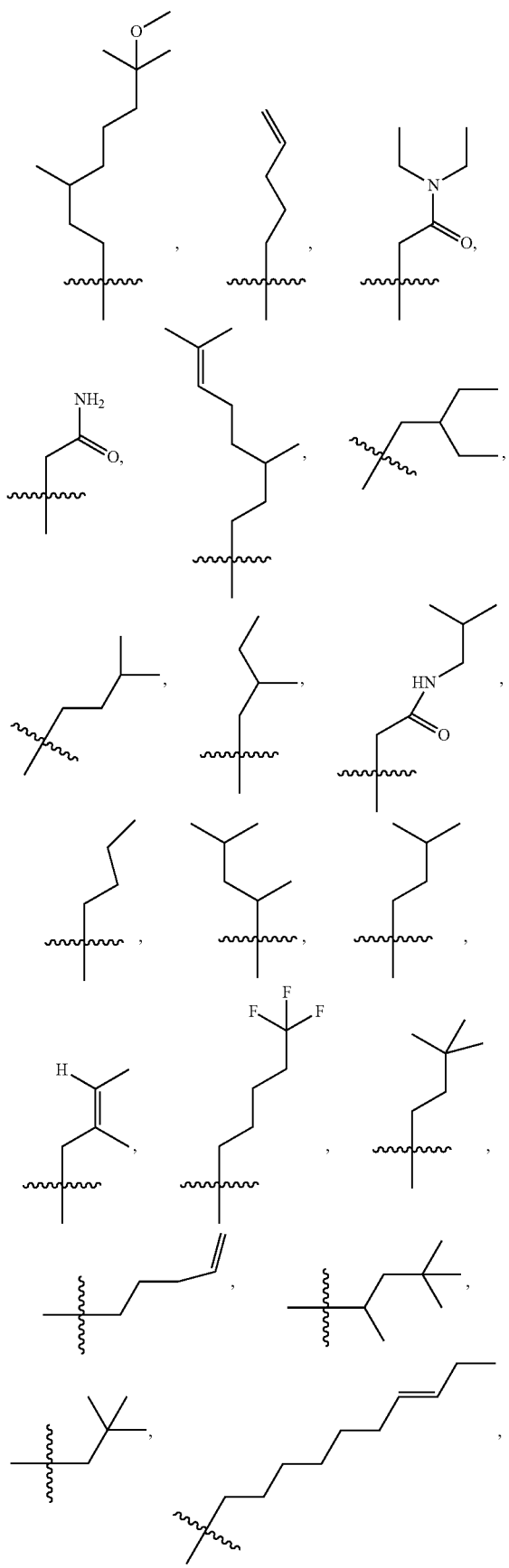

-continued

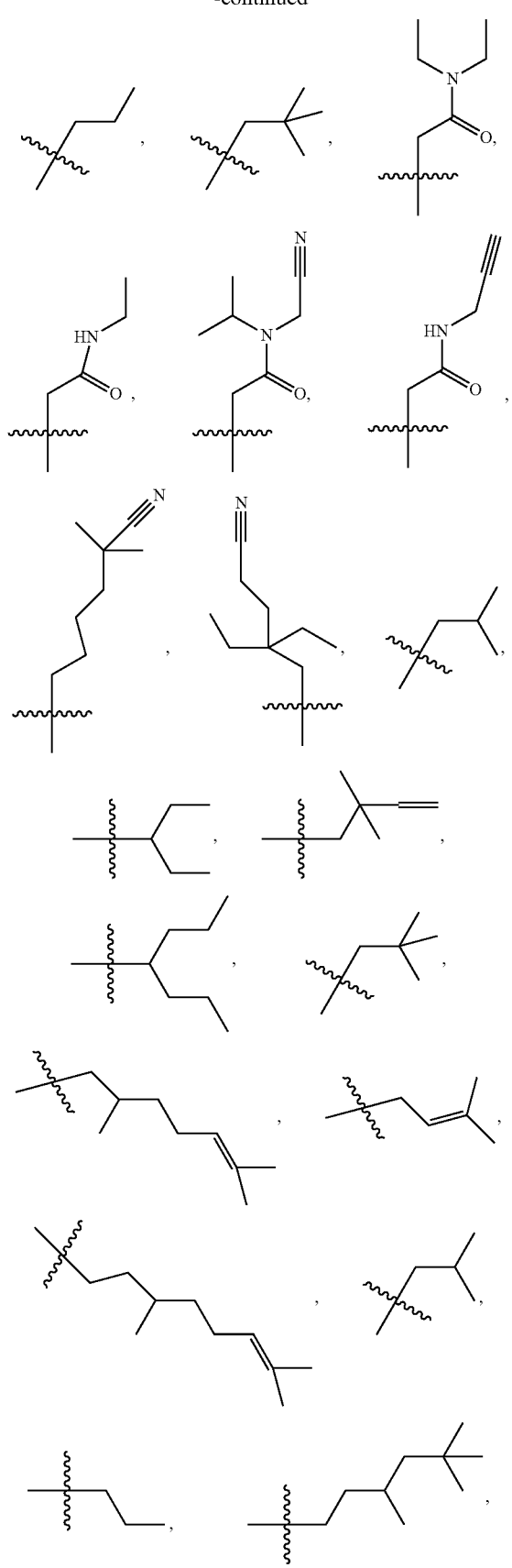

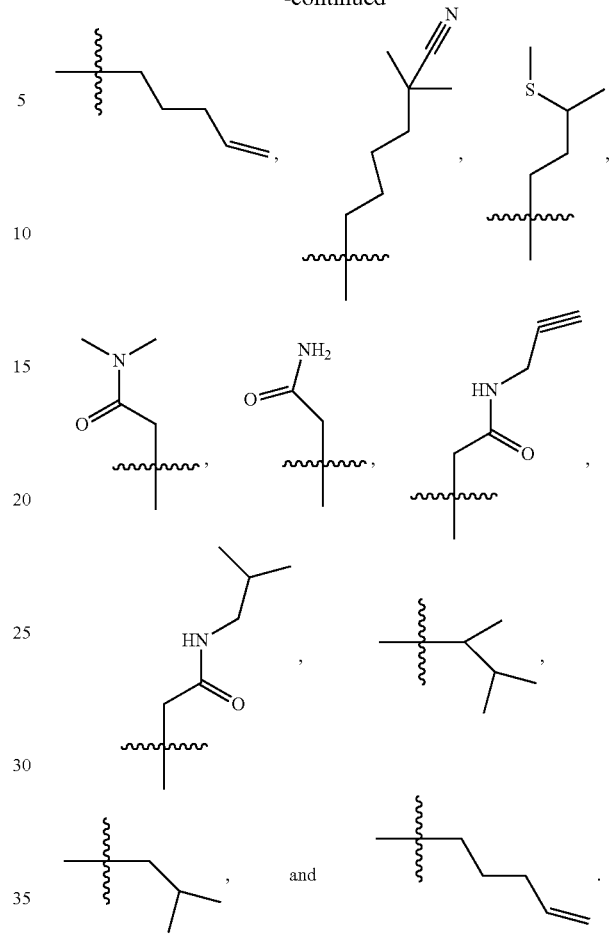

16. The method of claim 12, wherein q is 0 and $R_{2a}$ is hydrogen.

17. The method of claim 12, wherein one of $R_3$ and $R'_3$ is a branched or straight optionally substituted $C_{1-4}$ aliphatic wherein up to two carbon units of $R_3$ or $R'_3$ are optionally and independently replaced by —C(O)—, —CONH—, or —S(O)$_2$—, and the remaining $R_3$ or $R'_3$ is hydrogen.

18. The method of claim 17, wherein one of $R_3$ and $R'_3$ is straight optionally substituted $C_{2-4}$ aliphatic wherein a first carbon unit is optionally and independently replaced by —CONH—.

19. The method of claim 18, wherein one of $R_3$ and $R'_3$ is an optionally substituted (methylcarbonyl)amino, and the remaining $R_3$ or $R'_3$ is hydrogen.

20. The method of claim 12, wherein $R_3$ or $R'_3$ is independently selected from:

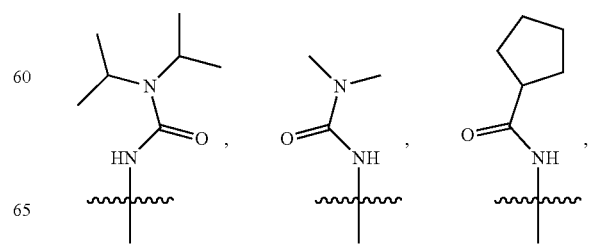

-continued
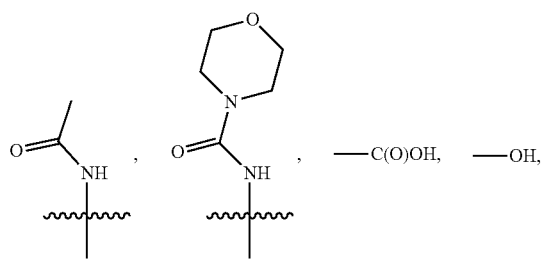
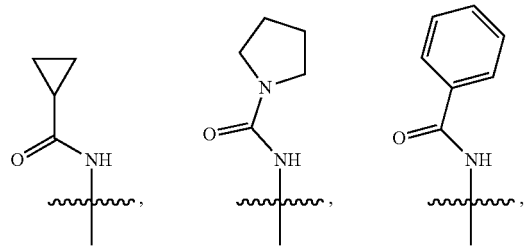
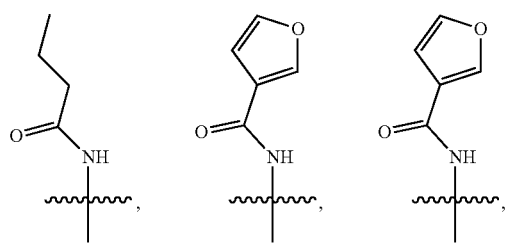
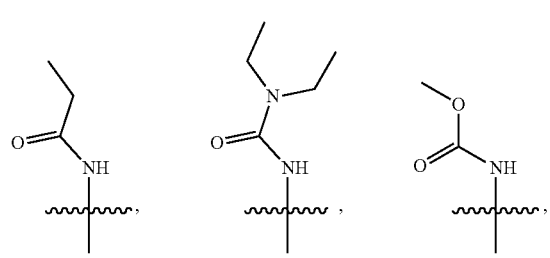
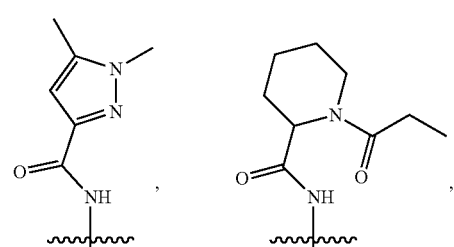
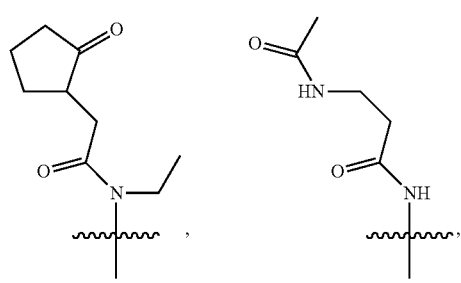
-continued
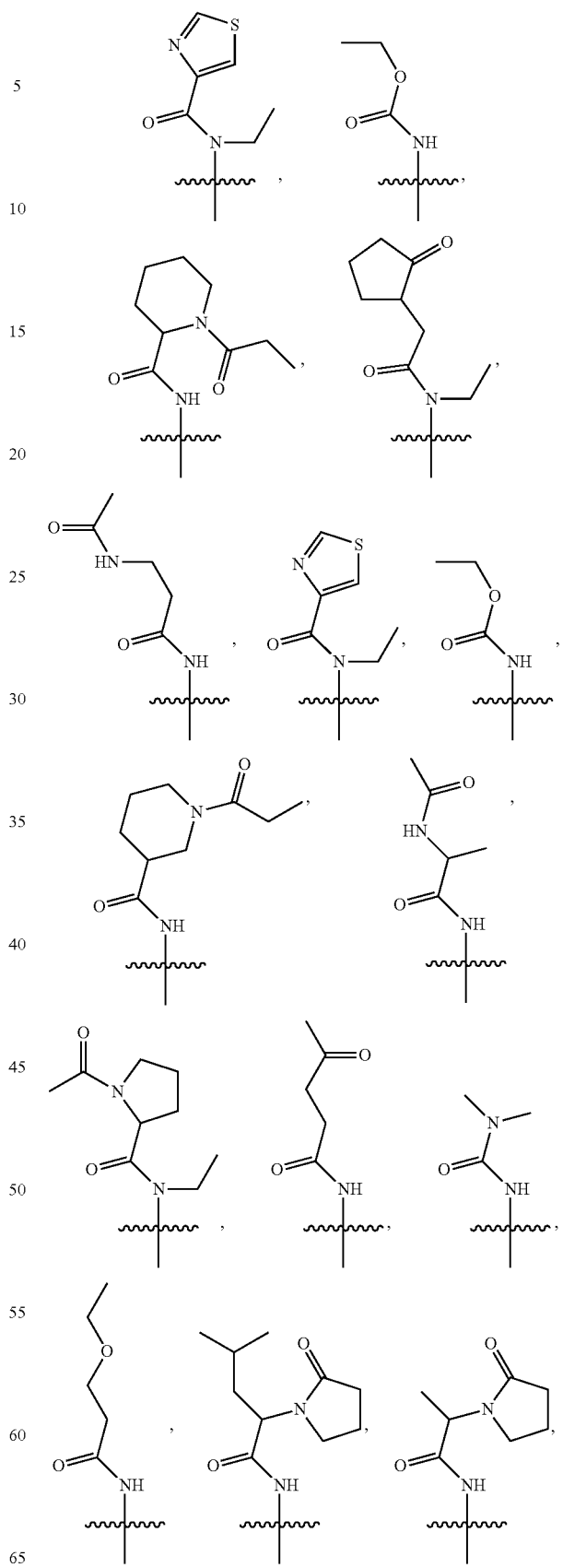

313
-continued
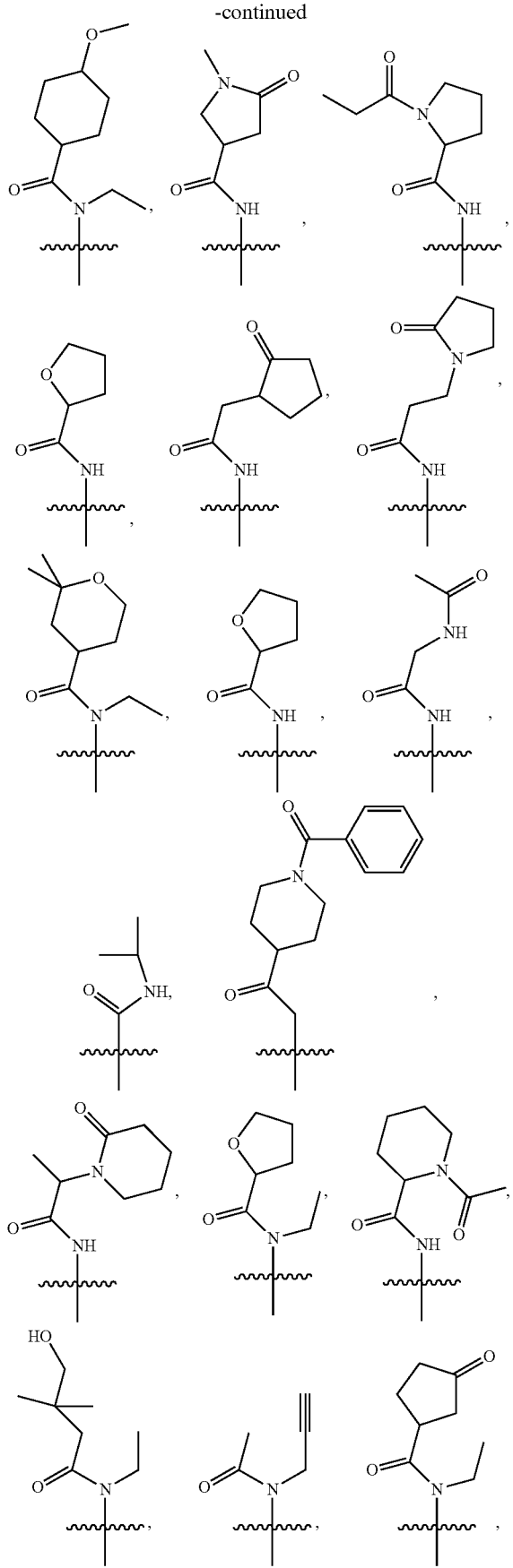
314
-continued
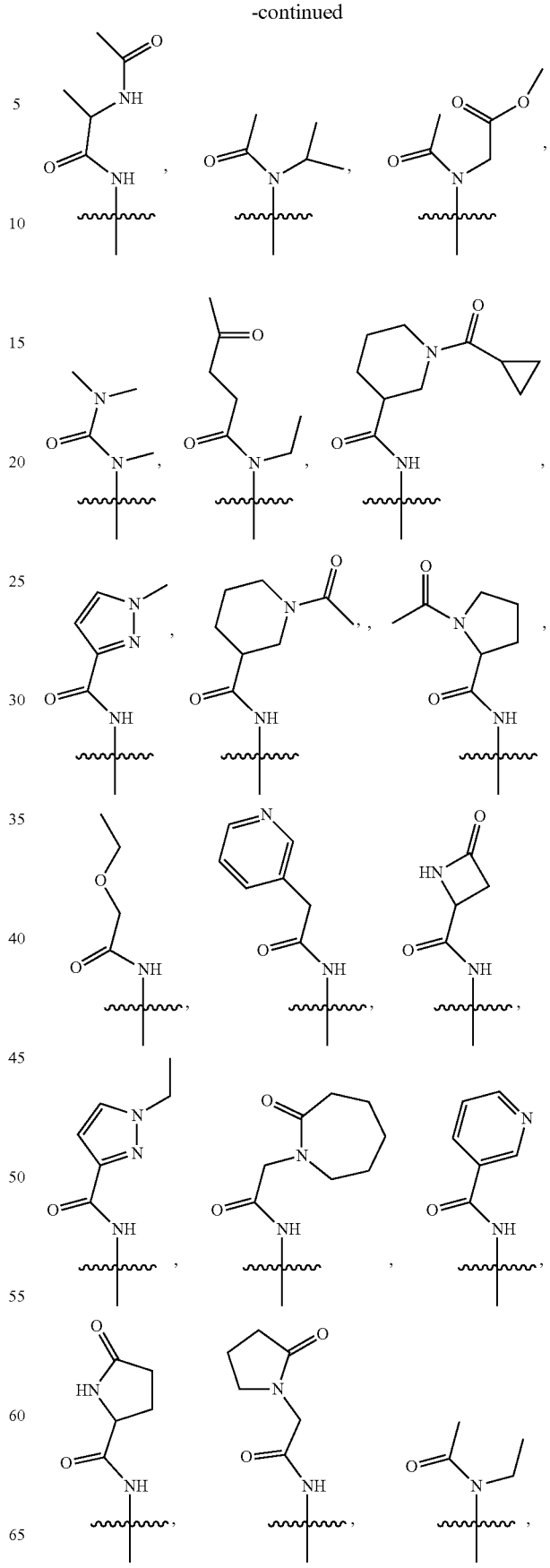

315
-continued

316
-continued

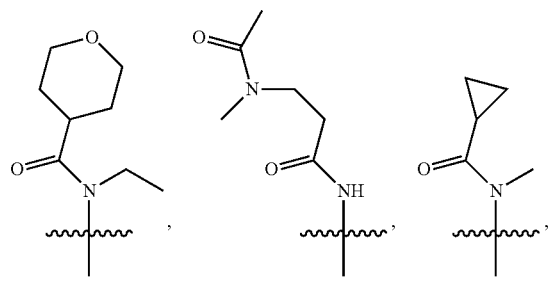
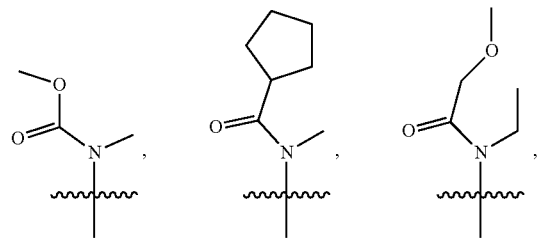
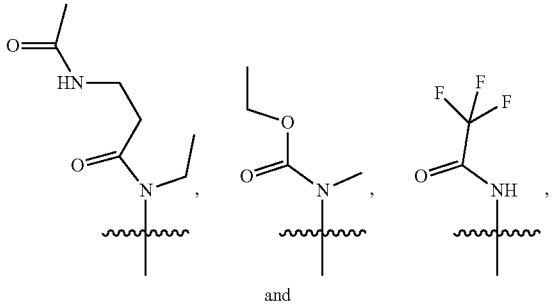
and
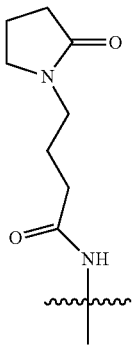
* * * * *